(12) United States Patent
Tangy et al.

(10) Patent No.: US 10,316,066 B2
(45) Date of Patent: Jun. 11, 2019

(54) DENGUE VIRUS CHIMERIC POLYEPITOPE COMPOSED OF FRAGMENTS OF NON-STRUCTURAL PROTEINS AND ITS USE IN AN IMMUNOGENIC COMPOSITION AGAINST DENGUE VIRUS INFECTION

(71) Applicants: INSTITUT PASTEUR, Paris (FR); CENTRE NATIONAL DE LA RECHERCHE SCIENTIFIQUE, Paris (FR)

(72) Inventors: Frederic Tangy, Les Lilas (FR); Anavaj Shakuntabai, Paris (FR); Etienne Simon-Loriere, Deuil-la-Barre (FR); Claude Roth, Paris (FR); Philippe Buchy, Juan les Pins (FR)

(73) Assignees: INSTITUT PASTEUR, Paris (FR); INSTITUT PASTEUR DU CAMBODGE, Phnom-Penh (KH); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/320,033

(22) PCT Filed: Jun. 22, 2015

(86) PCT No.: PCT/EP2015/064010
§ 371 (c)(1),
(2) Date: Dec. 19, 2016

(87) PCT Pub. No.: WO2015/197565
PCT Pub. Date: Dec. 30, 2015

(65) Prior Publication Data
US 2017/0158740 A1    Jun. 8, 2017

(30) Foreign Application Priority Data
Jun. 23, 2014   (EP) .................................. 14305984

(51) Int. Cl.
*A61K 39/12* (2006.01)
*C07K 14/005* (2006.01)
(Continued)

(52) U.S. Cl.
CPC ............ *C07K 14/005* (2013.01); *A61K 39/12* (2013.01); *C07K 14/1825* (2013.01); *C12N 7/00* (2013.01);
(Continued)

(58) Field of Classification Search
None
See application file for complete search history.

(56) References Cited

FOREIGN PATENT DOCUMENTS

WO        93/10239      5/1993
WO   2004/001051 A2   12/2003
(Continued)

OTHER PUBLICATIONS

Rivino et al. "Differential Targeting of Viral Components by CD4+ versus CD8+ T Lymphocytes in Dengue Virus Infection", J. Virol. 2013; 87(5): 2693-2706.*
(Continued)

*Primary Examiner* — Janet L Andres
*Assistant Examiner* — Stuart W Snyder
(74) *Attorney, Agent, or Firm* — Arrigo, Lee, Guttman & Mouta-Bellum LLP

(57) ABSTRACT

The present invention is directed to a dengue virus chimeric polyepitope composed of fragments of non-structural proteins and its use in an immunogenic composition against dengue virus infection. The present invention provides means, in particular polynucleotides, vectors, cells and methods to produce vectors expressing said chimeric polyepitopes, in particular vectors consisting of recombinant measles virus (MV) particles. The present invention also relates to the use of the recombinant MV particles, in
(Continued)

particular under the form of a composition or of a vaccine, for the prevention and/or treatment of a dengue virus infection.

10 Claims, 27 Drawing Sheets

Specification includes a Sequence Listing.

(51) Int. Cl.
*C07K 14/18* (2006.01)
*C12N 7/00* (2006.01)
*A61K 39/00* (2006.01)

(52) U.S. Cl.
CPC .............. *A61K 2039/525* (2013.01); *A61K 2039/5254* (2013.01); *A61K 2039/54* (2013.01); *A61K 2039/70* (2013.01); *C07K 2319/00* (2013.01); *C12N 2760/18441* (2013.01); *C12N 2760/18443* (2013.01); *C12N 2770/24134* (2013.01); *Y02A 50/386* (2018.01)

(56) References Cited

FOREIGN PATENT DOCUMENTS

| WO | WO 2004/001051 A2 * | 12/2004 | ............... C12N 7/00 |
| WO | 2011/110953 A2 | 9/2011 | |
| WO | 2011/163628 A2 | 12/2011 | |
| WO | WO 2011/163628 A2 * | 12/2011 | ............. A61K 39/12 |
| WO | 2012/178196 A2 | 12/2012 | |
| WO | WO 2012/178196 A2 * | 12/2012 | ............. A61K 39/12 |

OTHER PUBLICATIONS

Weiskopf et al. "Comprehensive analysis of dengue virus-specific responses supports an HLA-linked protective role for CD8+ T cells", Proc. Nat. Acad. Sci. 2013; 110(22): E2046-E2053.*
Brandler, Samantha, et al., "Pediatric Measles Vaccine Expressing a Dengue Antigen Induces Durable Serotype-Specific Neutralizing Antibodies to Dengue Virus," PLoS Negelected Tropical Diseases, vol. 1, Issue 1, e96, 2007.
Brandler, Samantha, et al., "Pediatric measles vaccine expressing a dengue tetravalent antigen elicits neutralizing antibodies against all for dengue viruses," Vaccine, vol. 28, pp. 6730-6739 (2010).
Rivino, Laura, et al., "Differential Targeting of Viral Components by CD4+ versus CD8+ T Lymphocytes in Dengue Virus Infection," Journal of Virology, vol. 87, No. 5, pp. 2693-2706 (2013).
Weiskopf, Daniela, "Comprehensive analysis of dengue virus-specific responses supports an HLA-linked protective role for CD8+ T cells," PNAS, vol. 110, No. 22, pp. E2046-E2053 (2013).
European Search Report, Application No. EP 14 30 5984, dated Dec. 2, 2014.
International Search Report, Application No. PCT/EP2015/064010, dated Oct. 1, 2015.

* cited by examiner

Figure 1

- Amino acid sequence of DENV2-NS polyepitope

KSIEDNPEIEDDIFRKKRLTIMDLHPGAGKTKRYLPAIVREAIKRGLRTLILAPTRVVAAEMEEALRGLPIRYQ
TPAIRAEHTGREIVDLMCHATFTMRLLSPVRVPNYNLIIMDEAHFTDPASIAARGYISTRVEMGEAAGIFM
TATPPGSRDPFPQSNAPIMDEEREIPERSWNSGHEWVTDEDCAHWKEAKMLLDNINTPEGIIPSMFEPE
REKVDAIDGEYRLRGEARKTFVDLMRRGDLPVWLAYKVAAEGINYADRRWCFDGIKNNQILEENVEVEI
WTKEGERKKLKPRWLDARIYSDPLALKEFKEFAAGITTQESESNILDIDLRPASAWTLYAVATTFVTPMLRH
SIENSSVNVSLTAIANQATVLMGLGKGWPLSKMDIGVPLLAIGCYSQVLDIIGKRIEKIKQEHETSWHYDQ
DHPYKTWAYHGSYETKQTGSASSMVNGVVRLLTKPWDVVPMVTQMAMTDTTPFGQQRVFKEKVDTR
TQEPKEGTKKLMKITAEWLWKELGKKKTPRMCTREEFTRKVRSNA

- Amino acid sequence of DENV3-NS polyepitope

AEPDGPTPELEEEMFKKRNLTIMDLHPGSGKTRKYLPAIVREAIKRRLRTLILAPTRVVAAEMEEALKGLPIR
YQTTATKSEHTGREIVDLMCHATFTMRLLSPVRVPNYNLIIMDEAHFTDPASIAARGYISTRVGMGEAAAI
FMTATPPGTADAFPQSNAPIQDEERDIPERSWNSGNEWITDEDHAHWTEAKMLLDNINTPEGIIPALFE
PEREKSAAIDGEYRLKGESRKTFVELMRRGDLPVWLAHKVASEGIKYTDRKWCFDGQRNNQILEENMDV
EIWTKEGEKKKLRPRWLDARTYSDPLALKEFKDFAAGEPGVVSPTSYLDVDLHPASAWTLYAVATTVITP
MLRHTIENSTANVSLAAIANQAVVLMGLDKGWPISKMDLGVPLLALGCYSQVMDVIGERIKRIKEEHNST
WHYDDENPYKTWAYHGSYEVKATGSASSMINGVVKLLTKPWDVVPMVTQMAMTDTTPFGQQRVFK
EKVDTRTPRSMPGTRRVMGITAEWLWRTLGRNKKPRLCTREEFTKKVRTNA

- Amino acid sequence of DENV4-NS polyepitope

RIGEPDYEVDEDIFRKKRLTIMDLHPGAGKTKRILPSIVREALKRRLRTLILAPTRVVAAEMEEALRGLPIRYQ
TPAVKSEHTGREIVDLMCHATFTTRLLSSTRVPNYNLIVMDEAHFTDPSSVAARGYISTRVEMGEAAAIF
MTATPPGATDPFPQSNSPIEDIEREIPERSWNTGFDWITDEDHAHWTEAKMLLDNIYTPEGIIPTLFGPER
EKTQAIDGEFRLRGEQRKTFVELMRRGDLPVWLSYKVASAGISYKDREWCFTGERNNQILEENMEVEIW
TREGEKKKLRPRWLDARVYADPMALKDFKEFASGVKTETTILDVDLRPASAWTLYAVATTILTPMLRHTIE
NTSANLSLAAIANQAAVLMGLGKGWPLHRMDLGVPLLAMGCYSQVMTIIGRRLQRLQEEHKETWHYD
QENPYRTWAYHGSYEAPSTGSASSMVNGVVKLLTKPWDVIPMVTQLAMTDTTPFGQQRVFKEKVDTR
TPQPKPGTRMVMTTTANWLWALLGKKKNPRLCTREEFISKVRSNA

Figure 3

```
              ....|....|....|....|....|....|....|....|....|....|
                      10         20         30         40         50
DENV1-NS   ASQEGPLPEI EDEVFRKRNL TIMDLHPGSG KTRRYLPAIV REAIKRKLRT
DENV2-NS   KSIEDN-PEI EDDIFRKKRL TIMDLHPGAG KTKRYLPAIV REAIKRGLRT
DENV3-NS   AEPDGPTPEL EEEMFKKRNL TIMDLHPGSG KTRKYLPAIV REAIKRRLRT
DENV4-NS   RIGEPD-YEV DEDIFRKKRL TIMDLHPGAG KTKRILPSIV REALPRKRLRT

....|....|....|....|....|....|....|....|....|....|
                      60         70         80         90        100
DENV1-NS   LILAPTRVVA SEMAEALKGM PIRYQTTAVK SEHTGKEIVD LMCHATFTMR
DENV2-NS   LILAPTRVVA AEMEEALRGL PIRYQTPAIR AEHTGREIVD LMCHATFTMR
DENV3-NS   LILAPTRVVA AEMEEALKGL PIRYQTTATK SEHTGREIVD LMCHATFTMR
DENV4-NS   LILAPTRVVA AEMEEALRGL PIRYQTPAVK SEHTGREIVD LMCHATFTTR

....|....|....|....|....|....|....|....|....|....|
                     110        120        130        140        150
DENV1-NS   LLSPVRVPNY NMIIMDEAHF TDPSSIAARG YISTRVGMGE AAAIFMTATP
DENV2-NS   LLSPVRVPNY NLIIMDEAHF TDPASIAARG YISTRVGMGE AAGIFMTATP
DENV3-NS   LLSPVRVPNY NLIIMDEAHF TDPASIAARG YISTRVGMGE AAAIFMTATP
DENV4-NS   LLSSTRVPNY NLIVMDEAHF TDPSSVAARG YISTRVEMGE AAAIFMTATP

....|....|....|....|....|....|....|....|....|....|
                     160        170        180        190        200
DENV1-NS   PGSVEAFPQS NAVIQDEERD IPERSWNSGY EWITDEDHAH WTEAKMLLDN
DENV2-NS   PGSRDFPFQS NAPIMDEERE IPERSWNSGH EWVTDEDCAH WKEAKMLLDN
DENV3-NS   PGTADAFPQS NAPIQDEERD IPERSWNSGN EWITDEDHAH WTEAKMLLDN
DENV4-NS   PGATDFPFQS NSPIEDIERE IPERSWNTGF DWITDEDHAH WTEAKMLLDN

....|....|....|....|....|....|....|....|....|....|
                     210        220        230        240        250
DENV1-NS   INTPEGIIPA LFEPEREKSA AIDGEYRLRG EARKTFVELM RRGDLPVWLS
DENV2-NS   INTPEGIIPS MFEPEREKVD AIDGEYRLRG EARKTFVDLM RRGDLPVWLA
DENV3-NS   INTPEGIIPA LFEPEREKSA AIDGEYRLKG ESRKTFVELM RRGDLPVWLA
DENV4-NS   IYTPEGIIPT LFGPEREKTQ AIDGEFRLRG EQRKTFVELM RRGDLPVWLS

....|....|....|....|....|....|....|....|....|....|
                     260        270        280        290        300
DENV1-NS   YKVASEGFQY SDRRWCFDGE RNNQVLEENM DVEIWTKEGE RKKLRPRWLD
DENV2-NS   YKVAAEGINY ADRRWCFDGI RNNQILEENV EVEIWTKEGE RKKLKPRWLD
DENV3-NS   YKVASEGIKY TDRKWCFDGQ RNNQILEENM DVEIWTKEGE KKKLRPRWLD
DENV4-NS   YKVASAGISY KDREWCFTGE RNNQILEENM EVEIWTREGE KKKLRPRWLD

....|....|....|....|....|....|....|....|....|....|
                     310        320        330        340        350
DENV1-NS   ARTYSDPLAL REFKEFAAGV AVENHHHAAM LDVDLHPASA WTLYAVATTI
DENV2-NS   ARIYSDPLAL KEFKEFAAGI TTQESE-SNI LDIDLRPASA WTLYAVATTF
DENV3-NS   ARTYSDPLAL KEFKDFAAGE PGVVSP-TSY LDVDLHPASA WTLYAVATTV
DENV4-NS   ARVYADPMAL KDFKEFASGV KTE----TTI LDVDLRPASA WTLYAVATTI

....|....|....|....|....|....|....|....|....|....|
                     360        370        380        390        400
DENV1-NS   ITPMRRHTIE NTTANISLTA IANQAAILMG LDKGWPISKM DIGVPLLALG
DENV2-NS   VTPMLRHSIE NSSVNVSLTA IANQATVLMG LGKGWPLSKM DIGVPLLAIG
DENV3-NS   ITPMLRHTIE NSTANVSLAA IANQAVVLMG LDKGWPISKM DLGVPLLALG
DENV4-NS   LTPMLRHTIE NSTANLSLAA IANQAAVLMG LGKGWPLHRM DLGVPLLAMG

....|....|....|....|....|....|....|....|....|....|
                     410        420        430        440        450
DENV1-NS   CYSQVLDIIG QRIENIKHEH KSTWHYDEDN PYKTWAYHGS YEVKPSGSAS
DENV2-NS   CYSQVLDIIG KRIEKIKQEH ETSWHYDQDH PYKTWAYHGS YETKQTGSAS
DENV3-NS   CYSQVMDVIG ERIKRIKEEH NSTWHYDDEN PYKTWAYHGS YEVKATGSAS
DENV4-NS   CYSQVMTIIG RRLQRLQEEH KETWHYDQEN PYRTWAYHGS YEAPSTGSAS

....|....|....|....|....|....|....|....|....|....|
                     460        470        480        490        500
DENV1-NS   SMVNGVVKLL TKPWDVIPMV TQIAMTDTTP FGQQRVFKEK VDTRTPKAKR
DENV2-NS   SMVNGVVRLL TKPWDVVPMV TQMAMTDTTP FGQQRVFKEK VDTRTQEPKE
DENV3-NS   SMINGVVKLL TKPWDVVPMV TQMAMTDTTP FGQQRVFKEK VDTRTPRSMP
DENV4-NS   SMVNGVVKLL TKPWDVIPMV TQLAMTDTTP FGQQRVFKEK VDTRTPQRKP

....|....|....|.
                     510        520        530        539
DENV1-NS   GTAQIMEVTA KWLWGFLSRN KKPRICTREE FTRKVRSNA
DENV2-NS   GTKKLMKITA EWLWKELGKK KTPRMCTREE FTRKVRSNA
DENV3-NS   GTRVMGITA  EWLWRTLGRN KKPRLCTREE FTKKVRTNA
DENV4-NS   GTRMVMTTA  NWLWALIGKK KNPRLCTREE FISKVRSNA
```

Figure 4

```
         GCATCACAAGAAGGGCCCCTACCAGAGATTGAAGA
TGAGGTGTTTAGGAAAAGAAACTTAACAATAATGGACCTACATCCAGGAT
CAGGGAAAACAAGAAGATATCTCCCAGCCATAGTCCGTGAGGCCATAAAA
AGGAAGCTGCGCACACTAATTTTGGCTCCCACAAGGGTTGTCGCTTCCGA
AATGGCAGAGGCGCTCAAGGGAATGCCAATAAGGTACCAAACAACAGCAG
TGAAGAGTGAACACACAGGAAAGAGATAGTTGACCTCATGTGCCACGCC         Region 1
ACTTTCACCATGCGTCTCCTGTCTCCCGTGAGAGTTCCCAATTACAACAT         (NS3)
GATTATTATGGATGAAGCACATTTCACCGATCCATCCAGTATAGCAGCCA
GAGGGTACATCTCAACCCGAGTGGGCATGGGTGAAGCAGCTGCGATCTTC
ATGACAGCCACTCCTCCAGGATCAGTGGAGGCCTTTCCACAGAGCAATGC
AGTTATCCAAGATGAGGAAAGAGACATTCCTGAGAGATCATGGAACTCAG
GATATGAGTGGATCACTGACGAGGACCATGCTCATTGGACAGAAGCAAAA
ATGCTCCTTGACAACATAAACACACCAGAAGGAATTATCCCAGCTCTCTT
TGAGCCGGAGAGAGAAAGAGTGCAGCAATAGACGGGGAGTACAGACTGC
GGGGAGAAGCAAGGAAAACGTTCGTGGAGCTCATGAAGAGGAGATTTA         Region 2
CCAGTTTGGCTATCTTACAAAGTTGCCTCAGAAGGCTTCCAATACTCCGA         (NS3)
TAGAAGGTGGTGCTTTGATGGAGAAAGGAACAACCAGGTGTTGGAGGAAA
ACATGGACGTGGAGATCTGGACAAAGGAGGGAGAAAGAAAGAAATTACGA
CCCCGCTGGTTGGACGCCAGAACATACTCTGATCCACTGGCCCTGCGCGA
GTTCAAAGAGTTCGCAGCAGGAGTGGCTGTTGAAAATCACCACCATGCCG
CAATGCTGGACGTAGACTTACATCCAGCTTCAGCCTGGACCCTCTATGCA
GTGGCCACAACAATTATCACTCCCATGATGAGGCACACAATAGAAAACAC         Region 3
AACGGCAAACATTTCCCTGACAGCCATTGCAAACCAGGCGGCTATATTGA         (NS4b)
TGGGACTTGACAAAGGATGGCCAATATCGAAGATGGACATAGGAGTTCCA
CTTCTCGCCTTGGGGTGCTATTCCCAGGTGCTGGATATCATTGGCCAGAG
GATAGAGAACATAAAACATGAACATAAGTCAACATGGCATTATGATGAGG
ACAATCCATATAAAACATGGGCCTATCACGGATCATATGAGGTCAAGCCA
TCAGGATCAGCCTCATCCATGGTCAATGGCGTGGTGAAACTGCTCACCAA
ACCATGGGATGTCATCCCCATGGTCACACAAATAGCCATGACTGACACCA         Region 4
CACCCTTTGGACAACAGAGGGTGTTCAAAGAGAAAGTTGACACGCGCACA         (NS5)
CCAAAAGCAAAACGAGGCACAGCACAAATCATGGAGGTGACAGCCAAATG
GTTATGGGGTTTTCTTTCTAGAAACAAAAAACCAAGAATTTGTACAAGAG
AGGAGTTCACAAGAAAAGTCAGGTCAAACGCA
```

Figure 5

```
                            GCATCACAGGAGGGACCACTGCCCGAAATTGAGGA
CGAAGTGTTTAGAAAGCGAAATCTGACTATTATGGACCTGCACCCCGGAT
CTGGCAAGACCCGGAGATACCTGCCAGCCATCGTGAGGGAGGCTATTAAG
CGGAAACTGAGAACACTGATCCTGGCCCCAACTCGCGTGGTCGCTTCCGA
AATGGCTGAGGCCCTGAAAGGCATGCCCATCCGGTATCAGACCACAGCAG
TGAAGTCTGAACATACCGGCAAGGAGATTGTGGACCTGATGTGCCACGCC    Region 1
ACTTTCACCATGCGACTGCTGAGCCCAGTGCGGGTCCCCAACTACAATAT    (NS3)
GATCATTATGGACGAGGCCCACTTTACTGATCCCAGCTCCATCGCCGCTA
GAGGATATATTTCCACCAGGGTGGGAATGGGCGAGGCAGCAGCTATCTTC
ATGACAGCAACTCCCCCTGGCAGCGTGGAGGCATTTCCTCAGTCCAACGC
CGTCATCCAGGACGAGGAGCGGGACATTCTGAGCGGAGCTGGAATTCTG
GGTACGAATGGATCACAGACGAGGATCATGCACACTGGACTGAAGCCAAG
ATGCTGCTGGACAACATTAATACTCCTGAGGGAATCATTCCAGCTCTGTT
CGAGCCCGAAAGAGAGAAGTCTGCAGCCATCGACGGCGAGTATAGACTGA
GGGGAGAGGCCCGGAAGACCTTCGTGGAACTGATGAGGCGCGGCGATCTG    Region 2
CCCGTGTGGCTGAGTTACAAGGTCGCTTCAGAGGGATTCCAGTATAGTGA    (NS3)
CCGACGGTGGTGCTTTGATGGCGAACGCAACAATCAGGTGCTGGAGGAGA
ACATGGATGTCGAGATTTGGACAAAGGAAGGCGAGCGGAAGAAACTGCGC
CCACGATGGCTGGACGCTCGGACTTACAGCGATCCCCTGGCACTGAGAGA
ATTCAAAGAGTTTGCTGCAGGGGTGGCCGTCGAGAATCACCATCACGCCG
CTATGCTGGACGTGGATCTGCATCCTGCCAGTGCTTGGACCCTGTATGCA
GTGGCCACTACCATCATTACCCCAATGATGCGCCACACAATCGAGAACAC    Region 3
AACTGCCAATATCTCACTGACAGCTATTGCAAACCAGGCAGCCATTCTGA    (NS4b)
TGGGACTGGACAAAGGCTGGCCCATCAGCAAGATGGATATTGGCGTGCCT
CTGCTGGCCCTGGGGTGTTACAGTCAGGTGCTGGACATCATTGGCCAGAG
GATCGAGAACATTAAGCATGAGCACAAATCAACCTGGCATTACGACGAAG
ATAATCCCTATAAGACATGGCCTACCACGGAAGCTATGAGGTGAAACCT
TCAGGCAGCGCCAGCAGCATGGTCAACGGGGTGGTCAAGCTGCTGACCAA    Region 4
ACCTTGGGACGTGATCCCAATGGTCACTCAGATTGCCATGACCGATACCA    (NS5)
CCCCATTCGGCCAGCAGCGGGTGTTCAAGGAGAAGGTGGACACCCGCACA
CCTAAGGCTAAACGAGGGACTGCACAGATCATGGAGGTGACCGCCAAGTG
GCTGTGGGGATTCCTGTCCAGGAACAAGAAGCCAAGAATCTGTACCAGGG
AAGAGTTCACAAGAAAGGTCCGGTCAAACGCC
```

| Peptide | Sequence | |
|---|---|---|
| 1 | VKSEHTGKEIVDLMC | Pool 1 |
| 2 | HTGKEIVDLMCHATF | |
| 3 | EIVDLMCHATFTMRL | |
| 4 | LMCHATFTMRLLSPV | |
| 5 | ATFTMRLLSPVRVPN | |
| 6 | MRLLSPVRVPNYNMI | |
| 7 | EFKEFAAGVAVENHH | |
| 8 | FAAGVAVENHHHAAM | |
| 9 | VAVENHHHAAMLDVD | |
| 10 | NHHHAAMLDVDLHPA | |
| 11 | AAMLDVDLHPASAWT | |
| 12 | DVDLHPASAWTLYAV | |
| 13 | HPASAWTLYAVATTI | |
| 14 | AWTLYAVATTIITPM | |
| 15 | YAVATTIITPMMRHT | |
| 16 | TTIITPMMRHTIENT | |
| 17 | TPMMRHTIENTTANI | |
| 18 | RHTIENTTANISLTA | |
| 19 | ENTTANISLTAIANQ | |
| 20 | ANISLTAIANQAAIL | Pool 2 |
| 21 | GWPISKMDIGVPLLA | |
| 22 | SKMDIGVPLLALGCY | |
| 23 | IGVPLLALGCYSQVL | |
| 24 | DEDNPYKTWAYHGSY | |
| 25 | PYKTWAYHGSYEVKP | |
| 26 | WAYHGSYEVKPSGSA | |
| 27 | GSYEVKPSGSASSMV | |
| 28 | VKPSGSASSMVNGVV | |
| 29 | GSASSMVNGVVKLLT | |
| 30 | SMVNGVVKLLTKPWD | |
| 31 | GVVKLLTKPWDVIPM | |
| 32 | LLTKPWDVIPMVTQI | |
| 33 | PWDVIPMVTQIAMTD | |
| 34 | IPMVTQIAMTDTTPF | |
| 35 | TQIAMTDTTPFGQQR | |
| 36 | MTDTTPFGQQRVFKE | |
| 37 | FTMRLLSPV | |
| 38 | VAVENHHHAAM | |
| 39 | LYAVATTII | |
| 40 | TAIANQAAI | |
| 41 | SSMVNGVVKL | |

Figure 9

```
  1         10        20        30        40        50        60
ASQEGPLPEIEDEVFRKRNLTIMDLHPGSGKTRRYLPAIVREAIKRKLRTLILAPTRVVASE
                                     P30                ‾‾‾‾‾‾‾‾‾‾
                                   ‾‾‾‾‾‾                  P36
                                    P451

70        80        90       100       110       120
MAEALKGMPIRYQTTAVKSEHTGKEIVDLMCHATFTMRLLSPVRVPNYNMIIMDEAHFTDPS
‾

130       140       150       160       170       180
SIAARGYISTRVGMGEAAAIFMTATPPGSVEAFPQSNAVIQDEERDIPERSWNSGYEWITDE
                                                 ‾‾‾‾‾‾‾‾‾‾‾‾‾
                                                     P453

190       200       210       220       230       240
DHAHWTEAKMLLDNINTPEGIIPALFEPEREKSAAIDGEYRLRGEARKTFVELMRRGDLPVW
                ‾‾‾‾‾‾‾‾‾‾                                ‾‾‾‾
                   P49                                     P50

250       260       270       280       290       300         1
LSYKVASEGFQYSDRRWCFDGERNNQVLEENMDVEIWTKEGERKKLRPRWLDARTYSDPLAL
‾‾‾‾‾    ‾‾‾‾‾‾‾‾‾                                 ‾‾‾‾‾‾‾‾‾‾‾‾
 P50        P32                                        P17

320       330       340       350       360       370
REFKEFAAGVAVENHHHAAMLDVDLHPASAWTLYAVATTIITPMMRHTIENTTANISLTAIA
‾‾‾‾‾‾‾‾‾                ‾‾‾‾‾‾‾‾      ‾‾‾‾‾‾‾‾
  P30                      P21             P33
                              ‾‾‾‾‾‾‾‾
                                P51

380       390       400       410       420       430
NQAAILMGLDKGWPISKMDIGVPLLALGCYSQVLDIIGQRIENIKHEHKSTWHYDEDNPYKT 440       450       460       470       480       490
WAYHGSYEVKPSGSASSMVNGVVKLLTKPWDVIPMVTQIAMTDTTPFGQQRVFKEKVDTRTP
                ‾‾‾‾‾‾‾‾‾‾‾‾
                   P56

500       510       520       530
KAKRGTAQIMEVTAKWLWGFLSRNKKPRICTREEFTRKVRSNA
                        ‾‾‾‾‾‾‾‾‾‾
                           P15
```

Epitopes / HLA restriction

1-185 Region 1 (NS3)          P30, P451, P56 / HLA-A2
186-319 Region 2 (NS3)    P15, P30, P36 / HLA-B7
320-405 Region 3 (NS4b)       P21, P49, P50, P51, P453 / HLA-B35
406-539 Region 4 (NS5)

<u>Figure 14</u>

| Nb | HLA RESTRICTION (REFERENCES) | PEPTIDE SYNTHESIZED[a, b] | POSITION | + SFC[c] |
|---|---|---|---|---|
| P20 | B35 (5) | LPEIEDEVF | NS3-1 (7-15) | - |
| P19 | B35 (5, 9) | HPGSGKTRRY | NS3-1 (26-35) | - |
| P30 | A31 (1, 7), B7 (6, 9) | RYLPAIVREAI | NS3-1 (34-44) | B7 |
| P451 | A2 (10) | YLPAIVREA | NS3-1 (35-43) | A2 |
| P11 | A31 (1, 7), B7 (6, 9) | LPAIVREAI | NS3-1 (36-44) | - |
| P36 | B7 (1, 2, 9), B35 (9) | APTRVVASEM | NS3-1 (54-63) | B7 |
| P48 | B7 (1, 9), A2,11; B35,62 (3) | EMAEALKGMPIRYQT | NS3-1 (62-76) | - |
| P12 | ND (2), B7 (9) | SPVRVPNYNM | NS3-1 (103-112) | - |
| P454 | B7 (10) | VPNYNMIIM | NS3-1 (107-115) | - |
| P18 | ND (2), B35 (5, 9) | DPSSIAARGY | NS3-1 (122-131) | - |
| P457 | B7 (10) | AVIQDEERDI | NS3-1 (162-171) | - |
| P453 | B58 (1, 7) | RSWNSGYEW | NS3-1 (174-182) | B35 |
| P49 | B35 (1, 2, 3, 4, 9) | TPEGIIPAL | NS3-2 (203-211) | B35 |
| P28 | A11 (9) | KTFVELMRR | NS3-2 (234-242) | NT |
| P2 | B55 (1), A2 (9) | ELMRRGDLPV | NS3-2 (238-247) | - |
| P450 | A2 (10) | DLMRRGDLPV | NS3-2 (238-247) | - |
| P50 | nd (2), B35 (5) | LPVWLSYKVA | NS3-2 (245-254) | B35 |
| P32 | A24 (1, 2, 6, 9, 11) | QYSDRRWCF | NS3-2 (259-267) | A24 |
| P73 | A24 (1, 2, 6, 11) | NYADRRWCF | NS3-2 (259-267) | NT |
| P74 | A24 (13) | NYADRKWCF | NS3-2 (259-267) | NT |
| P75 | A24 (13) | KYTDRKWCF | NS3-2 (259-267) | NT |
| P76 | A24 (13) | SYKDREWCF | NS3-2 (259-267) | NT |
| P35 | B7 (8, 9) | RPRWLDART | NS3-2 (295-303) | - |
| P17 | A24 (1, 7, 8) | LDARTYSDPLALREFKEF | NS3-2 (299-316) | A24 |
| P29 | A24 (1, 7, 8) | RIYSDPLALK | NS3-2 (302-311) | - |

| | ↓ FROM FIG. 18 | | ↓ FROM FIG. 18 | |
|---|---|---|---|---|
| P452 | A11, A24 (1, 7, 8) | RTYSDPLALR | NS3-2 (302-311) | NT |
| P21 | B7, B35 (9) | HPASAWTLY | NS4b (336-344) | B35 |
| P16 | B7, B35 (9) | PASAWTLY | NS4b (337-344) | - |
| P13 | B35 (9) | HPASAWTLYA | NS4b (336-345) | NT |
| P51 | A2 (6) B35 (9) | TLYAVATTI | NS4b (342-350) | B35 |
| P52 | B35 (9) | VATTIITPM | NS4b (346-354) | - |
| P33 | A24 (9) | ITPMMRHTI | NS4b (351-359) | A24 |
| P14 | A24 (9) | TPMMRHTIEN | NS4b (352-361) | - |
| P22 | B35 (5, 9) | IANQAAILM | NS4b (371-379) | - |
| P456 | A11 (10) | AAILMGLDK | NS4b (375-383) | NT |
| P53 | A2 (6) | KMDIGVPLL | NS4b (389-397) | - |
| P54 | B35 (9) | VPLLALGCY | NS4b (394-402) | - |
| P55 | A2,11, B35,62 (3) | DNPYKTWAYH | NS5 (429-438) | - |
| P24 | B35 (9) | WAYHGSYEV | NS5 (435-443) | - |
| P56 | A2 (6) | SMVNGVVKL | NS5 (435-443) | A2 |
| P5 | B55 (1), A2,24, B55,61 (3), A2 (8) | LLTKPWDVIPMVTQI | NS5 (459-473) | - |
| P6 | " | LLTKPWDVIP | NS5 (459-468) | - |
| P7 | " | LTKPWDVIPM | NS5 (460-469) | - |
| P8 | " | TKPWDVIPMV | NS5 (461-470) | - |
| P9 | " | KPWDVIPMVT | NS5 (462-471) | - |
| P10 | " | PWDVIPMVTQ | NS5 (463-472) | - |
| P27 | " | WDVIPMVTQI | NS5 (464-473) | - |
| P455 | B7 (9) | IPMVTQIAM | NS5 (467-475) | - |
| P34 | A68, B35 (1) | DTTPFGQQR | NS5 (477-485) | - |
| P23 | B35 (9) | TPFGQQRVF | NS5 (479-487) | - |

| | ↓ FROM FIG. 18 (CONT.) | | | ↓ FROM FIG. 18 (CONT.) | |
|---|---|---|---|---|---|
| P3 | A2,32, B35,62 (3), B7 (7, 8) | TAKWLWGFLSRNKKPRICTR | NS5 (509-528) | - |
| P4 | A2,32, B35,62 (3) | WGFLSRNKK | NS5 (514-522) | - |
| P15 | B7 (5, 8, 9) | KPRICTREEF | NS5 (522-531) | B7 |

FIG. 18 (CONT. 2)

| HLA CLASS II RESTRICTION (REFERENCES) | PEPTIDE SEQUENCE | POSITION |
|---|---|---|
| HLA-DR2 (NASCIMENTO, E., 2013) | PELEEEMFKKRNLTI | NS3-1 (8-22) |
| MALOY M. MANGADA, 2005 | RKLTIMDLHPGSGKT | NS3-1 (18-32) |
| HLA-DR15 (SIMMONS, ET AL., 2006) | TKRYLPPAIVREAIKR | NS3-1 (32-46) |
| HLA-DR15 (ZENG, L., ET AL., 1996) | RKYLPAIVRE | NS3-1 (33-42) |
| HLA-DR3 (NASCIMENTO, E., 2013) | LPAIVREAIKRRLRT | NS3-1 (36-50) |
| HLA-DR3 (NASCIMENTO, E., 2013) | VREAIKRRLRTLILA | NS3-1 (40-54) |
| HLA-DR15 (KURANE, I., 1998) | TRVVAAEMEEA | NS3-1 (56-66) |
| HLA-DRB1*15:01 (MALOY M. MANGADA, 2005) | PTRVVAAEMEEAMKG | NS3-1 (55-69) |
| HLA-DR15 (MORAN, E., 2008) | ALKGMPIRYQTTAVK | NS3-1 (66-80) |
| HLA-DR4 (NASCIMENTO, E., 2013) | KGLPIRYQTTATKSE | NS3-1 (68-82) |
| HLA-DR4 (NASCIMENTO, E., 2013) | IRYQTTATKSEHTGR | NS3-1 (72-86) |
| HLA-DPw2 (MALOY M. MANGADA, 2005) | HTGREIVDLMCHATE | NS3-1 (83-97) |
| HLA-DPA1*01:03/DPB1*02:01 (FALTA, MT., 2013) | REIVDLMCHATF | NS3-1 (86-97) |
| HLA-DPw2 (KURANE, I., ET AL., 1993) | EIVDLMCHAT | NS3-1 (87-96) |
| HLA-DPw2 (OKAMOTO, Y., 1998) | VDLMCHATFT | NS3-1 (89-98) |
| HLA-DRB1*01:01 (WEISKOPF, D., 2013) | TFTMRLLSPVRVPNY | NS3-1 (96-110) |
| RIVINO, L., 2013 | PNYNLIIMDEAHFTD | NS3-1 (108-122) |
| HLA-DR2 (NASCIMENTO, E., 2013) | ASIAARGYISTRVGM | NS3-1 (124-138) |
| HLA-DR4 (NASCIMENTO, E., 2013) | EAAAIFMTATPPGTA | NS3-1 (139-154) |
| MALOY M. MANGADA, 2005 | REGEKKKLRPRWLDR | NS3-2 (287-301) |
| HLA-DR2 (NASCIMENTO, E., 2013) | PLALKEFKDFAAGRK | NS3-2 (307-319) |
| HLA-DR3 (NASCIMENTO, E., 2013) | KEEHSSTWHYDDENPYK | NS5 (417-433) |
| HLA-DR2 (NASCIMENTO, E., 2013) | TWHYDDENPYKTWAYHG | NS5 (423-439) |
| HLA-DR2 (NASCIMENTO, E., 2013) | DENPYKTWAYHGSYEVK | NS5 (427-444) |
| RIVINO ET AL., 2013 | KTWAYHGSYETKQTG | NS5 (433-447) |

| p30 | NS POLYEPITOPE | R | Y | L | P | A | I | V | R | E | A | I |
|---|---|---|---|---|---|---|---|---|---|---|---|---|
| | SEROTYPE 1 | - | - | | - | - | - | - | - | - | | - |
| | SEROTYPE 2 | - | - | | - | - | - | - | - | - | | - |
| | SEROTYPE 3 | K | - | | - | - | - | - | - | - | | - |
| | SEROTYPE 4 | - | I | | - | S | - | - | - | - | | L |

| p451 | NS POLYEPITOPE | Y | L | P | A | I | V | R | E | A |
|---|---|---|---|---|---|---|---|---|---|---|
| | SEROTYPE 1 | - | | - | - | - | - | - | - | |
| | SEROTYPE 2 | - | | - | - | - | - | - | - | |
| | SEROTYPE 3 | - | | - | - | - | - | - | - | |
| | SEROTYPE 4 | I | | - | S | - | - | - | - | |

| p56 | NS POLYEPITOPE | S | M | V | N | G | V | V | K | L |
|---|---|---|---|---|---|---|---|---|---|---|
| | SEROTYPE 1 | - | | - | - | - | - | - | K/R | |
| | SEROTYPE 2 | - | | - | - | - | - | - | R/K | |
| | SEROTYPE 3 | - | | I | - | - | - | - | - | |
| | SEROTYPE 4 | - | | - | - | - | - | - | - | |

*FIG. 20A*

| p17 | NS POLYEPITOPE | L | D | A | R | T | Y | S | D | P | L | A | L | R | E | F | K | E | F |
|---|---|---|---|---|---|---|---|---|---|---|---|---|---|---|---|---|---|---|---|
| | SEROTYPE 1 | - | - | - | - | - | - | - | - | - | - | - | - | - | - | - | - | - | - |
| | SEROTYPE 2 | - | - | - | - | I | - | - | - | - | - | - | - | K | - | - | - | - | - |
| | SEROTYPE 3 | K | - | - | - | - | - | - | - | - | - | - | - | K | - | - | - | D | - |
| | SEROTYPE 4 | - | I | - | - | V | - | A | - | - | M | - | - | K | D | - | - | - | - |

| p32 | NS POLYEPITOPE | Q | Y | S | D | R | R | W | C | F |
|---|---|---|---|---|---|---|---|---|---|---|
| | SEROTYPE 1 | - | - | - | - | - | - | - | - | - |
| | SEROTYPE 2 | N | - | A | - | - | R/K | - | - | - |
| | SEROTYPE 3 | K | - | T | - | - | K | - | - | - |
| | SEROTYPE 4 | S | - | K | - | - | E | - | - | - |

| p33 | NS POLYEPITOPE | I | T | P | M | M | R | H | T | I |
|---|---|---|---|---|---|---|---|---|---|---|
| | SEROTYPE 1 | - | - | - | - | - | - | - | - | - |
| | SEROTYPE 2 | V | - | - | - | L | - | - | S | - |
| | SEROTYPE 3 | - | - | - | - | L | - | - | - | - |
| | SEROTYPE 4 | L | - | - | - | L | - | - | - | - |

*FIG. 20B*

| p15 | NS POLYEPITOPE | K | P | R | I | C | T | R | E | E | F |
|---|---|---|---|---|---|---|---|---|---|---|---|
| | SEROTYPE 1 | - | | - | - | - | - | - | - | | - |
| | SEROTYPE 2 | T | | - | M | - | - | - | K/R | | - |
| | SEROTYPE 3 | K/R | | - | L | - | - | H | - | | - |
| | SEROTYPE 4 | N | | - | L | - | - | - | - | | - |

| p30 | NS POLYEPITOPE | R | Y | L | P | A | I | V | R | E | A | I |
|---|---|---|---|---|---|---|---|---|---|---|---|---|
| | SEROTYPE 1 | - | - | | - | - | - | - | - | - | | - |
| | SEROTYPE 2 | - | - | | - | - | - | - | - | - | | - |
| | SEROTYPE 3 | K | - | | - | - | - | - | - | - | | - |
| | SEROTYPE 4 | - | I | | - | S | - | - | - | - | | L |

| p36 | NS POLYEPITOPE | A | P | T | R | V | V | A | S | E | M |
|---|---|---|---|---|---|---|---|---|---|---|---|
| | SEROTYPE 1 | - | | - | - | - | - | - | - | | - |
| | SEROTYPE 2 | - | | - | - | - | - | - | A | | - |
| | SEROTYPE 3 | - | | - | - | - | - | - | A | | - |
| | SEROTYPE 4 | - | | - | - | - | - | - | A | | - |

*FIG. 20C*

| p21 | NS POLYEPITOPE | H | P | A | S | A | W | T | L | Y |
|---|---|---|---|---|---|---|---|---|---|---|
| | SEROTYPE 1 | H/R | - | - | - | - | - | - | - | - |
| | SEROTYPE 2 | R | - | - | - | - | - | - | - | - |
| | SEROTYPE 3 | - | - | - | - | - | - | - | - | - |
| | SEROTYPE 4 | R | - | - | - | - | - | - | - | - |

| p49 | NS POLYEPITOPE | T | P | E | G | I | I | P | A | L |
|---|---|---|---|---|---|---|---|---|---|---|
| | SEROTYPE 1 | - | - | - | - | - | - | - | - | - |
| | SEROTYPE 2 | - | - | - | - | - | - | - | S | M |
| | SEROTYPE 3 | - | - | - | - | - | - | - | - | - |
| | SEROTYPE 4 | - | - | - | - | - | - | - | T | - |

| p50 | NS POLYEPITOPE | L | P | V | W | L | S | Y | K | V | A |
|---|---|---|---|---|---|---|---|---|---|---|---|
| | SEROTYPE 1 | - | - | - | - | - | - | - | - | - | - |
| | SEROTYPE 2 | - | - | - | - | - | A | - | K/R | - | - |
| | SEROTYPE 3 | - | - | - | - | - | A | H | - | - | - |
| | SEROTYPE 4 | - | - | - | - | - | - | - | - | - | - |

| p51 | NS POLYEPITOPE | T | L | Y | A | V | A | T | T | I |
|---|---|---|---|---|---|---|---|---|---|---|
| | SEROTYPE 1 | - | - | - | - | - | - | - | - | I/V |
| | SEROTYPE 2 | - | - | - | - | - | - | - | - | F |
| | SEROTYPE 3 | - | - | - | - | - | - | - | - | V |
| | SEROTYPE 4 | - | - | - | - | - | - | - | - | - |

| p453 | NS POLYEPITOPE | R | S | W | N | S | G | Y | E | W |
|---|---|---|---|---|---|---|---|---|---|---|
| | SEROTYPE 1 | - | - | - | - | - | - | - | E/D | - |
| | SEROTYPE 2 | - | - | - | - | - | - | H | - | - |
| | SEROTYPE 3 | - | - | - | - | - | - | N | - | - |
| | SEROTYPE 4 | - | - | - | - | T | - | F | D | - |

*FIG. 20D*

SEQUENCE LISTING

<160> NUMBER OF SEQ ID NOS: 152

<210> SEQ ID NO 1
<211> LENGTH: 1617
<212> TYPE: DNA
<213> ORGANISM: Artificial Sequence
<220> FEATURE:
<223> OTHER INFORMATION: Native nucleotide sequence of the
      polynucleotide encoding the chimeric polyepitope of DENV1

<400> SEQUENCE: 1

| | |
|---|---|
| gcatcacaag aagggcccct accagagatt gaagatgagg tgtttaggaa aagaaactta | 60 |
| acaataatgg acctacatcc aggatcaggg aaaacaagaa gatatctccc agccatagtc | 120 |
| cgtgaggcca taaaaggaa gctgcgcaca ctaattttgg ctcccacaag ggttgtcgct | 180 |
| tccgaaatgg cagaggcgct caagggaatg ccaataaggt accaaacaac agcagtgaag | 240 |
| agtgaacaca caggaaaaga gatagttgac ctcatgtgcc acgccacttt caccatgcgt | 300 |
| ctcctgtctc ccgtgagagt tcccaattac aacatgatta ttatggatga agcacatttc | 360 |
| accgatccat ccagtatagc agccagaggg tacatctcaa cccgagtggg catgggtgaa | 420 |
| gcagctgcga tcttcatgac agccactcct ccaggatcag tggaggcctt tccacagagc | 480 |
| aatgcagtta tccaagatga ggaaagagac attcctgaga gatcatggaa ctcaggatat | 540 |
| gagtggatca ctgacgagga ccatgctcat tggacagaag caaaaatgct ccttgacaac | 600 |
| ataaacacac agaaggaat tatcccagct ctctttgagc cggagagaga aaagagtgca | 660 |
| gcaatagacg gggagtacag actgcgggga gaagcaagga aaacgttcgt ggagctcatg | 720 |
| agaagaggag atttaccagt ttggctatct tacaaagttg cctcagaagg cttccaatac | 780 |
| tccgatagaa ggtggtgctt tgatggagaa aggaacaacc aggtgttgga ggaaaacatg | 840 |
| gacgtggaga tctggacaaa ggagggagaa agaaagaaat tacgaccccg ctggttggac | 900 |
| gccagaacat actctgatcc actggccctg cgcgagttca aagagttcgc agcaggagtg | 960 |
| gctgttgaaa tcaccacca tgccgcaatg ctggacgtag acttacatcc agcttcagcc | 1020 |
| tggaccctct atgcagtggc cacaacaatt atcactccca tgatgaggca cacaatagaa | 1080 |
| aacacaacgg caaacatttc cctgacagcc attgcaaacc aggcggctat attgatggga | 1140 |
| cttgacaaag gatggccaat atcgaagatg gacataggag ttccacttct cgccttgggg | 1200 |
| tgctattccc aggtgctgga tatcattggc cagaggatag agaacataaa acatgaacat | 1260 |
| aagtcaacat ggcattatga tgaggacaat ccatataaaa catgggccta tcacggatca | 1320 |
| tatgaggtca agccatcagg atcagcctca tccatggtca atggcgtggt gaaactgctc | 1380 |
| accaaaccat gggatgtcat ccccatggtc acacaaatag ccatgactga caccacaccc | 1440 |
| tttggacaac agagggtgtt caaagagaaa gttgacacgc gcacaccaaa gcaaaacga | 1500 |
| ggcacagcac aaatcatgga ggtgacagcc aatggttat ggggttttct ttctagaaac | 1560 |
| aaaaaaccaa gaatttgtac aagagaggag ttcacaagaa aagtcaggtc aaacgca | 1617 |

<210> SEQ ID NO 2
<211> LENGTH: 1617
<212> TYPE: DNA
<213> ORGANISM: Artificial Sequence
<220> FEATURE:
<223> OTHER INFORMATION: Optimised nucleotide sequence of the
      polynucleotide encoding the chimeric polyepitope of DENV1 (human
      codon optimised, measles optimised)

<400> SEQUENCE: 2

```
gcatcacagg agggaccact gcccgaaatt gaggacgaag tgtttagaaa gcgaaatctg      60
actattatgg acctgcaccc cggatctggc aagacccgga gatacctgcc agccatcgtg     120
agggaggcta ttaagcggaa actgagaaca ctgatcctgg ccccaactcg cgtggtcgct     180
tccgaaatgg ctgaggccct gaaaggcatg cccatccggt atcagaccac agcagtgaag     240
tctgaacata ccggcaagga gattgtggac ctgatgtgcc acgccacttt caccatgcga     300
ctgctgagcc cagtgcgggt ccccaactac aatatgatca ttatggacga ggcccacttt     360
actgatccca gctccatcgc cgctagagga tatatttcca ccagggtggg aatgggcgag     420
gcagcagcta tcttcatgac agcaactccc cctggcagcg tggaggcatt tcctcagtcc     480
aacgccgtca tccaggacga ggagcgggac attcctgagc ggagctggaa ttctgggtac     540
gaatggatca cagacgagga tcatgcacac tggactgaag ccaagatgct gctggacaac     600
attaatactc ctgagggaat cattccagct ctgttcgagc ccgaaagaga aagtctgca     660
gccatcgacg gcgagtatag actgagggga gaggcccgga agaccttcgt ggaactgatg     720
aggcgcggcg atctgcccgt gtggctgagt tacaaggtcg cttcagaggg attccagtat     780
agtgaccgac ggtggtgctt tgatggcgaa cgcaacaatc aggtgctgga ggagaacatg     840
gatgtcgaga tttggacaaa ggaaggcgag cggaagaaac tgcgcccacg atggctggac     900
gctcggactt acagcgatcc cctggcactg agagaattca agagtttgc tgcaggggtg     960
gccgtcgaga tcaccatca cgccgctatg ctggacgtgg atctgcatcc tgccagtgct    1020
tggaccctgt atgcagtggc cactaccatc attaccccca tgatgcgcca cacaatcgag    1080
aacacaactg ccaatatctc actgacagct attgcaaacc aggcagccat tctgatggga    1140
ctggacaaag gctggcccat cagcaagatg gatattggcg tgcctctgct ggccctgggg    1200
tgttacagtc aggtgctgga catcattggc cagaggatcg agaacattaa gcatgagcac    1260
aaatcaacct ggcattacga cgaagataat ccctataaga catgggccta ccacggaagc    1320
tatgaggtga aaccttcagg cagcgccagc agcatggtca acggggtggt caagctgctg    1380
accaaacctt gggacgtgat cccaatggtc actcagattg ccatgaccga taccacccca    1440
ttcggccagc agcgggtgtt caaggagaag gtggacaccc gcacacctaa ggctaaacga    1500
gggactgcac agatcatgga ggtgaccgcc aagtggctgt ggggattcct gtccaggaac    1560
aagaagccaa gaatctgtac cagggaagag ttcacaagaa aggtccggtc aaacgcc       1617
```

<210> SEQ ID NO 3
<211> LENGTH: 539
<212> TYPE: PRT
<213> ORGANISM: Artificial Sequence
<220> FEATURE:
<223> OTHER INFORMATION: Amino acid sequence of the chimeric polyepitope
      of DENV1

<400> SEQUENCE: 3

Ala Ser Gln Glu Gly Pro Leu Pro Glu Ile Glu Asp Glu Val Phe Arg
1 5 10 15

Lys Arg Asn Leu Thr Ile Met Asp Leu His Pro Gly Ser Gly Lys Thr
20 25 30

Arg Arg Tyr Leu Pro Ala Ile Val Arg Glu Ala Ile Lys Arg Lys Leu
35 40 45

Arg Thr Leu Ile Leu Ala Pro Thr Arg Val Val Ala Ser Glu Met Ala
50 55 60

Glu Ala Leu Lys Gly Met Pro Ile Arg Tyr Gln Thr Thr Ala Val Lys
65 70 75 80

```
Ser Glu His Thr Gly Lys Glu Ile Val Asp Leu Met Cys His Ala Thr
                85                  90                  95
Phe Thr Met Arg Leu Leu Ser Pro Val Arg Val Pro Asn Tyr Asn Met
            100                 105                 110
Ile Ile Met Asp Glu Ala His Phe Thr Asp Pro Ser Ser Ile Ala Ala
        115                 120                 125
Arg Gly Tyr Ile Ser Thr Arg Val Gly Met Gly Glu Ala Ala Ala Ile
    130                 135                 140
Phe Met Thr Ala Thr Pro Pro Gly Ser Val Glu Ala Phe Pro Gln Ser
145                 150                 155                 160
Asn Ala Val Ile Gln Asp Glu Arg Asp Ile Pro Glu Arg Ser Trp
                165                 170                 175
Asn Ser Gly Tyr Glu Trp Ile Thr Asp Glu Asp His Ala His Trp Thr
                180                 185                 190
Glu Ala Lys Met Leu Leu Asp Asn Ile Asn Thr Pro Glu Gly Ile Ile
            195                 200                 205
Pro Ala Leu Phe Glu Pro Glu Arg Glu Lys Ser Ala Ala Ile Asp Gly
        210                 215                 220
Glu Tyr Arg Leu Arg Gly Glu Ala Arg Lys Thr Phe Val Glu Leu Met
225                 230                 235                 240
Arg Arg Gly Asp Leu Pro Val Trp Leu Ser Tyr Lys Val Ala Ser Glu
                245                 250                 255
Gly Phe Gln Tyr Ser Asp Arg Arg Trp Cys Phe Asp Gly Glu Arg Asn
                260                 265                 270
Asn Gln Val Leu Glu Glu Asn Met Asp Val Glu Ile Trp Thr Lys Glu
            275                 280                 285
Gly Glu Arg Lys Lys Leu Arg Pro Arg Trp Leu Asp Ala Arg Thr Tyr
        290                 295                 300
Ser Asp Pro Leu Ala Leu Arg Glu Phe Lys Glu Phe Ala Ala Gly Val
305                 310                 315                 320
Ala Val Glu Asn His His His Ala Ala Met Leu Asp Val Asp Leu His
                325                 330                 335
Pro Ala Ser Ala Trp Thr Leu Tyr Ala Val Ala Thr Thr Ile Ile Thr
                340                 345                 350
Pro Met Met Arg His Thr Ile Glu Asn Thr Thr Ala Asn Ile Ser Leu
            355                 360                 365
Thr Ala Ile Ala Asn Gln Ala Ala Ile Leu Met Gly Leu Asp Lys Gly
        370                 375                 380
Trp Pro Ile Ser Lys Met Asp Ile Gly Val Pro Leu Leu Ala Leu Gly
385                 390                 395                 400
Cys Tyr Ser Gln Val Leu Asp Ile Gly Gln Arg Ile Glu Asn Ile
                405                 410                 415
Lys His Glu His Lys Ser Thr Trp His Tyr Asp Glu Asp Asn Pro Tyr
                420                 425                 430
Lys Thr Trp Ala Tyr His Gly Ser Tyr Glu Val Lys Pro Ser Gly Ser
            435                 440                 445
Ala Ser Ser Met Val Asn Gly Val Val Lys Leu Leu Thr Lys Pro Trp
        450                 455                 460
Asp Val Ile Pro Met Val Thr Gln Ile Ala Met Thr Asp Thr Thr Pro
465                 470                 475                 480
Phe Gly Gln Gln Arg Val Phe Lys Glu Lys Val Asp Thr Arg Thr Pro
                485                 490                 495
```

Lys Ala Lys Arg Gly Thr Ala Gln Ile Met Glu Val Thr Ala Lys Trp
              500                 505                 510

Leu Trp Gly Phe Leu Ser Arg Asn Lys Lys Pro Arg Ile Cys Thr Arg
        515                 520                 525

Glu Glu Phe Thr Arg Lys Val Arg Ser Asn Ala
        530                 535

<210> SEQ ID NO 4
<211> LENGTH: 555
<212> TYPE: DNA
<213> ORGANISM: Artificial Sequence
<220> FEATURE:
<223> OTHER INFORMATION: Native nucleotide sequence of the
      polynucleotide encoding the first region of NS3 of DENV1

<400> SEQUENCE: 4
gcatcacaag aagggcccct accagagatt gaagatgagg tgtttaggaa agaaacttaa    60
acaataatgg acctacatcc aggatcaggg aaaacaagaa gatatctccc agccatagtc   120
cgtgaggcca taaaaggaa gctgcgcaca ctaattttgg ctcccacaag ggttgtcgct   180
tccgaaatgg cagaggcgct caagggaatg ccaataaggt accaaacaac agcagtgaag   240
agtgaacaca caggaaaaga gatagttgac ctcatgtgcc acgccacttt caccatgcgt   300
ctcctgtctc ccgtgagagt tcccaattac aacatgatta ttatggatga agcacatttc   360
accgatccat ccagtatagc agccagaggg tacatctcaa cccgagtggg catgggtgaa   420
gcagctgcga tcttcatgac agccactcct ccaggatcag tggaggcctt ccacagagc   480 aatgcagtta tccaagatga ggaaagagac attcctgaga gatcatggaa ctcaggatat   540
gagtggatca ctgac                                                   555

<210> SEQ ID NO 5
<211> LENGTH: 555
<212> TYPE: DNA
<213> ORGANISM: Artificial Sequence
<220> FEATURE:
<223> OTHER INFORMATION: Optimised nucleotide sequence of the
      polynucleotide encoding the first region of NS3 of DENV1

<400> SEQUENCE: 5
gcatcacagg agggaccact gcccgaaatt gaggacgaag tgtttagaaa gcgaaatctg    60
actattatgg acctgcaccc cggatctggc aagacccgga gatacctgcc agccatcgtg   120
agggaggcta ttaagcggaa actgagaaca ctgatcctgg ccccaactcg cgtggtcgct   180
tccgaaatgg ctgaggccct gaaaggcatg cccatccggt atcagaccac agcagtgaag   240
tctgaacata ccggcaagga gattgtggac ctgatgtgcc acgccacttt caccatgcga   300
ctgctgagcc cagtgcgggt ccccaactac aatatgatca ttatggacga ggcccacttt   360
actgatccca gctccatcgc cgctagagga tatatttcca ccagggtggg aatgggcgag   420
gcagcagcta tcttcatgac agcaactccc cctggcagcg tggaggcatt cctcagtcc   480 aacgccgtca tccaggacga ggagcgggac attcctgagc ggagctggaa ttctgggtac   540
gaatggatca cagac                                                   555

<210> SEQ ID NO 6
<211> LENGTH: 185
<212> TYPE: PRT
<213> ORGANISM: Artificial Sequence
<220> FEATURE:
<223> OTHER INFORMATION: Amino acid sequence of the first region of NS3
      of DENV1

<400> SEQUENCE: 6

Ala Ser Gln Glu Gly Pro Leu Pro Glu Ile Glu Asp Glu Val Phe Arg
1               5                   10                  15

Lys Arg Asn Leu Thr Ile Met Asp Leu His Pro Gly Ser Gly Lys Thr
            20                  25                  30

Arg Arg Tyr Leu Pro Ala Ile Val Arg Glu Ala Ile Lys Arg Lys Leu
        35                  40                  45

Arg Thr Leu Ile Leu Ala Pro Thr Arg Val Val Ala Ser Glu Met Ala
    50                  55                  60

Glu Ala Leu Lys Gly Met Pro Ile Arg Tyr Gln Thr Thr Ala Val Lys
65                  70                  75                  80

Ser Glu His Thr Gly Lys Glu Ile Val Asp Leu Met Cys His Ala Thr
                85                  90                  95

Phe Thr Met Arg Leu Leu Ser Pro Val Arg Val Pro Asn Tyr Asn Met
            100                 105                 110

Ile Ile Met Asp Glu Ala His Phe Thr Asp Pro Ser Ser Ile Ala Ala
        115                 120                 125

Arg Gly Tyr Ile Ser Thr Arg Val Gly Met Gly Glu Ala Ala Ala Ile
    130                 135                 140

Phe Met Thr Ala Thr Pro Pro Gly Ser Val Glu Ala Phe Pro Gln Ser
145                 150                 155                 160

Asn Ala Val Ile Gln Asp Glu Glu Arg Asp Ile Pro Glu Arg Ser Trp
                165                 170                 175

Asn Ser Gly Tyr Glu Trp Ile Thr Asp
            180                 185

<210> SEQ ID NO 7
<211> LENGTH: 402
<212> TYPE: DNA
<213> ORGANISM: Artificial Sequence
<220> FEATURE:
<223> OTHER INFORMATION: Native nucleotide sequence of the
      polynucleotide encoding the second region of NS3 of DENV1

<400> SEQUENCE: 7
gaggaccatg ctcattggac agaagcaaaa atgctccttg acaacataaa cacaccagaa    60
ggaattatcc cagctctctt tgagccggag agagaaaaga gtgcagcaat agacggggag   120
tacagactgc ggggagaagc aaggaaaacg ttcgtggagc tcatgagaag aggagattta   180
ccagtttggc tatcttacaa agttgcctca gaaggcttcc aatactccga tagaaggtgg   240
tgctttgatg gagaaaggaa caaccaggtg ttggaggaaa acatggacgt ggagatctgg   300
acaaaggagg gagaaagaaa gaaattacga ccccgctggt tggacgccag aacatactct   360
gatccactgg ccctgcgcga gttcaaagag ttcgcagcag ga                      402

<210> SEQ ID NO 8
<211> LENGTH: 402
<212> TYPE: DNA
<213> ORGANISM: Artificial Sequence
<220> FEATURE:
<223> OTHER INFORMATION: Optimised nucleotide sequence of the
      polynucleotide encoding the second region of NS3 of DENV1

<400> SEQUENCE: 8
gaggatcatg cacactggac tgaagccaag atgctgctgg acaacattaa tactcctgag    60
ggaatcattc cagctctgtt cgagcccgaa agagagaagt ctgcagccat cgacggcgag   120

```
tatagactga ggggagaggc ccggaagacc ttcgtggaac tgatgaggcg cggcgatctg      180
cccgtgtggc tgagttacaa ggtcgcttca gagggattcc agtatagtga ccgacggtgg      240
tgctttgatg gcgaacgcaa caatcaggtg ctggaggaga acatggatgt cgagatttgg      300
acaaaggaag gcgagcggaa gaaactgcgc ccacgatggc tggacgctcg gacttacagc      360
gatcccctgg cactgagaga attcaaagag tttgctgcag gg                        402

<210> SEQ ID NO 9
<211> LENGTH: 134
<212> TYPE: PRT
<213> ORGANISM: Artificial Sequence
<220> FEATURE:
<223> OTHER INFORMATION: Amino acid sequence of the second region of NS3
      of DENV1

<400> SEQUENCE: 9

Glu Asp His Ala His Trp Thr Glu Ala Lys Met Leu Leu Asp Asn Ile
1               5                   10                  15

Asn Thr Pro Glu Gly Ile Ile Pro Ala Leu Phe Glu Pro Glu Arg Glu
            20                  25                  30

Lys Ser Ala Ala Ile Asp Gly Glu Tyr Arg Leu Arg Gly Glu Ala Arg
        35                  40                  45

Lys Thr Phe Val Glu Leu Met Arg Arg Gly Asp Leu Pro Val Trp Leu
    50                  55                  60

Ser Tyr Lys Val Ala Ser Glu Gly Phe Gln Tyr Ser Asp Arg Arg Trp
65                  70                  75                  80

Cys Phe Asp Gly Glu Arg Asn Asn Gln Val Leu Glu Glu Asn Met Asp
                85                  90                  95

Val Glu Ile Trp Thr Lys Glu Gly Glu Arg Lys Lys Leu Arg Pro Arg
            100                 105                 110

Trp Leu Asp Ala Arg Thr Tyr Ser Asp Pro Leu Ala Leu Arg Glu Phe
        115                 120                 125

Lys Glu Phe Ala Ala Gly
    130

<210> SEQ ID NO 10
<211> LENGTH: 258
<212> TYPE: DNA
<213> ORGANISM: Artificial Sequence
<220> FEATURE:
<223> OTHER INFORMATION: Native nucleotide sequence of the
      polynucleotide encoding the NS4b fragment of DENV1

<400> SEQUENCE: 10
gtggctgttg aaaatcacca ccatgccgca atgctggacg tagacttaca tccagcttca      60
gcctggaccc tctatgcagt ggccacaaca attatcactc ccatgatgag gcacacaata      120
gaaaacacaa cggcaaacat ttccctgaca gccattgcaa accaggcggc tatattgatg      180
ggacttgaca aggatggcc aatatcgaag atggacatag agttccact tctcgccttg       240 gggtgctatt cccaggtg                                                    258

<210> SEQ ID NO 11
<211> LENGTH: 258
<212> TYPE: DNA
<213> ORGANISM: Artificial Sequence
<220> FEATURE:
<223> OTHER INFORMATION: Optimised nucleotide sequence of the
      polynucleotide encoding the NS4b fragment of DENV1

<400> SEQUENCE: 11
```
gtggccgtcg agaatcacca tcacgccgct atgctggacg tggatctgca tcctgccagt 60
gcttggaccc tgtatgcagt ggccactacc atcattaccc caatgatgcg ccacacaatc 120
gagaacacaa ctgccaatat ctcactgaca gctattgcaa accaggcagc cattctgatg 180
ggactggaca aaggctggcc catcagcaag atggatattg gcgtgcctct gctggccctg 240
gggtgttaca gtcaggtg 258

<210> SEQ ID NO 12
<211> LENGTH: 86
<212> TYPE: PRT
<213> ORGANISM: Artificial Sequence
<220> FEATURE:
<223> OTHER INFORMATION: Amino acid sequence of the NS4b fragment of DENV1

<400> SEQUENCE: 12

```
Val Ala Val Glu Asn His His His Ala Ala Met Leu Asp Val Asp Leu
1               5                   10                  15

His Pro Ala Ser Ala Trp Thr Leu Tyr Ala Val Ala Thr Thr Ile Ile
            20                  25                  30

Thr Pro Met Met Arg His Thr Ile Glu Asn Thr Thr Ala Asn Ile Ser
        35                  40                  45

Leu Thr Ala Ile Ala Asn Gln Ala Ala Ile Leu Met Gly Leu Asp Lys
    50                  55                  60

Gly Trp Pro Ile Ser Lys Met Asp Ile Gly Val Pro Leu Leu Ala Leu
65                  70                  75                  80

Gly Cys Tyr Ser Gln Val
                85
```

<210> SEQ ID NO 13
<211> LENGTH: 402
<212> TYPE: DNA
<213> ORGANISM: Artificial Sequence
<220> FEATURE:
<223> OTHER INFORMATION: Native nucleotide sequence of the polynucleotide encoding the NS5 fragment of DENV1

<400> SEQUENCE: 13
ctggatatca ttggccagag gatagagaac ataaaacatg aacataagtc aacatggcat 60
tatgatgagg acaatccata taaaacatgg gcctatcacg gatcatatga ggtcaagcca 120
tcaggatcag cctcatccat ggtcaatggc gtggtgaaac tgctcaccaa accatgggat 180
gtcatcccca tggtcacaca aatagccatg actgacacca caccctttgg acaacagagg 240
gtgttcaaag agaaagttga cacgcgcaca ccaaaagcaa aacgaggcac agcacaaatc 300
atggaggtga cagccaaatg gttatggggt tttctttcta gaaacaaaaa accaagaatt 360
tgtacaagag aggagttcac aagaaaagtc aggtcaaacg ca 402

<210> SEQ ID NO 14
<211> LENGTH: 402
<212> TYPE: DNA
<213> ORGANISM: Artificial Sequence
<220> FEATURE:
<223> OTHER INFORMATION: Optimised nucleotide sequence of the polynucleotide encoding the NS5 fragment of DENV1

<400> SEQUENCE: 14
ctggacatca ttggccagag gatcgagaac attaagcatg agcacaaatc aacctggcat 60
tacgacgaag ataatcccta taagacatgg gcctaccacg gaagctatga ggtgaaacct 120

-continued

```
tcaggcagcg ccagcagcat ggtcaacggg gtggtcaagc tgctgaccaa accttgggac    180
gtgatcccaa tggtcactca gattgccatg accgatacca ccccattcgg ccagcagcgg    240
gtgttcaagg agaaggtgga cacccgcaca cctaaggcta aacgagggac tgcacagatc    300
atggaggtga ccgccaagtg gctgtgggga ttcctgtcca ggaacaagaa gccaagaatc    360
tgtaccaggg aagagttcac aagaaaggtc cggtcaaacg cc                      402

<210> SEQ ID NO 15
<211> LENGTH: 134
<212> TYPE: PRT
<213> ORGANISM: Artificial Sequence
<220> FEATURE:
<223> OTHER INFORMATION: Amino acid sequence of the NS5 fragment of
      DENV1

<400> SEQUENCE: 15

Leu Asp Ile Ile Gly Gln Arg Ile Glu Asn Ile Lys His Glu His Lys
1               5                   10                  15

Ser Thr Trp His Tyr Asp Glu Asp Asn Pro Tyr Lys Thr Trp Ala Tyr
            20                  25                  30

His Gly Ser Tyr Glu Val Lys Pro Ser Gly Ser Ala Ser Ser Met Val
        35                  40                  45

Asn Gly Val Val Lys Leu Leu Thr Lys Pro Trp Asp Val Ile Pro Met
    50                  55                  60

Val Thr Gln Ile Ala Met Thr Asp Thr Thr Pro Phe Gly Gln Gln Arg
65                  70                  75                  80

Val Phe Lys Glu Lys Val Asp Thr Arg Thr Pro Lys Ala Lys Arg Gly
                85                  90                  95

Thr Ala Gln Ile Met Glu Val Thr Ala Lys Trp Leu Trp Gly Phe Leu
            100                 105                 110

Ser Arg Asn Lys Lys Pro Arg Ile Cys Thr Arg Glu Glu Phe Thr Arg
        115                 120                 125

Lys Val Arg Ser Asn Ala
    130

<210> SEQ ID NO 16
<211> LENGTH: 9
<212> TYPE: PRT
<213> ORGANISM: Artificial Sequence
<220> FEATURE:
<223> OTHER INFORMATION: Amino acid sequence of the P20 epitope

<400> SEQUENCE: 16

Leu Pro Glu Ile Glu Asp Glu Val Phe
1               5

<210> SEQ ID NO 17
<211> LENGTH: 10
<212> TYPE: PRT
<213> ORGANISM: Artificial Sequence
<220> FEATURE:
<223> OTHER INFORMATION: Amino acid sequence of the P19 epitope

<400> SEQUENCE: 17

His Pro Gly Ser Gly Lys Thr Arg Arg Tyr
1               5                   10

<210> SEQ ID NO 18
<211> LENGTH: 11
<212> TYPE: PRT
```

```
<213> ORGANISM: Artificial Sequence
<220> FEATURE:
<223> OTHER INFORMATION: Amino acid sequence of the P30 epitope

<400> SEQUENCE: 18

Arg Tyr Leu Pro Ala Ile Val Arg Glu Ala Ile
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Amino acid sequence of the P451 epitope

<400> SEQUENCE: 19

Tyr Leu Pro Ala Ile Val Arg Glu Ala
1               5

<210> SEQ ID NO 20
<211> LENGTH: 9
<212> TYPE: PRT
<213> ORGANISM: Artificial Sequence
<220> FEATURE:
<223> OTHER INFORMATION: Amino acid sequence of the P11 epitope

<400> SEQUENCE: 20

Leu Pro Ala Ile Val Arg Glu Ala Ile
1               5

<210> SEQ ID NO 21
<211> LENGTH: 10
<212> TYPE: PRT
<213> ORGANISM: Artificial Sequence
<220> FEATURE:
<223> OTHER INFORMATION: Amino acid sequence of the P36 epitope

<400> SEQUENCE: 21

Ala Pro Thr Arg Val Val Ala Ser Glu Met
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Amino acid sequence of the P48 EPITOPE

<400> SEQUENCE: 22

Glu Met Ala Glu Ala Leu Lys Gly Met Pro Ile Arg Tyr Gln Thr
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: Amino acid sequence of the P12 epitope

<400> SEQUENCE: 23

Ser Pro Val Arg Val Pro Asn Tyr Asn Met
1               5                   10

<210> SEQ ID NO 24
<211> LENGTH: 9
<212> TYPE: PRT
<213> ORGANISM: Artificial Sequence
```

```
<220> FEATURE:
<223> OTHER INFORMATION: Amino acid sequence of the P454 epitope

<400> SEQUENCE: 24

Val Pro Asn Tyr Asn Met Ile Ile Met
1               5

<210> SEQ ID NO 25
<211> LENGTH: 10
<212> TYPE: PRT
<213> ORGANISM: Artificial Sequence
<220> FEATURE:
<223> OTHER INFORMATION: Amino acid sequence of the P18 epitope

<400> SEQUENCE: 25

Asp Pro Ser Ser Ile Ala Ala Arg Gly Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Amino acid sequence of the P457 epitope

<400> SEQUENCE: 26

Ala Val Ile Gln Asp Glu Glu Arg Asp Ile
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Amino acid sequence of the P453 epitope

<400> SEQUENCE: 27

Arg Ser Trp Asn Ser Gly Tyr Glu Trp
1               5

<210> SEQ ID NO 28
<211> LENGTH: 9
<212> TYPE: PRT
<213> ORGANISM: Artificial Sequence
<220> FEATURE:
<223> OTHER INFORMATION: Amino acid sequence of the P49 epitope

<400> SEQUENCE: 28

Thr Pro Glu Gly Ile Ile Pro Ala Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Amino acid sequence of the P28 epitope

<400> SEQUENCE: 29

Lys Thr Phe Val Glu Leu Met Arg Arg
1               5

<210> SEQ ID NO 30
<211> LENGTH: 10
<212> TYPE: PRT
<213> ORGANISM: Artificial Sequence
<220> FEATURE:
```

```
<223> OTHER INFORMATION: Amino acid sequence of the P2 epitope

<400> SEQUENCE: 30

Glu Leu Met Arg Arg Gly Asp Le

```
<400> SEQUENCE: 36

Lys Tyr Thr Asp Arg Lys Trp Cys Phe
1               5

<210> SEQ ID NO 37
<211> LENGTH: 9
<212> TYPE: PRT
<213> ORGANISM: Artificial Sequence
<220> FEATURE:
<223> OTHER INFORMATION: Amino acid sequence of the P76 epitope

<400> SEQUENCE: 37

Ser Tyr Lys Asp Arg Glu Trp Cys Phe
1               5

<210> SEQ ID NO 38
<211> LENGTH: 9
<212> TYPE: PRT
<213> ORGANISM: Artificial Sequence
<220> FEATURE:
<223> OTHER INFORMATION: Amino acid sequence of the P35 epitope

<400> SEQUENCE: 38

Arg Pro Arg Trp Leu Asp Ala Arg Thr
1               5

<210> SEQ ID NO 39
<211> LENGTH: 18
<212> TYPE: PRT
<213> ORGANISM: Artificial Sequence
<220> FEATURE:
<223> OTHER INFORMATION: Amino acid sequence of the P17 epitope

<400> SEQUENCE: 39

Leu Asp Ala Arg Thr Tyr Ser Asp Pro Leu Ala Leu Arg Glu Phe Lys
1               5                   10                  15

Glu Phe

<210> SEQ ID NO 40
<211> LENGTH: 10
<212> TYPE: PRT
<213> ORGANISM: Artificial Sequence
<220> FEATURE:
<223> OTHER INFORMATION: Amino acid sequence of the P29 epitope

<400> SEQUENCE: 40

Arg Ile Tyr Ser Asp Pro Leu Ala Leu Lys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Amino acid sequence of the P452 epitope

<400> SEQUENCE: 41

Arg Thr Tyr Ser Asp Pro Leu Ala Leu Arg
1               5                   10

<210> SEQ ID NO 42
<211> LENGTH: 9
<212> TYPE: PRT
<213> ORGANISM: Artificial Sequence
<220> FEATURE:
```

```
<223> OTHER INFORMATION: Amino acid sequence of the P21 epitope

<400> SEQUENCE: 42

His Pro Ala Ser Ala Trp Thr Leu Tyr
1               5

<210> SEQ ID NO 43
<211> LENGTH: 8
<212> TYPE: PRT
<213> ORGANISM: Artificial Sequence
<220> FEATURE:
<223> OTHER INFORMATION: Amino acid sequence of the P16 epitope

<400> SEQUENCE: 43

Pro Ala Ser Ala Trp Thr Leu Tyr
1               5

<210> SEQ ID NO 44
<211> LENGTH: 10
<212> TYPE: PRT
<213> ORGANISM: Artificial Sequence
<220> FEATURE:
<223> OTHER INFORMATION: Amino acid sequence of the P13 epitope

<400> SEQUENCE: 44

His Pro Ala Ser Ala Trp Thr Leu Tyr Ala
1               5                   10

<210> SEQ ID NO 45
<211> LENGTH: 9
<212> TYPE: PRT
<213> ORGANISM: Artificial Sequence
<220> FEATURE:
<223> OTHER INFORMATION: Amino acid sequence of the P51 epitope

<400> SEQUENCE: 45

Thr Leu Tyr Ala Val Ala Thr Thr Ile
1               5

<210> SEQ ID NO 46
<211> LENGTH: 9
<212> TYPE: PRT
<213> ORGANISM: Artificial Sequence
<220> FEATURE:
<223> OTHER INFORMATION: Amino acid sequence of the P52 epitope

<400> SEQUENCE: 46

Val Ala Thr Thr Ile Ile Thr Pro Met
1               5

<210> SEQ ID NO 47
<211> LENGTH: 9
<212> TYPE: PRT
<213> ORGANISM: Artificial Sequence
<220> FEATURE:
<223> OTHER INFORMATION: Amino acid sequence of the P33 epitope

<400> SEQUENCE: 47

Ile Thr Pro Met Met Arg His Thr Ile
1               5

<210> SEQ ID NO 48
<211> LENGTH: 10
<212> TYPE: PRT
<213> ORGANISM: Artificial Sequence
<220> FEATURE:
<223> OTHER INFORMATION: Amino acid sequence of the P14 epitope
```

```
<400> SEQUENCE: 48

Thr Pro Met Met Arg His Thr Ile Glu Asn
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Amino acid sequence of the P22 epitope

<400> SEQUENCE: 49

Ile Ala Asn Gln Ala Ala Ile Leu Met
1               5

<210> SEQ ID NO 50
<211> LENGTH: 9
<212> TYPE: PRT
<213> ORGANISM: Artificial Sequence
<220> FEATURE:
<223> OTHER INFORMATION: Amino acid sequence of the P456 epitope

<400> SEQUENCE: 50

Ala Ala Ile Leu Met Gly Leu Asp Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Amino acid sequence of the P53 epitope

<400> SEQUENCE: 51

Lys Met Asp Ile Gly Val Pro Leu Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Amino acid sequence of the P54 epitope

<400> SEQUENCE: 52

Val Pro Leu Leu Ala Leu Gly Cys Tyr
1               5

<210> SEQ ID NO 53
<211> LENGTH: 10
<212> TYPE: PRT
<213> ORGANISM: Artificial Sequence
<220> FEATURE:
<223> OTHER INFORMATION: Amino acid sequence of the P55 epitope

<400> SEQUENCE: 53

Asp Asn Pro Tyr Lys Thr Trp Ala Tyr His
1               5                   10

<210> SEQ ID NO 54
<211> LENGTH: 9
<212> TYPE: PRT
<213> ORGANISM: Artificial Sequence
<220> FEATURE:
<223> OTHER INFORMATION: Amino acid sequence of the P24 epitope
```

```
<400> SEQUENCE: 54

Trp Ala Tyr His Gly Ser Tyr Glu Val
1               5

<210> SEQ ID NO 55
<211> LENGTH: 9
<212> TYPE: PRT
<213> ORGANISM: Artificial Sequence
<220> FEATURE:
<223> OTHER INFORMATION: Amino acid sequence of the P56 epitope

<400> SEQUENCE: 55

Ser Met Val Asn Gly Val Val Lys Leu
1               5

<210> SEQ ID NO 56
<211> LENGTH: 15
<212> TYPE: PRT
<213> ORGANISM: Artificial Sequence
<220> FEATURE:
<223> OTHER INFORMATION: Amino acid sequence of the P5 epitope

<400> SEQUENCE: 56

Leu Leu Thr Lys Pro Trp Asp Val Ile Pro Met Val Thr Gln Ile
1               5                   10                  15

<210> SEQ ID NO 57
<211> LENGTH: 10
<212> TYPE: PRT
<213> ORGANISM: Artificial Sequence
<220> FEATURE:
<223> OTHER INFORMATION: Amino acid sequence of the P6 epitope

<400> SEQUENCE: 57

Leu Leu Thr Lys Pro Trp Asp Val Ile Pro
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Amino acid sequence of the P7 epitope

<400> SEQUENCE: 58

Leu Thr Lys Pro Trp Asp Val Ile Pro Met
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Amino acid sequence of the P8 epitope

<400> SEQUENCE: 59

Thr Lys Pro Trp Asp Val Ile Pro Met Val
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Amino acid sequence of the P9 epitope

<400> SEQUENCE: 60
```

```
Lys Pro Trp Asp Val Ile Pro Met Val Thr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Amino acid sequence of the P10 epitope

<400> SEQUENCE: 61

Pro Trp Asp Val Ile Pro Met Val Thr Gln
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Amino acid sequence of the P27 epitope

<400> SEQUENCE: 62

Trp Asp Val Ile Pro Met Val Thr Gln Ile
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Amino acid sequence of the P455 epitope

<400> SEQUENCE: 63

Ile Pro Met Val Thr Gln Ile Ala Met
1               5

<210> SEQ ID NO 64
<211> LENGTH: 9
<212> TYPE: PRT
<213> ORGANISM: Artificial Sequence
<220> FEATURE:
<223> OTHER INFORMATION: Amino acid sequence of the P34 epitope

<400> SEQUENCE: 64

Asp Thr Thr Pro Phe Gly Gln Gln Arg
1               5

<210> SEQ ID NO 65
<211> LENGTH: 9
<212> TYPE: PRT
<213> ORGANISM: Artificial Sequence
<220> FEATURE:
<223> OTHER INFORMATION: Amino acid sequence of the P23 epitope

<400> SEQUENCE: 65

Thr Pro Phe Gly Gln Gln Arg Val Phe
1               5

<210> SEQ ID NO 66
<211> LENGTH: 20
<212> TYPE: PRT
<213> ORGANISM: Artificial Sequence
<220> FEATURE:
<223> OTHER INFORMATION: Amino acid sequence of the P3 epitope

<400> SEQUENCE: 66
```

```
Thr Ala Lys Trp Leu Trp Gly Phe Leu Ser Arg Asn Lys Lys Pro Arg
1               5                   10                  15

Ile Cys Thr Arg
            20

<210> SEQ ID NO 67
<211> LENGTH: 9
<212> TYPE: PRT
<213> ORGANISM: Artificial Sequence
<220> FEATURE:
<223> OTHER INFORMATION: Amino acid sequence of the P4 epitope

<400> SEQUENCE: 67

Trp Gly Phe Leu Ser Arg Asn Lys Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Amino acid sequence of the P15 epitope

<400> SEQUENCE: 68

Lys Pro Arg Ile Cys Thr Arg Glu Glu Phe
1               5                   10

<210> SEQ ID NO 69
<211> LENGTH: 15
<212> TYPE: PRT
<213> ORGANISM: Artificial Sequence
<220> FEATURE:
<223> OTHER INFORMATION: Amino acid sequence of the peptide at position
      8-22 of the first region of NS3

<400> SEQUENCE: 69

Pro Glu Leu Glu Glu Glu Met Phe Lys Lys Arg Asn Leu Thr Ile
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Amino acid sequence of the peptide at position
      18-32 of the first region of NS3

<400> SEQUENCE: 70

Arg Lys Leu Thr Ile Met Asp Leu His Pro Gly Ser Gly Lys Thr
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Amino acid sequence of the peptide at position
      32-46 of the first region of NS3

<400> SEQUENCE: 71

Thr Lys Arg Tyr Leu Pro Ala Ile Val Arg Glu Ala Ile Lys Arg
1               5                   10                  15

<210> SEQ ID NO 72
<211> LENGTH: 10
<212> TYPE: PRT
<213> ORGANISM: Artificial Sequence
```

```
<220> FEATURE:
<223> OTHER INFORMATION: Amino acid sequence of the peptide at position
      33-42 of the first region of NS3

<400> SEQUENCE: 72

Arg Lys Tyr Leu Pro Ala Ile Val Arg Glu
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Amino acid sequence of the peptide at position
      36-50 of the first region of NS3

<400> SEQUENCE: 73

Leu Pro Ala Ile Val Arg Glu Ala Ile Lys Arg Arg Leu Arg Thr
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Amino acid sequence of the peptide at position
      40-54 of the first region of NS3

<400> SEQUENCE: 74

Val Arg Glu Ala Ile Lys Arg Arg Leu Arg Thr Leu Ile Leu Ala
1               5                   10                  15

<210> SEQ ID NO 75
<211> LENGTH: 11
<212> TYPE: PRT
<213> ORGANISM: Artificial Sequence
<220> FEATURE:
<223> OTHER INFORMATION: Amino acid sequence of the peptide at position
      56-66 of the first region of NS3

<400> SEQUENCE: 75

Thr Arg Val Val Ala Ala Glu Met Glu Glu Ala
1               5                   10

<210> SEQ ID NO 76
<211> LENGTH: 15
<212> TYPE: PRT
<213> ORGANISM: Artificial Sequence
<220> FEATURE:
<223> OTHER INFORMATION: Amino acid sequence of the peptide at position
      55-69 of the first region of NS3

<400> SEQUENCE: 76

Pro Thr Arg Val Val Ala Ala Glu Met Glu Glu Ala Met Lys Gly
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Amino acid sequence of the peptide at position
      66-80 of the first region of NS3

<400> SEQUENCE: 77

Ala Leu Lys Gly Met Pro Ile Arg Tyr Gln Thr Thr Ala Val Lys
1               5                   10                  15
```

<210> SEQ ID NO 78
<211> LENGTH: 15
<212> TYPE: PRT
<213> ORGANISM: Artificial Sequence
<220> FEATURE:
<223> OTHER INFORMATION: Amino acid sequence of the peptide at position
      68-82 of the first region of NS3

<400> SEQUENCE: 78

Lys Gly Leu Pro Ile Arg Tyr Gln Thr Thr Ala Thr Lys Ser Glu
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Amino acid sequence of the peptide at position
      72-86 of the first region of NS3

<400> SEQUENCE: 79

Ile Arg Tyr Gln Thr Thr Ala Thr Lys Ser Glu His Thr Gly Arg
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Amino acid sequence of the peptide at position
      83-97 of the first region of NS3

<400> SEQUENCE: 80

His Thr Gly Arg Glu Ile Val Asp Leu Met Cys His Ala Thr Glu
1               5                   10                  15

<210> SEQ ID NO 81
<211> LENGTH: 12
<212> TYPE: PRT
<213> ORGANISM: Artificial Sequence
<220> FEATURE:
<223> OTHER INFORMATION: Amino acid sequence of the peptide at position
      86-97 of the first region of NS3

<400> SEQUENCE: 81

Arg Glu Ile Val Asp Leu Met Cys His Ala Thr Phe
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Amino acid sequence of the peptide at position
      87-96 of the first region of NS3

<400> SEQUENCE: 82

Glu Ile Val Asp Leu Met Cys His Ala Thr
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Amino acid sequence of the peptide at position
      89-98 of the first region of NS3

-continued

```
<400> SEQUENCE: 83

Val Asp Leu Met Cys His Ala Thr Phe Thr
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Amino acid sequence of the peptide at position
      96-110 of the first region of NS3

<400> SEQUENCE: 84

Thr Phe Thr Met Arg Leu Leu Ser Pro Val Arg Val Pro Asn Tyr
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Amino acid sequence of the peptide at position
      108-122 of the first region of NS3

<400> SEQUENCE: 85

Pro Asn Tyr Asn Leu Ile Ile Met Asp Glu Ala His Phe Thr Asp
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Amino acid sequence of the peptide at position
      124-138 of the first region of NS3

<400> SEQUENCE: 86

Ala Ser Ile Ala Ala Arg Gly Tyr Ile Ser Thr Arg Val Gly Met
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Amino acid sequence of the peptide at position
      139-154 of the first region of NS3

<400> SEQUENCE: 87

Glu Ala Ala Ala Ile Phe Met Thr Ala Thr Pro Pro Gly Thr Ala
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Amino acid sequence of the peptide at position
      287-301 of the second region of NS3

<400> SEQUENCE: 88

Arg Glu Gly Glu Lys Lys Lys Leu Arg Pro Arg Trp Leu Asp Arg
1               5                   10                  15

<210> SEQ ID NO 89
<211> LENGTH: 15
<212> TYPE: PRT
```

```
<213> ORGANISM: Artificial Sequence
<220> FEATURE:
<223> OTHER INFORMATION: Amino acid sequence of the peptide at position
      307-319 of the second region of NS3

<400> SEQUENCE: 89

Pro Leu Ala Leu Lys Glu Phe Lys Asp Phe Ala Ala Gly Arg Lys
1               5                   10                  15

<210> SEQ ID NO 90
<211> LENGTH: 17
<212> TYPE: PRT
<213> ORGANISM: Artificial Sequence
<220> FEATURE:
<223> OTHER INFORMATION: Amino acid sequence of the peptide at position
      417-433 of NS5

<400> SEQUENCE: 90

Lys Glu Glu His Ser Ser Thr Trp His Tyr Asp Asp Glu Asn Pro Tyr
1               5                   10                  15

Lys

<210> SEQ ID NO 91
<211> LENGTH: 17
<212> TYPE: PRT
<213> ORGANISM: Artificial Sequence
<220> FEATURE:
<223> OTHER INFORMATION: Amino acid sequence of the peptide at position
      423-439 of NS5

<400> SEQUENCE: 91

Thr Trp His Tyr Asp Asp Glu Asn Pro Tyr Lys Thr Trp Ala Tyr His
1               5                   10                  15

Gly

<210> SEQ ID NO 92
<211> LENGTH: 17
<212> TYPE: PRT
<213> ORGANISM: Artificial Sequence
<220> FEATURE:
<223> OTHER INFORMATION: Amino acid sequence of the peptide at position
      427-444 of NS5

<400> SEQUENCE: 92

Asp Glu Asn Pro Tyr Lys Thr Trp Ala Tyr His Gly Ser Tyr Glu Val
1               5                   10                  15

Lys

<210> SEQ ID NO 93
<211> LENGTH: 15
<212> TYPE: PRT
<213> ORGANISM: Artificial Sequence
<220> FEATURE:
<223> OTHER INFORMATION: Amino acid sequence of the peptide at position
      433-447 of NS5

<400> SEQUENCE: 93

Lys Thr Trp Ala Tyr His Gly Ser Tyr Glu Thr Lys Gln Thr Gly
1               5                   10                  15

<210> SEQ ID NO 94
<211> LENGTH: 17
<212> TYPE: PRT
<213> ORGANISM: Artificial Sequence
<220> FEATURE:
<223> OTHER INFORMATION: Amino acid sequence of the peptide at position
```

```
                    451-473 of NS5

<400> SEQUENCE: 94

Ser Met Ile Asn Gly Val Val Lys Leu Leu Thr Lys Pro Trp Asp Val
1               5                   10                  15

Val

<210> SEQ ID NO 95
<211> LENGTH: 9
<212> TYPE: PRT
<213> ORGANISM: Artificial Sequence
<220> FEATURE:
<223> OTHER INFORMATION: Amino acid sequence of the peptide at position
      462-471 of NS5

<400> SEQUENCE: 95

Lys Pro Trp Asp Val Leu Pro Met Val
1               5

<210> SEQ ID NO 96
<211> LENGTH: 17
<212> TYPE: PRT
<213> ORGANISM: Artificial Sequence
<220> FEATURE:
<223> OTHER INFORMATION: Amino acid sequence of the peptide at position
      457-463 of NS5

<400> SEQUENCE: 96

Val Lys Leu Leu Thr Lys Pro Trp Asp Val Val Pro Met Val Thr Gln
1               5                   10                  15

Met

<210> SEQ ID NO 97
<211> LENGTH: 18
<212> TYPE: PRT
<213> ORGANISM: Artificial Sequence
<220> FEATURE:
<223> OTHER INFORMATION: Amino acid sequence of the peptide at position
      469-485 of NS5

<400> SEQUENCE: 97

Met Val Thr Gln Met Ala Met Thr Asp Thr Thr Pro Phe Gly Gln Gln
1               5                   10                  15

Arg Val

<210> SEQ ID NO 98
<211> LENGTH: 15
<212> TYPE: PRT
<213> ORGANISM: Artificial Sequence
<220> FEATURE:
<223> OTHER INFORMATION: Synthetic peptide

<400> SEQUENCE: 98

Val Lys Ser Glu His Thr Gly Lys Glu Ile Val Asp Leu Met Cys
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic peptide

<400> SEQUENCE: 99

His Thr Gly Lys Glu Ile Val Asp Leu Met Cys His Ala Thr Phe
```

```
<210> SEQ ID NO 100
<211> LENGTH: 15
<212> TYPE: PRT
<213> ORGANISM: Artificial Sequence
<220> FEATURE:
<223> OTHER INFORMATION: Synthetic peptide

<400> SEQUENCE: 100

Glu Ile Val Asp Leu Met Cys His Ala Thr Phe Thr Met Arg Leu
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic peptide

<400> SEQUENCE: 101

Leu Met Cys His Ala Thr Phe Thr Met Arg Leu Leu Ser Pro Val
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic peptide

<400> SEQUENCE: 102

Ala Thr Phe Thr Met Arg Leu Leu Ser Pro Val Arg Val Pro Asn
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Synthetic peptide

<400> SEQUENCE: 103

Met Arg Leu Leu Ser Pro Val Arg Val Pro Asn Tyr Asn Met Ile
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Synthetic peptide

<400> SEQUENCE: 104

Glu Phe Lys Glu Phe Ala Ala Gly Val Ala Val Glu Asn His His
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Synthetic peptide

<400> SEQUENCE: 105

Phe Ala Ala Gly Val Ala Val Glu Asn His His His Ala Ala Met
1               5                   10                  15
```

<210> SEQ ID NO 106
<211> LENGTH: 15
<212> TYPE: PRT
<213> ORGANISM: Artificial Sequence
<220> FEATURE:
<223> OTHER INFORMATION: Synthetic peptide

<400> SEQUENCE: 106

Val Ala Val Glu Asn His His His Ala Ala Met Leu Asp Val Asp
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: Synthetic peptide

<400> SEQUENCE: 107

Asn His His His Ala Ala Met Leu Asp Val Asp Leu His Pro Ala
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic peptide

<400> SEQUENCE: 108

Ala Ala Met Leu Asp Val Asp Leu His Pro Ala Ser Ala Trp Thr
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic peptide

<400> SEQUENCE: 109

Asp Val Asp Leu His Pro Ala Ser Ala Trp Thr Leu Tyr Ala Val
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic peptide

<400> SEQUENCE: 110

His Pro Ala Ser Ala Trp Thr Leu Tyr Ala Val Ala Thr Thr Ile
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic peptide

<400> SEQUENCE: 111

Ala Trp Thr Leu Tyr Ala Val Ala Thr Thr Ile Ile Thr Pro Met
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: Synthetic peptide

<400> SEQUENCE: 112

Tyr Ala Val Ala Thr Thr Ile Ile Thr Pro Met Met Arg His Thr
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic peptide

<400> SEQUENCE: 113

Thr Thr Ile Ile Thr Pro Met Met Arg His Thr Ile Glu Asn Thr
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic peptide

<400> SEQUENCE: 114

Thr Pro Met Met Arg His Thr Ile Glu Asn Thr Thr Ala Asn Ile
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic peptide

<400> SEQUENCE: 115

Arg His Thr Ile Glu Asn Thr Thr Ala Asn Ile Ser Leu Thr Ala
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic peptide

<400> SEQUENCE: 116

Glu Asn Thr Thr Ala Asn Ile Ser Leu Thr Ala Ile Ala Asn Gln
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic peptide

<400> SEQUENCE: 117

Ala Asn Ile Ser Leu Thr Ala Ile Ala Asn Gln Ala Ala Ile Leu
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Synthetic peptide

<400> SEQUENCE: 118

Gly Trp Pro Ile Ser Lys Met Asp Ile Gly Val Pro Leu Leu Ala
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetic peptide

<400> SEQUENCE: 119

Ser Lys Met Asp Ile Gly Val Pro Leu Leu Ala Leu Gly Cys Tyr
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Synthetic peptide

<400> SEQUENCE: 120

Ile Gly Val Pro Leu Leu Ala Leu Gly Cys Tyr Ser Gln Val Leu
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Synthetic peptide

<400> SEQUENCE: 121

Asp Glu Asp Asn Pro Tyr Lys Thr Trp Ala Tyr His Gly Ser Tyr
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Synthetic peptide

<400> SEQUENCE: 122

Pro Tyr Lys Thr Trp Ala Tyr His Gly Ser Tyr Glu Val Lys Pro
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Synthetic peptide

<400> SEQUENCE: 123

Trp Ala Tyr His Gly Ser Tyr Glu Val Lys Pro Ser Gly Ser Ala
1               5                   10                  15

<210> SEQ ID NO 124

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 124

Gly Ser Tyr Glu Val Lys Pro Ser Gly Ser Ala Ser Ser Met Val
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Synthetic peptide

<400> SEQUENCE: 125

Val Lys Pro Ser Gly Ser Ala Ser Ser Met Val Asn Gly Val Val
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Synthetic peptide

<400> SEQUENCE: 126

Gly Ser Ala Ser Ser Met Val Asn Gly Val Val Lys Leu Leu Thr
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Synthetic peptide

<400> SEQUENCE: 127

Ser Met Val Asn Gly Val Val Lys Leu Leu Thr Lys Pro Trp Asp
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic peptide

<400> SEQUENCE: 128

Gly Val Val Lys Leu Leu Thr Lys Pro Trp Asp Val Ile Pro Met
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic peptide

<400> SEQUENCE: 129

Leu Leu Thr Lys Pro Trp Asp Val Ile Pro Met Val Thr Gln Ile
1               5                   10                  15

<210> SEQ ID NO 130
<211> LENGTH: 15
```

<212> TYPE: PRT
<213> ORGANISM: Artificial Sequence
<220> FEATURE:
<223> OTHER INFORMATION: Synthetic peptide

<400> SEQUENCE: 130

Pro Trp Asp Val Ile Pro Met Val Thr Gln Ile Ala Met Thr Asp
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic peptide

<400> SEQUENCE: 131

Ile Pro Met Val Thr Gln Ile Ala Met Thr Asp Thr Thr Pro Phe
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic peptide

<400> SEQUENCE: 132

Thr Gln Ile Ala Met Thr Asp Thr Thr Pro Phe Gly Gln Gln Arg
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic peptide

<400> SEQUENCE: 133

Met Thr Asp Thr Thr Pro Phe Gly Gln Gln Arg Val Phe Lys Glu
1               5                   10                  15

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide

<400> SEQUENCE: 134

Phe Thr Met Arg Leu Leu Ser Pro Val
1               5

<210> SEQ ID NO 135
<211> LENGTH: 11
<212> TYPE: PRT
<213> ORGANISM: Artificial Sequence
<220> FEATURE:
<223> OTHER INFORMATION: Synthetic peptide

<400> SEQUENCE: 135

Val Ala Val Glu Asn His His His Ala Ala Met
1               5                   10

<210> SEQ ID NO 136
<211> LENGTH: 9
<212> TYPE: PRT

<213> ORGANISM: Artificial Sequence
<220> FEATURE:
<223> OTHER INFORMATION: Synthetic peptide

<400> SEQUENCE: 136

Leu Tyr Ala Val Ala Thr Thr Ile Ile
1 5

<210> SEQ ID NO 137
<211> LENGTH: 9
<212> TYPE: PRT
<213> ORGANISM: Artificial Sequence
<220> FEATURE:
<223> OTHER INFORMATION: Synthetic peptide

<400> SEQUENCE: 137

Thr Ala Ile Ala Asn Gln Ala Ala Ile
1 5

<210> SEQ ID NO 138
<211> LENGTH: 10
<212> TYPE: PRT
<213> ORGANISM: Artificial Sequence
<220> FEATURE:
<223> OTHER INFORMATION: Synthetic peptide

<400> SEQUENCE: 138

Ser Ser Met Val Asn Gly Val Val Lys Leu
1 5 10

<210> SEQ ID NO 139
<211> LENGTH: 22363
<212> TYPE: DNA
<213> ORGANISM: Artificial Sequence
<220> FEATURE:
<223> OTHER INFORMATION: Complete optimised nucleotide sequence of the polynucleotide encoding pTM-MVDVax6
<220> FEATURE:
<221> NAME/KEY: misc_feature
<222> LOCATION: (1)..(8)
<223> OTHER INFORMATION: NotI
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammerhead ribozyme
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1768)..(1888)
<223> OTHER INFORMATION: MV N-P intergenic
<220> FEATURE:
<221> NAME/KEY: misc_feature
<222> LOCATION: (1889)..(3412)
<223> OTHER INFORMATION: MV P ORF
<220> FEATURE:
<221> NAME/KEY: misc_feature
<222> LOCATION: (3413)..(3531)
<223> OTHER INFORMATION: MV ATU2
<220> FEATURE:
<221> NAME/KEY: misc_feature
<222> LOCATION: (3532)..(5085)
<223> OTHER INFORMATION: DENV tetra EDIII + ectoM
<220> FEATURE:
<221> NAME/KEY: misc_feature
<222> LOCATION: (5086)..(5181)
<223> OTHER INFORMATION: MV P-M intergenic
<220> FEATURE:
<221> NAME/KEY: misc_feature
<222> LOCATION: (5182)..(6189)
<223> OTHER INFORMATION: MV M ORF
<220> FEATURE:
<221> NAME/KEY: misc_feature
<222> LOCATION: (6190)..(7192)
<223> OTHER INFORMATION: MV M-F intergenic
<220> FEATURE:
<221> NAME/KEY: misc_feature
<222> LOCATION: (7193)..(8854)
<223> OTHER INFORMATION: MV F ORF
<220> FEATURE:
<221> NAME/KEY: misc_feature
<222> LOCATION: (8855)..(9014)
<223> OTHER INFORMATION: MV-F-H intergenic
<220> FEATURE:
<221> NAME/KEY: misc_feature
<222> LOCATION: (9015)..(10868)
<223> OTHER INFORMATION: MV H ORF
<220> FEATURE:
<221> NAME/KEY: misc_feature
<222> LOCATION: (10869)..(10995)
<223> OTHER INFORMATION: MV ATU3
<220> FEATURE:
<221> NAME/KEY: misc_feature
<222> LOCATION: (10996)..(12618)
<223> OTHER INFORMATION: DENV1 NS polyepitope
<220> FEATURE:
<221> NAME/KEY: misc_feature
<222> LOCATION: (12619)..(12712)
<223> OTHER INFORMATION: MV H-L intergenic
<220> FEATURE:
<221> NAME/KEY: misc_feature
<222> LOCATION: (12713)..(19263)
<223> OTHER INFORMATION: MV L ORF
<220> FEATURE:
<221> NAME/KEY: misc_feature
<222> LOCATION: (19264)..(19372)
<223> OTHER INFORMATION: MV Trailer
<220> FEATURE:
<221> NAME/KEY: misc_feature
<222> LOCATION: (19373)..(19456)
<223> OTHER INFORMATION: HDV ribozyme
<220> FEATURE:
<221> NAME/KEY: misc_feature
<222> LOCATION: (19457)..(19598)
<223> OTHER INFORMATION: T7 terminator
<220> FEATURE:
<221> NAME/KEY: misc_feature
<222> LOCATION: (19599)..(19606)
<223> OTHER INFORMATION: Not I
<220> FEATURE:
<221> NAME/KEY: misc_feature
<222> LOCATION: (19607)..(22363)
<223> OTHER INFORMATION: pTM plasmid

<400> SEQUENCE: 139
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420
tccttatttg tggagtctcc aggtcaattg attcagagga tcaccgatga ccctgacgtt 480

```
agcataaggc tgttagaggt tgtccagagt gaccagtcac aatctggcct taccttcgca    540
tcaagaggta ccaacatgga ggatgaggcg gaccaatact tttcacatga tgatccaatt    600
agtagtgatc aatccaggtt cggatggttc gggaacaagg aaatctcaga tattgaagtg    660
caagaccctg agggattcaa catgattctg ggtaccatcc tagcccaaat ttgggtcttg    720
ctcgcaaagg cggttacggc cccagacacg gcagctgatt cggagctaag aaggtggata    780
aagtacaccc aacaaagaag ggtagttggt gaatttagat tggagagaaa atggttggat    840
gtggtgagga acaggattgc cgaggacctc tccttacgcc gattcatggt cgctctaatc    900
ctggatatca agagaacacc cggaaacaaa cccaggattg ctgaaatgat atgtgacatt    960
gatacatata tcgtagaggc aggattagcc agttttatcc tgactattaa gtttgggata   1020
gaaactatgt atcctgctct tggactgcat gaatttgctg gtgagttatc cacacttgag   1080
tccttgatga acctttacca gcaaatgggg gaaactgcac cctacatggt aatcctggag   1140
aactcaattc agaacaagtt cagtgcagga tcatacccte tgctctggag ctatgccatg   1200
ggagtaggag tggaacttga aaactccatg ggaggtttga ctttggccg atcttacttt   1260 gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg acccagaca agcccaagta   1440 tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccctaga cattgacact   1620 gcaacggagt ccagccaaga tccgcaggac agtcgaaggt cagctgacgc cctgcttagg   1680
ctgcaagcca tggcaggaat ctcggaagaa caaggctcag acacgacac ccctatagtg   1740 tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat tggagccaat ggcagaagag caggcacgcc atgtcaaaaa   1920
cggactggaa tgcatcccgg gctctcaaggc cgagcccatc ggctcactgg ccatcgagga   1980
agctatggca gcatggtcag aaatatcaga caacccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atcccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
```

```
gataatctcc aagctagaat cactgctgtt attgaaggga gaagttgagt caattaagaa    2940
gcagatcaac aggcaaaata tcagcatatc caccctggaa ggacacctct caagcatcat    3000
gatcgccatt cctggacttg gaaggatcc caacgacccc actgcagatg tcgaaatcaa     3060
tcccgacttg aaaccatca taggcagaga ttcaggccga gcactggccg aagttctcaa     3120
gaaacccgtt gccagccgac aactccaagg aatgacaaat ggacggacca gttccagagg    3180
acagctgctg aaggaatttc agctaaagcc gatcgggaaa aagatgagct cagccgtcgg    3240
gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata ataatgaagt agctacagct    3420
caacttacct gccaaccca tgccagtcga cccaactagc ctaccctcca tcattgttat     3480
aaaaaactta ggaaccaggt ccacacagcc gccagcccat caacgcgtac gatgggcatc    3540
atattcattc ttcttatgct ggttacaccg tctatggcgg agaaacttcg aatcaaaggt    3600
atgagctata cgatgtgcag cggcaagttc aagatcgaga aggaaatggc tgaaacccag    3660
cacggtacaa ctgtggtcaa agtcaaatat gaggggctg cgctccctg taaagtaccc      3720
attgagatta gggacgtcaa taagagaag gtggtaggtc gcatcatctc cagtacacct     3780
ttggccgaga acacgaactc cgtcacaaac atagagttgg aacccccgtt cggagactca    3840
tacattgtga tcggggtggg caactctgca ctcacactgc attggttcaa gaagggaagc    3900
agtatcggcc gcaggataa gagagacaaa ctgaaattga aggtatgtc ctatgccatg      3960
tgcacgaata ctttcgttct caagaaagaa gtatctgaga ctcagcacgg aaccatcctg    4020
atcaaagtcg agtacaaagg agaagacgtg ccctgtaaga tcccattcag taccgaggat    4080
ggacagggca aggcccataa cggcaggctg ataaccgcca accctgtggt tacaaagaag    4140
gaagagccag tcaatatcga agctgagcca ccgttcgggg agagcaacat agtaattggc    4200
ataggggata atgcttttgaa gatcaactgg tacaagaaag gaagctccat tggccgaaga   4260
gataagcgcg acaaactcca gctgaaagga atgagctact ccatgtgtac tgggaagttc    4320
aagattgtca aggaaatcgc cgaaactcag catggcacta ttgtgatccg cgtgcagtat    4380
gaaggcgatg gtagcccctg caagatacca tttgaaaatca ccgatttgga gaaacggcac   4440
gtcctgggtc ggctcattac cgtgaaccca atcgtgaccg agaaggacag tccagttaat    4500
atcgaggccg agcctccttt cggcgacagt tacatcattg tagggtgga ccagggcaa     4560
ctgaagctga actggttcaa gaaaggcagc agtataggac ggcgggataa acgggacaaa    4620
ctcacactga aaggcatgtc atacgttatg tgcaccggct cattcaaact ggagaaggaa    4680
gttgcagaga cacagcatgg gaccgtgctc gtgcaggtca aatacgaggg caccgacgct    4740
ccttgcaaga ttccgttcag tacacaggac gagaaaggcg tgactcagaa cggcagattg    4800
attacagcga accctatcgt gactgacaag gagaagccag ttaacatcga gactgagccg    4860
cctttcggag aatcatacat tatcgtggga gccggcgaga aggcactgaa actcagctgg    4920
ttcaagaagg gcagctcaat cggtcggaga gacaagcggt ctgtcgccct cgcaccgcac    4980
gtgggcctgg gtctggaaac gaggaccgag acgtggatga gttccgaagg cgcatggaag    5040
caaatccaga aagtggagac gtgggccctc aggcatccgt aatgagcgcg cagcgcttag    5100
acgtctcgcg atcgatacta gtacaaccta aatccattat aaaaaactta ggagcaaagt    5160
gattgcctcc caaggtccac aatgacagag acctacgact tcgacaagtc ggcatgggac    5220
```

```
atcaaagggt cgatcgctcc gatacaaccc accacctaca gtgatggcag gctggtgccc    5280
caggtcagag tcatagatcc tggtctaggc gacaggaagg atgaatgctt tatgtacatg    5340
tttctgctgg gggttgttga ggacagcgat tccctagggc ctccaatcgg gcgagcattt    5400
gggttcctgc ccttaggtgt tggcagatcc acagcaaagc ccgaaaaact cctcaaagag    5460
gccactgagc ttgacatagt tgttagacgt acagcagggc tcaatgaaaa actggtgttc    5520
tacaacaaca ccccactaac tctcctcaca ccttggagaa aggtcctaac aacagggagt    5580
gtcttcaacg caaaccaagt gtgcaatgcg gttaatctga taccgctcga taccccgcag    5640
aggttccgtg ttgtttatat gagcatcacc cgtctttcgg ataacgggta ttacaccgtt    5700
cctagaagaa tgctggaatt cagatcggtc aatgcagtgg ccttcaacct gctggtgacc    5760
cttaggattg acaaggcgat aggccctggg aagatcatcg acaatacaga gcaacttcct    5820
gaggcaacat ttatggtcca catcgggaac ttcaggagaa agaagagtga agtctactct    5880
gccgattatt gcaaaatgaa aatcgaaaag atgggcctgg tttttgcact tggtgggata    5940
gggggcacca gtcttcacat tagaagcaca ggcaaaatga gcaagactct ccatgcacaa    6000
ctcgggttca agaagacctt atgttacccg ctgatggata tcaatgaaga ccttaatcga    6060
ttactctgga ggagcagatg caagatagta agaatccagg cagttttgca gccatcagtt    6120
cctcaagaat tccgcatttta cgacgacgtg atcataaatg atgaccaagg actattcaaa    6180
gttctgtaga ccgtagtgcc cagcaatgcc cgaaaacgac ccccctcaca atgcagccca    6240
gaaggcccgg acaaaaaagc cccctccgaa agactccacg gaccaagcga gaggccagcc    6300
agcagccgac ggcaagcgcg aacaccaggc ggccccagca cagaacagcc ctgacacaag    6360
gccaccacca gccaccccaa tctgcatcct cctcgtggga ccccgagga ccaacccca    6420 aggctgcccc cgatccaaac caccaaccgc atccccacca ccccgggaa agaaacccc    6480 agcaattgga aggcccctcc ccctcttcct caacacaaga actccacaac cgaaccgcac    6540
aagcgaccga ggtgacccaa ccgcaggcat ccgactccct agacagatcc tctctccccg    6600
gcaaactaaa caaaacttag ggccaaggaa catacacacc caacagaacc cagaccccgg    6660
cccacggcgc cgcgccccca accccgaca accagaggga gccccaacc aatcccgccg    6720 gctccccgg tgcccacagg cagggacacc aaccccgaa cagacccagc acccaaccat    6780
cgacaatcca agacggggg gcccccccaa aaaaggccc ccaggggccg acagccagca    6840
ccgcgaggaa gccccaccac cccacacacg accacggcaa ccaaaccaga acccagacca    6900 cccctggggcca ccagctccca gactcggcca tcacccccgca gaaaggaaag gccacaaccc    6960
gcgcacccca gccccgatcc ggcggggagc cacccaaccc gaaccagcac ccaagagcga    7020
tccccgaagg acccccgaac cgcaaaggac atcagtatcc cacagcctct ccaagtcccc    7080
cggtctcctc ctcttctcga agggaccaaa agatcaatcc accacaccg acgacactca    7140 actccccacc cctaaaggag acaccggaa tcccagaatc aagactcatc caatgtccat    7200
catgggtctc aaggtgaacg tctctgccat attcatggca gtactgttaa ctctccaaac    7260
acccaccggt caaatccatt ggggcaatct ctctaagata ggggtggtag aataggaag    7320 tgcaagctac aaagttatga ctcgttccag ccatcaatca ttagtcataa aattaatgcc    7380
caatataact ctcctcaata actgcacgag ggtagagatt gcagaataca ggagactact    7440
gagaacagtt ttggaaccaa ttagagatgc acttaatgca atgacccaga atataagacc    7500
ggttcagagt gtagcttcaa gtaggagaca caagagattt gcgggagtag tcctggcagg    7560
tgcggcccta ggcgttgcca cagctgctca gataacagcc ggcattgcac ttcaccagtc    7620
```

```
catgctgaac tctcaagcca tcgacaatct gagagcgagc ctggaaacta ctaatcaggc    7680
aattgagaca atcagacaag cagggcagga gatgatattg gctgttcagg gtgtccaaga    7740
ctacatcaat aatgagctga taccgtctat gaaccaacta tcttgtgatt taatcggcca    7800
gaagctcggg ctcaaattgc tcagatacta tacagaaatc ctgtcattat ttggccccag    7860
tttacgggac cccatatctg cggagatatc tatccaggct ttgagctatg cgcttggagg    7920
agacatcaat aaggtgttag aaaagctcgg atacagtgga ggtgatttac tgggcatctt    7980
agagagcgga ggaataaagg cccggataac tcacgtcgac acagagtcct acttcattgt    8040
cctcagtata gcctatccga cgctgtccga gattaagggg gtgattgtcc accggctaga    8100
gggggtctcg tacaacatag gctctcaaga gtggtatacc actgtgccca gtatgttgc     8160 aacccaaggg taccttatct cgaattttga tgagtcatcg tgtactttca tgccagaggg    8220
gactgtgtgc agccaaaatg ccttgtaccc gatgagtcct ctgctccaag aatgcctccg    8280
ggggtacacc aagtcctgtg ctcgtacact cgtatccggg tcttttggga accggttcat    8340
tttatcacaa gggaacctaa tagccaattg tgcatcaatc ctttgcaagt gttacacaac    8400
aggaacgatc attaatcaag accctgacaa gatcctaaca tacattgctg ccgatcactg    8460
cccggtagtc gaggtgaacg gcgtgaccat ccaagtcggg agcaggaggt atccagacgc    8520
tgtgtacttg cacagaattg acctcggtcc tcccatatca ttggagaggt tggacgtagg    8580
gacaaatctg gggaatgcaa ttgctaagtt ggaggatgcc aaggaattgt tggagtcatc    8640
ggaccagata ttgaggagta tgaaaggttt atcgagcact agcatagtct acatcctgat    8700
tgcagtgtgt cttggagggt tgatagggat ccccgcttta atatgttgct gcaggggggcg   8760 ttgtaacaaa aagggagaac aagttggtat gtcaagacca ggcctaaagc ctgatcttac    8820
gggaacatca aaatcctatg taaggtcgct ctgatcctct acaactcttg aaacacaaat    8880
gtcccacaag tctcctcttc gtcatcaagc aaccaccgca cccagcatca agcccacctg    8940
aaattatctc cggcttccct ctggccgaac aatatcggta gttaatcaaa acttagggtg    9000
caagatcatc cacaatgtca ccacaacgag accggataaa tgccttctac aaagataacc    9060
cccatcccaa gggaagtagg atagtcatta acagagaaca tcttatgatt gatagaccctt   9120 atgttttgct ggctgttctg tttgtcatgt ttctgagctt gatcggggttg ctagccattg    9180 caggcattag acttcatcgg gcagccatct acaccgcaga gatccataaa agcctcagca    9240
ccaatctaga tgtaactaac tcaatcgagc atcaggtcaa ggacgtgctg acaccactct    9300
tcaaaatcat cggtgatgaa gtgggcctga ggacacctca gagattcact gacctagtga    9360
aattaatctc tgacaagatt aaattcctta tccggatag ggagtacgac ttcagagatc     9420
tcacttggtg tatcaacccg ccagagagaa tcaaattgga ttatgatcaa tactgtgcag    9480
atgtggctgc tgaagagctc atgaatgcat ggtgaactc aactctactg gagaccagaa     9540
caaccaatca gttcctagct gtctcaaagg gaaactgctc agggcccact acaatcagag    9600
gtcaattctc aaacatgtcg ctgtccctgt tagacttgta tttaggtcga ggttacaatg    9660
tgtcatctat agtcactatg acatcccagg gaatgtatgg gggaacttac ctagtggaaa    9720
agcctaatct gagcagcaaa aggtcagagt tgtcacaact gagcatgtac cgagtgtttg    9780
aagtaggtgt tatcagaaat ccgggtttgg gggctccggt gttccatatg acaaactatc    9840
ttgagcaacc agtcagtaat gatctcagca actgtatggt ggctttgggg gagctcaaac    9900
tcgcagccct ttgtcacggg gaagattcta tcacaattcc ctatcaggga tcagggaaag    9960
```

```
gtgtcagctt ccagctcgtc aagctaggtg tctggaaatc cccaaccgac atgcaatcct    10020
gggtcccctt atcaacggat gatccagtga tagacaggct ttacctctca tctcacagag    10080
gtgttatcgc tgacaatcaa gcaaaatggg ctgtcccgac aacacgaaca gatgacaagt    10140
tgcgaatgga gacatgcttc caacaggcgt gtaagggtaa aatccaagca ctctgcgaga    10200
atcccgagtg ggcaccattg aaggataaca ggattccttc atacggggtc ttgtctgttg    10260
atctgagtct gacagttgag cttaaaatca aaattgcttc gggattcggg ccattgatca    10320
cacacggttc agggatggac ctatacaaat ccaaccacaa caatgtgtat tggctgacta    10380
tcccgccaat gaagaaccta gccttaggtg taatcaacac attggagtgg ataccgagat    10440
tcaaggttag tccctacctc ttcactgtcc caattaagga agcaggcgaa gactgccatg    10500
ccccaacata cctacctgcg gaggtggatg gtgatgtcaa actcagttcc aatctggtga    10560
ttctacctgg tcaagatctc caatatgttt tggcaaccta cgatacttcc agggttgaac    10620
atgctgtggt ttattacgtt tacagcccaa gccgctcatt ttcttacttt tatccttttta   10680 ggttgcctat aaagggggtc cccatcgaat tacaagtgga atgcttcaca tgggaccaaa    10740
aactctggtg ccgtcacttc tgtgtgcttg cggactcaga atctggtgga catatcactc    10800
actctgggat ggtgggcatg ggagtcagct gcacagtcac ccgggaagat ggaaccaatc    10860 gcagatagggg ctgctagtga accaatcaca tgatgtcacc cagacatcag gcatacccac    10920
tagtctaccc tccatcattg ttataaaaaa cttaggaacc aggtccacac agccgccagc    10980
ccatcaacgc gtacgatggc atcacaggag ggaccactgc ccgaaattga ggacgaagtg    11040
tttagaaagc gaaatctgac tattatggac ctgcaccccg gatctggcaa gacccggaga    11100
tacctgccag ccatcgtgag ggaggctatt aagcggaaac tgagaacact gatcctggcc    11160
ccaactcgcg tggtcgcttc cgaaatggct gaggccctga aaggcatgcc catccggtat    11220
cagaccacag cagtgaagtc tgaacatacc ggcaaggaga ttgtggacct gatgtgccac    11280
gccactttca ccatgcgact gctgagccca gtgcgggtcc ccaactacaa tatgatcatt    11340
atggacgagg cccactttac tgatcccagc tccatcgccg ctagaggata tatttccacc    11400
agggtgggaa tgggcgaggc agcagctatc ttcatgacag caactccccc tggcagcgtg    11460
gaggcatttc ctcagtccaa cgccgtcatc caggacgagg agcgggacat tcctgagcgg    11520
agctggaatt ctgggtacga atggatcaca gacgaggatc atgcacactg gactgaagcc    11580
aagatgctgc tggacaacat taatactcct gagggaatca ttccagctct gttcgagccc    11640
gaaagagaga gtctgcagc catcgacggc gagtatagac tgaggggaga ggcccggaag    11700
accttcgtgg aactgatgag gcgcggcgat ctgcccgtgt ggctgagtta caaggtcgct    11760
tcagagggat tccagtatag tgaccgacgg tggtgctttg atggcgaacg caacaatcag    11820
gtgctggagg agaacatgga tgtcgagatt tggacaaagg aaggcgagcg gaagaaactg    11880
cgcccacgat ggctggacgc tcggacttac agcgatcccc tggcactgag agaattcaaa    11940
gagtttgctg caggggtggc cgtcgagaat caccatcacg ccgctatgct ggacgtggat    12000
ctgcatcctg ccagtgcttg gacccctgta tgcagtggcca ctaccatcat taccccaatg    12060
atgcgccaca caatcgagaa cacaactgcc aatatctcac tgcagctat tgcaaaccag    12120 gcagccattc tgatgggact ggacaaaggc tggcccatca gcaagatgga tattggcgtg    12180
cctctgctgg ccctggggtg ttacagtcag gtgctggaca tcattggcca gaggatcgag    12240
aacattaagc atgagcacaa atcaacctgg cattacgacg aagataatcc ctataagaca    12300
tgggcctacc acggaagcta tgaggtgaaa ccttcaggca gcgccagcag catggtcaac    12360
```

```
ggggtggtca agctgctgac caaaccttgg gacgtgatcc caatggtcac tcagattgcc   12420
atgaccgata ccaccccatt cggccagcag cgggtgttca aggagaaggt ggacacccgc   12480
acacctaagg ctaaacgagg gactgcacag atcatggagg tgaccgccaa gtggctgtgg   12540
ggattcctgt ccaggaacaa gaagccaaga atctgtacca gggaagagtt cacaagaaag   12600
gtccggtcaa acgcctaatg agcgcgcagc gcttagacgt ctcgcgatcg atgctagtgt   12660
gaaatagaca tcagaattaa gaaaaacgta gggtccaagt ggttccccgt tatggactcg   12720
ctatctgtca accagatctt ataccctgaa gttcacctag atagcccgat agttaccaat   12780
aagatagtag ccatcctgga gtatgctcga gtccctcacg cttacagcct ggaggaccct   12840
acactgtgtc agaacatcaa gcaccgccta aaaaacggat tttccaacca atgattata    12900 aacaatgtgg aagttgggaa tgtcatcaag tccaagctta ggagttatcc ggcccactct   12960
catattccat atccaaattg taatcaggat ttatttaaca tagaagacaa agagtcaacg   13020
aggaagatcc gtgaactcct caaaaagggg aattcgctgt actccaaagt cagtgataag   13080
gttttccaat gcttaaggga cactaactca cggcttggcc taggctccga attgagggag   13140
gacatcaagg agaaagttat taacttggga gtttacatgc acagctccca gtggtttgag   13200 cccttttctgt tttggtttac agtcaagact gagatgaggt cagtgattaa atcacaaacc   13260
catacttgcc ataggaggag acacacacct gtattcttca ctggtagttc agttgagttg   13320
ctaatctctc gtgaccttgt tgctataatc agtaaagagt ctcaacatgt atattacctg   13380
acatttgaac tggttttgat gtattgtgat gtcatagagg ggaggttaat gacagagacc   13440
gctatgacta ttgatgctag gtatacagag cttctaggaa gagtcagata catgtggaaa   13500
ctgatagatg gtttcttccc tgcactcggg aatccaactt atcaaattgt agccatgctg   13560
gagcctcttt cacttgctta cctgcagctg agggatataa cagtagaact cagaggtgct   13620
ttccttaacc actgctttac tgaaatacat gatgttcttg accaaaacgg gtttctgat   13680 gaaggtactt atcatgagtt aactgaagct ctagattaca ttttcataac tgatgacata   13740
catctgacag gggagatttt ctcattttc agaagtttcg gccacccag acttgaagca    13800 gtaacggctg ctgaaaatgt taggaaatac atgaatcagc ctaaagtcat tgtgtatgag   13860
actctgatga aggtcatgc catattttgt ggaatcataa tcaacggcta tcgtgacagg   13920
cacggaggca gttggccacc gctgaccctc cccctgcatg ctgcagacac aatccggaat   13980
gctcaagctt caggtgaagg gttaacacat gagcagtgcg ttgataactg gaaatctttt   14040
gctggagtga aatttggctg ctttatgcct cttagcctgg atagtgatct gacaatgtac   14100
ctaaaggaca aggcacttgc tgctctccaa agggaatggg attcagttta cccgaaagag   14160
ttcctgcgtt acgaccctcc caagggaacc gggtcacgga ggcttgtaga tgttttcctt   14220
aatgattcga gctttgaccc atatgatgtg ataatgtatg ttgtaagtgg agcttacctc   14280
catgaccctg agttcaacct gtcttacagc ctgaaagaaa aggagatcaa ggaaacaggt   14340 agacttttttg ctaaaatgac ttacaaaatg aaggcatgcc aagtgattgc tgaaaatcta   14400
atctcaaacg ggattggcaa atattttaag gacaatggga tggccaagga tgagcacgat   14460
ttgactaagg cactccacac tctagctgtc tcaggagtcc ccaaagatct caaagaaagt   14520 cacaggggg ggccagtctt aaaaacctac tcccgaagcc cagtccacac aagtaccagg   14580
aacgtgagag cagcaaaagg gtttataggg ttccctcaag taattcggca ggaccaagac   14640
actgatcatc cggagaatat ggaagcttac gagacagtca gtgcatttat cacgactgat   14700
```

```
ctcaagaagt actgccttaa ttggagatat gagaccatca gcttgtttgc acagaggcta    14760
aatgagattt acggattgcc ctcattttc cagtggctgc ataagaggct tgagacctct     14820
gtcctgtatg taagtgaccc tcattgcccc cccgaccttg acgcccatat cccgttatat    14880
aaagtcccca atgatcaaat cttcattaag tacccctatgg gaggtataga agggtattgt   14940
cagaagctgt ggaccatcag caccattccc tatctatacc tggctgctta tgagagcgga   15000
gtaaggattg cttcgttagt gcaaggggac aatcagacca tagccgtaac aaaaagggta   15060
cccagcacat ggccctacaa ccttaagaaa cgggaagctg ctagagtaac tagagattac   15120
tttgtaattc ttaggcaaag gctacatgat attggccatc acctcaaggc aaatgagaca   15180
attgtttcat cacattttt tgtctattca aaaggaatat attatgatgg gctacttgtg    15240
tcccaatcac tcaagagcat cgcaagatgt gtattctggt cagagactat agttgatgaa   15300
acaagggcag catgcagtaa tattgctaca acaatggcta aaagcatcga gagaggttat   15360
gaccgttacc ttgcatattc cctgaacgtc ctaaaagtga tacagcaaat tctgatctct   15420
cttggcttca caatcaattc aaccatgacc cgggatgtag tcatacccct cctcacaaac   15480
aacgacctct taataaggat ggcactgttg cccgctccta ttggggggat gaattatctg   15540
aatatgagca ggctgtttgt cagaaacatc ggtgatccag taacatcatc aattgctgat   15600
ctcaagagaa tgattctcgc ctcactaatg cctgaagaga ccctccatca agtaatgaca   15660
caacaaccgg gggactcttc attcctagac tgggctagcg acccttactc agcaaatctt   15720
gtatgtgtcc agagcatcac tagactcctc aagaacataa ctgcaaggtt tgtcctgatc   15780
catagtccaa acccaatgtt aaaaggatta ttccatgatg acagtaaaga agaggacgag   15840
ggactggcgg cattcctcat ggacaggcat attatagtac ctagggcagc tcatgaaatc   15900
ctggatcata gtgtcacagg ggcaagagag tctattgcag gcatgctgga taccacaaaa   15960
ggcttgattc gagccagcat gaggaagggg gggttaacct ctcgagtgat aaccagattg   16020
tccaattatg actatgaaca attcagagca gggatggtgc tattgacagg aagaaagaga   16080
aatgtcctca ttgacaaaga gtcatgttca gtgcagctgg cgagagctct aagaagccat   16140
atgtgggcga ggctagctcg aggacggcct atttacggcc ttgaggtccc tgatgtacta   16200
gaatctatgc gaggccacct tattcggcgt catgagacat gtgtcatctg cgagtgtgga   16260
tcagtcaact acgatggtt ttttgtcccc tcgggttgcc aactggatga tattgacaag    16320
gaaacatcat ccttgagagt cccatatatt ggttctacca ctgatgagag aacagacatg   16380
aagcttgcct tcgtaagagc cccaagtcga tccttgcgat ctgctgttag aatagcaaca   16440
gtgtactcat gggcttacgg tgatgatgat agctcttgga acgaagcctg gttgttggct   16500
aggcaaaggg ccaatgtgag cctggaggag ctaaggtgtaga tcactcccat ctcaacttcg  16560
actaatttag cgcataggtt gagggatcgt agcactcaag tgaaatactc aggtacatcc   16620
cttgtccgag tggcgaggta taccacaatc tccaacgaca atctctcatt tgtcatatca   16680
gataagaagg ttgatactaa ctttatatac caacaaggaa tgcttctagg gttgggtgtt   16740
ttagaaacat tgtttcgact cgagaaagat accggatcat ctaacacggt attacatctt   16800
cacgtcgaaa cagattgttg cgtgatcccg atgatagatc atcccaggat acccagctcc   16860
cgcaagctag agctgagggc agagctatgt accaacccat tgatatatga taatgcacct   16920
ttaattgaca gagatgcaac aaggctatac acccagagcc ataggaggca ccttgtggaa   16980
tttgttacat ggtccacacc ccaactatat cacattttag ctaagtccac agcactatct   17040
atgattgacc tggtaacaaa atttgagaag gaccatatga atgaaatttc agctctcata   17100
```

```
ggggatgacg atatcaatag tttcataact gagtttctgc tcatagagcc aagattattc   17160
actatctact tgggccagtg tgcggccatc aattgggcat ttgatgtaca ttatcataga   17220
ccatcaggga aatatcagat gggtgagctg ttgtcatcgt tcctttctag aatgagcaaa   17280
ggagtgttta aggtgcttgt caatgctcta agccacccaa agatctacaa gaaattctgg   17340
cattgtggta ttatagagcc tatccatggt ccttcacttg atgctcaaaa cttgcacaca   17400
actgtgtgca acatggttta cacatgctat atgacctacc tcgacctgtt gttgaatgaa   17460
gagttagaag agttcacatt tctcttgtgt gaaagcgacg aggatgtagt accggacaga   17520
ttcgacaaca tccaggcaaa acactatgt gttctggcag atttgtactg tcaaccaggg    17580
acctgcccac caattcgagg tctaagaccg gtagagaaat gtgcagttct aaccgaccat   17640
atcaaggcag aggctatgtt atctccagca ggatcttcgt ggaacataaa tccaattatt   17700
gtagaccatt actcatgctc tctgacttat ctccggcgag gatcgatcaa acagataaga   17760
ttgagagttg atccaggatt cattttcgac gccctcgctg aggtaaatgt cagtcagcca   17820
aagatcggca gcaacaacat ctcaaatatg agcatcaagg ctttcagacc cccacacgat   17880
gatgttgcaa aattgctcaa agatatcaac acaagcaagc acaatcttcc catttcaggg   17940
ggcaatctcg ccaattatga aatccatgct ttccgcagaa tcgggttgaa ctcatctgct   18000
tgctacaaag ctgttgagat atcaacatta attaggagat gccttgagcc aggggaggac   18060
ggcttgttct tgggtgaggg atcgggttct atgttgatca cttataaaga gatacttaaa   18120
ctaaacaagt gcttctataa tagtgggggtt tccgccaatt ctagatctgg tcaaagggaa   18180
ttagcaccct atccctccga agttggcctt gtcgaacaca gaatgggagt aggtaatatt   18240
gtcaaagtgc tctttaacgg gaggcccgaa gtcacgtggg taggcagtgt agattgcttc   18300
aatttcatag ttagtaatat ccctacctct agtgtggggt ttatccattc agatatagag   18360
accttgcctg acaaagatac tatagagaag ctagaggaat tggcagccat cttatcgatg   18420
gctctgctcc tgggcaaaat aggatcaata ctggtgatta agcttatgcc tttcagcggg   18480
gattttgttc agggatttat aagttatgta gggtctcatt atagagaagt gaaccttgta   18540
taccctagat acagcaactt catctctact gaatcttatt tggttatgac agatctcaag   18600
gctaaccggc taatgaatcc tgaaaagatt aagcagcaga taattgaatc atctgtgagg   18660
acttcacctg gacttatagg tcacatccta tccattaagc aactaagctg catacaagca   18720
attgtgggag acgcagttag tagaggtgat atcaatccta ctctgaaaaa acttacacct   18780
atagagcagg tgctgatcaa ttgcgggttg gcaattaacg gacctaagct gtgcaaagaa   18840
ttgatccacc atgatgttgc ctcagggcaa gatggattgc ttaattctat actcatcctc   18900
tacagggagt tggcaagatt caaagacaac caaagaagtc aacaagggat gttccacgct   18960
taccccgtat tggtaagtag caggcaacga gaacttatat ctaggatcac ccgcaaattc   19020
tgggggcaca ttcttcttta ctccgggaac aaaaagttga taaataagtt tatccagaat   19080
ctcaagtccg gctatctgat actagactta caccagaata tcttcgttaa gaatctatcc   19140
aagtcagaga aacagattat tatgacgggg ggtttgaaac gtgagtgggt ttttaaggta   19200
acagtcaagg agaccaaaga atggtataag ttagtcggat acagtgccct gattaaggac   19260
taattggttg aactccggaa ccctaatcct gccctaggtg gttaggcatt atttgcaata   19320
tattaaagaa aactttgaaa atacgaagtt tctattccca gctttgtctg gtggccggca   19380
tggtcccagc ctcctcgctg gcgccggctg ggcaacattc gagggaccc gtcccctcgg    19440
```

-continued

```
taatggcgaa tgggacgcgg ccgatccggc tgctaacaaa gcccgaaagg aagctgagtt    19500
ggctgctgcc accgctgagc aataactagc ataacccctt ggggcctcta acgggtctt     19560
gagggggtttt ttgctgaaag gaggaactat atccggatgc ggccgcgggc cctatggtac   19620
ccagcttttg ttcccttag tgagggttaa ttccgagctt ggcgtaatca tggtcatagc    19680
tgtttcctgt gtgaaattgt tatccgctca caattccaca acataggag gccggaagca    19740
taaagtgtaa agcctggggt gcctaatgag tgaggtaact cacattaatt gcgttgcgct   19800
cactgcccgc tttccagtcg ggaaacctgt cgtgccagct gcattaatga atcggccaac  19860
gcgcggggag aggcggtttg cgtattgggc gctcttccgc ttcctcgctc actgactcgc  19920
tgcgctcggt cgttcggctg cggcgagcgg tatcagctca ctcaaaggcg gtaatacggt  19980
tatccacaga atcaggggat aacgcaggaa agaacatgtg agcaaaaggc cagcaaaagg  20040
ccaggaaccg taaaaaggcc gcgttgctgg cgttttttcca taggctcggc cccctgacg  20100
agcatcacaa aaatcgacgc tcaagtcaga ggtggcgaaa cccgacagga ctataaagat  20160
accaggcgtt cccccctgga agctccctcg tgcgctctcc tgttccgacc ctgccgctta  20220
ccggatacct gtccgccttt ctcccttcgg gaagcgtggc gctttctcaa tgctcacgct  20280
gtaggtatct cagttcggtg taggtcgttc gctccaagct gggctgtgtg cacgaacccc  20340
ccgttcagcc cgaccgctgc gccttatccg gtaactatcg tcttgagtcc aacccggtaa  20400
gacacgactt atcgccactg gcagcagcca ctggtaacag gattagcaga gcgaggtatg  20460
taggcggtgc tacagagttc ttgaagtggt ggcctaacta cggctacact agaaggacag  20520
tatttggtat ctgcgctctg ctgaagccag ttaccttcgg aaaaagagtt ggtagctctt  20580
gatccggcaa acaaaccacc gctggtagcg gtggtttttt tgtttgcaag cagcagatta  20640
cgcgcagaaa aaaggatctc aagaagatc ctttgatctt ttctacgggg tctgacgctc  20700
agtggaacga aaactcacgt taagggattt tggtcatgag attatcaaaa aggatcttca  20760
cctagatcct tttaaattaa aaatgaagtt ttaaatcaat ctaaagtata tatgagtaaa  20820
cttggtctga cagttaccaa tgcttaatca gtgaggcacc tatctcagcg atctgtctat  20880
ttcgttcatc catagttgcc tgactgcccg tcgtgtagat aactacgata cgggagggct  20940
taccatctgg ccccagtgct gcaatgatac cgcgagaccc acgctcaccg gctccagatt  21000
tatcagcaat aaaccagcca gccggaaggg ccgagcgcag aagtggtcct gcaactttat  21060
ccgcctccat ccagtctatt aattgttgcc gggaagctag agtaagtagt tcgccagtta  21120
atagtttgcg caacgttgtt gccattgcta caggcatcgt ggtgtcacgc tcgtcgtttg  21180
gtatggcttc attcagctcc ggttcccaac gatcaaggcg agttacatga tcccccatgt  21240
tgtgaaaaaa agcggttagc tccttcggtc ctccgatcgt tgtcagaagt aagttggccg  21300
cagtgttatc actcatgctt atggcagcac tgcataattc tcttactgtc atgccatccg  21360
taagatgctt ttctgtgact ggtgagtact caaccaagtc attctgagaa tagtgtatgc  21420
ggcgaccgag ttgctcttgc ccggcgtcaa tacgggataa taccgcgcca catagcagaa  21480
ctttaaaagt gctcatcatt ggaaaacgtt cttcggggcg aaaactctca aggatcttac  21540
cgctgttgag atccagttcg atgtaaccca ctcgtgcacc caactgatct tcagcatctt  21600
ttactttcac cagcgtttct gggtgagcaa aaacaggaag gcaaaatgcc gcaaaaaagg  21660
gaataagggc gacacggaaa tgttgaatac tcatactctt ccttttttcaa tattattgaa  21720
gcatttatca gggttattgt ctcatgagcg gatacatatt tgaatgtatt tagaaaaata  21780
aacaaatagg ggttccgcgc acatttcccc gaaaagtgcc acctgaaatt gtaaacgtta  21840
```

```
atattttgtt aaaattcgcg ttaaatttt gttaaatcag ctcatttttt aaccaatagg    21900
ccgaaatcgg caaaatccct tataaatcaa aagaatagac cgagatagggg ttgagtgttg   21960 ttccagtttg gaacaagagt ccactattaa agaacgtgga ctccaacgtc aaagggcgaa    22020
aaaccgtcta tcagggcgat ggcccactac gtgaaccatc accctaatca agttttttgg   22080
ggtcgaggtg ccgtaaagca ctaaatcgga accctaaagg gagcccccga tttagagctt    22140
gacggggaaa gccggcgaac gtggcgagaa aggaagggaa gaaagcgaaa ggagcgggcg    22200
ctagggcgct ggcaagtgta gcggtcacgc tgcgcgtaac caccacaccc gccgcgctta    22260
atgcgccgct acagggcgcg tcccattcgc cattcaggct gcgcaactgt tgggaagggc   22320
gatcggtgcg ggcctcttcg ctattacgcc agccaccgcg gtg                      22363
```

<210> SEQ ID NO 140
<211> LENGTH: 20701
<212> TYPE: DNA
<213> ORGANISM: Artificial Sequence
<220> FEATURE:
<223> OTHER INFORMATION: Complete optimised nucleotide sequence of the polynucleotide encoding pTM-MVDVax7
<220> FEATURE:
<221> NAME/KEY: misc_feature
<222> LOCATION: (1)..(8)
<223> OTHER INFORMATION: NotI
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammerhead ribozyme
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1768)..(1888)
<223> OTHER INFORMATION: MV N-P intergenic
<220> FEATURE:
<221> NAME/KEY: misc_feature
<222> LOCATION: (1889)..(3412)
<223> OTHER INFORMATION: MV P ORF
<220> FEATURE:
<221> NAME/KEY: misc_feature
<222> LOCATION: (3413)..(3531)
<223> OTHER INFORMATION: MV ATU2
<220> FEATURE:
<221> NAME/KEY: misc_feature
<222> LOCATION: (3532)..(5154)
<223> OTHER INFORMATION: DENV1 NS polyepitope
<220> FEATURE:
<221> NAME/KEY: misc_feature
<222> LOCATION: (5155)..(5253)
<223> OTHER INFORMATION: MV P-M intergenic
<220> FEATURE:
<221> NAME/KEY: misc_feature
<222> LOCATION: (5254)..(6261)
<223> OTHER INFORMATION: MV M ORF
<220> FEATURE:
<221> NAME/KEY: misc_feature
<222> LOCATION: (6262)..(7264)
<223> OTHER INFORMATION: MV M-F intergenic
<220> FEATURE:
<221> NAME/KEY: misc_feature
<222> LOCATION: (7265)..(8926)
<223> OTHER INFORMATION: MV F ORF
<220> FEATURE:
<221> NAME/KEY: misc_feature
<222> LOCATION: (8927)..(9086)
<223> OTHER INFORMATION: MV-F-H intergenic
<220> FEATURE:
<221> NAME/KEY: misc_feature
<222> LOCATION: (9087)..(10940)
<223> OTHER INFORMATION: MV H ORF
<220> FEATURE:
<221> NAME/KEY: misc_feature
<222> LOCATION: (10941)..(11049)
<223> OTHER INFORMATION: MV H-L intergenic
<220> FEATURE:
<221> NAME/KEY: misc_feature
<222> LOCATION: (11050)..(17601)
<223> OTHER INFORMATION: MV L ORF
<220> FEATURE:
<221> NAME/KEY: misc_feature
<222> LOCATION: (17602)..(17710)
<223> OTHER INFORMATION: MV Trailer
<220> FEATURE:
<221> NAME/KEY: misc_feature
<222> LOCATION: (17711)..(17794)
<223> OTHER INFORMATION: HDV ribozyme
<220> FEATURE:
<221> NAME/KEY: misc_feature
<222> LOCATION: (17795)..(17936)
<223> OTHER INFORMATION: T7 terminator
<220> FEATURE:
<221> NAME/KEY: misc_feature
<222> LOCATION: (17937)..(17944)
<223> OTHER INFORMATION: Not I
<220> FEATURE:
<221> NAME/KEY: misc_feature
<222> LOCATION: (17945)..(20701)
<223> OTHER INFORMATION: pTM plasmid

<400> SEQUENCE: 140
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420
tccttatttg tggagtctcc aggtcaattg attcagagga tcaccgatga ccctgacgtt 480
agcataaggc tgttagaggt tgtccagagt gaccagtcac aatctggcct taccttcgca 540
tcaagaggta ccaacatgga ggatgaggcg gaccaatact tttcacatga tgatccaatt 600
agtagtgatc aatccaggtt cggatggttc gggaacaagg aaatctcaga tattgaagtg 660
caagaccctg agggattcaa catgattctg ggtaccatcc tagcccaaat ttgggtcttg 720
ctcgcaaagg cggttacggc cccagacacg gcagctgatt cggagctaag aaggtggata 780
aagtacaccc aacaaagaag ggtagttggt gaatttagat tggagagaaa atggttggat 840
gtggtgagga acaggattgc cgaggacctc tccttacgcc gattcatggt cgctctaatc 900
ctggatatca agagaacacc cggaaacaaa cccaggattg ctgaaatgat atgtgacatt 960
gatacatata tcgtagaggc aggattagcc agttttatcc tgactattaa gtttgggata 1020
gaaactatgt atcctgctct tggactgcat gaatttgctg gtgagttatc cacacttgag 1080
tccttgatga acctttacca gcaaatgggg gaaactgcac cctacatggt aatcctggag 1140
aactcaattc agaacaagtt cagtgcagga tcataccctc tgctctggag ctatgccatg 1200

```
ggagtaggag tggaacttga aaactccatg ggaggtttga actttggccg atcttacttt      1260
gatccagcat attttagatt agggcaagag atggtaagga ggtcagctgg aaaggtcagt      1320
tccacattgg catctgaact cggtatcact gccgaggatg caaggcttgt ttcagagatt      1380
gcaatgcata ctactgagga caagatcagt agagcggttg acccagaca agcccaagta       1440 tcatttctac acggtgatca aagtgagaat gagctaccga gattggggg caaggaagat       1500 aggagggtca aacagagtcg aggagaagcc agggagagct acagagaaac cgggcccagc      1560
agagcaagtg atgcgagagc tgcccatctt ccaaccggca caccctaga cattgacact       1620 gcaacggagt ccagccaaga tccgcaggac agtcgaaggt cagctgacgc cctgcttagg      1680
ctgcaagcca tggcaggaat ctcggaagaa caaggctcag acacggacac ccctatagtg      1740
tacaatgaca gaaatcttct agactaggtg cgagaggccg agggccagaa caacatccgc      1800
ctaccatcca tcattgttat aaaaaactta ggaaccaggt ccacacagcc gccagcccat      1860
caaccatcca ctcccacgat ggagccaat ggcagaagag caggcacgcc atgtcaaaaa       1920
cggactggaa tgcatccggg ctctcaaggc cgagcccatc ggctcactgg ccatcgagga      1980
agctatggca gcatggtcag aaatatcaga aacccagga caggagcgag ccacctgcag       2040
ggaagagaag gcaggcagtt cgggtctcag caaaccatgc ctctcagcaa ttggatcaac      2100
tgaaggcggt gcacctcgca tccgcggtca gggacctgga gagagcgatg acgacgctga     2160
aactttggga atcccccaa gaaatctcca ggcatcaagc actgggttac agtgttatta      2220
cgtttatgat cacagcggtg aagcggttaa gggaatccaa gatgctgact ctatcatggt      2280
tcaatcaggc cttgatggtg atagcaccct ctcaggagga caatgaat ctgaaaacag        2340 cgatgtggat attggcgaac ctgataccga gggatatgct atcactgacc ggggatctgc      2400
tcccatctct atggggttca gggcttctga tgttgaaact gcagaaggag gggagatcca     2460
cgagctcctg agactccaat ccagaggcaa caactttccg aagcttggga aaactctcaa     2520
tgttcctccg ccccccggacc ccggtagggc cagcacttcc gggacaccca ttaaaaaggg   2580
cacagacgcg agattagcct catttggaac ggagatcgcg tctttattga caggtggtgc     2640
aacccaatgt gctcgaaagt cacccctcgga accatcaggg ccaggtgcac ctgcggggaa   2700
tgtccccgag tgtgtgagca atgccgcact gatacaggag tggacacccg aatctggtac    2760
cacaatctcc ccgagatccc agaataatga agaaggggga gactattatg atgatgagct    2820
gttctctgat gtccaagata ttaaaacagc cttggccaaa atacacgagg ataatcagaa     2880
gataatctcc aagctagaat cactgctgtt attgaaggga gaagttgagt caattaagaa    2940
gcagatcaac aggcaaaata tcagcatatc cacccctggaa ggacacctct caagcatcat    3000
gatcgccatt cctggacttg gaaggatcc caacgacccc actgcagatg tcgaaatcaa      3060
tcccgacttg aaacccatca taggcagaga ttcaggccga gcactggccg aagttctcaa    3120
gaaacccgtt gccagccgac aactccaagg aatgacaaat ggacggacca gttccagagg    3180
acagctgctg aaggaatttc agctaaagcc gatcgggaaa agatgagct cagccgtcgg     3240 gtttgttcct gacaccggcc ctgcatcacg cagtgtaatc cgctccatta taaaatccag    3300
ccggctagag gaggatcgga agcgttacct gatgactctc cttgatgata tcaaaggagc    3360
caatgatctt gccaagttcc accagatgct gatgaagata ataatgaagt agctacagct    3420
caacttacct gccaaccca tgccagtcga cccaactagc ctacccctcca tcattgttat    3480 aaaaaactta ggaaccaggt ccacacagcc gccagcccat caacgcgtac gatggcatca    3540
caggagggac cactgcccga aattgaggac gaagtgttta gaaagcgaaa tctgactatt    3600
```

```
atggacctgc accccggatc tggcaagacc cggagatacc tgccagccat cgtgagggag    3660
gctattaagc ggaaactgag aacactgatc ctggccccaa ctcgcgtggt cgcttccgaa    3720
atggctgagg ccctgaaagg catgcccatc cggtatcaga ccacagcagt gaagtctgaa    3780
cataccggca aggagattgt ggacctgatg tgccacgcca ctttcaccat gcgactgctg    3840
agcccagtgc gggtccccaa ctacaatatg atcattatgg acgaggccca ctttactgat    3900
cccagctcca tcgccgctag aggatatatt tccaccaggg tgggaatggg cgaggcagca    3960
gctatcttca tgacagcaac tccccctggc agcgtggagg catttcctca gtccaacgcc    4020
gtcatccagg acgaggagcg ggacattcct gagcggagct ggaattctgg gtacgaatgg    4080
atcacagacg aggatcatgc acactggact gaagccaaga tgctgctgga acacattaat    4140
actcctgagg gaatcattcc agctctgttc gagcccgaaa gagagaagtc tgcagccatc    4200
gacggcgagt atagactgag gggagaggcc cggaagacct tcgtggaact gatgaggcgc    4260
ggcgatctgc ccgtgtggct gagttacaag gtcgcttcag agggattcca gtatagtgac    4320
cgacggtggt gctttgatgg cgaacgcaac aatcaggtgc tggaggagaa catggatgtc    4380
gagatttgga caaaggaagg cgagcggaag aaactgcgcc cacgatggct ggacgctcgg    4440
acttacagcg atccctggc actgagagaa ttcaaagagt ttgctgcagg ggtggccgtc    4500
gagaatcacc atcacgccgc tatgctggac gtggatctgc atcctgccag tgcttggacc    4560
ctgtatgcag tggccactac catcattacc ccaatgatgc gccacacaat cgagaacaca    4620
actgccaata tctcactgac agctattgca aaccaggcag ccattctgat gggactggac    4680
aaaggctggc ccatcagcaa gatggatatt ggcgtgcctc tgctggccct ggggtgttac    4740
agtcaggtgc tggacatcat tggccagagg atcgagaaca ttaagcatga gcacaaatca    4800
acctggcatt acgacgaaga taatccctat aagacatggg cctaccacgg aagctatgag    4860
gtgaaacctt caggcagcgc cagcagcatg gtcaacgggg tggtcaagct gctgaccaaa    4920
ccttgggacg tgatcccaat ggtcactcag attgccatga ccgataccac cccattcggc    4980
cagcagcggg tgttcaagga aaggtggac acccgcacac ctaaggctaa acgagggact    5040
gcacagatca tggaggtgac cgccaagtgg ctgtggggat tcctgtccag gaacaagaag    5100
ccaagaatct gtaccaggga agagttcaca agaaaggtcc ggtcaaacgc ctaatgagcg    5160
cgcagcgctt agacgtctcg cgatcgatac tagtacaacc taaatccatt ataaaaaact    5220
taggagcaaa gtgattgcct cccaaggtcc acaatgacag agacctacga cttcgacaag    5280
tcggcatggg acatcaaagg gtcgatcgct ccgatacaac ccaccaccta cagtgatggc    5340
aggctggtgc cccaggtcag agtcatagat cctggtctag cgacaggaa ggatgaatgc    5400 tttatgtaca tgtttctgct gggggttgtt gaggacagcg attccctagg gcctccaatc    5460
gggcgagcat ttgggttcct gcccttaggt gttggcagat ccacagcaaa gcccgaaaaa    5520
ctcctcaaag aggccactga gcttgacata gttgttagac gtacagcagg gctcaatgaa    5580
aaactggtgt tctacaacaa cacccccacta actctcctca caccttggag aaaggtccta    5640
acaacaggga gtgtcttcaa cgcaaaccaa gtgtgcaatg cggttaatct gataccgctc    5700
gataccccgc agaggttccg tgttgtttat atgagcatca ccgtctttc ggataacggg    5760 tattacaccg ttcctagaag aatgctggaa ttcagatcgg tcaatgcagt ggccttcaac    5820
ctgctggtga cccttaggat tgacaaggcg ataggccctg ggaagatcat cgacaataca    5880
gagcaacttc ctgaggcaac atttatggtc cacatcggga acttcaggag aaagaagagt    5940
```

```
gaagtctact ctgccgatta ttgcaaaatg aaaatcgaaa agatgggcct ggttttttgca    6000 cttggtggga taggggggcac cagtcttcac attagaagca caggcaaaat gagcaagact    6060
ctccatgcac aactcgggtt caagaagacc ttatgttacc cgctgatgga tatcaatgaa    6120
gaccttaatc gattactctg gaggagcaga tgcaagatag taagaatcca ggcagttttg    6180
cagccatcag ttcctcaaga attccgcatt tacgacgacg tgatcataaa tgatgaccaa    6240
ggactattca aagttctgta daccgtagtg cccagcaatg cccgaaaacg accccctca     6300 caatgacagc cagaaggccc ggacaaaaaa gcccctccg aaagactcca cggaccaagc     6360
gagaggccag ccagcagccg acggcaagcg cgaacaccag gcggcccag cacagaacag    6420 ccctgacaca aggccaccac cagccacccc aatctgcatc ctcctcgtgg acccccgag    6480 gaccaacccc caaggctgcc cccgatccaa accaccaacc gcatccccac caccccgg     6540 aaagaaaccc ccagcaattg aaggccccct cccctcttc ctcaacacaa gaactccaca    6600
accgaaccgc acaagcgacc gaggtgaccc aaccgcaggc atccgactcc ctagacagat    6660
cctctctccc cggcaaacta aacaaaactt agggccaagg aacatacaca cccaacagaa    6720
cccagacccc ggcccacggc gccgcgcccc caaccccga caaccagagg gagccccaa     6780 ccaatcccgc cggctccccc ggtgcccaca ggcagggaca ccaaccccg aacagaccca    6840 gcacccaacc atcgacaatc caagacgggg gggcccccc aaaaaaaggc cccaggggc     6900 cgacagccag caccgcgagg aagcccaccc accccacaca cgaccacggc aaccaaacca    6960
gaacccagac caccctgggc caccagctcc cagactcggc catcaccccg cagaaaggaa    7020
aggcacaaac ccgcgcaccc cagccccgat ccggcgggga gccacccaac ccgaaccagc    7080
acccaagagc gatccccgaa ggaccccga accgcaaagg acatcagtat cccacagcct    7140
ctccaagtcc cccggtctcc tcctcttctc gaagggacca aagatcaat ccaccacacc     7200 cgacgacact caactcccca ccctaaagg agacaccggg aatcccagaa tcaagactca    7260
tccaatgtcc atcatgggtc tcaaggtgaa cgtctctgcc atattcatgg cagtactgtt    7320
aactctccaa acacccaccg gtcaaatcca ttgggggcaat ctctctaaga tagggggtgg   7380
aggaatagga agtgcaagct acaaagttat gactcgttcc agccatcaat cattagtcat    7440
aaaattaatg cccaatataa ctctcctcaa taactgcacg agggtagaga ttgcagaata    7500
caggagacta ctgagaacag ttttggaacc aattagagat gcacttaatg caatgaccca    7560
gaatataaga ccggttcaga gtgtagcttc aagtaggaga cacaagagat ttgcgggagt    7620
agtcctggca ggtgcggccc taggcgttgc cacagctgct cagataacag ccggcattgc    7680
acttcaccag tccatgctga actctcaagc catcgacaat ctgagagcga gcctggaaac    7740
tactaatcag gcaattgaga caatcagaca agcagggcag gagatgatat tggctgttca    7800
gggtgtccaa gactacatca ataatgagct gataccgtct atgaaccaac tatcttgtga    7860
tttaatcggc cagaagctcg ggctcaaatt gctcagatac tatacagaaa tcctgtcatt    7920
atttggcccc agtttacggg accccatatc tgcggagata tctatccagg ctttgagcta    7980
tgcgcttgga ggagacatca ataaggtgtt agaaaagctc ggatacagtg gaggtgattt    8040
actgggcatc ttagagagcg gaggaataaa ggcccgata actcacgtcg acacagagtc    8100
ctacttcatt gtcctcagta tagcctatcc gacgctgtcc gagattaagg gggtgattgt    8160
ccaccggcta gaggggggtct cgtacaacat aggctctcaa gagtggtata ccactgtgcc    8220
caagtatgtt gcaaacccaag ggtaccttat ctcgaatttt gatgagtcat cgtgtacttt    8280
catgccagag gggactgtgt gcagccaaaa tgccttgtac ccgatgagtc ctctgctcca    8340
```

```
agaatgcctc cggggtaca ccaagtcctg tgctcgtaca ctcgtatccg ggtcttttgg   8400
gaaccggttc attttatcac aagggaacct aatagccaat tgtgcatcaa tcctttgcaa   8460
gtgttacaca acaggaacga tcattaatca agaccctgac aagatcctaa catacattgc   8520
tgccgatcac tgcccggtag tcgaggtgaa cggcgtgacc atccaagtcg ggagcaggag   8580
gtatccagac gctgtgtact tgcacagaat tgacctcggt cctcccatat cattggagag   8640
gttggacgta gggacaaatc tggggaatgc aattgctaag ttggaggatg ccaaggaatt   8700
gttggagtca tcggaccaga tattgaggag tatgaaaggt ttatcgagca ctagcatagt   8760
ctacatcctg attgcagtgt gtcttggagg gttgataggg atccccgctt taatatgttg   8820
ctgcaggggg cgttgtaaca aaagggaga acaagttggt atgtcaagac caggcctaaa   8880
gcctgatctt acgggaacat caaaatccta tgtaaggtcg ctctgatcct ctacaactct   8940
tgaaacacaa atgtcccaca agtctcctct tcgtcatcaa gcaaccaccg cacccagcat   9000
caagcccacc tgaaattatc tccggcttcc ctctggccga acaatatcgg tagttaatca   9060
aaacttaggg tgcaagatca tccacaatgt caccacaacg agaccggata aatgccttct   9120
acaaagataa ccccatccc aagggaagta ggatagtcat taacagagaa catcttatga   9180
ttgatagacc ttatgttttg ctggctgttc tgtttgtcat gtttctgagc ttgatcgggt   9240
tgctagccat tgcaggcatt agacttcatc gggcagccat ctacaccgca gagatccata   9300
aaagcctcag caccaatcta gatgtaacta actcaatcga gcatcaggtc aaggacgtgc   9360
tgacaccact cttcaaaatc atcggtgatg aagtgggcct gaggacacct cagagattca   9420
ctgacctagt gaaattaatc tctgacaaga ttaaattcct taatccggat agggagtacg   9480
acttcagaga tctcacttgg tgtatcaacc cgccagagag aatcaaattg gattatgatc   9540
aatactgtgc agatgtggct gctgaagagc tcatgaatgc attggtgaac tcaactctac   9600
tggagaccag aacaaccaat cagttcctag ctgtctcaaa gggaaactgc tcagggccca   9660
ctacaatcag aggtcaattc tcaaacatgt cgctgtccct gttagacttg tatttaggtc   9720
gaggttacaa tgtgtcatct atagtcacta tgacatccca gggaatgtat ggggaactt   9780 acctagtgga aaagcctaat ctgagcagca aaggtcaga gttgtcacaa ctgagcatgt   9840
accgagtgtt tgaagtaggt gttatcagaa atccgggttt gggggctccg gtgttccata   9900
tgacaaacta tcttgagcaa ccagtcagta atgatctcag caactgtatg gtggctttgg   9960
gggagctcaa actcgcagcc ctttgtcacg gggaagattc tatcacaatt ccctatcagg   10020
gatcagggaa aggtgtcagc ttccagctcg tcaagctagg tgtctggaaa tccccaaccg   10080
acatgcaatc ctgggtcccc ttatcaacgg atgatccagt gatagacagg ctttacctct   10140
catctcacag aggtgttatc gctgacaatc aagcaaaatg gctgtcccg acaacacgaa   10200 cagatgacaa gttgcgaatg gagacatgct tccaacaggc gtgtaagggt aaaatccaag   10260
cactctgcga gaatcccgag tgggcaccat tgaaggataa caggattcct tcatacgggg   10320
tcttgtctgt tgatctgagt ctgacagttg agcttaaaat caaaattgct tcgggattcg   10380
ggccattgat cacacacggt tcagggatgg acctatacaa atccaaccac aacaatgtgt   10440
attggctgac tatcccgcca atgaagaacc tagccttagg tgtaatcaac acattggagt   10500
ggataccgag attcaaggtt agtccctacc tcttcactgt cccaattaag gaagcaggcg   10560
aagactgcca tgccccaaca tacctacctg cggaggtgga tggtgatgtc aaactcagtt   10620
ccaatctggt gattctacct ggtcaagatc tccaatatgt tttggcaacc tacgatactt   10680
```

```
ccagggttga acatgctgtg gtttattacg tttacagccc aagccgctca ttttcttact   10740
tttatccttt taggttgcct ataaaggggg tccccatcga attacaagtg gaatgcttca   10800
catgggacca aaaactctgg tgccgtcact tctgtgtgct tgcggactca gaatctggtg   10860
gacatatcac tcactctggg atggtgggca tgggagtcag ctgcacagtc acccgggaag   10920
atggaaccaa tcgcagatag ggctgctagt gaaccaatca catgatgtca cccagacatc   10980
aggcataccc actagtgtga aatagacatc agaattaaga aaaacgtagg gtccaagtgg   11040
ttccccgtta tggactcgct atctgtcaac cagatcttat accctgaagt tcacctagat   11100
agcccgatag ttaccaataa gatagtagcc atcctggagt atgctcgagt ccctcacgct   11160
tacagcctgg aggaccctac actgtgtcag aacatcaagc accgcctaaa aaacggattt   11220
tccaaccaaa tgattataaa caatgtggaa gttgggaatg tcatcaagtc caagcttagg   11280
agttatccgg cccactctca tattccatat ccaaattgta atcaggattt atttaacata   11340
gaagacaaag agtcaacgag gaagatccgt gaactcctca aaaggggaa ttcgctgtac    11400
tccaaagtca gtgataaggt tttccaatgc ttaaggaca ctaactcacg gcttggccta    11460
ggctccgaat tgagggagga catcaaggag aaagttatta acttgggagt ttacatgcac   11520
agctcccagt ggtttgagcc cttctctgtt tggtttacag tcaagactga gatgaggtca   11580
gtgattaaat cacaaaccca tacttgccat aggaggagac acacacctgt attcttcact   11640
ggtagttcag ttgagttgct aatctctcgt gaccttgttg ctataatcag taaagagtct   11700
caacatgtat attacctgac atttgaactg gttttgatgt attgtgatgt catagagggg   11760
aggttaatga cagagaccgc tatgactatt gatgctaggt atacagagct tctaggaaga   11820
gtcagataca tgtggaaact gatagatggt ttcttccctg cactcgggaa tccaacttat   11880
caaattgtag cctgctgga gcctctttca cttgcttacc tgcagctgag ggatataaca    11940
gtagaactca gaggtgcttt ccttaaccac tgctttactg aaatacatga tgttcttgac   12000
caaaacgggt tttctgatga aggtactat catgagttaa ctgaagctct agattacatt    12060
ttcataactg atgacataca tctgacaggg gagattttct cattttttcag aagtttcggc   12120
cacccccagac ttgaagcagt aacgctgctg aaaatgtta ggaaatacat gaatcagcct    12180
aaagtcattg tgtatgagac tctgatgaaa ggtcatgcca tattttgtgg aatcataatc   12240
aacggctatc gtgacaggca cggaggcagt tggccaccgc tgaccctccc cctgcatgct   12300
gcagacacaa tccggaatgc tcaagcttca ggtgaagggt taacacatga gcagtgcgtt   12360
gataactgga atctttttgc tggagtgaaa tttggctgct ttatgcctct agcctggat    12420
agtgatctga caatgtacct aaaggacaag gcacttgctg ctctccaaag ggaatgggat   12480
tcagtttacc cgaaagagtt cctgcgttac gaccctccca agggaaccgg gtcacggagg   12540
cttgtagatg ttttccttaa tgattcgagc tttgacccat atgatgtgat aatgtatgtt   12600
gtaagtggag cttacctcca tgaccctgag ttcaacctgt cttacagcct gaaagaaaag   12660
gagatcaagg aaacaggtag acttttttgct aaaatgactt acaaaatgag gcatgccaa    12720
gtgattgctg aaaatctaat ctcaaacggg attggcaaat attttaagga caatgggatg   12780
gccaaggatg agcacgattt gactaaggca ctccacactc tagctgtctc aggagtcccc   12840
aaagatctca agaaagtca caggggggg ccagtcttaa aacctactc ccgaagccca      12900
gtccacacaa gtaccaggaa cgtgagagca gcaaagggt ttatagggtt ccctcaagta    12960
attcggcagg accaagacac tgatcatccg gagaatatgg aagcttacga gacagtcagt   13020
gcatttatca cgactgatct caagaagtac tgccttaatt ggagatatga gaccatcagc   13080
```

```
ttgtttgcac agaggctaaa tgagatttac ggattgccct cattttttcca gtggctgcat    13140 aagaggcttg agacctctgt cctgtatgta agtgaccctc attgccccccc cgaccttgac    13200 gcccatatcc cgttatataa agtccccaat gatcaaatct tcattaagta ccctatggga    13260
ggtatagaag ggtattgtca gaagctgtgg accatcagca ccattcccta tctatacctg    13320
gctgcttatg agagcggagt aaggattgct tcgttagtgc aaggggacaa tcagaccata    13380
gccgtaacaa aaagggtacc cagcacatgg ccctacaacc ttaagaaacg ggaagctgct    13440
agagtaacta gagattactt tgtaattctt aggcaaaggc tacatgatat tggccatcac    13500
ctcaaggcaa atgagacaat tgtttcatca catttttttg tctattcaaa aggaatatat    13560
tatgatgggc tacttgtgtc ccaatcactc aagagcatcg caagatgtgt attctggtca    13620
gagactatag ttgatgaaac aagggcagca tgcagtaata ttgctacaac aatggctaaa    13680
agcatcgaga gaggttatga ccgttacctt gcatattccc tgaacgtcct aaaagtgata    13740
cagcaaattc tgatctctct tggcttcaca atcaattcaa ccatgacccg ggatgtagtc    13800
atacccctcc tcacaaacaa cgacctctta ataaggatgg cactgttgcc cgctcctatt    13860 gggggggatga attatctgaa tatgagcagg ctgtttgtca gaaacatcgg tgatccagta    13920
acatcatcaa ttgctgatct caagagaatg attctcgcct cactaatgcc tgaagagacc    13980
ctccatcaag taatgacaca acaaccgggg gactcttcat tcctagactg gctagcgac    14040 ccttactcag caaatcttgt atgtgtccag agcatcacta gactcctcaa gaacataact    14100
gcaaggtttg tcctgatcca tagtccaaac ccaatgttaa aaggattatt ccatgatgac    14160
agtaaagaag aggacgaggg actggcggca ttcctcatgg acaggcatat tatagtacct    14220
agggcagctc atgaaatcct ggatcatagt gtcacagggg caagagagtc tattgcaggc    14280
atgctggata ccacaaaagg cttgattcga gccagcatga ggaaggggg gttaacctct    14340 cgagtgataa ccagattgtc caattatgac tatgaacaat tcagagcagg gatggtgcta    14400
ttgacaggaa gaaagagaaa tgtcctcatt gacaaagagt catgttcagt gcagctggcg    14460
agagctctaa gaagccatat gtgggcgagg ctagctcgag gacggcctat ttacggcctt    14520
gaggtccctg atgtactaga atctatgcga ggccaccttta tcggcgtca tgagacatgt    14580 gtcatctgcg agtgtggatc agtcaactac ggatggtttt tgtcccctc gggttgccaa    14640 ctggatgata ttgacaagga acatcatcc ttgagagtcc catatattgg ttctaccact    14700
gatgagagaa cagacatgaa gcttgccttc gtaagagccc caagtcgatc cttgcgatct    14760
gctgttagaa tagcaacagt gtactcatgg gcttacggtg atgatgatag ctcttggaac    14820
gaagcctggt tgttggctag gcaaaggggcc aatgtgagcc tggaggagct aagggtgatc    14880
actcccatct caacttcgac taatttagcg cataggttga gggatcgtag cactcaagtg    14940
aaatactcag gtacatccct tgtccgagtg gcgaggtata ccacaatctc caacgacaat    15000
ctctcatttg tcatatcaga taagaaggtt gatactaact ttatataccca acaaggaatg    15060 cttctagggt tgggtgtttt agaaacattg tttcgactcg agaaagatac cggatcatct    15120
aacacggtat tacatcttca cgtcgaaaca gattgttgcg tgatcccgat gatagatcat    15180
cccaggatac ccagctcccg caagctagag ctgggggcag agctatgtac caacccattg    15240
atatatgata atgcaccttt aattgacaga gatgcaacaa ggctatacac ccagagccat    15300
aggaggcacc ttgtggaatt tgttacatgg tccacacccc aactatatca cattttagct    15360
aagtccacag cactatctat gattgacctg gtaacaaaat ttgagaagga ccatatgaat    15420
```

```
gaaatttcag ctctcatagg ggatgacgat atcaatagtt tcataactga gtttctgctc   15480
atagagccaa gattattcac tatctacttg ggccagtgtg cggccatcaa ttgggcattt   15540
gatgtacatt atcatagacc atcagggaaa tatcagatgg gtgagctgtt gtcatcgttc   15600
ctttctagaa tgagcaaagg agtgtttaag gtgcttgtca atgctctaag ccacccaaag   15660
atctacaaga aattctggca ttgtggtatt atagagccta tccatggtcc ttcacttgat   15720
gctcaaaact tgcacacaac tgtgtgcaac atggtttaca catgctatat gacctacctc   15780
gacctgttgt tgaatgaaga gttagaagag ttcacatttc tcttgtgtga aagcgacgag   15840
gatgtagtac cggacagatt cgacaacatc caggcaaaac acttatgtgt tctggcagat   15900
ttgtactgtc aaccagggac ctgcccacca attcgaggtc taagaccggt agagaaatgt   15960
gcagttctaa ccgaccatat caaggcgagg gctatgttat ctccagcagg atcttcgtgg   16020
aacataaatc caattattgt agaccattac tcatgctctc tgacttatct ccggcgagga   16080
tcgatcaaac agataagatt gagagttgat ccaggattca ttttcgacgc cctcgctgag   16140
gtaaatgtca gtcagccaaa gatcggcagc aacaacatct caaatatgag catcaaggct   16200
ttcagacccc cacacgatga tgttgcaaaa ttgctcaaag atatcaacac aagcaagcac   16260
aatcttccca tttcaggggg caatctcgcc aattatgaaa tccatgcttt ccgcagaatc   16320
gggttgaact catctgcttg ctacaaagct gttgagatat caacattaat taggagatgc   16380
cttgagccag gggaggacgg cttgttcttg ggtgagggat cgggttctat gttgatcact   16440
tataaagaga tacttaaact aaacaagtgc ttctataata gtggggtttc cgccaattct   16500
agatctggtc aaagggaatt agcaccctat ccctccgaag ttggccttgt cgaacacaga   16560
atgggagtag gtaatattgt caaagtgctc tttaacggga ggcccgaagt cacgtgggta   16620
ggcagtgtag attgcttcaa tttcatagtt agtaatatcc ctacctctag tgtgggggttt   16680 atccattcag atatagagac cttgcctgac aaagatacta tagagaagct agaggaattg   16740
gcagccatct tatcgatggc tctgctcctg ggcaaaatag gatcaatact ggtgattaag   16800
cttatgcctt tcagcgggga ttttgttcag ggatttataa gttatgtagg gtctcattat   16860
agagaagtga accttgtata ccctagatac agcaacttca tctctactga atcttatttg   16920
gttatgacag atctcaaggc taaccggcta atgaatcctg aaaagattaa gcagcagata   16980
attgaatcat ctgtgaggac ttcacctgga cttataggtc acatcctatc cattaagcaa   17040
ctaagctgca tacaagcaat tgtgggagac gcagttagta gaggtgatat caatcctact   17100
ctgaaaaaac ttacacctat agagcaggtg ctgatcaatt gcgggttggc aattaacgga   17160
cctaagctgt gcaaagaatt gatccaccat gatgttgcct cagggcaaga tggattgctt   17220
aattctatac tcatcctcta cagggagttg caagattca aagacaacca agaagtcaa   17280 caagggatgt tccacgctta ccccgtattg gtaagtagca ggcaacgaga acttatatct   17340
aggatcaccc gcaaattctg ggggcacatt cttctttact ccgggaacaa aaagttgata   17400 aataagtttta tccagaatct caagtccggc tatctgatac tagacttaca ccagaatatc   17460
ttcgttaaga atctatccaa gtcagagaaa cagattatta tgacgggggg tttgaaacgt   17520
gagtgggttt ttaaggtaac agtcaaggag accaaagaat ggtataagtt agtcggatac   17580
agtgccctga ttaaggacta attggttgaa ctccggaacc ctaatcctgc cctaggtggt   17640
taggcattat ttgcaatata ttaaagaaaa ctttgaaaat acgaagtttc tattcccagc   17700
tttgtctggt ggccggcatg gtcccagcct cctcgctggc gccggctggg caacattccg   17760
aggggaccgt cccctcggta atggcgaatg ggacgcggcc gatccggctg ctaacaaagc   17820
```

```
ccgaaaggaa gctgagttgg ctgctgccac cgctgagcaa taactagcat aaccccttgg   17880
ggcctctaaa cgggtcttga gggttttttt gctgaaagga ggaactatat ccggatgcgg   17940
ccgcgggccc tatggtaccc agcttttgtt ccctttagtg agggttaatt ccgagcttgg   18000
cgtaatcatg gtcatagctg tttcctgtgt gaaattgtta ccgctcaca attccacaca    18060 acataggagc cggaagcata aagtgtaaag cctggggtgc ctaatgagtg aggtaactca   18120
cattaattgc gttgcgctca ctgcccgctt tccagtcggg aaacctgtcg tgccagctgc   18180
attaatgaat cggccaacgc gcggggagag gcggtttgcg tattgggcgc tcttccgctt   18240
cctcgctcac tgactcgctg cgctcggtcg ttcggctgcg gcgagcggta tcagctcact   18300
caaaggcggt aatacggtta tccacagaat caggggataa cgcaggaaag aacatgtgag   18360
caaaaggcca gcaaaaggcc aggaaccgta aaaaggccgc gttgctggcg ttttccata    18420 ggctcggccc ccctgacgag catcacaaaa atcgacgctc aagtcagagg tggcgaaacc   18480
cgacaggact ataaagatac caggcgttcc cccctggaag ctccctcgtg cgctctcctg   18540
ttccgaccct gccgcttacc ggatacctgt ccgcctttct cccttcggga agcgtggcgc   18600
tttctcaatg ctcacgctgt aggtatctca gttcggtgta ggtcgttcgc tccaagctgg   18660
gctgtgtgca cgaaccccc gttcagcccg accgctgcgc cttatccggt aactatcgtc   18720
ttgagtccaa cccggtaaga cacgacttat cgccactggc agcagccact ggtaacagga   18780
ttagcagagc gaggtatgta ggcggtgcta cagagttctt gaagtggtgg cctaactacg   18840
gctacactag aaggacagta tttggtatct gcgctctgct gaagccagtt accttcggaa   18900
aaagagttgg tagctcttga tccggcaaac aaaccaccgc tggtagcggt ggtttttttg   18960
tttgcaagca gcagattacg cgcagaaaaa aaggatctca agaagatcct ttgatctttt   19020
ctacggggtc tgacgctcag tggaacgaaa actcacgtta agggattttg gtcatgagat   19080
tatcaaaaag gatcttcacc tagatccttt taaattaaaa atgaagtttt aaatcaatct   19140
aaagtatata tgagtaaact tggtctgaca gttaccaatg cttaatcagt gaggcaccta   19200
tctcagcgat ctgtctattt cgttcatcca tagttgcctg actgcccgtc gtgtagataa   19260
ctacgatacg ggagggctta ccatctggcc ccagtgctgc aatgataccg cgagacccac   19320
gctcaccggc tccagattta tcagcaataa accagccagc cggaagggcc gagcgcagaa   19380
gtggtcctgc aactttatcc gcctccatcc agtctattaa ttgttgccgg gaagctagag   19440
taagtagttc gccagttaat agtttgcgca acgttgttgc cattgctaca ggcatcgtgg   19500
tgtcacgctc gtcgtttggt atggcttcat tcagctccgg ttcccaacga tcaaggcgag   19560
ttacatgatc ccccatgttg tgaaaaaaag cggttagctc cttcggtcct ccgatcgttg   19620
tcagaagtaa gttggccgca gtgttatcac tcatgcttat ggcagcactg cataattctc   19680
ttactgtcat gccatccgta agatgctttt ctgtgactgg tgagtactca accaagtcat   19740
tctgagaata gtgtatgcgg cgaccgagtt gctcttgccc ggcgtcaata cgggataata   19800
ccgcgccaca tagcagaact ttaaaagtgc tcatcattgg aaaacgttct cgggcgaa    19860 aactctcaag gatcttaccg ctgttgagat ccagttcgat gtaacccact cgtgcaccca   19920
actgatcttc agcatctttt actttcacca gcgtttctgg gtgagcaaaa acaggaaggc   19980
aaaatgccgc aaaaaaggga ataagggcga cacggaaatg ttgaatactc atactcttcc   20040
tttttcaata ttattgaagc atttatcagg gttattgtct catgagcgga tacatatttg   20100
aatgtattta gaaaaataaa caaatagggg ttccgcgcac atttccccga aaagtgccac   20160
```

```
ctgaaattgt aaacgttaat attttgttaa aattcgcgtt aaattttgt taaatcagct   20220 cattttttaa ccaataggcc gaaatcggca aatccctta taaatcaaaa gaatagaccg   20280
agatagggtt gagtgttgtt ccagtttgga acaagagtcc actattaaag aacgtggact   20340
ccaacgtcaa agggcgaaaa accgtctatc agggcgatgg cccactacgt gaaccatcac   20400
cctaatcaag ttttttgggg tcgaggtgcc gtaaagcact aaatcggaac cctaaaggga   20460 gccccccgatt tagagcttga cggggaaagc cggcgaacgt ggcgagaaag gaagggaaga   20520
aagcgaaagg agcgggcgct agggcgctgg caagtgtagc ggtcacgctg cgcgtaacca   20580
ccacacccgc cgcgcttaat gcgccgctac agggcgcgtc ccattcgcca ttcaggctgc   20640
gcaactgttg ggaagggcga tcggtgcggg cctcttcgct attacgccag ccaccgcggt   20700
g                                                                  20701
```

<210> SEQ ID NO 141
<211> LENGTH: 20701
<212> TYPE: DNA
<213> ORGANISM: Artificial Sequence
<220> FEATURE:
<223> OTHER INFORMATION: Complete optimised nucleotide sequence of the
      polynucleotide encoding pTM-MVDVax8
<220> FEATURE:
<221> NAME/KEY: misc_feature
<222> LOCATION: (1)..(8)
<223> OTHER INFORMATION: NotI
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammerhead ribozyme
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1768)..(1888)
<223> OTHER INFORMATION: MV N-P intergenic
<220> FEATURE:
<221> NAME/KEY: misc_feature
<222> LOCATION: (1889)..(3412)
<223> OTHER INFORMATION: MV P ORF
<220> FEATURE:
<221> NAME/KEY: misc_feature
<222> LOCATION: (3413)..(3519)
<223> OTHER INFORMATION: MV P-M intergenic
<220> FEATURE:
<221> NAME/KEY: misc_feature
<222> LOCATION: (3520)..(4527)
<223> OTHER INFORMATION: MV M ORF
<220> FEATURE:
<221> NAME/KEY: misc_feature
<222> LOCATION: (4528)..(5530)
<223> OTHER INFORMATION: MV M-F intergenic
<220> FEATURE:
<221> NAME/KEY: misc_feature
<222> LOCATION: (5531)..(7192)
<223> OTHER INFORMATION: MV F ORF
<220> FEATURE:
<221> NAME/KEY: misc_feature
<222> LOCATION: (7193)..(7352)
<223> OTHER INFORMATION: MV-F-H intergenic
<220> FEATURE:
<221> NAME/KEY: misc_feature
<222> LOCATION: (7353)..(9206)

<223> OTHER INFORMATION: MV H ORF
<220> FEATURE:
<221> NAME/KEY: misc_feature
<222> LOCATION: (9207)..(9333)
<223> OTHER INFORMATION: MV ATU3
<220> FEATURE:
<221> NAME/KEY: misc_feature
<222> LOCATION: (9334)..(10956)
<223> OTHER INFORMATION: DENV1 NS polyepitope
<220> FEATURE:
<221> NAME/KEY: misc_feature
<222> LOCATION: (10957)..(11049)
<223> OTHER INFORMATION: MV H-L intergenic
<220> FEATURE:
<221> NAME/KEY: misc_feature
<222> LOCATION: (11050)..(17601)
<223> OTHER INFORMATION: MV L ORF
<220> FEATURE:
<221> NAME/KEY: misc_feature
<222> LOCATION: (17602)..(17710)
<223> OTHER INFORMATION: MV Trailer
<220> FEATURE:
<221> NAME/KEY: misc_feature
<222> LOCATION: (17711)..(17794)
<223> OTHER INFORMATION: HDV ribozyme
<220> FEATURE:
<221> NAME/KEY: misc_feature
<222> LOCATION: (17795)..(17936)
<223> OTHER INFORMATION: T7 terminator
<220> FEATURE:
<221> NAME/KEY: misc_feature
<222> LOCATION: (17937)..(17944)
<223> OTHER INFORMATION: Not I
<220> FEATURE:
<221> NAME/KEY: misc_feature
<222> LOCATION: (17945)..(20701)
<223> OTHER INFORMATION: pTM plasmid

<400> SEQUENCE: 141
gcggccgcta atacgactca ctatagggcc aactttgttt ggtctgatga gtccgtgagg 60
acgaaacccg gagtcccggg tcaccaaaca aagttgggta aggatagttc aatcaatgat 120
catcttctag tgcacttagg attcaagatc ctattatcag ggacaagagc aggattaggg 180
atatccgaga tggccacact tttaaggagc ttagcattgt tcaaaagaaa caaggacaaa 240
ccacccatta catcaggatc cggtggagcc atcagaggaa tcaaacacat tattatagta 300
ccaatccctg gagattcctc aattaccact cgatccagac ttctggaccg gttggtgagg 360
ttaattggaa acccggatgt gagcgggccc aaactaacag gggcactaat aggtatatta 420
tccttatttg tggagtctcc aggtcaattg attcagagga tcaccgatga ccctgacgtt 480
agcataaggc tgttagaggt tgtccagagt gaccagtcac aatctggcct taccttcgca 540
tcaagaggta ccaacatgga ggatgaggcg gaccaatact tttcacatga tgatccaatt 600
agtagtgatc aatccaggtt cggatggttc gggaacaagg aaatctcaga tattgaagtg 660
caagaccctg agggattcaa catgattctg ggtaccatcc tagcccaaat ttgggtcttg 720
ctcgcaaagg cggttacggc cccagacacg gcagctgatt cggagctaag aaggtggata 780
aagtacaccc aacaaagaag ggtagttggt gaatttagat tggagagaaa atggttggat 840
gtggtgagga acaggattgc cgaggacctc tccttacgcc gattcatggt cgctctaatc 900
ctggatatca agagaacacc cggaaacaaa cccaggattg ctgaaatgat atgtgacatt 960
gatacatata tcgtagaggc aggattagcc agttttatcc tgactattaa gtttgggata 1020
gaaactatgt atcctgctct tggactgcat gaatttgctg gtgagttatc cacacttgag 1080
tccttgatga acctttacca gcaaatgggg gaaactgcac cctacatggt aatcctggag 1140
aactcaattc agaacaagtt cagtgcagga tcataccctc tgctctggag ctatgccatg 1200

```
ggagtaggag tggaacttga aaactccatg ggaggtttga actttggccg atcttacttt   1260
gatccagcat attttagatt agggcaagag atggtaagga ggtcagctgg aaaggtcagt   1320
tccacattgg catctgaact cggtatcact gccgaggatg caaggcttgt ttcagagatt   1380
gcaatgcata ctactgagga caagatcagt agagcggttg acccagaca agcccaagta    1440 tcatttctac acggtgatca aagtgagaat gagctaccga gattggggg caaggaagat    1500 aggagggtca aacagagtcg aggagaagcc agggagagct acagagaaac cgggcccagc   1560
agagcaagtg atgcgagagc tgcccatctt ccaaccggca caccctaga cattgacact    1620 gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat ggagccaat ggcagaagag caggcacgcc atgtcaaaaa    1920
cggactggaa tgcatccggg ctctcaaggc cgagcccatc ggctcactgg ccatcgagga   1980
agctatggca gcatggtcag aaatatcaga acccagga caggagcgag ccacctgcag     2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg gaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata ataatgaagt agctacagct   3420
caacttacct gccaacccca tgccagtcga cccaactagt acaacctaaa tccattataa   3480
aaaacttagg agcaaagtga ttgcctccca aggtccacaa tgacagagac ctacgacttc   3540
```

```
gacaagtcgg catgggacat caaagggtcg atcgctccga tacaacccac cacctacagt   3600
gatggcaggc tggtgcccca ggtcagagtc atagatcctg gtctaggcga caggaaggat   3660
gaatgcttta tgtacatgtt tctgctgggg gttgttgagg acagcgattc cctagggcct   3720
ccaatcgggc gagcatttgg gttcctgccc ttaggtgttg gcagatccac agcaaagccc   3780
gaaaaactcc tcaaagaggc cactgagctt gacatagttg ttagacgtac agcagggctc   3840
aatgaaaaac tggtgttcta caacaacacc ccactaactc tcctcacacc ttggagaaag   3900
gtcctaacaa cagggagtgt cttcaacgca aaccaagtgt gcaatgcggt taatctgata   3960
ccgctcgata ccccgcagag gttccgtgtt gtttatatga gcatcacccg tctttcggat   4020
aacgggtatt acaccgttcc tagaagaatg ctggaattca gatcggtcaa tgcagtggcc   4080
ttcaacctgc tggtgaccct taggattgac aaggcgatag ccctgggaa gatcatcgac    4140
aatacagagc aacttcctga ggcaacattt atggtccaca tcgggaactt caggagaaag   4200
aagagtgaag tctactctgc cgattattgc aaaatgaaaa tcgaaagat gggcctggtt    4260
tttgcacttg gtgggatagg gggcaccagt cttcacatta gaagcacagg caaaatgagc   4320
aagactctcc atgcacaact cgggttcaag aagaccttat gttacccgct gatggatatc   4380
aatgaagacc ttaatcgatt actctggagg agcagatgca agatagtaag aatccaggca   4440
gttttgcagc catcagttcc tcaagaattc cgcatttacg acgacgtgat cataaatgat   4500
gaccaaggac tattcaaagt tctgtagacc gtagtgccca gcaatgcccg aaaacgaccc   4560
ccctcacaat gacagccaga aggcccggac aaaaagccc cctccgaaag actccacgga    4620
ccaagcgaga ggccagccag cagccgacgg caagcgcgaa caccaggcgg ccccagcaca   4680
gaacagccct gacacaaggc caccaccagc caccccaatc tgcatcctcc tcgtgggacc   4740
cccgaggacc aaccccccaag gctgcccccg atccaaacca ccaaccgcat ccccaccacc   4800
cccgggaaag aaaccccccag caattggaag gcccctcccc ctcttcctca acacaagaac   4860
tccacaaccg aaccgcacaa gcgaccgagg tgacccaacc gcaggcatcc gactccctag   4920
acagatcctc tctccccggc aaactaaaca aaacttaggg ccaaggaaca tacacaccca   4980
acagaaccca gaccccggcc cacggcgccg cgccccaac cccgacaac cagagggagc    5040
ccccaaccaa tcccgccggc tccccggtg cccacaggca gggacaccaa ccccgaaca    5100
gacccagcac ccaaccatcg acaatccaag acgggggc cccccaaaa aaaggccccc      5160
aggggccgac agccagcacc gcgaggaagc ccacccaccc cacacacgac cacggcaacc   5220
aaaccagaac ccagaccacc ctgggccacc agctcccaga ctcggccatc accccgcaga   5280
aaggaaaggc cacaacccgc gcaccccagc ccgatccgg cggggagcca cccaacccga    5340
accagcaccc aagagcgatc cccgaaggac ccccgaaccg caaaggacat cagtatccca   5400
cagcctctcc aagtccccg gtctcctcct cttctcgaag ggaccaaaag atcaatccac    5460
cacacccgac gacactcaac tccccacccc taaaggagac accggaaatc ccagaatcaa   5520
gactcatcca atgtccatca tgggtctcaa ggtgaacgtc tctgccatat tcatggcagt   5580
actgttaact ctccaaacac ccaccggtca atccattgg ggcaatctct ctaagatagg    5640
ggtggtagga ataggaagtg caagctacaa agttatgact cgttccagcc atcaatcatt   5700
agtcataaaa ttaatgccca atataactct cctcaataac tgcacgaggg tagagattgc   5760
agaatacagg agactactga gaacagtttt ggaaccaatt agagatgcac ttaatgcaat   5820
gacccagaat ataagaccgg ttcagagtgt agcttcaagt aggagacaca agagatttgc   5880
gggagtagtc ctggcaggtg cggccctagg cgttgccaca gctgctcaga taacagccgg   5940
```

```
cattgcactt caccagtcca tgctgaactc tcaagccatc gacaatctga gagcgagcct    6000
ggaaactact aatcaggcaa ttgagacaat cagacaagca gggcaggaga tgatattggc    6060
tgttcagggt gtccaagact acatcaataa tgagctgata ccgtctatga accaactatc    6120
ttgtgattta atcggccaga agctcggget caaattgctc agatactata cagaaatcct    6180
gtcattattt ggccccagtt tacgggaccc catatctgcg gagatatcta tccaggcttt    6240
gagctatgcg cttggaggag acatcaataa ggtgttagaa aagctcggat acagtggagg    6300
tgatttactg ggcatcttag agagcggagg aataaaggcc cggataactc acgtcgacac    6360
agagtcctac ttcattgtcc tcagtatagc ctatccgacg ctgtccgaga ttaagggggt    6420
gattgtccac cggctagagg gggtctcgta aacataggc tctcaagagt ggtataccac     6480
tgtgcccaag tatgttgcaa cccaagggta ccttatctcg aattttgatg agtcatcgtg    6540
tactttcatg ccagagggga ctgtgtgcag ccaaaatgcc ttgtacccga tgagtcctct    6600
gctccaagaa tgcctccggg ggtacaccaa gtcctgtgct cgtacactcg tatccgggtc    6660
ttttgggaac cggttcattt tatcacaagg gaacctaata gccaattgtg catcaatcct    6720
ttgcaagtgt tacacaacag gaacgatcat taatcaagac cctgacaaga tcctaacata    6780
cattgctgcc gatcactgcc cggtagtcga ggtgaacggc gtgaccatcc aagtcgggag    6840
caggaggtat ccagacgctg tgtacttgca cagaattgac ctcggtcctc ccatatcatt    6900
ggagaggttg gacgtaggga caaatctggg gaatgcaatt gctaagttgg aggatgccaa    6960
ggaattgttg gagtcatcgg accagatatt gaggagtatg aaaggtttat cgagcactag    7020
catagtctac atcctgattg cagtgtgtct tggaggggttg atagggatcc ccgctttaat    7080
atgttgctgc aggggggcgtt gtaacaaaaa gggagaacaa gttggtatgt caagaccagg    7140
cctaaagcct gatcttacgg gaacatcaaa atcctatgta aggtcgctct gatcctctac    7200
aactcttgaa acacaaatgt cccacaagtc tcctcttcgt catcaagcaa ccaccgcacc    7260
cagcatcaag cccacctgaa attatctccg gcttccctct ggccgaacaa tatcggtagt    7320
taatcaaaac ttagggtgca agatcatcca caatgtcacc acaacgagac cggataaatg    7380
ccttctacaa agataacccc catcccaagg gaagtaggat agtcattaac agagaacatc    7440
ttatgattga tagaccttat gttttgctgg ctgttctgtt tgtcatgttt ctgagcttga    7500
tcgggttgct agccattgca ggcattagac ttcatcgggc agccatctac accgcagaga    7560
tccataaaag cctcagcacc aatctagatg taactaactc aatcgagcat caggtcaagg    7620
acgtgctgac accactcttc aaaatcatcg gtgatgaagt gggcctgagg acacctcaga    7680
gattcactga cctagtgaaa ttaatctctg acaagattaa attccttaat ccggataggg    7740
agtacgactt cagagatctc acttggtgta tcaacccgcc agagagaatc aaattggatt    7800
atgatcaata ctgtgcagat gtggctgctg aagagctcat gaatgcattg gtgaactcaa    7860
ctctactgga gaccagaaca accaatcagt tcctagctgt ctcaaaggga aactgctcag    7920
ggcccactac aatcagaggt caattctcaa acatgtcgct gtccctgtta gacttgtatt    7980
taggtcgagg ttacaatgtg tcatctatag tcactatgac atcccaggga atgtatgggg    8040
gaacttacct agtggaaaag cctaatctga gcagcaaaag gtcagagttg tcacaactga    8100
gcatgtaccg agtgtttgaa gtaggtgtta tcagaaatcc gggtttgggg ctccggtgt     8160 tccatatgac aaactatctt gagcaaccag tcagtaatga tctcagcaac tgtatggtgg    8220
ctttggggga gctcaaactc gcagcccttt gtcacgggga agattctatc acaattccct    8280
```

```
atcagggatc agggaaaggt gtcagcttcc agctcgtcaa gctaggtgtc tggaaatccc   8340
caaccgacat gcaatcctgg gtccccttat caacggatga tccagtgata gacaggcttt   8400
acctctcatc tcacagaggt gttatcgctg acaatcaagc aaaatgggct gtcccgacaa   8460
cacgaacaga tgacaagttg cgaatggaga catgcttcca acaggcgtgt aagggtaaaa   8520
tccaagcact ctgcgagaat cccgagtggg caccattgaa ggataacagg attccttcat   8580
acggggtctt gtctgttgat ctgagtctga cagttgagct taaaatcaaa attgcttcgg   8640
gattcgggcc attgatcaca cacggttcag ggatggacct atacaaatcc aaccacaaca   8700
atgtgtattg gctgactatc ccgccaatga agaacctagc cttaggtgta atcaacacat   8760
tggagtggat accgagattc aaggttagtc cctacctctt cactgtccca attaaggaag   8820
caggcgaaga ctgccatgcc caacatacc tacctgcgga ggtggatggt gatgtcaaac   8880
tcagttccaa tctggtgatt ctacctggtc aagatctcca atatgttttg gcaacctacg   8940
atacttccag ggttgaacat gctgtggttt attacgttta cagcccaagc cgctcatttt   9000 cttacttta tcctttttagg ttgcctataa aggggtccc catcgaatta caagtggaat   9060
gcttcacatg ggaccaaaaa ctctggtgcc gtcacttctg tgtgcttgcg gactcagaat   9120
ctggtggaca tatcactcac tctgggatgg tgggcatggg agtcagctgc acagtcaccc   9180
gggaagatgg aaccaatcgc agatagggct gctagtgaac caatcacatg atgtcaccca   9240
gacatcaggc atacccacta gtctaccctc catcattgtt ataaaaaact taggaaccag   9300
gtccacacag ccgccagccc atcaacgcgt acgatggcat cacaggaggg accactgccc   9360
gaaattgagg acgaagtgtt tagaaagcga aatctgacta ttatggacct gcaccccgga   9420
tctggcaaga cccggagata cctgccagcc atcgtgaggg aggctattaa gcggaaactg   9480
agaacactga tcctggcccc aactcgcgtg gtcgcttccg aaatggctga ggccctgaaa   9540
ggcatgccca tccggtatca gaccacagca gtgaagtctg aacataccgg caaggagatt   9600
gtggacctga tgtgccacgc cactttcacc atgcgactgc tgagcccagt gcgggtcccc   9660
aactacaata tgatcattat ggacgaggcc cactttactg atcccagctc catcgccgct   9720
agaggatata tttccaccag ggtgggaatg gcgaggcag cagctatctt catgacagca   9780 actcccctg gcagcgtgga ggcatttcct cagtccaacg ccgtcatcca ggacgaggag   9840
cgggacattc ctgagcggag ctggaattct gggtacgaat ggatcacaga cgaggatcat   9900
gcacactgga ctgaagccaa gatgctgctg acaacatta atactcctga gggaatcatt   9960
ccagctctgt tcgagcccga aagagagaag tctgcagcca tcgacggcga gtatagactc  10020
aggggagagg cccggaagac cttcgtggaa ctgatgaggc gcggcgatct gcccgtgtgg  10080
ctgagttaca aggtcgcttc agagggattc cagtatagtg accgacggtg gtgctttgat  10140
ggcgaacgca acaatcaggt gctggaggag aacatggatg tcgagatttg gacaaaggaa  10200
ggcgagcgga agaaactgcg cccacgatgg ctggacgctc ggacttacag cgatcccctg  10260
gcactgagag aattcaaaga gttttgctgca gggggtggccg tcgagaatca ccatcacgcc  10320
gctatgctgg acgtggatct gcatcctgcc agtgcttgga ccctgtatgc agtggccact  10380
accatcatta cccaatgat gcgccacaca atcgagaaca caactgccaa tatctcactg  10440
acagctattg caaccaggc agccattctg atgggactgg acaaaggctg gccatcagc  10500 aagatgata ttggcgtgcc tctgctggcc ctggggtgtt acagtcaggt gctgacatc  10560 attggccaga ggatcgagaa cattaagcat gagcacaaat caacctggca ttacgacgaa  10620
gataatccct ataagacatg ggcctaccac ggaagctatg aggtgaaacc ttcaggcagc  10680
```

```
gccagcagca tggtcaacgg ggtggtcaag ctgctgacca aaccttggga cgtgatccca   10740
atggtcactc agattgccat gaccgatacc accccattcg gccagcagcg ggtgttcaag   10800
gagaaggtgg acacccgcac acctaaggct aaacgaggga ctgcacagat catggaggtg   10860
accgccaagt ggctgtgggg attcctgtcc aggaacaaga agccaagaat ctgtaccagg   10920
gaagagttca caagaaaggt ccggtcaaac gcctaatgag cgcgcagcgc ttagacgtct   10980
cgcgatcgat gctagtgtga aatagacatc agaattaaga aaaacgtagg gtccaagtgg   11040
ttccccgtta tggactcgct atctgtcaac cagatcttat accctgaagt tcacctagat   11100
agcccgatag ttaccaataa gatagtagcc atcctggagt atgctcgagt ccctcacgct   11160
tacagcctgg aggaccctac actgtgtcag aacatcaagc accgcctaaa aaacggattt   11220
tccaaccaaa tgattataaa caatgtggaa gttgggaatg tcatcaagtc caagcttagg   11280
agttatccgg cccactctca tattccatat ccaaattgta atcaggattt atttaacata   11340
gaagacaaag agtcaacgag gaagatccgt gaactcctca aaaggggaa ttcgctgtac   11400 tccaaagtca gtgataaggt tttccaatgc ttaagggaca ctaactcacg gcttggccta   11460
ggctccgaat tgagggagga catcaaggag aaagttatta acttgggagt ttacatgcac   11520
agctcccagt ggtttgagcc cttttctgttt tggtttacag tcaagactga gatgaggtca   11580
gtgattaaat cacaaaccca tacttgccat aggaggagac acacacctgt attcttcact   11640
ggtagttcag ttgagttgct aatctctcgt gaccttgttg ctataatcag taaagagtct   11700
caacatgtat attacctgac atttgaactg gttttgatgt attgtgatgt catagagggg   11760
aggttaatga cagagaccgc tatgactatt gatgctaggt atacagagct tctaggaaga   11820
gtcagataca tgtggaaact gatagatggt ttcttccctg cactcgggaa tccaactttat  11880 caaattgtag ccatgctgga gcctctttca cttgcttacc tgcagctgag ggatataaca   11940
gtagaactca gaggtgcttt ccttaaccac tgctttactg aaatacatga tgttcttgac   12000
caaaacgggt tttctgatga aggtacttat catgagttaa ctgaagctct agattacatt   12060
ttcataactg atgacataca tctgacaggg gagattttct catttttcag aagtttcggc   12120
caccccagac ttgaagcagt aacggctgct gaaaatgtta ggaaatacat gaatcagcct   12180
aaagtcattg tgtatgagac tctgatgaaa ggtcatgcca tattttgtgg aatcataatc   12240
aacggctatc gtgacaggca cggaggcagt tggccaccgc tgaccctccc cctgcatgct   12300
gcagacacaa tccggaatgc tcaagcttca ggtgaagggt taacacatga gcagtgcgtt   12360
gataactgga aatcttttgc tggagtgaaa tttggctgct ttatgcctct tagcctggat   12420
agtgatctga caatgtacct aaaggacaag gcacttgctg ctctccaaag ggaatgggat   12480
tcagtttacc cgaaagagtt cctgcgttac gaccctccca agggaaccgg gtcacggagg   12540
cttgtagatg tttccttaa tgattcgagc tttgacccat atgatgtgat aatgtatgtt   12600
gtaagtggag cttacctcca tgaccctgag ttcaacctgt cttacagcct gaaagaaaag   12660
gagatcaagg aaacaggtag acttttttgct aaaatgactt acaaaatgag gcatgccaa   12720 gtgattgctg aaaatctaat ctcaaacggg attggcaaat attttaagga caatgggatg   12780
gccaaggatg agcacgattt gactaaggca ctccacactc tagctgtctc aggagtcccc   12840
aaagatctca agaaagtca caggggggg ccagtcttaa aaacctactc ccgaagccca   12900
gtccacacaa gtaccaggaa cgtgagagca gcaaagggt ttatagggt ccctcaagta   12960 attcggcagg accaagacac tgatcatccg gagaatatgg aagcttacga gacagtcagt   13020
```

```
gcatttatca cgactgatct caagaagtac tgccttaatt ggagatatga gaccatcagc    13080
ttgtttgcac agaggctaaa tgagatttac ggattgccct cattttccca gtggctgcat    13140
aagaggcttg agacctctgt cctgtatgta agtgaccctc attgccccccc cgaccttgac    13200 gcccatatcc cgttatataa agtccccaat gatcaaatct tcattaagta ccctatggga    13260
ggtatagaag ggtattgtca gaagctgtgg accatcagca ccattcccta tctatacctg    13320
gctgcttatg agagcggagt aaggattgct tcgttagtgc aaggggacaa tcagaccata    13380
gccgtaacaa aagggtacc cagcacatgg ccctacaacc ttaagaaacg ggaagctgct    13440
agagtaacta gagattactt tgtaattctt aggcaaaggc tacatgatat tggccatcac    13500
ctcaaggcaa atgagacaat tgtttcatca catttttttg tctattcaaa aggaatatat    13560
tatgatgggc tacttgtgtc ccaatcactc aagagcatcg caagatgtgt attctggtca    13620
gagactatag ttgatgaaac aagggcagca tgcagtaata ttgctacaac aatggctaaa    13680
agcatcgaga gaggttatga ccgttacctt gcatattccc tgaacgtcct aaaagtgata    13740 cagcaaaattc tgatctctct tggcttcaca atcaattcaa ccatgacccg ggatgtagtc    13800 ataccccctcc tcacaaacaa cgacctctta ataaggatgg cactgttgcc cgctcctatt    13860 gggggggatga attatctgaa tatgagcagg ctgtttgtca gaaacatcgg tgatccagta    13920
acatcatcaa ttgctgatct caagagaatg attctcgcct cactaatgcc tgaagagacc    13980
ctccatcaag taatgacaca acaaccgggg gactcttcat tcctagactg ggctagcgac    14040
ccttactcag caaatcttgt atgtgtccag agcatcacta gactcctcaa gaacataact    14100
gcaaggtttg tcctgatcca tagtccaaac ccaatgttaa aaggattatt ccatgatgac    14160
agtaaagaag aggacgaggg actggcggca ttcctcatgg acaggcatat tatagtacct    14220
agggcagctc atgaaatcct ggatcatagt gtcacagggg caagagagtc tattgcaggc    14280
atgctggata ccacaaaagg cttgattcga gccagcatga ggaagggggg gttaacctct    14340
cgagtgataa ccagattgtc caattatgac tatgaacaat tcagagcagg gatggtgcta    14400
ttgacaggaa gaaagagaaa tgtcctcatt gacaaagagt catgttcagt gcagctggcg    14460
agagctctaa gaagccatat gtgggcgagg ctagctcgag gacggcctat ttacggcctt    14520
gaggtccctg atgtactaga atctatgcga ggccacctta ttcggcgtca tgagacatgt    14580
gtcatctgcg agtgtggatc agtcaactac ggatggtttt tgtcccctc gggttgccaa    14640 ctggatgata ttgacaagga aacatcatcc ttgagagtcc catatattgg ttctaccact    14700
gatgagagaa cagacatgaa gcttgccttc gtaagagccc caagtcgatc cttgcgatct    14760
gctgttagaa tagcaacagt gtactcatgg gcttacggtg atgatgatag ctcttggaac    14820
gaagcctggt tgttggctag gcaaagggcc aatgtgagcc tggaggagct aagggtgatc    14880
actcccatct caacttcgac taatttagcg cataggttga gggatcgtag cactcaagtg    14940
aaatactcag gtacatccct tgtccgagtg gcgaggtata ccacaatctc caacgacaat    15000
ctctcatttg tcatatcaga taagaaggtt gatactaact ttatatacca acaaggaatg    15060
cttctagggt tgggtgtttt agaaacattg tttcgactcg agaaagatac cggatcatct    15120
aacacggtat tacatcttca cgtcgaaaca gattgttgcg tgatcccgat gatagatcat    15180
cccaggatac ccagctcccg caagctagag ctgagggcag agctatgtac caacccattg    15240
atatatgata atgcaccttt aattgacaga gatgcaacaa ggctatacac ccagagccat    15300
aggaggcacc ttgtggaatt tgttacatgg tccacacccc aactatatca catttttagct    15360 aagtccacag cactatctat gattgacctg gtaacaaaat ttgagaagga ccatatgaat    15420
```

```
gaaatttcag ctctcatagg ggatgacgat atcaatagtt tcataactga gtttctgctc   15480
atagagccaa gattattcac tatctacttg ggccagtgtg cggccatcaa ttgggcattt   15540
gatgtacatt atcatagacc atcagggaaa tatcagatgg gtgagctgtt gtcatcgttc   15600
cttctagaa tgagcaaagg agtgtttaag gtgcttgtca atgctctaag ccacccaaag   15660
atctacaaga aattctggca ttgtggtatt atagagccta tccatggtcc ttcacttgat   15720
gctcaaaact tgcacacaac tgtgtgcaac atggtttaca catgctatat gacctacctc   15780
gacctgttgt tgaatgaaga gttagaagag ttcacatttc tcttgtgtga aagcgacgag   15840
gatgtagtac cggacagatt cgacaacatc caggcaaaac acttatgtgt tctggcagat   15900
ttgtactgtc aaccagggac ctgcccacca attcgaggtc taagaccggt agagaaatgt   15960
gcagttctaa ccgaccatat caaggcagag gctatgttat ctccagcagg atcttcgtgg   16020
aacataaatc caattattgt agaccattac tcatgctctc tgacttatct ccggcgagga   16080
tcgatcaaac agataagatt gagagttgat ccaggattca ttttcgacgc cctcgctgag   16140
gtaaatgtca gtcagccaaa gatcggcagc aacaacatct caaatatgag catcaaggct   16200
ttcagacccc cacacgatga tgttgcaaaa ttgctcaaag atatcaacac aagcaagcac   16260
aatcttccca tttcagggg caatctcgcc aattatgaaa tccatgcttt ccgcagaatc   16320
gggttgaact catctgcttg ctacaaagct gttgagatat caacattaat taggagatgc   16380
cttgagccag gggaggacgg cttgttcttg ggtgagggat cgggttctat gttgatcact   16440
tataaagaga tacttaaact aaacaagtgc ttctataata gtggggtttc cgccaattct   16500
agatctggtc aaagggaatt agcaccctat ccctccgaag ttggccttgt cgaacacaga   16560
atgggagtag gtaatattgt caaagtgctc tttaacggga ggcccgaagt cacgtgggta   16620
ggcagtgtag attgcttcaa tttcatagtt agtaatatcc ctacctctag tgtggggttt   16680
atccattcag atatagagac cttgcctgac aaagatacta tagagaagct agaggaattg   16740
gcagccatct tatcgatggc tctgctcctg ggcaaaatag gatcaatact ggtgattaag   16800
cttatgcctt tcagcgggga ttttgttcag ggatttataa gttatgtagg gtctcattat   16860
agagaagtga accttgtata ccctagatac agcaacttca tctctactga atcttatttg   16920
gttatgacag atctcaaggc taaccggcta atgaatcctg aaaagattaa gcagcagata   16980
attgaatcat ctgtgaggac ttcacctgga cttataggtc acatcctatc cattaagcaa   17040
ctaagctgca tacaagcaat tgtgggagac gcagttagta gaggtgatat caatcctact   17100
ctgaaaaaac ttacacctat agagcaggtg ctgatcaatt gcgggttggc aattaacgga   17160
cctaagctgt gcaaagaatt gatccaccat gatgttgcct cagggcaaga tggattgctt   17220
aattctatac tcatcctcta cagggagttg gcaagattca aagacaacca agaagtcaa   17280
caagggatgt tccacgctta ccccgtattg gtaagtagca ggcaacgaga acttatatct   17340
aggatcaccc gcaaattctg ggggcacatt cttctttact ccgggaacaa aaagttgata   17400
aataagttta tccagaatct caagtccggc tatctgatac tagacttaca ccagaatatc   17460
ttcgttaaga atctatccaa gtcagagaaa cagattatta tgacgggggg tttgaaacgt   17520
gagtgggttt ttaaggtaac agtcaaggag accaaagaat ggtataagtt agtcggatac   17580
agtgccctga ttaaggacta attggttgaa ctccggaacc ctaatcctgc cctaggtggt   17640
taggcattat ttgcaatata ttaaagaaaa ctttgaaaat acgaagtttc tattcccagc   17700
tttgtctggt ggccggcatg gtcccagcct cctcgctggc gccggctggg caacattccg   17760
```

-continued

```
aggggaccgt cccctcggta atggcgaatg ggacgcggcc gatccggctg ctaacaaagc   17820
ccgaaaggaa gctgagttgg ctgctgccac cgctgagcaa taactagcat aaccccttgg   17880
ggcctctaaa cgggtcttga ggggttttt gctgaaagga ggaactatat ccggatgcgg   17940
ccgcgggccc tatggtaccc agcttttgtt ccctttagtg agggttaatt ccgagcttgg   18000
cgtaatcatg gtcatagctg tttcctgtgt gaaattgtta tccgctcaca attccacaca   18060
acataggagc cggaagcata aagtgtaaag cctggggtgc ctaatgagtg aggtaactca   18120
cattaattgc gttgcgctca ctgcccgctt tccagtcggg aaacctgtcg tgccagctgc   18180
attaatgaat cggccaacgc gcggggagag gcggtttgcg tattgggcgc tcttccgctt   18240
cctcgctcac tgactcgctg cgctcggtcg ttcggctgcg gcgagcggta tcagctcact   18300
caaaggcggt aatacggtta tccacagaat caggggataa cgcaggaaag aacatgtgag   18360
caaaaggcca gcaaaaggcc aggaaccgta aaaaggccgc gttgctggcg ttttttccata   18420
ggctcggccc ccctgacgag catcacaaaa atcgacgctc aagtcagagg tggcgaaacc   18480
cgacaggact ataaagatac caggcgttcc ccctggaag ctccctcgtg cgctctcctg   18540
ttccgaccct gccgcttacc ggatacctgt ccgcctttct cccttcggga agcgtggcgc   18600
tttctcaatg ctcacgctgt aggtatctca gttcggtgta ggtcgttcgc tccaagctgg   18660
gctgtgtgca cgaaccccc gttcagcccg accgctgcgc cttatccggt aactatcgtc   18720
ttgagtccaa cccggtaaga cacgacttat cgccactggc agcagccact ggtaacagga   18780
ttagcagagc gaggtatgta ggcggtgcta cagagttctt gaagtggtgg cctaactacg   18840
gctacactag aaggacagta tttggtatct gcgctctgct gaagccagtt accttcggaa   18900
aaagagttgg tagctcttga tccggcaaac aaaccaccgc tggtagcggt ggttttttg   18960
tttgcaagca gcagattacg cgcagaaaaa aaggatctca agaagatcct ttgatctttt   19020
ctacggggtc tgacgctcag tggaacgaaa actcacgtta agggattttg gtcatgagat   19080
tatcaaaaag gatcttcacc tagatccttt taaattaaaa atgaagtttt aaatcaatct   19140
aaagtatata tgagtaaact tggtctgaca gttaccaatg cttaatcagt gaggcaccta   19200
tctcagcgat ctgtctattt cgttcatcca tagttgcctg actgcccgtc gtgtagataa   19260
ctacgatacg ggagggctta ccatctggcc ccagtgctgc aatgataccg cgagacccac   19320
gctcaccggc tccagattta tcagcaataa accagccagc cggaagggcc gagcgcagaa   19380
gtggtcctgc aactttatcc gcctccatcc agtctattaa ttgttgccgg gaagctagag   19440
taagtagttc gccagttaat agtttgcgca acgttgttgc cattgctaca ggcatcgtgg   19500
tgtcacgctc gtcgtttggt atggcttcat tcagctccgg ttcccaacga tcaaggcgag   19560
ttacatgatc ccccatgttg tgaaaaaaag cggttagctc cttcggtcct ccgatcgttg   19620
tcagaagtaa gttggccgca gtgttatcac tcatgcttat ggcagcactg cataattctc   19680
ttactgtcat gccatccgta agatgctttt ctgtgactgg tgagtactca accaagtcat   19740
tctgagaata gtgtatgcgg cgaccgagtt gctcttgccc ggcgtcaata cgggataata   19800
ccgcgccaca tagcagaact ttaaaagtgc tcatcattgg aaaacgttct cgggggcgaa   19860
aactctcaag gatcttaccg ctgttgagat ccagttcgat gtaacccact cgtgcaccca   19920
actgatcttc agcatctttt actttcacca gcgtttctgg gtgagcaaaa acaggaaggc   19980
aaaatgccgc aaaaaaggga ataagggcga cacggaaatg ttgaatactc atactcttcc   20040
tttttcaata ttattgaagc atttatcagg gttattgtct catgagcgga tacatatttg   20100
aatgtattta gaaaaataaa caaataggg ttccgcgcac atttccccga aaagtgccac   20160
```

```
ctgaaattgt aaacgttaat attttgttaa aattcgcgtt aaattttttgt taaatcagct    20220 cattttttaa ccaataggcc gaaatcggca aatcccctta taaatcaaaa gaatagaccg    20280
agatagggtt gagtgttgtt ccagtttgga acaagagtcc actattaaag aacgtggact    20340
ccaacgtcaa agggcgaaaa accgtctatc agggcgatgg cccactacgt gaaccatcac    20400
cctaatcaag ttttttgggg tcgaggtgcc gtaaagcact aaatcggaac cctaaaggga    20460 gccccccgatt tagagcttga cggggaaagc cggcgaacgt ggcgagaaag gaagggaaga    20520
aagcgaaagg agcgggcgct agggcgctgg caagtgtagc ggtcacgctg cgcgtaacca    20580
ccacacccgc cgcgcttaat gcgccgctac agggcgcgtc ccattcgcca ttcaggctgc    20640
gcaactgttg ggaagggcga tcggtgcggg cctcttcgct attacgccag ccaccgcggt    20700
g                                                                    20701
```

```
<210> SEQ ID NO 142
<211> LENGTH: 22261
<212> TYPE: DNA
<213> ORGANISM: Artificial Sequence
<220> FEATURE:
<223> OTHER INFORMATION: Complete optimised nucleotide sequence of the
      polynucleotide encoding pTM-MVDVax9
<220> FEATURE:
<221> NAME/KEY: misc_feature
<222> LOCATION: (1 )..(8)
<223> OTHER INFORMATION: NotI
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammerhead ribozyme
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1768)..(1888)
<223> OTHER INFORMATION: MV N-P intergenic
<220> FEATURE:
<221> NAME/KEY: misc_feature
<222> LOCATION: (1889)..(3412)
<223> OTHER INFORMATION: MV P ORF
<220> FEATURE:
<221> NAME/KEY: misc_feature
<222> LOCATION: (3413)..(3531)
<223> OTHER INFORMATION: MV ATU2
<220> FEATURE:
<221> NAME/KEY: misc_feature
<222> LOCATION: (3532)..(6717)
<223> OTHER INFORMATION: DENV tetra EDIII/ectoM/DENV1 NS polyepitope
<220> FEATURE:
<221> NAME/KEY: misc_feature
<222> LOCATION: (6718)..(6813)
<223> OTHER INFORMATION: MV P-M intergenic
<220> FEATURE:
<221> NAME/KEY: misc_feature
<222> LOCATION: (6814)..(7821)
<223> OTHER INFORMATION: MV M ORF
<220> FEATURE:
<221> NAME/KEY: misc_feature
<222> LOCATION: (7822)..(8824)
<223> OTHER INFORMATION: MV M-F intergenic
<220> FEATURE:
<221> NAME/KEY: misc_feature
```

```
<222> LOCATION: (8825)..(10486)
<223> OTHER INFORMATION: MV F ORF
<220> FEATURE:
<221> NAME/KEY: misc_feature
<222> LOCATION: (10487)..(10646)
<223> OTHER INFORMATION: MV-F-H intergenic
<220> FEATURE:
<221> NAME/KEY: misc_feature
<222> LOCATION: (10647)..(12500)
<223> OTHER INFORMATION: MV H ORF
<220> FEATURE:
<221> NAME/KEY: misc_feature
<222> LOCATION: (12501)..(12609)
<223> OTHER INFORMATION: MV H-L intergenic
<220> FEATURE:
<221> NAME/KEY: misc_feature
<222> LOCATION: (12610)..(19161)
<223> OTHER INFORMATION: MV L ORF
<220> FEATURE:
<221> NAME/KEY: misc_feature
<222> LOCATION: (19162)..(19270)
<223> OTHER INFORMATION: MV Trailer
<220> FEATURE:
<221> NAME/KEY: misc_feature
<222> LOCATION: (19271)..(19354)
<223> OTHER INFORMATION: HDV ribozyme
<220> FEATURE:
<221> NAME/KEY: misc_feature
<222> LOCATION: (19355)..(19496)
<223> OTHER INFORMATION: T7 terminator
<220> FEATURE:
<221> NAME/KEY: misc_feature
<222> LOCATION: (19497)..(19504)
<223> OTHER INFORMATION: Not I
<220> FEATURE:
<221> NAME/KEY: misc_feature
<222> LOCATION: (19506)..(22261)
<223> OTHER INFORMATION: pTM plasmid

<400> SEQUENCE: 142
gcggccgcta atacgactca ctatagggcc aactttgttt ggtctgatga gtccgtgagg      60
acgaaacccg gagtcccggg tcaccaaaca aagttgggta aggatagttc aatcaatgat     120
catcttctag tgcacttagg attcaagatc ctattatcag ggacaagagc aggattaggg     180
atatccgaga tggccacact tttaaggagc ttagcattgt tcaaaagaaa caaggacaaa     240
ccacccatta catcaggatc cggtggagcc atcagaggaa tcaaacacat tattatagta     300
ccaatccctg gagattcctc aattaccact cgatccagac ttctggaccg gttggtgagg     360
ttaattggaa acccggatgt gagcgggccc aaactaacag gggcactaat aggtatatta     420
tccttatttg tggagtctcc aggtcaattg attcagagga tcaccgatga ccctgacgtt     480
agcataaggc tgttagaggt tgtccagagt gaccagtcac aatctggcct taccttcgca     540
tcaagaggta ccaacatgga ggatgaggcg gaccaatact tttcacatga tgatccaatt     600
agtagtgatc aatccaggtt cggatggttc gggaacaagg aaatctcaga tattgaagtg     660
caagaccctg agggattcaa catgattctg ggtaccatcc tagcccaaat ttgggtcttg     720
ctcgcaaagg cggttacggc cccagacacg gcagctgatt cggagctaag aaggtggata     780
aagtacaccc aacaaagaag ggtagttggt gaatttagat tggagagaaa atggttggat     840
gtggtgagga acaggattgc cgaggacctc tccttacgcc gattcatggt cgctctaatc     900
ctggatatca gagaacacc cggaaacaaa cccaggattc tgaaatgat atgtgacatt     960 gatacatata tcgtagaggc aggattagcc agttttatcc tgactattaa gtttgggata    1020
gaaactatgt atcctgctct tggactgcat gaatttgctg gtgagttatc cacacttgag    1080
tccttgatga accttttacca gcaaatgggg gaaactgcac cctacatggt aatcctggag    1140
```

-continued

| | | | | | |
|---|---|---|---|---|---|
| aactcaattc | agaacaagtt | cagtgcagga | tcatacccte | tgctctggag | ctatgccatg | 1200 |
| ggagtaggag | tggaacttga | aaactccatg | ggaggtttga | actttggccg | atcttacttt | 1260 |
| gatccagcat | attttagatt | agggcaagag | atggtaagga | ggtcagctgg | aaaggtcagt | 1320 |
| tccacattgg | catctgaact | cggtatcact | gccgaggatg | caaggcttgt | ttcagagatt | 1380 |
| gcaatgcata | ctactgagga | caagatcagt | agagcggttg | gacccagaca | agcccaagta | 1440 |
| tcatttctac | acggtgatca | aagtgagaat | gagctaccga | gattggggg | caaggaagat | 1500 |
| aggagggtca | aacagagtcg | aggagaagcc | agggagagct | acagagaaac | cgggcccagc | 1560 |
| agagcaagtg | atgcgagagc | tgcccatctt | ccaaccggca | cacccctaga | cattgacact | 1620 |
| gcaacggagt | ccagccaaga | tccgcaggac | agtcgaaggt | cagctgacgc | cctgcttagg | 1680 |
| ctgcaagcca | tggcaggaat | ctcggaagaa | caaggctcag | acacggacac | ccctatagtg | 1740 |
| tacaatgaca | gaaatcttct | agactaggtg | cgagaggccg | agggccagaa | caacatccgc | 1800 |
| ctaccatcca | tcattgttat | aaaaaactta | ggaaccaggt | ccacacagcc | gccagcccat | 1860 |
| caaccatcca | ctcccacgat | tggagccaat | ggcagaagag | caggcacgcc | atgtcaaaaa | 1920 |
| cggactggaa | tgcatcccggg | ctctcaaggc | cgagcccatc | ggctcactgg | ccatcgagga | 1980 |
| agctatggca | gcatggtcag | aaatatcaga | aacccagga | caggagcgag | ccacctgcag | 2040 |
| ggaagagaag | gcaggcagtt | cgggtctcag | caaaccatgc | ctctcagcaa | ttggatcaac | 2100 |
| tgaaggcggt | gcacctcgca | tccgcggtca | gggacctgga | gagagcgatg | acgacgctga | 2160 |
| aactttggga | atcccccaa | gaaatctcca | ggcatcaagc | actgggttac | agtgttatta | 2220 |
| cgtttatgat | cacagcggtg | aagcggttaa | gggaatccaa | gatgctgact | ctatcatggt | 2280 |
| tcaatcaggc | cttgatggtg | atagcaccct | ctcaggagga | gacaatgaat | ctgaaaacag | 2340 |
| cgatgtggat | attggcgaac | ctgataccga | gggatatgct | atcactgacc | ggggatctgc | 2400 |
| tcccatctct | atggggttca | gggcttctga | tgttgaaact | gcagaaggag | gggagatcca | 2460 |
| cgagctcctg | agactccaat | ccagaggcaa | caactttccg | aagcttggga | aaactctcaa | 2520 |
| tgttcctccg | ccccggacc | ccggtagggc | cagcacttcc | gggacaccca | ttaaaaaggg | 2580 |
| cacagacgcg | agattagcct | catttggaac | ggagatcgcg | tctttattga | caggtggtgc | 2640 |
| aacccaatgt | gctcgaaagt | caccctcgga | accatcaggg | ccaggtgcac | ctgcgggaa | 2700 |
| tgtccccgag | tgtgtgagca | atgccgcact | gatacaggag | tggacacccg | aatctggtac | 2760 |
| cacaatctcc | ccgagatccc | agaataatga | agaaggggga | gactattatg | atgatgagct | 2820 |
| gttctctgat | gtccaagata | ttaaaacagc | cttggccaaa | atacacgagg | ataatcagaa | 2880 |
| gataatctcc | aagctagaat | cactgctgtt | attgaaggga | gaagttgagt | caattaagaa | 2940 |
| gcagatcaac | aggcaaaata | tcagcatatc | caccctggaa | ggacacctct | caagcatcat | 3000 |
| gatcgccatt | cctggacttg | ggaaggatcc | caacgacccc | actgcagatg | tcgaaatcaa | 3060 |
| tcccgacttg | aaaccatca | taggcagaga | ttcaggccga | gcactggccg | aagttctcaa | 3120 |
| gaaacccgtt | gccagccgac | aactccaagg | aatgacaaat | ggacggacca | gttccagagg | 3180 |
| acagctgctg | aaggaatttc | agctaaagcc | gatcgggaaa | aagatgagct | cagccgtcgg | 3240 |
| gtttgttcct | gacaccggcc | ctgcatcacg | cagtgtaatc | cgctccatta | taaaatccag | 3300 |
| ccggctagag | gaggatcgga | agcgttacct | gatgactctc | cttgatgata | tcaaaggagc | 3360 |
| caatgatctt | gccaagttcc | accagatgct | gatgaagata | ataatgaagt | agctacagct | 3420 |
| caacttacct | gccaacccca | tgccagtcga | cccaactagc | ctaccctcca | tcattgttat | 3480 |
| aaaaaactta | ggaaccaggt | ccacacagcc | gccagcccat | caacgcgtac | gatgggcatc | 3540 |

```
atattcattc ttcttatgct ggttacaccg tctatggcgg agaaacttcg aatcaaaggt   3600
atgagctata cgatgtgcag cggcaagttc aagatcgaga aggaaatggc tgaaacccag   3660
cacggtacaa ctgtggtcaa agtcaaatat gaggggctg gcgctccctg taaagtaccc    3720
attgagatta gggacgtcaa taagagaag gtggtaggtc gcatcatctc cagtacacct    3780
ttggccgaga acacgaactc cgtcacaaac atagagttgg aaccccgtt cggagactca    3840 tacattgtga tcgggtggg caactctgca ctcacactgc attggttcaa gagggaagc    3900 agtatcggcc gcagggataa gagagacaaa ctgaaattga aggtatgtc ctatgccatg    3960 tgcacgaata ctttcgttct caagaaagaa gtatctgaga ctcagcacgg aaccatcctg   4020
atcaaagtcg agtacaaagg agaagacgtg ccctgtaaga tcccattcag taccgaggat   4080
ggacagggca aggcccataa cggcaggctg ataaccgcca accctgtggt tacaaagaag   4140
gaagagccag tcaatatcga agctgagcca ccgttcgggg agagcaacat agtaattggc   4200
ataggggata atgctttgaa gatcaactgg tacaagaaag gaagctccat tggccgaaga   4260
gataagcgcg acaaactcca gctgaaagga atgagctact ccatgtgtac tgggaagttc   4320
aagattgtca aggaaatcgc cgaaactcag catggcacta ttgtgatccg cgtgcagtat   4380
gaaggcgatg gtagcccctg caagatacca tttgaaatca ccgatttgga gaacggcac    4440 gtcctgggtc ggctcattac cgtgaaccca atcgtgaccg agaaggacag tccagttaat   4500
atcgaggccg agcctccttt cggcgacagt tacatcattg tagggtgga accagggcaa    4560 ctgaagctga actggttcaa gaaaggcagc agtataggac ggcgggataa acgggacaaa   4620
ctcacactga aaggcatgtc atacgttatg tgcaccggct cattcaaact ggagaaggaa   4680
gttgcagaga cacagcatgg gaccgtgctc gtgcaggtca aatacgaggg caccgacgct   4740
ccttgcaaga ttccgttcag tacacaggac gagaaaggcg tgactcagaa cggcagattg   4800
attacagcga accctatcgt gactgacaag gagaagccag ttaacatcga gactgagccg   4860
cctttcggag aatcatacat tatcgtggga gccggcgaga aggcactgaa actcagctgg   4920
ttcaagaagg gcagctcaat cggtcggaga gacaagcgt ctgtcgccct cgcaccgcac    4980
gtgggcctgg gtctggaaac gaggaccgag acgtggatga gttccgaagg cgcatggaag   5040
caaatccaga aagtggagac gtgggccctc aggcatccgc ggagagataa acgagcatca   5100
caggagggac cactgcccga aattgaggac gaagtgttta aaagcgaaa tctgactatt    5160 atggacctgc accccggatc tggcaagacc cggagatacc tgccagccat cgtgagggag   5220
gctattaagc ggaaactgag aacactgatc ctggccccaa ctcgcgtggt cgcttccgaa   5280
atggctgagg ccctgaaagg catgcccatc cggtatcaga ccacagcagt gaagtctgaa   5340
cataccggca aggagattgt ggacctgatg tgccacgcca ctttcaccat cgcgactgctg   5400 agcccagtgc gggtccccaa ctacaatatg atcattatgg acgaggccca ctttactgat   5460
cccagctcca tcgccgctag aggatatatt tccaccaggg tgggaatggg cgaggcagca   5520
gctatcttca tgacagcaac tccccctggc agcgtggagg catttcctca gtccaacgcc   5580
gtcatccagg acgaggagcg ggacattcct gagcggagct ggaattctgg gtacgaatgg   5640
atcacagacg aggatcatgc acactggact gaagccaaga tgctgctgga caacattaat   5700
actcctgagg gaatcattcc agctctgttc gagcccgaaa gagagaagtc tgcagccatc   5760
gacggcgagt atagactgag gggagaggcc cggaagacct tcgtggaact gatgaggcgc   5820
ggcgatctgc ccgtgtggct gagttacaag gtcgcttcag agggattcca gtatagtgac   5880
```

-continued

```
cgacggtggt gctttgatgg cgaacgcaac aatcaggtgc tggaggagaa catggatgtc      5940
gagatttgga caaaggaagg cgagcggaag aaactgcgcc cacgatggct ggacgctcgg      6000
acttacagcg atccctggc actgagagaa ttcaaagagt ttgctgcagg ggtggccgtc       6060
gagaatcacc atcacgccgc tatgctggac gtggatctgc atcctgccag tgcttggacc      6120
ctgtatgcag tggccactac catcattacc ccaatgatgc gccacacaat cgagaacaca      6180
actgccaata tctcactgac agctattgca aaccaggcag ccattctgat gggactggac      6240
aaaggctggc ccatcagcaa gatggatatt ggcgtgcctc tgctggccct ggggtgttac      6300
agtcaggtgc tggacatcat tggccagagg atcgagaaca ttaagcatga gcacaaatca      6360
acctggcatt acgacgaaga taatccctat aagacatggg cctaccacgg aagctatgag      6420
gtgaaaccct caggcagcgc cagcagcatg gtcaacgggg tggtcaagct gctgaccaaa      6480
ccttgggacg tgatcccaat ggtcactcag attgccatga ccgataccac cccattcggc      6540
cagcagcggg tgttcaagga aaggtggac acccgcacac ctaaggctaa acgagggact      6600
gcacagatca tggaggtgac cgccaagtgg ctgtggggat tcctgtccag gaacaagaag      6660
ccaagaatct gtaccaggga agagttcaca agaaaggtcc ggtcaaacgc taatgagcg      6720 cgcagcgctt agacgtctcg cgatcgatac tagtacaacc taaatccatt ataaaaaact      6780
taggagcaaa gtgattgcct cccaaggtcc acaatgacag agacctacga cttcgacaag      6840
tcggcatggg acatcaaagg gtcgatcgct ccgatacaac ccaccaccta cagtgatggc      6900
aggctggtgc cccaggtcag agtcatagat cctggtctag gcgacaggaa ggatgaatgc      6960
tttatgtaca tgtttctgct ggggggttgtt gaggacagcg attccctagg gcctccaatc      7020
gggcgagcat ttgggttcct gcccttaggt gttggcagat ccacagcaaa gcccgaaaaa      7080
ctcctcaaag aggccactga gcttgacata gttgttagac gtacagcagg gctcaatgaa      7140
aaactggtgt tctacaacaa caccccacta actctcctca caccttggag aaaggtccta      7200
acaacaggga gtgtcttcaa cgcaaaccaa gtgtgcaatg cggttaatct gataccgctc      7260
gataccccgc agaggttccg tgttgtttat atgagcatca cccgtctttc ggataacggg      7320
tattacaccg ttcctagaag aatgctggaa ttcagatcgg tcaatgcagt ggccttcaac      7380
ctgctggtga cccttaggat tgacaaggcg ataggccctg gaagatcat cgacaataca      7440 gagcaacttc ctgaggcaac atttatggtc cacatcggga acttcaggag aaagaagagt      7500
gaagtctact ctgccgatta ttgcaaaatg aaaatcgaaa agatgggcct ggttttgca     7560 cttggtggga taggggcac cagtcttcac attagaagca caggcaaaat gagcaagact      7620
ctccatgcac aactcgggtt caagaagacc ttatgttacc cgctgatgga tatcaatgaa      7680
gaccttaatc gattactctg gaggagcaga tgcaagatag taagaatcca ggcagttttg      7740
cagccatcag ttcctcaaga attccgcatt tacgacgacg tgatcataaa tgatgaccaa      7800
ggactattca aagttctgta gaccgtagtg cccagcaatg cccgaaaacg accccccctca     7860 caatgacagc cagaaggccc ggacaaaaaa gcccctccg aaagactcca cggaccaagc      7920
gagaggccag ccagcagccg acggcaagcg cgaacaccag gcggcccag cacagaacag      7980 ccctgacaca aggccaccac cagccacccc aatctgcatc ctcctcgtgg acccccgag      8040 gaccaacccc caaggctgcc cccgatccaa accaccaacc gcatcccac caccccggg      8100 aaagaaaccc ccagcaattg gaaggcccct cccctctcc tcaacacaa gaactccaca      8160 accgaaccgc acaagcgacc gaggtgaccc aaccgcagg atccgactcc ctagacagat      8220
cctctctccc cggcaaacta aacaaaactt agggccaagg aacatacaca cccaacagaa      8280
```

```
cccagacccc ggcccacggc gccgcgcccc caaccccccga caaccagagg gagccccccaa   8340 ccaatcccgc cggctccccc ggtgcccaca ggcagggaca ccaaccccg  aacagaccca    8400 gcacccaacc atcgacaatc aagacgggg  gggccccccc aaaaaaaggc ccccaggggc    8460
cgacagccag caccgcgagg aagcccaccc acccacaca  cgaccacggc aaccaaacca    8520
gaacccagac caccctgggc caccagctcc cagactcggc catcaccccg cagaaaggaa    8580
aggccacaac ccgcgcaccc cagccccgat ccggcgggga gccacccaac ccgaaccagc    8640
acccaagagc gatccccgaa ggaccccga  accgcaaagg acatcagtat cccacagcct    8700
ctccaagtcc cccggtctcc tcctcttctc gaagggacca aaagatcaat ccaccacacc    8760
cgacgacact caactcccca cccctaaagg agacaccggg aatcccagaa tcaagactca    8820
tccaatgtcc atcatgggtc tcaaggtgaa cgtctctgcc atattcatgg cagtactgtt    8880
aactctccaa acacccaccg gtcaaatcca ttggggcaat ctctctaaga tagggtggt     8940 aggaatagga agtgcaagct acaaagttat gactcgttcc agccatcaat cattagtcat    9000
aaaattaatg cccaatataa ctctcctcaa taactgcacg agggtagaga ttgcagaata    9060
caggagacta ctgagaacag ttttggaacc aattagagat gcacttaatg caatgaccca    9120
gaatataaga ccggttcaga gtgtagcttc aagtaggaga cacaagagat ttgcgggagt    9180
agtcctggca ggtgcggccc taggcgttgc cacagctgct cagataacag ccggcattgc    9240
acttcaccag tccatgctga actctcaagc catcgacaat ctgagagcga gcctggaaac    9300
tactaatcag gcaattgaga caatcagaca agcagggcag gagatgatat tggctgttca    9360
gggtgtccaa gactacatca ataatgagct gataccgtct atgaaccaac tatcttgtga    9420
tttaatcggc cagaagctcg ggctcaaatt gctcagatac tatacagaaa tcctgtcatt    9480
atttggcccc agtttacggg accccatatc tgcggagata tctatccagg ctttgagcta    9540
tgcgcttgga ggagacatca ataaggtgtt agaaaagctc ggatacagtg gaggtgattt    9600
actgggcatc ttagagagcg gaggaataaa ggcccggata actcacgtcg acacagagtc    9660
ctacttcatt gtcctcagta tagcctatcg gacgctgtcc gagattaagg gggtgattgt    9720
ccaccggcta gaggggtct  cgtacaacat aggctctcaa gagtggtata ccactgtgcc    9780
caagtatgtt gcaacccaag ggtaccttat ctcgaatttt gatgagtcat cgtgtacttt    9840
catgccagag gggactgtgt gcagccaaaa tgccttgtac ccgatgagtc ctctgctcca    9900
agaatgcctc cgggggtaca ccaagtcctg tgctcgtaca ctcgtatccg ggtcttttgg    9960
gaaccggttc attttatcac aagggaacct aatagccaat tgtgcatcaa tcctttgcaa   10020
gtgttacaca acaggaacga tcattaatca agaccctgac aagatcctaa catacattgc   10080
tgccgatcac tgcccggtag tcgaggtgaa cggcgtgacc atccaagtcg ggagcaggag   10140
gtatccagac gctgtgtact tgcacagaat tgacctcggt cctcccatat cattggagag   10200
gttggacgta gggacaaatc tggggaatgc aattgctaag ttggaggatg ccaaggaatt   10260
gttggagtca tcggaccaga tattgaggag tatgaaaggt ttatcgagca ctagcatagt   10320
ctacatcctg attgcagtgt gtcttggagg gttgataggg atccccgctt taatatgttg   10380
ctgcaggggg cgttgtaaca aaaagggaga acaagttggt atgtcaagac caggcctaaa   10440
gcctgatctt acgggaacat caaaatccta tgtaaggtcg ctctgatcct ctacaactct   10500
tgaaacacaa atgtcccaca agtctcctct tcgtcatcaa gcaaccaccg cacccagcat   10560
caagcccacc tgaaattatc tccggcttcc ctctggccga acaatatcgg tagttaatca   10620
```

```
aaacttaggg tgcaagatca tccacaatgt caccacaacg agaccggata aatgccttct    10680
acaaagataa cccccatccc aagggaagta ggatagtcat taacagagaa catcttatga    10740
ttgatagacc ttatgttttg ctggctgttc tgtttgtcat gtttctgagc ttgatcgggt    10800
tgctagccat tgcaggcatt agacttcatc gggcagccat ctacaccgca gagatccata    10860
aaagcctcag caccaatcta gatgtaacta actcaatcga gcatcaggtc aaggacgtgc    10920
tgacaccact cttcaaaatc atcggtgatg aagtgggcct gaggacacct cagagattca    10980
ctgacctagt gaaattaatc tctgacaaga ttaaattcct taatccggat agggagtacg    11040
acttcagaga tctcacttgg tgtatcaacc cgccagagag aatcaaattg gattatgatc    11100
aatactgtgc agatgtggct gctgaagagc tcatgaatgc attggtgaac tcaactctac    11160
tggagaccag aacaaccaat cagttcctag ctgtctcaaa gggaaactgc tcagggccca    11220
ctacaatcag aggtcaattc tcaaacatgt cgctgtccct gttagacttg tatttaggtc    11280
gaggttacaa tgtgtcatct atagtcacta tgacatccca gggaatgtat ggggggaactt   11340
acctagtgga aaagcctaat ctgagcagca aaaggtcaga gttgtcacaa ctgagcatgt    11400
accgagtgtt tgaagtaggt gttatcagaa atcggggttt gggggctccg gtgttccata    11460
tgacaaacta tcttgagcaa ccagtcagta atgatctcag caactgtatg gtggctttgg    11520
gggagctcaa actcgcagcc ctttgtcacg gggaagattc tatcacaatt ccctatcagg    11580
gatcaggaa aggtgtcagc ttccagctcg tcaagctagg tgtctggaaa tccccaaccg     11640
acatgcaatc ctgggtcccc ttatcaacgg atgatccagt gatagacagg cttttacctct   11700
catctcacag aggtgttatc gctgacaatc aagcaaaatg ggctgtcccg acaacacgaa    11760
cagatgacaa gttgcgaatg gagacatgct ccaacaggc gtgtaagggt aaaatccaag     11820
cactctgcga gaatcccgag tgggcaccat tgaaggataa caggattcct tcatacgggg   11880
tcttgtctgt tgatctgagt ctgacagttg agcttaaaat caaaattgct tcgggattcg    11940
ggccattgat cacacacggt tcagggatgg acctatacaa atccaaccac aacaatgtgt    12000
attggctgac tatcccgcca atgaagaacc tagccttagg tgtaatcaac acattggagt    12060
ggatacccag attcaaggtt agtccctacc tcttcactgt cccaattaag gaagcaggcg    12120
aagactgcca tgccccaaca tacctacctg cggaggtgga tggtgatgtc aaactcagtt    12180
ccaatcggt gattctacct ggtcaagatc tccaatatgt tttggcaacc tacgatactt     12240
ccagggttga acatgctgtg gtttattacg tttacagccc aagccgctca ttttcttact    12300
tttatccttt taggttgcct ataaagggg tccccatcga attacaagtg gaatgcttca    12360
catgggacca aaaactctgg tgccgtcact tctgtgtgct tgcggactca gaatctggtg    12420
gacatatcac tcactctggg atggtgggca tgggagtcag ctgcacagtc acccgggaag    12480
atggaaccaa tcgcagatag ggctgctagt gaaccaatca catgatgtca cccagacatc    12540
aggcataccc actagtgtga aatagacatc agaattaaga aaacgtagg gtccaagtgg     12600
ttccccgtta tggactcgct atctgtcaac cagatcttat accctgaagt tcacctagat    12660
agcccgatag ttaccaataa gatagtagcc atcctggagt atgctcgagt ccctcacgct    12720
tacagcctgg aggaccctac actgtgtcag aacatcaagc accgcctaaa aaacggatttt   12780
tccaaccaaa tgattataaa caatgtggaa gttgggaatg tcatcaagtc caagcttagg    12840
agttatccgg cccactctca tattccatat ccaaattgta atcaggatttt atttaacata   12900
gaagacaaag agtcaacgag gaagatccgt gaactcctca aaaaggggaa ttcgctgtac    12960
tccaaagtca gtgataaggt tttccaatgc ttaagggaca ctaactcacg gcttggccta    13020
```

```
ggctccgaat tgagggagga catcaaggag aaagttatta acttgggagt ttacatgcac    13080
agctcccagt ggtttgagcc ctttctgttt tggtttacag tcaagactga gatgaggtca    13140
gtgattaaat cacaaaccca tacttgccat aggaggagac acacacctgt attcttcact    13200
ggtagttcag ttgagttgct aatctctcgt gaccttgttg ctataatcag taaagagtct    13260
caacatgtat attacctgac atttgaactg gttttgatgt attgtgatgt catagagggg    13320
aggttaatga cagagaccgc tatgactatt gatgctaggt atacagagct tctaggaaga    13380
gtcagataca tgtggaaact gatagatggt ttcttccctg cactcgggaa tccaacttat    13440
caaattgtag ccatgctgga gcctctttca cttgcttacc tgcagctgag ggatataaca    13500
gtagaactca gaggtgcttt ccttaaccac tgctttactg aaatacatga tgttcttgac    13560
caaaacgggt tttctgatga aggtactat catgagttaa ctgaagctct agattacatt    13620
ttcataactg atgacataca tctgacaggg gagattttct catttttcag aagtttcggc    13680
caccccagac ttgaagcagt aacggctgct gaaaatgtta ggaaatacat gaatcagcct    13740
aaagtcattg tgtatgagac tctgatgaaa ggtcatgcca tattttgtgg aatcataatc    13800
aacggctatc gtgacaggca cggaggcagt tggccaccgc tgaccctccc cctgcatgct    13860
gcagacacaa tccggaatgc tcaagcttca ggtgaagggt taacacatga gcagtgcgtt    13920
gataactgga aatcttttgc tggagtgaaa tttggctgct ttatgcctct tagcctggat    13980
agtgatctga caatgtacct aaaggacaag gcacttgctg ctctccaaag ggaatgggat    14040
tcagtttacc cgaaagagtt cctgcgttac gaccctccca agggaaccgg gtcacggagg    14100
cttgtagatg ttttccttaa tgattcgagc tttgacccat atgatgtgat aatgtatgtt    14160
gtaagtggag cttacctcca tgaccctgag ttcaacctgt cttacagcct gaaagaaaag    14220
gagatcaagg aaacaggtag acttttttgct aaaatgactt acaaaatgag ggcatgccaa    14280
gtgattgctg aaaatctaat ctcaaacggg attggcaaat attttaagga caatgggatg    14340
gccaaggatg agcacgattt gactaaggca ctccacactc tagctgtctc aggagtcccc    14400
aaagatctca agaaagtca caggggggggg ccagtcttaa aaacctactc ccgaagccca    14460
gtccacacaa gtaccaggaa cgtgagagca gcaaaagggt ttatagggtt ccctcaagta    14520
attcggcagg accaagacac tgatcatccg gagaatatgg aagcttacga gacagtcagt    14580
gcatttatca cgactgatct caagaagtac tgccttaatt ggagatatga gaccatcagc    14640
ttgtttgcac agaggctaaa tgagatttac ggattgccct catttttcca gtggctgcat    14700
aagaggcttg agacctctgt cctgtatgta agtgaccctc attgcccccc cgaccttgac    14760
gcccatatcc cgttatataa agtccccaat gatcaaatct tcattaagta ccctatggga    14820
ggtatagaag ggtattgtca gaagctgtgg accatcagca ccattcccta tctatacctg    14880
gctgcttatg agagcggagt aaggattgct tcgttagtgc aaggggacaa tcagaccata    14940
gccgtaacaa aagggtacc cagcacatgg ccctacaacc ttaagaaacg ggaagctgct    15000
agagtaacta gagattactt tgtaattctt aggcaaaggc tacatgatat tggccatcac    15060
ctcaaggcaa atgagacaat tgtttcatca cattttttg tctattcaaa aggaatatat    15120
tatgatgggc tacttgtgtc ccaatcactc aagagcatcg caagatgtgt attctggtca    15180
gagactatag ttgatgaaac aagggcagca tgcagtaata ttgctacaac aatggctaaa    15240
agcatcgaga gaggttatga ccgttacctt gcatattccc tgaacgtcct aaaagtgata    15300
cagcaaattc tgatctctct tggcttcaca atcaattcaa ccatgacccg ggatgtagtc    15360
```

```
ataccoctcc tcacaaacaa cgacctctta ataaggatgg cactgttgcc cgctcctatt    15420 gggggatga attatctgaa tatgagcagg ctgtttgtca gaaacatcgg tgatccagta    15480
acatcatcaa ttgctgatct caagagaatg attctcgcct cactaatgcc tgaagagacc    15540
ctccatcaag taatgacaca acaaccgggg gactcttcat tcctagactg ggctagcgac    15600
ccttactcag caaatcttgt atgtgtccag agcatcacta gactcctcaa gaacataact    15660
gcaaggtttg tcctgatcca tagtccaaac ccaatgttaa aaggattatt ccatgatgac    15720
agtaaagaag aggacgaggg actggcggca ttcctcatgg acaggcatat tatagtacct    15780
agggcagctc atgaaatcct ggatcatagt gtcacagggg caagagagtc tattgcaggc    15840
atgctggata ccacaaaagg cttgattcga gccagcatga ggaagggggg gttaacctct    15900
cgagtgataa ccagattgtc caattatgac tatgaacaat tcagagcagg gatggtgcta    15960
ttgacaggaa gaaagagaaa tgtcctcatt gacaaagagt catgttcagt gcagctggcg    16020
agagctctaa gaagccatat gtgggcgagg ctagctcgag gacggcctat ttacggcctt    16080
gaggtccctg atgtactaga atctatgcga ggccaccta ttcggcgtca tgagacatgt    16140
gtcatctgcg agtgtggatc agtcaactac ggatggtttt ttgtcccctc gggttgccaa    16200
ctggatgata ttgacaagga acatcatcc ttgagagtcc catatattgg ttctaccact    16260
gatgagagaa cagacatgaa gcttgccttc gtaagagccc caagtcgatc cttgcgatct    16320
gctgttagaa tagcaacagt gtactcatgg gcttacggtg atgatgatag ctcttggaac    16380
gaagcctggt tgttggctag gcaaagggcc aatgtgagcc tggaggagct aagggtgatc    16440
actcccatct caacttcgac taatttagcg cataggttga gggatcgtag cactcaagtg    16500
aaatactcag gtacatccct tgtccgagtg gcgaggtata ccacaatctc caacgacaat    16560
ctctcatttg tcatatcaga taagaaggtt gatactaact ttatataccca acaaggaatg    16620 cttctagggt tgggtgtttt agaaacattg tttcgactcg agaaagatac cggatcatct    16680
aacacggtat tacatcttca cgtcgaaaca gattgttgcg tgatcccgat gatagatcat    16740
cccaggatac ccagctcccg caagctagag ctgagggcag agctatgtac caacccattg    16800
atatatgata atgcaccttt aattgacaga gatgcaacaa ggctatacac ccagagccat    16860
aggaggcacc ttgtggaatt tgttacatgg tccacacccc aactatatca cattttagct    16920
aagtccacag cactatctat gattgacctg gtaacaaaat ttgagaagga ccatatgaat    16980
gaaatttcag ctctcatagg ggatgacgat atcaatagtt tcataactga gtttctgctc    17040
atagagccaa gattattcac tatctacttg ggccagtgtg cggccatcaa ttgggcattt    17100
gatgtacatt atcatagacc atcagggaaa tatcagatgg gtgagctgtt gtcatcgttc    17160
ctttctagaa tgagcaaagg agtgtttaag gtgcttgtca atgctctaag ccacccaaag    17220
atctacaaga aattctggca ttgtggtatt atagagccta tccatggtcc ttcacttgat    17280
gctcaaaact tgcacacaac tgtgtgcaac atggttaca catgctatat gacctacctc    17340
gacctgttgt tgaatgaaga gttagaagag ttcacatttc tcttgtgtga aagcgacgag    17400
gatgtagtac cggacagatt cgacaacatc caggcaaaac acttatgtgt tctggcagat    17460
ttgtactgtc aaccagggac ctgcccacca attcgaggtc taagaccggt agagaaatgt    17520
gcagttctaa ccgaccatat caaggcagag gctatgttat ctccagcagg atcttcgtgg    17580
aacataaatc caattattgt agaccattac tcatgctctc tgacttatct ccggcgagga    17640
tcgatcaaac agataagatt gagagttgat ccaggattca ttttcgacgc cctcgctgag    17700
gtaaatgtca gtcagccaaa gatcggcagc aacaacatct caaatatgag catcaaggct    17760
```

```
ttcagacccc cacacgatga tgttgcaaaa ttgctcaaag atatcaacac aagcaagcac    17820
aatcttccca tttcaggggg caatctcgcc aattatgaaa tccatgcttt ccgcagaatc    17880
gggttgaact catctgcttg ctacaaagct gttgagatat caacattaat taggagatgc    17940
cttgagccag gggaggacgg cttgttcttg ggtgagggat cgggttctat gttgatcact    18000
tataaagaga tacttaaact aaacaagtgc ttctataata gtggggtttc cgccaattct    18060
agatctggtc aaagggaatt agcaccctat ccctccgaag ttggccttgt cgaacacaga    18120
atgggagtag gtaatattgt caaagtgctc tttaacggga ggcccgaagt cacgtgggta    18180
ggcagtgtag attgcttcaa tttcatagtt agtaatatcc ctacctctag tgtgggggttt   18240 atccattcag atatagagac cttgcctgac aaagatacta tagagaagct agaggaattg    18300
gcagccatct tatcgatggc tctgctcctg ggcaaaatag gatcaatact ggtgattaag    18360
cttatgcctt tcagcgggga ttttgttcag ggatttataa gttatgtagg gtctcattat    18420
agagaagtga accttgtata ccctagatac agcaacttca tctctactga atcttatttg    18480
gttatgacag atctcaaggc taaccggcta atgaatcctg aaaagattaa gcagcagata    18540
attgaatcat ctgtgaggac ttcacctgga cttataggtc acatcctatc cattaagcaa    18600
ctaagctgca tacaagcaat tgtgggagac gcagttagta gaggtgatat caatcctact    18660
ctgaaaaaac ttacacctat agagcaggtg ctgatcaatt gcgggttggc aattaacgga    18720
cctaagctgt gcaaagaatt gatccaccat gatgttgcct cagggcaaga tggattgctt    18780
aattctatac tcatcctcta cagggagttg gcaagattca aagacaacca aagaagtcaa    18840
caagggatgt tccacgctta ccccgtattg gtaagtagca ggcaacgaga acttatatct    18900
aggatcaccc gcaaattctg ggggcacatt cttctttact ccgggaacaa aaagttgata    18960
aataagttta tccagaatct caagtccggc tatctgatac tagacttaca ccagaatatc    19020
ttcgttaaga atctatccaa gtcagagaaa cagattatta tgacgggggg tttgaaacgt    19080
gagtgggttt ttaaggtaac agtcaaggag accaaagaat ggtataagtt agtcggatac    19140
agtgccctga ttaaggacta attggttgaa ctccggaacc ctaatcctgc cctaggtggt    19200
taggcattat ttgcaatata ttaaagaaaa cttttgaaaat acgaagtttc tattcccagc    19260
tttgtctggt ggccggcatg gtcccagcct cctcgctggc gccggctggg caacattccg    19320
aggggaccgt ccccctcggta atggcgaatg ggacgcggcc gatccggctg ctaacaaagc    19380
ccgaaaggaa gctgagttgg ctgctgccac cgctgagcaa taactagcat aaccccttgg    19440
ggcctctaaa cgggtcttga gggggttttt tgctgaaagga ggaactatat ccggatgcgg    19500
ccgcgggccc tatggtaccc agcttttgtt ccctttagtg agggttaatt ccgagcttgg    19560
cgtaatcatg gtcatagctg tttcctgtgt gaaattgtta tccgctcaca attccacaca    19620
acataggagc cggaagcata aagtgtaaag cctggggtgc ctaatgagtg aggtaactca    19680
cattaattgc gttgcgctca ctgcccgctt tccagtcggg aaacctgtcg tgccagctgc    19740
attaatgaat cggccaacgc gcggggagag gcggtttgcg tattgggcgc tcttccgctt    19800
cctcgctcac tgactcgctg cgctcggtcg ttcggctgcg gcgagcggta tcagctcact    19860
caaaggcggt aatacggtta tccacagaat caggggataa cgcaggaaag aacatgtgag    19920
caaaaggcca gcaaaaggcc aggaaccgta aaaaggccgc gttgctggcg ttttttccata    19980 ggctcggccc ccctgacgag catcacaaaa atcgacgctc aagtcagagg tggcgaaacc    20040
cgacaggact ataaagatac caggcgttcc cccctggaag ctccctcgtg cgctctcctg    20100
```

```
ttccgaccct gccgcttacc ggatacctgt ccgcctttct cccttcggga agcgtggcgc   20160
tttctcaatg ctcacgctgt aggtatctca gttcggtgta ggtcgttcgc tccaagctgg   20220
gctgtgtgca cgaaccccccc gttcagcccg accgctgcgc cttatccggt aactatcgtc   20280
ttgagtccaa cccggtaaga cacgacttat cgccactggc agcagccact ggtaacagga   20340
ttagcagagc gaggtatgta ggcggtgcta cagagttctt gaagtggtgg cctaactacg   20400
gctacactag aaggacagta tttggtatct gcgctctgct gaagccagtt accttcggaa   20460
aaagagttgg tagctcttga tccggcaaac aaaccaccgc tggtagcggt ggtttttttg   20520
tttgcaagca gcagattacg cgcagaaaaa aaggatctca agaagatcct ttgatctttt   20580
ctacggggtc tgacgctcag tggaacgaaa actcacgtta agggattttg gtcatgagat   20640
tatcaaaaag gatcttcacc tagatccttt taaattaaaa atgaagtttt aaatcaatct   20700
aaagtatata tgagtaaact tggtctgaca gttaccaatg cttaatcagt gaggcaccta   20760
tctcagcgat ctgtctattt cgttcatcca tagttgcctg actgcccgtc gtgtagataa   20820
ctacgatacg ggagggctta ccatctggcc ccagtgctgc aatgataccg cgagacccac   20880
gctcaccggc tccagattta tcagcaataa accagccagc cggaagggcc gagcgcagaa   20940
gtggtcctgc aactttatcc gcctccatcc agtctattaa ttgttgccgg gaagctagag   21000
taagtagttc gccagttaat agtttgcgca acgttgttgc cattgctaca ggcatcgtgg   21060
tgtcacgctc gtcgtttggt atggcttcat tcagctccgg ttcccaacga tcaaggcgag   21120
ttacatgatc ccccatgttg tgaaaaaaag cggttagctc cttcggtcct ccgatcgttg   21180
tcagaagtaa gttggccgca gtgttatcac tcatgcttat ggcagcactg cataattctc   21240
ttactgtcat gccatccgta agatgctttt ctgtgactgg tgagtactca accaagtcat   21300
tctgagaata gtgtatgcgg cgaccgagtt gctcttgccc ggcgtcaata cgggataata   21360
ccgcgccaca tagcagaact ttaaaagtgc tcatcattgg aaaacgttct cgggggcgaa   21420
aactctcaag gatcttaccg ctgttgagat ccagttcgat gtaacccact cgtgcaccca   21480
actgatcttc agcatctttt actttcacca gcgtttctgg gtgagcaaaa acaggaaggc   21540
aaaatgccgc aaaaaaggga ataagggcga cacggaaatg ttgaatactc atactcttcc   21600 ttttcaata ttattgaagc atttatcagg gttattgtct catgagcgga tacatatttg   21660
aatgtattta gaaaaataaa caaataggggg ttccgcgcac atttccccga aaagtgccac   21720
ctgaaattgt aaacgttaat attttgttaa aattcgcgtt aaatttttgt taaatcagct   21780 catttttaa ccaataggcc gaaatcggca aaatccctta taaatcaaaa gaatagaccg   21840
agatagggtt gagtgttgtt ccagtttgga acaagagtcc actattaaag aacgtggact   21900
ccaacgtcaa agggcgaaaa accgtctatc agggcgatgg cccactacgt gaaccatcac   21960
cctaatcaag ttttttgggg tcgaggtgcc gtaaagcact aaatcggaac cctaaaggga   22020 gccccccgatt tagagcttga cggggaaagc cggcgaacgt ggcgagaaag gaagggaaga   22080
aagcgaaagg agcgggcgct agggcgctgg caagtgtagc ggtcacgctg cgcgtaacca   22140
ccacacccgc cgcgcttaat gcgccgctac agggcgcgtc ccattcgcca ttcaggctgc   22200
gcaactgttg ggaagggcga tcggtgcggg cctcttcgct attacgccag ccaccgcggt   22260
g                                                                   22261
```

<210> SEQ ID NO 143
<211> LENGTH: 22363
<212> TYPE: DNA
<213> ORGANISM: Artificial Sequence

```
<220> FEATURE:
<223> OTHER INFORMATION: Complete optimised nucleotide sequence of the
      polynucleotide encoding pTM-MVDVax10
<220> FEATURE:
<221> NAME/KEY: misc_feature
<222> LOCATION: (1)..(8)
<223> OTHER INFORMATION: NotI
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammerhead ribozyme
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1768)..(1888)
<223> OTHER INFORMATION: MV N-P intergenic
<220> FEATURE:
<221> NAME/KEY: misc_feature
<222> LOCATION: (1889)..(3412)
<223> OTHER INFORMATION: MV P ORF
<220> FEATURE:
<221> NAME/KEY: misc_feature
<222> LOCATION: (3413)..(3531)
<223> OTHER INFORMATION: MV ATU2
<220> FEATURE:
<221> NAME/KEY: misc_feature
<222> LOCATION: (3532)..(5154)
<223> OTHER INFORMATION: DENV1 NS polyepitope
<220> FEATURE:
<221> NAME/KEY: misc_feature
<222> LOCATION: (5155)..(5253)
<223> OTHER INFORMATION: MV P-M intergenic
<220> FEATURE:
<221> NAME/KEY: misc_feature
<222> LOCATION: (5254)..(6261)
<223> OTHER INFORMATION: MV M ORF
<220> FEATURE:
<221> NAME/KEY: misc_feature
<222> LOCATION: (6262)..(7264)
<223> OTHER INFORMATION: MV M-F intergenic
<220> FEATURE:
<221> NAME/KEY: misc_feature
<222> LOCATION: (7265)..(8926)
<223> OTHER INFORMATION: MV F ORF
<220> FEATURE:
<221> NAME/KEY: misc_feature
<222> LOCATION: (8927)..(9086)
<223> OTHER INFORMATION: MV-F-H intergenic
<220> FEATURE:
<221> NAME/KEY: misc_feature
<222> LOCATION: (9087)..(10940)
<223> OTHER INFORMATION: MV H ORF
<220> FEATURE:
<221> NAME/KEY: misc_feature
<222> LOCATION: (10941)..(11067)
<223> OTHER INFORMATION: MV ATU3
<220> FEATURE:
<221> NAME/KEY: misc_feature
<222> LOCATION: (11068)..(12618)
<223> OTHER INFORMATION: DENV tetra EDIII + ectoM
<220> FEATURE:
<221> NAME/KEY: misc_feature
<222> LOCATION: (12619)..(12711)
<223> OTHER INFORMATION: MV H-L intergenic
<220> FEATURE:
<221> NAME/KEY: misc_feature
<222> LOCATION: (12712)..(19263)
<223> OTHER INFORMATION: MV L ORF

```
<220> FEATURE:
<221> NAME/KEY: misc_feature
<222> LOCATION: (19264)..(19372)
<223> OTHER INFORMATION: MV Trailer
<220> FEATURE:
<221> NAME/KEY: misc_feature
<222> LOCATION: (19373)..(19456)
<223> OTHER INFORMATION: HDV ribozyme
<220> FEATURE:
<221> NAME/KEY: misc_feature
<222> LOCATION: (19457)..(19598)
<223> OTHER INFORMATION: T7 terminator
<220> FEATURE:
<221> NAME/KEY: misc_feature
<222> LOCATION: (19599)..(19606)
<223> OTHER INFORMATION: Not I
<220> FEATURE:
<221> NAME/KEY: misc_feature
<222> LOCATION: (19607)..(122363)
<223> OTHER INFORMATION: pTM plasmid

<400> SEQUENCE: 143
```

| | | | | |
|---|---|---|---|---|
| gcggccgcta | atacgactca | ctatagggcc | aactttgttt | ggtctgatga | gtccgtgagg | 60 |
| acgaaacccg | gagtcccggg | tcaccaaaca | aagttgggta | aggatagttc | aatcaatgat | 120 |
| catcttctag | tgcacttagg | attcaagatc | ctattatcag | ggacaagagc | aggattaggg | 180 |
| atatccgaga | tggccacact | tttaaggagc | ttagcattgt | tcaaaagaaa | caaggacaaa | 240 |
| ccacccatta | catcaggatc | cggtggagcc | atcagaggaa | tcaaacacat | tattatagta | 300 |
| ccaatccctg | agattcctc | aattaccact | cgatccagac | ttctggaccg | gttggtgagg | 360 |
| ttaattggaa | acccggatgt | gagcgggccc | aaactaacag | gggcactaat | aggtatatta | 420 |
| tccttatttg | tggagtctcc | aggtcaattg | attcagagga | tcaccgatga | ccctgacgtt | 480 |
| agcataaggc | tgttagaggt | tgtccagagt | gaccagtcac | aatctggcct | taccttcgca | 540 |
| tcaagaggta | ccaacatgga | ggatgaggcg | gaccaatact | tttcacatga | tgatccaatt | 600 |
| agtagtgatc | aatccaggtt | cggatggttc | gggaacaagg | aaatctcaga | tattgaagtg | 660 |
| caagaccctg | agggattcaa | catgattctg | ggtaccatcc | tagcccaaat | ttgggtcttg | 720 |
| ctcgcaaagg | cggttacggc | cccagacacg | gcagctgatt | cggagctaag | aaggtggata | 780 |
| aagtacaccc | aacaaagaag | ggtagttggt | gaatttagat | tggagagaaa | atggttggat | 840 |
| gtggtgagga | acaggattgc | cgaggacctc | tccttacgcc | gattcatggt | cgctctaatc | 900 |
| ctggatatca | agagaacacc | cggaaacaaa | cccaggattg | ctgaaatgat | atgtgacatt | 960 |
| gatacatata | tcgtagaggc | aggattagcc | agttttatcc | tgactattaa | gtttgggata | 1020 |
| gaaactatgt | atcctgctct | tggactgcat | gaatttgctg | gtgagttatc | cacacttgag | 1080 |
| tccttgatga | acctttacca | gcaaatgggg | gaaactgcac | cctacatggt | aatcctggag | 1140 |
| aactcaattc | agaacaagtt | cagtgcagga | tcataccctc | tgctctggag | ctatgccatg | 1200 |
| ggagtaggag | tggaacttga | aaactccatg | ggaggtttga | actttggccg | atcttacttt | 1260 |
| gatccagcat | attttagatt | agggcaagag | atggtaagga | ggtcagctgg | aaaggtcagt | 1320 |
| tccacattgg | catctgaact | cggtatcact | gccgaggatg | caaggcttgt | ttcagagatt | 1380 |
| gcaatgcata | ctactgagga | caagatcagt | agagcggttg | gacccagaca | agcccaagta | 1440 |
| tcatttctac | acggtgatca | aagtgagaat | gagctaccga | gattgggggg | caaggaagat | 1500 |
| aggagggtca | acagagtcg | aggagaagcc | agggagagct | acagagaaac | cgggcccagc | 1560 |
| agagcaagtg | atgcgagagc | tgcccatctt | ccaaccggca | caccctaga | cattgacact | 1620 |
| gcaacggagt | ccagccaaga | tccgcaggac | agtcgaaggt | cagctgacgc | cctgcttagg | 1680 |

```
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat ggagccaatg gcagaagag caggcacgcc atgtcaaaaa    1920
cggactggaa tgcatccggg ctctcaaggc cgagcccatc ggctcactgg ccatcgagga   1980
agctatggca gcatggtcag aaatatcaga aacccaggga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atccccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca gggcttctga tgttgaaact gcagaaggag gggagatcca   2460
cgagctcctg agactccaat ccagaggcaa caactttccg aagcttggga aaactctcaa   2520
tgttcctccg cccccggacc ccggtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg gaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata taatgaagt agctacagct   3420
caacttacct gccaaccca tgccagtcga cccaactagc ctaccctcca tcattgttat   3480
aaaaaactta ggaaccaggt ccacacagcc gccagcccat caacgcgtac gatggcatca   3540
caggagggac cactgcccga aattgaggac gaagtgttta gaaagcgaaa tctgactatt   3600
atggacctgc accccggatc tggcaagacc cggagatacc tgccagccat cgtgagggag   3660
gctattaagc ggaaactgag aacactgatc ctggccccaa ctcgcgtggt cgcttccgaa   3720
atggctgagg ccctgaaagg catgcccatc cggtatcaga ccacagcagt gaagtctgaa   3780
cataccggca aggagattgt ggacctgatg tgccacgcca ctttcaccat cgactgctg   3840
agcccagtgc gggtccccaa ctacaatatg atcattatgg acgaggccca ctttactgat   3900
cccagctcca tcgccgctag aggatatatt tccaccaggg tgggaatggg cgaggcagca   3960
gctatcttca tgacagcaac tccccctggc agcgtggagg catttcctca gtccaacgcc   4020
gtcatccagg acgaggagcg ggacattcct gagcggagct ggaattctgg gtacgaatgg   4080
```

```
atcacagacg aggatcatgc acactggact gaagccaaga tgctgctgga caacattaat    4140
actcctgagg gaatcattcc agctctgttc gagcccgaaa gagagaagtc tgcagccatc    4200
gacggcgagt atagactgag gggagaggcc cggaagacct tcgtggaact gatgaggcgc    4260
ggcgatctgc ccgtgtggct gagttacaag gtcgcttcag agggattcca gtatagtgac    4320
cgacggtggt gctttgatgg cgaacgcaac aatcaggtgc tggaggagaa catggatgtc    4380
gagatttgga caaggaagg cgagcggaag aaactgcgcc cacgatggct ggacgctcgg    4440
acttacagcg atccctggc actgagagaa ttcaaagagt tgctgcagg ggtggccgtc    4500
gagaatcacc atcacgccgc tatgctggac gtggatctgc atcctgccag tgcttggacc    4560
ctgtatgcag tggccactac catcattacc ccaatgatgc gccacacaat cgagaacaca    4620
actgccaata tctcactgac agctattgca aaccaggcag ccattctgat gggactggac    4680
aaaggctggc ccatcagcaa gatggatatt ggcgtgcctc tgctggccct ggggtgttac    4740
agtcaggtgc tggacatcat tggccagagg atcgagaaca ttaagcatga gcacaaatca    4800
acctggcatt acgacgaaga taatccctat aagacatggg cctaccacgg aagctatgag    4860
gtgaaaccett caggcagcgc cagcagcatg gtcaacgggg tggtcaagct gctgaccaaa    4920
ccttgggacg tgatcccaat ggtcactcag attgccatga ccgataccac cccattcggc    4980
cagcagcggt tgttcaagga gaaggtggac acccgcacac ctaaggctaa acgagggact    5040
gcacagatca tggaggtgac cgccaagtgg ctgtggggat tcctgtccag gaacaagaag    5100
ccaagaatct gtaccaggga agagttcaca agaaaggtcc ggtcaaacgc taatgagcg    5160
cgcagcgctt agacgtctcg cgatcgatac tagtacaacc taaatccatt ataaaaaact    5220
taggagcaaa gtgattgcct cccaaggtcc acaatgacag agacctacga cttcgacaag    5280
tcggcatggg acatcaaagg gtcgatcgct ccgatacaac ccaccaccta cagtgatggc    5340
aggctggtgc cccaggtcag agtcatagat cctggtctag cgacaggaa ggatgaatgc    5400
tttatgtaca tgtttctgct ggggggttgtt gaggacagcg attccctagg gcctccaatc    5460
gggcgagcat ttgggttcct gcccttaggt gttggcagat ccacagcaaa gcccgaaaaa    5520
ctcctcaaag aggccactga gcttgacata gttgttagc gtacagcagg gctcaatgaa    5580
aaactggtgt tctacaacaa caccccacta actctcctca cccttggag aaaggtccta    5640
acaacaggga gtgtcttcaa cgcaaaccaa gtgtgcaatg cggttaatct gataccgctc    5700
gataccccgc agaggttccg tgttgtttat atgagcatca cccgtctttc ggataacggg    5760
tattacaccg ttcctagaag aatgctggaa ttcagatcgg tcaatgcagt ggccttcaac    5820
ctgctggtga cccttaggat tgacaaggcg ataggccctg ggaagatcat cgacaataca    5880
gagcaacttc ctgaggcaac atttatggtc cacatcggga acttcaggag aaagaagagt    5940
gaagtctact ctgccgatta ttgcaaaatg aaaatcgaaa agatgggcct ggttttttgca    6000
cttggtggga taggggcac cagtcttcac attagaagca caggcaaaat gagcaagact    6060
ctccatgcac aactcgggtt caagaagacc ttatgttacc cgctgatgga tatcaatgaa    6120
gaccttaatc gattactctg gaggagcaga tgcaagatag taagaatcca ggcagttttg    6180
cagccatcag ttcctcaaga attccgcatt tacgacgacg tgatcataaa tgatgaccaa    6240
ggactattca aagttctgta gaccgtagtg cccagcaatg cccgaaaacg accccctcta    6300
caatgacagc cagaaggccc ggacaaaaaa gcccctccg aaagactcca cggaccaagc    6360
gagaggccag ccagcagccg acggcaagcg cgaacaccag gcggcccag cacagaacag    6420
```

```
ccctgacaca aggccaccac cagccacccc aatctgcatc ctcctcgtgg gaccccgag    6480
gaccaacccc caaggctgcc cccgatccaa accaccaacc gcatccccac cacccccggg    6540
aaagaaaccc ccagcaattg aaggcccct ccccctcttc ctcaacacaa gaactccaca    6600
accgaaccgc acaagcgacc gaggtgaccc aaccgcaggc atccgactcc ctagacagat    6660
cctctctccc cggcaaacta acaaaaactt agggccaagg aacatacaca cccaacagaa    6720
cccagacccc ggcccacggc gccgcgcccc caaccccga caaccagagg gagcccccaa    6780
ccaatcccgc cggctccccc ggtgcccaca ggcagggaca ccaaccccg aacagaccca    6840
gcacccaacc atcgacaatc caagacgggg gggcccccc aaaaaaaggc cccaggggc    6900
cgacagccag caccgcgagg aagcccaccc accccacaca cgaccacggc aaccaaacca    6960
gaacccagac caccctgggc caccagctcc cagactcggc catcaccccg cagaaaggaa    7020
aggccacaac ccgcgcaccc cagccccgat ccggcgggga gccacccaac ccgaaccagc    7080
acccaagagc gatccccgaa ggaccccga accgcaaagg acatcagtat cccacagcct    7140
ctccaagtcc cccggtctcc tcctcttctc gaagggacca aaagatcaat ccaccacacc    7200
cgacgacact caactcccca cccctaaagg agacaccggg aatcccagaa tcaagactca    7260
tccaatgtcc atcatgggtc tcaaggtgaa cgtctctgcc atattcatgg cagtactgtt    7320
aactctccaa acaccaccg gtcaaatcca ttggggcaat ctctctaaga taggggtggt    7380
aggaatagga agtgcaagct acaaagttat gactcgttcc agccatcaat cattagtcat    7440
aaaattaatg cccaatataa ctctcctcaa taactgcacg agggtagaga ttgcagaata    7500
caggagacta ctgagaacag ttttggaacc aattagagat gcacttaatg caatgaccca    7560
gaatataaga ccggttcaga gtgtagcttc aagtaggaga cacaagagat ttgcgggagt    7620
agtcctggca ggtgcggccc taggcgttgc cacagctgct cagataacag ccggcattgc    7680
acttcaccag tccatgctga actctcaagc catcgacaat ctgagagcga gcctggaaac    7740
tactaatcag gcaattgaga caatcagaca agcagggcag gagatgatat tggctgttca    7800
gggtgtccaa gactacatca ataatgagct gataccgtct atgaaccaac tatcttgtga    7860
tttaatcggc cagaagctcg ggctcaaatt gctcagatac tatacagaaa tcctgtcatt    7920
atttggcccc agtttacggg accccatatc tgcggagata tctatccagg ctttgagcta    7980
tgcgcttgga ggagacatca ataaggtgtt agaaaagctc ggatacagtg gaggtgattt    8040
actgggcatc ttagagagcg gaggaataaa ggcccggata actcacgtcg acacagagtc    8100
ctacttcatt gtcctcagta tagcctatcc gacgctgtcc gagattaagg gggtgattgt    8160
ccaccggcta gaggggtct cgtacaacat aggctctcaa gagtggtata ccactgtgcc    8220
caagtatgtt gcaacccaag ggtaccttat ctcgaatttt gatgagtcat cgtgtactt    8280
catgccagag gggactgtgt gcagccaaaa tgccttgtac ccgatgagtc ctctgctcca    8340
agaatgcctc cgggggtaca ccaagtcctg tgctcgtaca ctcgtatccg ggtcttttgg    8400
gaaccggttc atttatcac aagggaacct aatagccaat tgtgcatcaa tcctttgcaa    8460
gtgttacaca acaggaacga tcattaatca agaccctgac aagatcctaa catacattgc    8520
tgccgatcac tgcccggtag tcgaggtgaa cggcgtgacc atccaagtcg ggagcaggag    8580
gtatccagac gctgtgtact tgcacagaat tgacctcggt cctcccatat cattggagag    8640
gttggacgta gggacaaatc tggggaatgc aattgctaag ttggaggatg ccaaggaatt    8700
gttggagtca tcggaccaga tattgaggag tatgaaggtt ttatcgagca ctagcatagt    8760
ctacatcctg attgcagtgt gtcttggagg gttgataggg atccccgctt taatatgttg    8820
```

```
ctgcaggggg cgttgtaaca aaaagggaga acaagttggt atgtcaagac caggcctaaa   8880
gcctgatctt acgggaacat caaaatccta tgtaaggtcg ctctgatcct ctacaactct   8940
tgaaacacaa atgtcccaca agtctcctct tcgtcatcaa gcaaccaccg cacccagcat   9000
caagcccacc tgaaattatc tccggcttcc ctctggccga acaatatcgg tagttaatca   9060
aaacttaggg tgcaagatca tccacaatgt caccacaacg agaccggata aatgccttct   9120
acaaagataa cccccatccc aagggaagta ggatagtcat taacagagaa catcttatga   9180
ttgatagacc ttatgttttg ctggctgttc tgtttgtcat gtttctgagc ttgatcgggt   9240
tgctagccat tgcaggcatt agacttcatc gggcagccat ctacaccgca gagatccata   9300
aaagcctcag caccaatcta gatgtaacta actcaatcga gcatcaggtc aaggacgtgc   9360
tgacaccact cttcaaaatc atcggtgatg aagtgggcct gaggacacct cagagattca   9420
ctgacctagt gaaattaatc tctgacaaga ttaaattcct taatccggat agggagtacg   9480
acttcagaga tctcacttgg tgtatcaacc cgccagagag aatcaaattg gattatgatc   9540
aatactgtgc agatgtggct gctgaagagc tcatgaatgc attggtgaac tcaactctac   9600
tggagaccag aacaaccaat cagttcctag ctgtctcaaa gggaaactgc tcagggccca   9660
ctacaatcag aggtcaattc tcaaacatgt cgctgtccct gttagacttg tatttaggtc   9720
gaggttacaa tgtgtcatct atagtcacta tgacatccca gggaatgtat ggggaactt    9780
acctagtgga aaagcctaat ctgagcagca aaggtcaga gttgtcacaa ctgagcatgt    9840
accgagtgtt tgaagtaggt gttatcagaa atccgggttt gggggctccg gtgttccata   9900
tgacaaacta tcttgagcaa ccagtcagta atgatctcag caactgtatg gtggctttgg   9960
gggagctcaa actcgcagcc ctttgtcacg gggaagattc tatcacaatt ccctatcagg  10020
gatcagggaa aggtgtcagc ttccagctcg tcaagctagg tgtctggaaa tccccaaccg  10080
acatgcaatc ctgggtcccc ttatcaacgg atgatccagt gatagacagg ctttacctct  10140
catctcacag aggtgttatc gctgacaatc aagcaaaatg gctgtcccg acaacacgaa   10200
cagatgacaa gttgcgaatg gagacatgct ccaacaggc gtgtaagggt aaaatccaag  10260
cactctgcga gaatcccgag tgggcaccat tgaaggataa caggattcct tcatacgggg  10320
tcttgtctgt tgatctgagt ctgacagttg agcttaaaat caaaattgct tcgggattcg  10380
ggccattgat cacacacggt tcaggatgg acctatacaa atccaaccac aacaatgtgt  10440
attggctgac tatcccgcca atgaagaacc tagccttagg tgtaatcaac acattggagt  10500
ggataccgag attcaaggtt agtccctacc tcttcactgt cccaattaag gaagcaggcg  10560
aagactgcca tgccccaaca tacctacctg cggaggtgga tggtgatgtc aaactcagtt  10620
ccaatcggt gattctacct ggtcaagatc tccaatatgt tttggcaacc tacgatactt  10680
ccagggttga acatgctgtg gtttattacg tttacagccc aagccgctca ttttcttact  10740
tttatccttt taggttgcct ataaaggggg tccccatcga attacaagtg gaatgcttca  10800
catgggacca aaaactctgg tgccgtcact tctgtgtgct tgcggactca gaatctggtg  10860
gacatatcac tcactctggg atggtgggca tgggagtcag ctgcacagtc acccgggaag  10920
atggaaccaa tcgcagatag ggctgctagt gaaccaatca catgatgtca cccagacatc  10980
aggcataccc actagtctac cctccatcat tgttataaaa aacttaggaa ccaggtccac  11040
acagccgcca gccatcaac gcgtacgatg ggcatcatat tcattcttct tatgctggtt   11100
acaccgtcta tggcggagaa acttcgaatc aaaggtatga gctatacgat gtgcagcggc  11160
```

```
aagttcaaga tcgagaagga aatggctgaa acccagcacg gtacaactgt ggtcaaagtc   11220
aaatatgagg gggctggcgc tccctgtaaa gtacccattg agattaggga cgtcaataaa   11280
gagaaggtgg taggtcgcat catctccagt acacctttgg ccgagaacac gaactccgtc   11340
acaaacatag agttggaacc cccgttcgga gactcataca ttgtgatcgg ggtgggcaac   11400
tctgcactca cactgcattg gttcaagaag ggaagcagta tcggccgcag ggataagaga   11460
gacaaactga aattgaaagg tatgtcctat gccatgtgca cgaatacttt cgttctcaag   11520
aaagaagtat ctgagactca gcacggaacc atcctgatca aagtcgagta caaaggagaa   11580
gacgtgccct gtaagatccc attcagtacc gaggatggac agggcaaggc cataacggc    11640 aggctgataa ccgccaaccc tgtggttaca aagaaggaag agccagtcaa tatcgaagct   11700
gagccaccgt tcggggagag caacatagta attggcatag gggataatgc tttgaagatc   11760
aactggtaca agaaaggaag ctccattggc cgaagagata gcgcgacaa actccagctg    11820 aaaggaatga gctactccat gtgtactggg aagttcaaga ttgtcaagga aatcgccgaa   11880
actcagcatg gcactattgt gatccgcgtg cagtatgaag gcgatggtag cccctgcaag   11940
ataccatttg aaatcaccga tttggagaaa cggcacgtcc tgggtcggct cattaccgtg   12000
aacccaatcg tgaccgagaa ggacagtcca gttaatatcg aggccgagcc tcctttcggc   12060
gacagttaca tcattgtagg ggtggaacca gggcaactga agctgaactg gttcaagaaa   12120
ggcagcagta taggacggcg ggataaacgg gacaaactca cactgaaagg catgtcatac   12180
gttatgtgca ccggctcatt caaactggag aaggaagttg cagagacaca gcatgggacc   12240
gtgctcgtgc aggtcaaata cgagggcacc gacgctcctt gcaagattcc gttcagtaca   12300
caggacgaga aaggcgtgac tcagaacggc agattgatta cagcgaaccc tatcgtgact   12360
gacaaggaga agccagttaa catcgagact gagccgcctt tcggagaatc atacattatc   12420
gtgggagccg gcgagaaggc actgaaactc agctggttca agaagggcag ctcaatcggt   12480
cggagagaca agcggtctgt cgccctcgca ccgcacgtgg gcctgggtct ggaaacgagg   12540
accgagacgt ggatgagttc cgaaggcgca tggaagcaaa tccagaaagt ggagacgtgg   12600
gccctcaggc atccgtaatg agcgcgcagc gcttagacgt ctcgcgatcg atgctagtgt   12660
gaaatagaca tcagaattaa gaaaaacgta gggtccaagt ggttcccgt tatggactcg    12720 ctatctgtca accagatctt ataccctgaa gttcacctag atagcccgat agttaccaat   12780
aagatagtag ccatcctgga gtatgctcga gtccctcacg cttacagcct ggaggaccct   12840
acactgtgtc agaacatcaa gcaccgccta aaaaacggat tttccaacca aatgattata   12900
aacaatgtgg aagttgggaa tgtcatcaag tccaagctta ggagttatcc ggcccactct   12960
catattccat atccaaattg taatcaggat ttatttaaca tagaagacaa agagtcaacg   13020
aggaagatcc gtgaactcct caaaaagggg aattcgctgt actccaaagt cagtgataag   13080
gttttccaat gcttaaggga cactaactca cggcttggcc taggctccga attgagggag   13140
gacatcaagg agaaagttat taacttggga gtttacatgc acagctccca gtggtttgag   13200 cccttttctgt tttggtttac agtcaagact gagatgaggt cagtgattaa atcacaaacc   13260
catacttgcc ataggaggag acacacacct gtattcttca ctggtagttc agttgagttg   13320
ctaatctctc gtgaccttgt tgctataatc agtaaagagt ctcaacatgt atattacctg   13380
acatttgaac tggttttgat gtattgtgat gtcatagagg ggaggttaat gacagagacc   13440
gctatgacta ttgatgctag gtatacagag cttctaggaa gagtcagata catgtggaaa   13500
ctgatagatg gtttcttccc tgcactcggg aatccaactt atcaaattgt agccatgctg   13560
```

```
gagcctcttt cacttgctta cctgcagctg agggatataa cagtagaact cagaggtgct   13620
ttccttaacc actgctttac tgaaatacat gatgttcttg accaaaacgg gttttctgat   13680
gaaggtactt atcatgagtt aactgaagct ctagattaca ttttcataac tgatgacata   13740
catctgacag gggagatttt ctcattttc agaagtttcg gccacccag acttgaagca     13800 gtaacggctg ctgaaaatgt taggaaatac atgaatcagc ctaaagtcat tgtgtatgag   13860
actctgatga aaggtcatgc catatttgt ggaatcataa tcaacggcta tcgtgacagg    13920
cacggaggca gttggccacc gctgaccctc ccctgcatg ctgcagacac aatccggaat    13980
gctcaagctt caggtgaagg gttaacacat gagcagtgcg ttgataactg gaaatctttt   14040
gctggagtga aatttggctg ctttatgcct cttagcctgg atagtgatct gacaatgtac   14100
ctaaaggaca aggcacttgc tgctctccaa agggaatggg attcagttta cccgaaagag   14160
ttcctgcgtt acgaccctcc caagggaacc gggtcacgga ggcttgtaga tgttttcctt   14220
aatgattcga gctttgaccc atatgatgtg ataatgtatg ttgtaagtgg agcttacctc   14280
catgaccctg agttcaacct gtcttacagc ctgaaagaaa aggagatcaa ggaaacaggt   14340
agactttttg ctaaaatgac ttacaaaatg agggcatgcc aagtgattgc tgaaaatcta   14400
atctcaaacg ggattggcaa atattttaag acaatgggga tggccaagga tgagcacgat   14460
ttgactaagg cactccacac tctagctgtc tcaggagtcc ccaaagatct caaagaaagt   14520
cacagggggg ggccagtctt aaaaacctac tcccgaagcc cagtccacac aagtaccagg   14580
aacgtgagag cagcaaaagg gtttataggg ttccctcaag taattcggca ggaccaagac   14640
actgatcatc cggagaatat ggaagcttac gagacagtca gtgcatttat cacgactgat   14700
ctcaagaagt actgccttaa ttggagatat gagaccatca gcttgtttgc acagaggcta   14760
aatgagattt acggattgcc ctcattttc cagtggctgc ataagaggct tgagacctct    14820
gtcctgtatg taagtgaccc tcattgcccc cccgaccttg acgcccatat cccgttatat   14880
aaagtcccca atgatcaaat cttcattaag taccctatgg gaggtataga agggtattgt   14940
cagaagctgt ggaccatcag caccattccc tatctatacc tggctgctta tgagagcgga   15000
gtaaggattg cttcgttagt gcaaggggac aatcagacca tagccgtaac aaaaagggta   15060
cccagcacat ggccctacaa ccttaagaaa cgggaagctg ctagagtaac tagagattac   15120
tttgtaattc ttaggcaaag gctacatgat attggccatc acctcaaggc aaatgagaca   15180
attgtttcat cacattttt tgtctattca aaaggaatat attatgatgg gctacttgtg   15240
tcccaatcac tcaagagcat cgcaagatgt gtattctggt cagagactat agttgatgaa   15300
acaagggcag catgcagtaa tattgctaca acaatggcta aaagcatcga gagaggttat   15360
gaccgttacc ttgcatattc cctgaacgtc ctaaaagtga tacagcaaat tctgatctct   15420
cttggcttca caatcaattc aaccatgacc cgggatgtag tcatacccct cctcacaaac   15480
aacgacctct taataaggat ggcactgttg cccgctccta ttgggggat gaattatctg    15540 aatatgagca ggctgtttgt cagaaacatc ggtgatccag taacatcatc aattgctgat   15600
ctcaagagaa tgattctcgc ctcactaatg cctgaagaga ccctccatca agtaatgaca   15660
caacaaccgg gggactcttc attcctagac tgggctagcg acccttactc agcaaatctt   15720
gtatgtgtcc agagcatcac tagactcctc aagaacataa ctgcaaggtt tgtcctgatc   15780
catagtccaa acccaatgtt aaaaggatta ttccatgatg acagtaaaga agaggacgag   15840
ggactggcgg cattcctcat ggacaggcat attatagtac ctagggcagc tcatgaaatc   15900
```

```
ctggatcata gtgtcacagg ggcaagagag tctattgcag gcatgctgga taccacaaaa   15960
ggcttgattc gagccagcat gaggaagggg gggttaacct ctcgagtgat aaccagattg   16020
tccaattatg actatgaaca attcagagca gggatggtgc tattgacagg aagaaagaga   16080
aatgtcctca ttgacaaaga gtcatgttca gtgcagctgg cgagagctct aagaagccat   16140
atgtgggcga ggctagctcg aggacggcct atttacggcc ttgaggtccc tgatgtacta   16200
gaatctatgc gaggccacct tattcggcgt catgagacat gtgtcatctg cgagtgtgga   16260
tcagtcaact acggatggtt ttttgtcccc tcgggttgcc aactggatga tattgacaag   16320
gaaacatcat ccttgagagt cccatatatt ggttctacca ctgatgagag aacagacatg   16380
aagcttgcct tcgtaagagc cccaagtcga tccttgcgat ctgctgttag aatagcaaca   16440
gtgtactcat gggcttacgg tgatgatgat agctcttgga acgaagcctg gttgttggct   16500
aggcaaaggg ccaatgtgag cctggaggag ctaagggtga tcactcccat ctcaacttcg   16560
actaatttag cgcataggtt gagggatcgt agcactcaag tgaaatactc aggtacatcc   16620
cttgtccgag tggcgaggta taccacaatc tccaacgaca atctctcatt tgtcatatca   16680
gataagaagg ttgatactaa ctttatatac caacaaggaa tgcttctagg gttgggtgtt   16740
ttagaaacat tgtttcgact cgagaaagat accggatcat ctaacacggt attacatctt   16800
cacgtcgaaa cagattgttg cgtgatcccg atgatagatc atcccaggat acccagctcc   16860
cgcaagctag agctgagggc agagctatgt accaacccat tgatatatga taatgcacct   16920
ttaattgaca gagatgcaac aaggctatac acccagagcc ataggaggca ccttgtggaa   16980
tttgttacat ggtccacacc ccaactatat cacattttag ctaagtccac agcactatct   17040
atgattgacc tggtaacaaa atttgagaag gaccatatga atgaaatttc agctctcata   17100
ggggatgacg atatcaatag tttcataact gagtttctgc tcatagagcc aagattattc   17160
actatctact tgggccagtg tgcggccatc aattgggcat ttgatgtaca ttatcataga   17220
ccatcaggga aatatcagat gggtgagctg ttgtcatcgt tccttctag aatgagcaaa   17280 ggagtgttta aggtgcttgt caatgctcta agccacccaa agatctacaa gaaattctgg   17340
cattgtggta ttatagagcc tatccatggt ccttcacttg atgctcaaaa cttgcacaca   17400
actgtgtgca acatggttta cacatgctat atgacctacc tcgacctgtt gttgaatgaa   17460
gagttagaag agttcacatt tctcttgtgt gaaagcgacg aggatgtagt accggacaga   17520
ttcgacaaca tccaggcaaa acacttatgt gttctggcag atttgtactg tcaaccaggg   17580
acctgcccac caattcgagg tctaagaccg gtagagaaat gtgcagttct aaccgaccat   17640
atcaaggcag aggctatgtt atctccagca ggatcttcgt ggaacataaa tccaattatt   17700
gtagaccatt actcatgctc tctgacttat ctccggcgag gatcgatcaa acagataaga   17760
ttgagagttg atccaggatt catttttcgac gccctcgctg aggtaaatgt cagtcagcca   17820
aagatcggca gcaacaacat ctcaaatatg agcatcaagg ctttcagacc cccacacgat   17880
gatgttgcaa aattgctcaa agatatcaac acaagcaagc acaatcttcc catttcaggg   17940
ggcaatctcg ccaattatga aatccatgct ttccgcagaa tcgggttgaa ctcatctgct   18000
tgctacaaag ctgttgagat atcaacatta attaggagat gccttgagcc aggggaggac   18060
ggcttgttct tgggtgaggg atcgggttct atgttgatca cttataaaga gatacttaaa   18120
ctaaacaagt gcttctataa tagtgggggtt tccgccaatt ctagatctgg tcaaagggaa   18180
ttagcaccct atccctccga agttggcctt gtcgaacaca gaatgggagt aggtaatatt   18240
gtcaaagtgc tctttaacgg gaggcccgaa gtcacgtggg taggcagtgt agattgcttc   18300
```

```
aatttcatag ttagtaatat ccctacctct agtgtggggt ttatccattc agatatagag   18360
accttgcctg acaaagatac tatagagaag ctagaggaat tggcagccat cttatcgatg   18420
gctctgctcc tgggcaaaat aggatcaata ctggtgatta agcttatgcc tttcagcggg   18480
gattttgttc agggatttat aagttatgta gggtctcatt atagagaagt gaaccttgta   18540
taccctagat acagcaactt catctctact gaatcttatt tggttatgac agatctcaag   18600
gctaaccggc taatgaatcc tgaaaagatt aagcagcaga taattgaatc atctgtgagg   18660
acttcacctg gacttatagg tcacatccta tccattaagc aactaagctg catacaagca   18720
attgtgggag acgcagttag tagaggtgat atcaatccta ctctgaaaaa acttacacct   18780
atagagcagg tgctgatcaa ttgcgggttg gcaattaacg gacctaagct gtgcaaagaa   18840
ttgatccacc atgatgttgc ctcagggcaa gatggattgc ttaattctat actcatcctc   18900
tacagggagt tggcaagatt caaagacaac caaagaagtc aacaagggat gttccacgct   18960
taccccgtat tggtaagtag caggcaacga gaacttatat ctaggatcac ccgcaaattc   19020
tgggggcaca ttcttcttta ctccgggaac aaaaagttga taaataagtt tatccagaat   19080
ctcaagtccg gctatctgat actagactta caccagaata tcttcgttaa gaatctatcc   19140
aagtcagaga aacagattat tatgacgggg ggtttgaaac gtgagtgggt ttttaaggta   19200
acagtcaagg agaccaaaga atggtataag ttagtcggat acagtgccct gattaaggac   19260
taattggttg aactccggaa ccctaatcct gccctaggtg gttaggcatt atttgcaata   19320
tattaaagaa aactttgaaa atacgaagtt ctattccca gctttgtctg gtggccggca   19380
tggtcccagc ctcctcgctg gcgccggctg ggcaacattc gaggggacc gtcccctcgg   19440 taatggcgaa tgggacgcgg ccgatccggc tgctaacaaa gcccgaaagg aagctgagtt   19500
ggctgctgcc accgctgagc aataactagc ataaccccctt ggggcctcta aacgggtctt   19560
gaggggtttt ttgctgaaag gaggaactat atccggatgc ggccgcgggc cctatggtac   19620
ccagcttttg ttccctttag tgagggttaa ttccgagctt ggcgtaatca tggtcatagc   19680
tgtttcctgt gtgaaattgt tatccgctca caattccaca caacatagga gccggaagca   19740
taaagtgtaa agcctgggt gcctaatgag tgaggtaact cacattaatt gcgttgcgct   19800
cactgcccgc tttccagtcg ggaaacctgt cgtgccagct gcattaatga atcggccaac   19860 gcgcgggag aggcggtttg cgtattgggc gctcttccgc ttcctcgctc actgactcgc   19920
tgcgctcggt cgttcggctg cggcgagcgg tatcagctca ctcaaaggcg gtaatacggt   19980
tatccacaga atcaggggat aacgcaggaa agaacatgtg agcaaaaggc cagcaaaagg   20040
ccaggaaccg taaaaaggcc gcgttgctgg cgttttttcca taggctcggc cccctgacg   20100 agcatcacaa aaatcgacgc tcaagtcaga ggtggcgaaa cccgacagga ctataaagat   20160
accaggcgtt ccccctgga agctccctcg tgcgctctcc tgttccgacc ctgccgctta   20220
ccggatacct gtccgccttt ctcccttcgg aagcgtggc gctttctcaa tgctcacgct   20280
gtaggtatct cagttcggtg taggtcgttc gctccaagct gggctgtgtg cacgaacccc   20340
ccgttcagcc cgaccgctgc gccttatccg gtaactatcg tcttgagtcc aacccggtaa   20400
gacacgactt atcgccactg gcagcagcca ctggtaacag gattagcaga gcgaggtatg   20460
taggcggtgc tacagagttc ttgaagtggt ggcctaacta cggctacact agaaggacag   20520
tatttggtat ctgcgctctg ctgaagccag ttaccttcgg aaaaagagtt ggtagctctt   20580
gatccggcaa acaaaccacc gctggtagcg gtggtttttt tgtttgcaag cagcagatta   20640
```

```
cgcgcagaaa aaaaggatct caagaagatc ctttgatctt ttctacgggg tctgacgctc    20700
agtggaacga aaactcacgt taagggattt tggtcatgag attatcaaaa aggatcttca    20760
cctagatcct tttaaattaa aaatgaagtt ttaaatcaat ctaaagtata tatgagtaaa    20820
cttggtctga cagttaccaa tgcttaatca gtgaggcacc tatctcagcg atctgtctat    20880
ttcgttcatc catagttgcc tgactgcccg tcgtgtagat aactacgata cgggagggct    20940
taccatctgg ccccagtgct gcaatgatac cgcgagaccc acgctcaccg gctccagatt    21000
tatcagcaat aaaccagcca gccggaaggg ccgagcgcag aagtggtcct gcaactttat    21060
ccgcctccat ccagtctatt aattgttgcc gggaagctag agtaagtagt tcgccagtta    21120
atagtttgcg caacgttgtt gccattgcta caggcatcgt ggtgtcacgc tcgtcgtttg    21180
gtatggcttc attcagctcc ggttcccaac gatcaaggcg agttacatga tcccccatgt    21240
tgtgaaaaaa agcggttagc tccttcggtc ctccgatcgt tgtcagaagt aagttggccg    21300
cagtgttatc actcatgctt atggcagcac tgcataattc tcttactgtc atgccatccg    21360
taagatgctt ttctgtgact ggtgagtact caaccaagtc attctgagaa tagtgtatgc    21420
ggcgaccgag ttgctcttgc ccggcgtcaa tacgggataa taccgcgcca catagcagaa    21480
ctttaaaagt gctcatcatt ggaaaacgtt cttcggggcg aaaactctca aggatcttac    21540
cgctgttgag atccagttcg atgtaaccca ctcgtgcacc caactgatct tcagcatctt    21600
ttactttcac cagcgtttct gggtgagcaa aaacaggaag gcaaaatgcc gcaaaaaagg    21660
gaataagggc gacacggaaa tgttgaatac tcatactctt ccttttcaa tattattgaa    21720 gcatttatca gggttattgt ctcatgagcg gatacatatt tgaatgtatt tagaaaaata    21780
aacaaatagg ggttccgcgc acatttcccc gaaaagtgcc acctgaaatt gtaaacgtta    21840
atattttgtt aaaattcgcg ttaaattttt gttaaatcag ctcatttttt aaccaatagg    21900
ccgaaatcgg caaaatccct tataaatcaa agaatagac cgagataggg ttgagtgttg    21960
ttccagtttg gaacaagagt ccactattaa agaacgtgga ctccaacgtc aaagggcgaa    22020
aaaccgtcta tcagggcgat ggcccactac gtgaaccatc accctaatca agttttttgg    22080
ggtcgaggtg ccgtaaagca ctaaatcgga accctaaagg agcccccga tttagagctt    22140 gacggggaaa gccggcgaac gtggcgagaa aggaaggaa gaaagcgaaa ggagcgggcg    22200
ctagggcgct ggcaagtgta gcggtcacgc tgcgcgtaac caccacccc gccgcgctta    22260 atgcgccgct acagggcgcg tcccattcgc cattcaggct gcgcaactgt tgggaagggc    22320
gatcggtgcg ggcctcttcg ctattacgcc agccaccgcg gtg                     22363
```

<210> SEQ ID NO 144
<211> LENGTH: 1554
<212> TYPE: DNA
<213> ORGANISM: Artificial Sequence
<220> FEATURE:
<223> OTHER INFORMATION: Nucleotide sequence of the polynucleotide
      encoding DENV tetra EDIII-ectoM

<400> SEQUENCE: 144

```
atgggcatca tattcattct tcttatgctg gttacaccgt ctatggcgga gaaacttcga      60
atcaaaggta tgagctatac gatgtgcagc ggcaagttca gatcgagaa ggaaatggct     120 gaaacccagc acgtacaac tgtggtcaaa gtcaaatatg aggggctgg cgctccctgt     180 aaagtaccca ttgagattag ggacgtcaat aaagagaagg tggtaggtcg catcatctcc     240
agtacacctt tggccgagaa cacgaactcc gtcacaaaca tagagttgga accccgttc     300
```

```
ggagactcat acattgtgat cggggtgggc aactctgcac tcacactgca ttggttcaag    360
aagggaagca gtatcggccg cagggataag agagacaaac tgaaattgaa aggtatgtcc    420
tatgccatgt gcacgaatac tttcgttctc aagaagaag tatctgagac tcagcacgga     480
accatcctga tcaaagtcga gtacaaagga gaagacgtgc cctgtaagat cccattcagt    540
accgaggatg acagggcaa ggcccataac ggcaggctga taaccgccaa ccctgtggtt     600
acaaagaagg aagagccagt caatatcgaa gctgagccac cgttcgggga gagcaacata    660
gtaattggca tagggataa tgctttgaag atcaactggt acaagaaagg aagctccatt     720
ggccgaagag ataagcgcga caaactccag ctgaaaggaa tgagctactc catgtgtact    780
gggaagttca agattgtcaa ggaaatcgcc gaaactcagc atggcactat tgtgatccgc    840
gtgcagtatg aaggcgatgg tagcccctgc aagataccat ttgaaatcac cgatttggag    900
aaacggcacg tcctgggtcg gctcattacc gtgaacccaa tcgtgaccga aggacagt      960
ccagttaata tcgaggccga gcctcctttc ggcgacagtt acatcattgt aggggtggaa   1020
ccagggcaac tgaagctgaa ctggttcaag aaaggcagca gtataggacg gcgggataaa   1080
cgggacaaac tcacactgaa aggcatgtca tacgttatgt gcaccggctc attcaaactg   1140
gagaaggaag ttgcagagac acagcatggg accgtgctcg tgcaggtcaa atacgagggc   1200
accgacgctc cttgcaagat tccgttcagt acacaggacg agaaaggcgt gactcagaac   1260
ggcagattga ttcagcgaa ccctatcgtg actgacaagg agaagccagt taacatcgag    1320
actgagccgc ctttcggaga atcatacatt atcgtgggag ccggcgagaa ggcactgaaa   1380
ctcagctggt tcaagaaggg cagctcaatc ggtcggagag acaagcggtc tgtcgccctc   1440
gcaccgcacg tgggcctggg tctggaaacg aggaccgaga cgtggatgag ttccgaaggc   1500
gcatggaagc aaatccagaa agtggagacg tgggccctca ggcatccgta atga         1554
```

<210> SEQ ID NO 145
<211> LENGTH: 516
<212> TYPE: PRT
<213> ORGANISM: Artificial Sequence
<220> FEATURE:
<223> OTHER INFORMATION: Amino acid sequence of DENV tetra EDIII-ectoM

<400> SEQUENCE: 145

```
Met Gly Ile Ile Phe Ile Leu Leu Met Leu Val Thr Pro Ser Met Ala
1               5                   10                  15

Glu Lys Leu Arg Ile Lys Gly Met Ser Tyr Thr Met Cys Ser Gly Lys
            20                  25                  30

Phe Lys Ile Glu Lys Glu Met Ala Glu Thr Gln His Gly Thr Thr Val
        35                  40                  45

Val Lys Val Lys Tyr Glu Gly Ala Gly Ala Pro Cys Lys Val Pro Ile
    50                  55                  60

Glu Ile Arg Asp Val Asn Lys Glu Lys Val Val Gly Arg Ile Ile Ser
65                  70                  75                  80

Ser Thr Pro Leu Ala Glu Asn Thr Asn Ser Val Thr Asn Ile Glu Leu
                85                  90                  95

Glu Pro Pro Phe Gly Asp Ser Tyr Ile Val Ile Gly Val Gly Asn Ser
            100                 105                 110

Ala Leu Thr Leu His Trp Phe Lys Lys Gly Ser Ser Ile Gly Arg Arg
        115                 120                 125

Asp Lys Arg Asp Lys Leu Lys Leu Lys Gly Met Ser Tyr Ala Met Cys
    130                 135                 140
```

Thr Asn Thr Phe Val Leu Lys Lys Glu Val Ser Glu Thr Gln His Gly
145                 150                 155                 160

Thr Ile Leu Ile Lys Val Glu Tyr Lys Gly Glu Asp Val Pro Cys Lys
            165                 170                 175

Ile Pro Phe Ser Thr Glu Asp Gly Gln Gly Lys Ala His Asn Gly Arg
        180                 185                 190

Leu Ile Thr Ala Asn Pro Val Val Thr Lys Lys Glu Glu Pro Val Asn
    195                 200                 205

Ile Glu Ala Glu Pro Pro Phe Gly Glu Ser Asn Ile Val Gly Ile
210                 215                 220

Gly Asp Asn Ala Leu Lys Ile Asn Trp Tyr Lys Lys Gly Ser Ser Ile
225                 230                 235                 240

Gly Arg Arg Asp Lys Arg Asp Lys Leu Gln Leu Lys Gly Met Ser Tyr
                245                 250                 255

Ser Met Cys Thr Gly Lys Phe Lys Ile Val Lys Glu Ile Ala Glu Thr
            260                 265                 270

Gln His Gly Thr Ile Val Ile Arg Val Gln Tyr Glu Gly Asp Gly Ser
        275                 280                 285

Pro Cys Lys Ile Pro Phe Glu Ile Thr Asp Leu Glu Lys Arg His Val
    290                 295                 300

Leu Gly Arg Leu Ile Thr Val Asn Pro Ile Val Thr Glu Lys Asp Ser
305                 310                 315                 320

Pro Val Asn Ile Glu Ala Glu Pro Pro Phe Gly Asp Ser Tyr Ile Ile
                325                 330                 335

Val Gly Val Glu Pro Gly Gln Leu Lys Leu Asn Trp Phe Lys Lys Gly
            340                 345                 350

Ser Ser Ile Gly Arg Arg Asp Lys Arg Asp Lys Leu Thr Leu Lys Gly
        355                 360                 365

Met Ser Tyr Val Met Cys Thr Gly Ser Phe Lys Leu Glu Lys Glu Val
370                 375                 380

Ala Glu Thr Gln His Gly Thr Val Leu Val Gln Val Lys Tyr Glu Gly
385                 390                 395                 400

Thr Asp Ala Pro Cys Lys Ile Pro Phe Ser Thr Gln Asp Glu Lys Gly
                405                 410                 415

Val Thr Gln Asn Gly Arg Leu Ile Thr Ala Asn Pro Ile Val Thr Asp
            420                 425                 430

Lys Glu Lys Pro Val Asn Ile Glu Thr Glu Pro Pro Phe Gly Glu Ser
        435                 440                 445

Tyr Ile Ile Val Gly Ala Gly Glu Lys Ala Leu Lys Leu Ser Trp Phe
450                 455                 460

Lys Lys Gly Ser Ser Ile Gly Arg Arg Asp Lys Arg Ser Val Ala Leu
465                 470                 475                 480

Ala Pro His Val Gly Leu Gly Leu Glu Thr Arg Thr Glu Thr Trp Met
                485                 490                 495

Ser Ser Glu Gly Ala Trp Lys Gln Ile Gln Lys Val Gly Thr Trp Ala
            500                 505                 510

Leu Arg His Pro
        515

<210> SEQ ID NO 146
<211> LENGTH: 537
<212> TYPE: PRT
<213> ORGANISM: Artificial Sequence
<220> FEATURE:
<223> OTHER INFORMATION: Amino acid sequence of the chimeric polyepitope of DENV2

<400> SEQUENCE: 146

```
Lys Ser Ile Glu Asp Asn Pro Glu Ile Glu Asp Asp Ile Phe Arg Lys
1               5                   10                  15

Lys Arg Leu Thr Ile Met Asp Leu His Pro Gly Ala Gly Lys Thr Lys
            20                  25                  30

Arg Tyr Leu Pro Ala Ile Val Arg Glu Ala Ile Lys Arg Gly Leu Arg
        35                  40                  45

Thr Leu Ile Leu Ala Pro Thr Arg Val Val Ala Ala Glu Met Glu Glu
    50                  55                  60

Ala Leu Arg Gly Leu Pro Ile Arg Tyr Gln Thr Pro Ala Ile Arg Ala
65                  70                  75                  80

Glu His Thr Gly Arg Glu Ile Val Asp Leu Met Cys His Ala Thr Phe
                85                  90                  95

Thr Met Arg Leu Leu Ser Pro Val Arg Val Pro Asn Tyr Asn Leu Ile
            100                 105                 110

Ile Met Asp Glu Ala His Phe Thr Asp Pro Ala Ser Ile Ala Ala Arg
        115                 120                 125

Gly Tyr Ile Ser Thr Arg Val Glu Met Gly Glu Ala Ala Gly Ile Phe
    130                 135                 140

Met Thr Ala Thr Pro Pro Gly Ser Arg Asp Pro Phe Pro Gln Ser Asn
145                 150                 155                 160

Ala Pro Ile Met Asp Glu Glu Arg Glu Ile Pro Glu Arg Ser Trp Asn
                165                 170                 175

Ser Gly His Glu Trp Val Thr Asp Glu Asp Cys Ala His Trp Lys Glu
            180                 185                 190

Ala Lys Met Leu Leu Asp Asn Ile Asn Thr Pro Glu Gly Ile Ile Pro
        195                 200                 205

Ser Met Phe Glu Pro Glu Arg Glu Lys Val Asp Ala Ile Asp Gly Glu
    210                 215                 220

Tyr Arg Leu Arg Gly Glu Ala Arg Lys Thr Phe Val Asp Leu Met Arg
225                 230                 235                 240

Arg Gly Asp Leu Pro Val Trp Leu Ala Tyr Lys Val Ala Ala Glu Gly
                245                 250                 255

Ile Asn Tyr Ala Asp Arg Arg Trp Cys Phe Asp Gly Ile Lys Asn Asn
            260                 265                 270

Gln Ile Leu Glu Glu Asn Val Glu Val Glu Ile Trp Thr Lys Glu Gly
        275                 280                 285

Glu Arg Lys Lys Leu Lys Pro Arg Trp Leu Asp Ala Arg Ile Tyr Ser
    290                 295                 300

Asp Pro Leu Ala Leu Lys Glu Phe Lys Glu Phe Ala Ala Gly Ile Thr
305                 310                 315                 320

Thr Gln Glu Ser Glu Ser Asn Ile Leu Asp Ile Asp Leu Arg Pro Ala
                325                 330                 335

Ser Ala Trp Thr Leu Tyr Ala Val Ala Thr Thr Phe Val Thr Pro Met
            340                 345                 350

Leu Arg His Ser Ile Glu Asn Ser Ser Val Asn Val Ser Leu Thr Ala
        355                 360                 365

Ile Ala Asn Gln Ala Thr Val Leu Met Gly Leu Gly Lys Gly Trp Pro
    370                 375                 380

Leu Ser Lys Met Asp Ile Gly Val Pro Leu Leu Ala Ile Gly Cys Tyr
385                 390                 395                 400
```

```
Ser Gln Val Leu Asp Ile Ile Gly Lys Arg Ile Glu Lys Ile Lys Gln
                405                 410                 415

Glu His Glu Thr Ser Trp His Tyr Asp Gln Asp His Pro Tyr Lys Thr
            420                 425                 430

Trp Ala Tyr His Gly Ser Tyr Glu Thr Lys Gln Thr Gly Ser Ala Ser
            435                 440                 445

Ser Met Val Asn Gly Val Val Arg Leu Leu Thr Lys Pro Trp Asp Val
    450                 455                 460

Val Pro Met Val Thr Gln Met Ala Met Thr Asp Thr Thr Pro Phe Gly
465                 470                 475                 480

Gln Gln Arg Val Phe Lys Glu Lys Val Asp Thr Arg Thr Gln Glu Pro
            485                 490                 495

Lys Glu Gly Thr Lys Lys Leu Met Lys Ile Thr Ala Glu Trp Leu Trp
            500                 505                 510

Lys Glu Leu Gly Lys Lys Lys Thr Pro Arg Met Cys Thr Arg Glu Glu
            515                 520                 525

Phe Thr Arg Lys Val Arg Ser Asn Ala
            530                 535

<210> SEQ ID NO 147
<211> LENGTH: 538
<212> TYPE: PRT
<213> ORGANISM: Artificial Sequence
<220> FEATURE:
<223> OTHER INFORMATION: Amino acid sequence of the chimeric polyepitope
      of DENV3

<400> SEQUENCE: 147

Ala Glu Pro Asp Gly Pro Thr Pro Glu Leu Glu Glu Glu Met Phe Lys
1               5                   10                  15

Lys Arg Asn Leu Thr Ile Met Asp Leu His Pro Gly Ser Gly Lys Thr
            20                  25                  30

Arg Lys Tyr Leu Pro Ala Ile Val Arg Glu Ala Ile Lys Arg Arg Leu
        35                  40                  45

Arg Thr Leu Ile Leu Ala Pro Thr Arg Val Val Ala Ala Glu Met Glu
    50                  55                  60

Glu Ala Leu Lys Gly Leu Pro Ile Arg Tyr Gln Thr Thr Ala Thr Lys
65                  70                  75                  80

Ser Glu His Thr Gly Arg Glu Ile Val Asp Leu Met Cys His Ala Thr
                85                  90                  95

Phe Thr Met Arg Leu Leu Ser Pro Val Arg Val Pro Asn Tyr Asn Leu
            100                 105                 110

Ile Ile Met Asp Glu Ala His Phe Thr Asp Pro Ala Ser Ile Ala Ala
        115                 120                 125

Arg Gly Tyr Ile Ser Thr Arg Val Gly Met Gly Glu Ala Ala Ala Ile
    130                 135                 140

Phe Met Thr Ala Thr Pro Pro Gly Thr Ala Asp Ala Phe Pro Gln Ser
145                 150                 155                 160

Asn Ala Pro Ile Gln Asp Glu Glu Arg Asp Ile Pro Glu Arg Ser Trp
                165                 170                 175

Asn Ser Gly Asn Glu Trp Ile Thr Asp Glu Asp His Ala His Trp Thr
            180                 185                 190

Glu Ala Lys Met Leu Leu Asp Asn Ile Asn Thr Pro Glu Gly Ile Ile
        195                 200                 205

Pro Ala Leu Phe Glu Pro Glu Arg Glu Lys Ser Ala Ala Ile Asp Gly
    210                 215                 220
```

Glu Tyr Arg Leu Lys Gly Glu Ser Arg Lys Thr Phe Val Glu Leu Met
225                 230                 235                 240

Arg Arg Gly Asp Leu Pro Val Trp Leu Ala His Lys Val Ala Ser Glu
            245                 250                 255

Gly Ile Lys Tyr Thr Asp Arg Lys Trp Cys Phe Asp Gly Gln Arg Asn
        260                 265                 270

Asn Gln Ile Leu Glu Glu Asn Met Asp Val Glu Ile Trp Thr Lys Glu
    275                 280                 285

Gly Glu Lys Lys Lys Leu Arg Pro Arg Trp Leu Asp Ala Arg Thr Tyr
290                 295                 300

Ser Asp Pro Leu Ala Leu Lys Glu Phe Lys Asp Phe Ala Ala Gly Glu
305                 310                 315                 320

Pro Gly Val Val Ser Pro Thr Ser Tyr Leu Asp Val Asp Leu His Pro
            325                 330                 335

Ala Ser Ala Trp Thr Leu Tyr Ala Val Ala Thr Thr Val Ile Thr Pro
        340                 345                 350

Met Leu Arg His Thr Ile Glu Asn Ser Thr Ala Asn Val Ser Leu Ala
    355                 360                 365

Ala Ile Ala Asn Gln Ala Val Val Leu Met Gly Leu Asp Lys Gly Trp
370                 375                 380

Pro Ile Ser Lys Met Asp Leu Gly Val Pro Leu Leu Ala Leu Gly Cys
385                 390                 395                 400

Tyr Ser Gln Val Met Asp Val Ile Gly Glu Arg Ile Lys Arg Ile Lys
            405                 410                 415

Glu Glu His Asn Ser Thr Trp His Tyr Asp Asp Glu Asn Pro Tyr Lys
        420                 425                 430

Thr Trp Ala Tyr His Gly Ser Tyr Glu Val Lys Ala Thr Gly Ser Ala
    435                 440                 445

Ser Ser Met Ile Asn Gly Val Val Lys Leu Leu Thr Lys Pro Trp Asp
450                 455                 460

Val Val Pro Met Val Thr Gln Met Ala Met Thr Asp Thr Thr Pro Phe
465                 470                 475                 480

Gly Gln Gln Arg Val Phe Lys Glu Lys Val Asp Thr Arg Thr Pro Arg
            485                 490                 495

Ser Met Pro Gly Thr Arg Arg Val Met Gly Ile Thr Ala Glu Trp Leu
        500                 505                 510

Trp Arg Thr Leu Gly Arg Asn Lys Lys Pro Arg Leu Cys Thr Arg Glu
    515                 520                 525

Glu Phe Thr Lys Lys Val Arg Thr Asn Ala
    530                 535

<210> SEQ ID NO 148
<211> LENGTH: 534
<212> TYPE: PRT
<213> ORGANISM: Artificial Sequence
<220> FEATURE:
<223> OTHER INFORMATION: Amino acid sequence of the chimeric polyepitope
      of DENV4

<400> SEQUENCE: 148

Arg Ile Gly Glu Pro Asp Tyr Glu Val Asp Glu Asp Ile Phe Arg Lys
1               5                   10                  15

Lys Arg Leu Thr Ile Met Asp Leu His Pro Gly Ala Gly Lys Thr Lys
            20                  25                  30

Arg Ile Leu Pro Ser Ile Val Arg Glu Ala Leu Lys Arg Arg Leu Arg

```
                35                  40                  45
Thr Leu Ile Leu Ala Pro Thr Arg Val Val Ala Ala Glu Met Glu Glu
 50                  55                  60
Ala Leu Arg Gly Leu Pro Ile Arg Tyr Gln Thr Pro Ala Val Lys Ser
 65                  70                  75                  80
Glu His Thr Gly Arg Glu Ile Val Asp Leu Met Cys His Ala Thr Phe
                 85                  90                  95
Thr Thr Arg Leu Leu Ser Ser Thr Arg Val Pro Asn Tyr Asn Leu Ile
                100                 105                 110
Val Met Asp Glu Ala His Phe Thr Asp Pro Ser Ser Val Ala Ala Arg
                115                 120                 125
Gly Tyr Ile Ser Thr Arg Val Glu Met Gly Glu Ala Ala Ile Phe
                130                 135                 140
Met Thr Ala Thr Pro Pro Gly Ala Thr Asp Pro Phe Pro Gln Ser Asn
145                 150                 155                 160
Ser Pro Ile Glu Asp Ile Glu Arg Glu Ile Pro Glu Arg Ser Trp Asn
                165                 170                 175
Thr Gly Phe Asp Trp Ile Thr Asp Glu Asp His Ala His Trp Thr Glu
                180                 185                 190
Ala Lys Met Leu Leu Asp Asn Ile Tyr Thr Pro Glu Gly Ile Ile Pro
                195                 200                 205
Thr Leu Phe Gly Pro Glu Arg Glu Lys Thr Gln Ala Ile Asp Gly Glu
                210                 215                 220
Phe Arg Leu Arg Gly Glu Gln Arg Lys Thr Phe Val Glu Leu Met Arg
225                 230                 235                 240
Arg Gly Asp Leu Pro Val Trp Leu Ser Tyr Lys Val Ala Ser Ala Gly
                245                 250                 255
Ile Ser Tyr Lys Asp Arg Glu Trp Cys Phe Thr Gly Glu Arg Asn Asn
                260                 265                 270
Gln Ile Leu Glu Glu Asn Met Glu Val Glu Ile Trp Thr Arg Glu Gly
                275                 280                 285
Glu Lys Lys Lys Leu Arg Pro Arg Trp Leu Asp Ala Arg Val Tyr Ala
                290                 295                 300
Asp Pro Met Ala Leu Lys Asp Phe Lys Glu Phe Ala Ser Gly Val Lys
305                 310                 315                 320
Thr Glu Thr Thr Ile Leu Asp Val Asp Leu Arg Pro Ala Ser Ala Trp
                325                 330                 335
Thr Leu Tyr Ala Val Ala Thr Thr Ile Leu Thr Pro Met Leu Arg His
                340                 345                 350
Thr Ile Glu Asn Thr Ser Ala Asn Leu Ser Leu Ala Ala Ile Ala Asn
                355                 360                 365
Gln Ala Val Leu Met Gly Leu Gly Lys Gly Trp Pro Leu His Arg
                370                 375                 380
Met Asp Leu Gly Val Pro Leu Leu Ala Met Gly Cys Tyr Ser Gln Val
385                 390                 395                 400
Met Thr Ile Ile Gly Arg Arg Leu Gln Arg Leu Gln Glu Glu His Lys
                405                 410                 415
Glu Thr Trp His Tyr Asp Gln Glu Asn Pro Tyr Arg Thr Trp Ala Tyr
                420                 425                 430
His Gly Ser Tyr Glu Ala Pro Ser Thr Gly Ser Ala Ser Ser Met Val
                435                 440                 445
Asn Gly Val Val Lys Leu Leu Thr Lys Pro Trp Asp Val Ile Pro Met
450                 455                 460
```

```
Val Thr Gln Leu Ala Met Thr Asp Thr Thr Pro Phe Gly Gln Gln Arg
465                 470                 475                 480

Val Phe Lys Glu Lys Val Asp Thr Arg Thr Pro Gln Pro Lys Pro Gly
                485                 490                 495

Thr Arg Met Val Met Thr Thr Thr Ala Asn Trp Leu Trp Ala Leu Leu
            500                 505                 510

Gly Lys Lys Lys Asn Pro Arg Leu Cys Thr Arg Glu Glu Phe Ile Ser
        515                 520                 525

Lys Val Arg Ser Asn Ala
        530

<210> SEQ ID NO 149
<211> LENGTH: 22243
<212> TYPE: DNA
<213> ORGANISM: Artificial Sequence
<220> FEATURE:
<223> OTHER INFORMATION: Complete optimised nucleotide sequence of the
      polynucleotide encoding pTM-MVDVax11
<220> FEATURE:
<221> NAME/KEY: misc_feature
<222> LOCATION: (1)..(8)
<223> OTHER INFORMATION: NotI
<220> FEATURE:
<221> NAME/KEY: misc_feature
<222> LOCATION: (9)..(28)
<223> OTHER INFORMATION: T7 promoter
<220> FEATURE:
<221> NAME/KEY: misc_feature
<222> LOCATION: (29)..(82)
<223> OTHER INFORMATION: Hammerhead ribozyme
<220> FEATURE:
<221> NAME/KEY: misc_feature
<222> LOCATION: (83)..(189)
<223> OTHER INFORMATION: MV Leader and N promoter
<220> FEATURE:
<221> NAME/KEY: misc_feature
<222> LOCATION: (190)..(1767)
<223> OTHER INFORMATION: MV N ORF
<220> FEATURE:
<221> NAME/KEY: misc_feature
<222> LOCATION: (1768)..(1888)
<223> OTHER INFORMATION: MV N-P intergenic
<220> FEATURE:
<221> NAME/KEY: misc_feature
<222> LOCATION: (1889)..(3412)
<223> OTHER INFORMATION: MV P ORF
<220> FEATURE:
<221> NAME/KEY: misc_feature
<222> LOCATION: (3413)..(3531)
<223> OTHER INFORMATION: MV ATU2
<220> FEATURE:
<221> NAME/KEY: misc_feature
<222> LOCATION: (3532)..(6699)
<223> OTHER INFORMATION: DENV1 NS polyepitope/DENV tetra EDIII/ectoM
<220> FEATURE:
<221> NAME/KEY: misc_feature
<222> LOCATION: (6700)..(6813)
<223> OTHER INFORMATION: MV P-M intergenic
<220> FEATURE:
<221> NAME/KEY: misc_feature
<222> LOCATION: (6814)..(7803)
<223> OTHER INFORMATION: MV M ORF
<220> FEATURE:
<221> NAME/KEY: misc_feature
<222> LOCATION: (7804)..(8806)
<223> OTHER INFORMATION: MV M-F intergenic
<220> FEATURE:
<221> NAME/KEY: misc_feature
<222> LOCATION: (8807)..(10468)
<223> OTHER INFORMATION: MV F ORF
<220> FEATURE:
<221> NAME/KEY: misc_feature
<222> LOCATION: (10469)..(10628)
```

```
<223> OTHER INFORMATION: MV-F-H intergenic
<220> FEATURE:
<221> NAME/KEY: misc_feature
<222> LOCATION: (10629)..(12482)
<223> OTHER INFORMATION: MV H ORF
<220> FEATURE:
<221> NAME/KEY: misc_feature
<222> LOCATION: (12483)..(12591)
<223> OTHER INFORMATION: MV H-L intergenic
<220> FEATURE:
<221> NAME/KEY: misc_feature
<222> LOCATION: (12592)..(19143)
<223> OTHER INFORMATION: MV L ORF
<220> FEATURE:
<221> NAME/KEY: misc_feature
<222> LOCATION: (19144)..(19252)
<223> OTHER INFORMATION: MV Trailer
<220> FEATURE:
<221> NAME/KEY: misc_feature
<222> LOCATION: (19253)..(19336)
<223> OTHER INFORMATION: HDV ribozyme
<220> FEATURE:
<221> NAME/KEY: misc_feature
<222> LOCATION: (19337)..(19478)
<223> OTHER INFORMATION: T7 terminator
<220> FEATURE:
<221> NAME/KEY: misc_feature
<222> LOCATION: (19479)..(19486)
<223> OTHER INFORMATION: Not I
<220> FEATURE:
<221> NAME/KEY: misc_feature
<222> LOCATION: (19487)..(22243)
<223> OTHER INFORMATION: Not I

<400> SEQUENCE: 149
gcggccgcta atacgactca ctatagggcc aactttgttt ggtctgatga gtccgtgagg    60
acgaaacccg gagtcccggg tcaccaaaca agttgggta aggatagttc aatcaatgat    120
catcttctag tgcacttagg attcaagatc ctattatcag gacaagagc aggattaggg    180
atatccgaga tggccacact tttaaggagc ttagcattgt tcaaaagaaa caaggacaaa    240
ccacccatta catcaggatc cggtggagcc atcagaggaa tcaaacacat tattatagta    300
ccaatccctg gagattcctc aattaccact cgatccagac ttctggaccg gttggtgagg    360
ttaattggaa acccggatgt gagcgggccc aaactaacag ggcactaat aggtatatta    420
tccttatttg tggagtctcc aggtcaattg attcagagga tcaccgatga ccctgacgtt    480
agcataaggc tgttagaggt tgtccagagt gaccagtcac aatctggcct taccttcgca    540
tcaagaggta ccaacatgga ggatgaggcg gaccaatact tttcacatga tgatccaatt    600
agtagtgatc aatccaggtt cggatggttc gggaacaagg aaatctcaga tattgaagtg    660
caagaccctg agggattcaa catgattctg ggtaccatcc tagcccaaat ttgggtcttg    720
ctcgcaaagg cggttacggc cccagacacg gcagctgatt cggagctaag aaggtggata    780
aagtacaccc aacaaagaag ggtagttggt gaatttagat tggagagaaa atggttggat    840
gtggtgagga acaggattgc cgaggacctc tccttacgcc gattcatggt cgctctaatc    900
ctggatatca agaacacc cggaaacaaa cccaggattg ctgaaatgat atgtgacatt    960
gatacatata tcgtagaggc aggattagcc agttttatcc tgactattaa gtttgggata    1020
gaaactatgt atcctgctct tggactgcat gaatttgctg gtgagttatc cacacttgag    1080
tccttgatga acctttacca gcaaatgggg gaaactgcac cctacatggt aatcctggag    1140
aactcaattc agaacaagtt cagtgcagga tcatacccctc tgctctggag ctatgccatg    1200
ggagtaggag tggaacttga aaactccatg ggaggtttga actttggccg atcttacttt    1260
gatccagcat attttagatt agggcaagag atggtaagga ggtcagctgg aaaggtcagt    1320
```

```
tccacattgg catctgaact cggtatcact gccgaggatg caaggcttgt tcagagatt   1380 gcaatgcata ctactgagga caagatcagt agagcggttg acccagaca agcccaagta   1440 tcatttctac acggtgatca aagtgagaat gagctaccga gattgggggg caaggaagat   1500
aggagggtca aacagagtcg aggagaagcc agggagagct acagagaaac cgggcccagc   1560
agagcaagtg atgcgagagc tgcccatctt ccaaccggca caccoctaga cattgacact   1620 gcaacggagt ccagccaaga tccgcaggac agtcgaaggt cagctgacgc cctgcttagg   1680
ctgcaagcca tggcaggaat ctcggaagaa caaggctcag acacggacac ccctatagtg   1740
tacaatgaca gaaatcttct agactaggtg cgagaggccg agggccagaa caacatccgc   1800
ctaccatcca tcattgttat aaaaaactta ggaaccaggt ccacacagcc gccagcccat   1860
caaccatcca ctcccacgat ggagccaat ggcagaagag caggcacgcc atgtcaaaaa   1920
cggactggaa tgcatccggg ctctcaaggc cgagcccatc ggctcactgg ccatcgagga   1980
agctatggca gcatggtcag aaatatcaga acccagga caggagcgag ccacctgcag   2040
ggaagagaag gcaggcagtt cgggtctcag caaaccatgc ctctcagcaa ttggatcaac   2100
tgaaggcggt gcacctcgca tccgcggtca gggacctgga gagagcgatg acgacgctga   2160
aactttggga atcccccaa gaaatctcca ggcatcaagc actgggttac agtgttatta   2220
cgtttatgat cacagcggtg aagcggttaa gggaatccaa gatgctgact ctatcatggt   2280
tcaatcaggc cttgatggtg atagcaccct ctcaggagga gacaatgaat ctgaaaacag   2340
cgatgtggat attggcgaac ctgataccga gggatatgct atcactgacc ggggatctgc   2400
tcccatctct atggggttca ggcttctga tgttgaaact gcagaaggag gggagatcca   2460
cgagctcctg agactccaat ccagaggcaa caactttccg aagcttggga aaactctcaa   2520
tgttcctccg ccccggacc ccgtagggc cagcacttcc gggacaccca ttaaaaaggg   2580
cacagacgcg agattagcct catttggaac ggagatcgcg tctttattga caggtggtgc   2640
aacccaatgt gctcgaaagt caccctcgga accatcaggg ccaggtgcac ctgcggggaa   2700
tgtccccgag tgtgtgagca atgccgcact gatacaggag tggacacccg aatctggtac   2760
cacaatctcc ccgagatccc agaataatga agaaggggga gactattatg atgatgagct   2820
gttctctgat gtccaagata ttaaaacagc cttggccaaa atacacgagg ataatcagaa   2880
gataatctcc aagctagaat cactgctgtt attgaaggga gaagttgagt caattaagaa   2940
gcagatcaac aggcaaaata tcagcatatc caccctggaa ggacacctct caagcatcat   3000
gatcgccatt cctggacttg ggaaggatcc caacgacccc actgcagatg tcgaaatcaa   3060
tcccgacttg aaacccatca taggcagaga ttcaggccga gcactggccg aagttctcaa   3120
gaaacccgtt gccagccgac aactccaagg aatgacaaat ggacggacca gttccagagg   3180
acagctgctg aaggaatttc agctaaagcc gatcgggaaa aagatgagct cagccgtcgg   3240
gtttgttcct gacaccggcc ctgcatcacg cagtgtaatc cgctccatta taaaatccag   3300
ccggctagag gaggatcgga agcgttacct gatgactctc cttgatgata tcaaaggagc   3360
caatgatctt gccaagttcc accagatgct gatgaagata taatgaagt agctacagct   3420 caacttacct gccaacccca tgccagtcga cccaactagc ctaccctcca tcattgttat   3480
aaaaaactta ggaaccaggt ccacacagcc gccagcccat caacgcgtac gatggcatca   3540
caggagggac cactgcccga aattgaggac gaagtgttta aaagcgaaa tctgactatt   3600 atggacctgc accccggatc tggcaagacc cggagatacc tgccagccat cgtgagggag   3660
```

```
gctattaagc ggaaactgag aacactgatc ctggccccaa ctcgcgtggt cgcttccgaa    3720
atggctgagg ccctgaaagg catgcccatc cggtatcaga ccacagcagt gaagtctgaa    3780
cataccggca aggagattgt ggacctgatg tgccacgcca ctttcaccat gcgactgctg    3840
agcccagtgc gggtccccaa ctacaatatg atcattatgg acgaggccca ctttactgat    3900
cccagctcca tcgccgctag aggatatatt tccaccaggg tgggaatggg cgaggcagca    3960
gctatcttca tgacagcaac tccccctggc agcgtggagg catttcctca gtccaacgcc    4020
gtcatccagg acgaggagcg ggacattcct gagcggagct ggaattctgg gtacgaatgg    4080
atcacagacg aggatcatgc acactggact gaagccaaga tgctgctgga caacattaat    4140
actcctgagg gaatcattcc agctctgttc gagcccgaaa gagagaagtc tgcagccatc    4200
gacggcgagt atagactgag gggagaggcc cggaagacct tcgtggaact gatgaggcgc    4260
ggcgatctgc ccgtgtggct gagttacaag gtcgcttcag agggattcca gtatagtgac    4320
cgacggtggt gctttgatgg cgaacgcaac aatcaggtgc tggaggagaa catggatgtc    4380
gagatttgga caaaggaagg cgagcggaag aaactgcgcc cacgatggct ggacgctcgg    4440
acttacagcg atcccctggc actgagagaa ttcaaagagt ttgctgcagg ggtggccgtc    4500
gagaatcacc atcacgccgc tatgctggac gtggatctgc atcctgccag tgcttggacc    4560
ctgtatgcag tggccactac catcattacc ccaatgatgc ccacacaat cgagaacaca    4620 actgccaata tctcactgac agctattgca accaggcag ccattctgat gggactggac    4680
aaaggctggc ccatcagcaa gatggatatt ggcgtgcctc tgctggccct ggggtgttac    4740
agtcaggtgc tggacatcat tggccagagg atcgagaaca ttaagcatga gcacaaatca    4800
acctggcatt acgacgaaga taatccctat aagacatggg cctaccacgg aagctatgag    4860
gtgaaacctt caggcagcgc cagcagcatg gtcaacgggg tggtcaagct gctgaccaaa    4920
ccttgggacg tgatcccaat ggtcactcag attgccatga ccgataccac cccattcggc    4980
cagcagcggg tgttcaagga aaggtggac acccgcacac ctaaggctaa cgagggact    5040 gcacagatca tggaggtgac cgccaagtgg ctgtgggat tcctgtccag gaacaagaag    5100
ccaagaatct gtaccaggga agagttcaca agaaaggtcc ggtcaaacgc cggcatcata    5160
ttcattcttc ttatgctggt tacaccgtct atggcggaga acttcgaat caaaggtatg    5220 agctatacga tgtgcagcgg caagttcaag atcgagaagg aaatggctga acccagcac    5280 ggtacaactg tggtcaaagt caaatatgag ggggctggcg ctccctgtaa agtacccatt    5340
gagattaggg acgtcaataa agagaaggtg gtaggtcgca tcatctccag tacacctttg    5400
gccgagaaca cgaactccgt cacaaacata gagttggaac cccgttcgg agactcatac    5460 attgtgatcg gggtgggcaa ctctgcactc acactgcatt ggttcaagaa gggaagcagt    5520
atcggccgca gggataagag agacaaactg aaattgaaag gtatgtccta tgccatgtgc    5580
acgaatactt tcgttctcaa gaagaagta tctgagactc agcacggaac catcctgatc    5640
aaagtcgagt acaaaggaga agacgtgccc tgtaagatcc cattcagtac cgaggatgga    5700
cagggcaagg cccataacgg caggctgata accgccaacc ctgtggttac aaagaaggaa    5760
gagccagtca atatcgaagc tgagccaccg ttcggggaga gcaacatagt aattggcata    5820
ggggataatg ctttgaagat caactggtac aagaaaggaa gctccattgg ccgaagagat    5880
aagcgcgaca aactccagct gaaaggaatg agctactcca tgtgtactgg gaagttcaag    5940
attgtcaagg aaatcgccga aactcagcat ggcactattg tgatccgcgt gcagtatgaa    6000
ggcgatggta gccctgcaa gataccattt gaaatcaccg atttggagaa acggcacgtc    6060
```

```
ctgggtcggc tcattaccgt gaacccaatc gtgaccgaga aggacagtcc agttaatatc   6120
gaggccgagc ctcctttcgg cgacagttac atcattgtag gggtggaacc agggcaactg   6180
aagctgaact ggttcaagaa aggcagcagt ataggacggc gggataaacg ggacaaactc   6240
acactgaaag gcatgtcata cgttatgtgc accggctcat tcaaactgga gaaggaagtt   6300
gcagagacac agcatgggac cgtgctcgtg caggtcaaat acgagggcac cgacgctcct   6360
tgcaagattc cgttcagtac acaggacgag aaaggcgtga ctcagaacgg cagattgatt   6420
acagcgaacc ctatcgtgac tgacaaggag aagccagtta acatcgagac tgagccgcct   6480
ttcggagaat catacattat cgtgggagcc ggcgagaagg cactgaaact cagctggttc   6540
aagaagggca gctcaatcgg tcggagagac aagcggtctg tcgccctcgc accgcacgtg   6600
ggcctgggtc tggaaacgag gaccgagacg tggatgagtt ccgaaggcgc atggaagcaa   6660
atccagaaag tggagacgtg ggccctcagg catccgtaag cgcgcagcgc ttagacgtct   6720
cgcgatcgat actagtacaa cctaaatcca ttataaaaaa cttaggagca aagtgattgc   6780
ctcccaaggt ccacaatgac agagacctac gacttcgaca agtcggcatg ggacatcaaa   6840
gggtcgatcg ctccgataca acccaccacc tacagtgatg gcaggctggt gccccaggtc   6900
agagtcatag atcctggtct aggcgacagg aaggatgaat gctttatgta catgtttctg   6960 ctggggttg ttgaggacag cgattcccta gggcctccaa tcgggcgagc atttgggttc   7020
ctgcccttag gtgttggcag atccacagca aagcccgaaa aactcctcaa agaggccact   7080
gagcttgaca tagttgttag acgtacagca gggctcaatg aaaaactggt gttctacaac   7140
aacaccccac taactctcct cacaccttgg agaaaggtcc taacaacagg gagtgtcttc   7200
aacgcaaacc aagtgtgcaa tgcggttaat ctgataccgc tcgataccc gcagaggttc   7260 cgtgttgttt atatgagcat cacccgtctt tcggataacg ggtattacac cgttcctaga   7320
agaatgctgg aattcagatc ggtcaatgca gtggccttca acctgctggt gacccttagg   7380
attgacaagg cgataggccc tgggaagatc atcgacaata cagagcaact tcctgaggca   7440
acatttatgg tccacatcgg gaacttcagg agaaagaaga gtgaagtcta ctctgccgat   7500
tattgcaaaa tgaaaatcga aaagatgggc ctggttttg cacttggtgg dataggcggc   7560
accagtcttc acattagaag cacaggcaaa atgagcaaga ctctccatgc acaactcggg   7620
ttcaagaaga ccttatgtta cccgctgatg gatatcaatg aagaccttaa tcgattactc   7680
tggaggagca gatgcaagat agtaagaatc caggcagttt tgcagccatc agttcctcaa   7740
gaattccgca tttacgacga cgtgatcata aatgatgacc aaggactatt caaagttctg   7800
tagaccgtag tgcccagcaa tgcccgaaaa cgaccccct cacaatgaca gccagaaggc   7860
ccggacaaaa aagccccctc cgaaagactc cacggaccaa gcgagaggcc agccagcagc   7920
cgacggcaag cgcgaacacc aggcggcccc agcacagaac agccctgaca caaggccacc   7980
accagccacc ccaatctgca tcctcctcgt gggaccccg aggaccaacc cccaaggctg   8040
cccccgatcc aaaccaccaa ccgcatcccc accacccccg ggaaagaaac ccccagcaat   8100
tggaaggccc ctcccctct tcctcaacac aagaactcca caaccgaacc gcacaagcga   8160
ccgaggtgac ccaaccgcag gcatccgact ccctagacag atcctctctc cccggcaaac   8220
taaacaaaac ttagggccaa ggaacataca cacccaacag aacccagacc ccggcccacg   8280
gcgccgcgcc cccaacccc gacaaccaga gggagccccc aaccaatccc gccggctccc   8340
ccggtgccca caggcaggga caccaacccc cgaacagacc cagcacccaa ccatcgacaa   8400
```

```
tccaagacgg ggggccccc ccaaaaaaag gccccccaggg gccgacagcc agcaccgcga   8460
ggaagcccac ccaccccaca cacgaccacg gcaaccaaac cagaacccag accaccctgg   8520
gccaccagct cccagactcg gccatcaccc cgcagaaagg aaaggccaca acccgcgcac   8580
cccagccccg atccggcggg gagccaccca acccgaacca gcacccaaga gcgatccccg   8640
aaggaccccc gaaccgcaaa ggacatcagt atcccacagc ctctccaagt cccccggtct   8700
cctcctcttc tcgaagggac caaaagatca atccaccaca cccgacgaca ctcaactccc   8760 caccccctaaa ggagacaccg ggaatcccag aatcaagact catccaatgt ccatcatggg   8820
tctcaaggtg aacgtctctg ccatattcat ggcagtactg ttaactctcc aaacaccccac  8880 cggtcaaatc cattggggca atctctctaa gatagggttg gtaggaatag gaagtgcaag   8940
ctacaaagtt atgactcgtt ccagccatca atcattagtc ataaaattaa tgcccaatat   9000
aactctcctc aataactgca cgagggtaga gattgcagaa tacaggagac tactgagaac   9060
agttttggaa ccaattagag atgcacttaa tgcaatgacc cagaatataa gaccggttca   9120
gagtgtagct tcaagtagga gacacaagag atttgcggga gtagtcctgg caggtgcggc   9180
cctaggcgtt gccacagctg ctcagataac agccggcatt gcacttcacc agtccatgct   9240
gaactctcaa gccatcgaca atctgagagc gagcctggaa actactaatc aggcaattga   9300
gacaatcaga caagcagggc aggagatgat attggctgtt caggggtgtcc aagactacat   9360 caataatgag ctgataccgt ctatgaacca actatcttgt gatttaatcg gccagaagct   9420
cgggctcaaa ttgctcagat actatacaga aatcctgtca ttatttggcc ccagtttacg   9480
ggaccccata tctgcggaga tatctatcca ggctttgagc tatgcgcttg gaggagacat   9540
caataaggtg ttagaaaagc tcggatacag tggaggtgat ttactgggca tcttagagag   9600
cggaggaata aaggcccgga taactcacgt cgacacagag tcctacttca ttgtcctcag   9660
tatagcctat ccgacgctgt ccgagattaa ggggtgatt gtccaccggc tagagggggt   9720
ctcgtacaac ataggctctc aagagtggta taccactgtg cccaagtatg ttgcaaccca   9780
agggtacctt atctcgaatt ttgatgagtc atcgtgtact ttcatgccag aggggactgt   9840
gtgcagccaa aatgccttgt acccgatgag tcctctgctc caagaatgcc tccggggta   9900 caccaagtcc tgtgctcgta cactcgtatc cgggtctttt gggaaccggt tcattttatc   9960
acaagggaac ctaatagcca attgtgcatc aatcctttgc aagtgttaca caacaggaac  10020
gatcattaat caagaccctg acaagatcct aacatacatt gctgccgatc actgccggt  10080 agtcgaggtg aacggcgtga ccatccaagt cgggagcagg aggtatccag acgctgtgta  10140
cttgcacaga attgaccctcg gtcctccat atcattggag aggttggacg tagggacaaa  10200 tctgggaat gcaattgcta agttggagga tgccaaggaa ttgttggagt catcggacca  10260
gatattgagg agtatgaaag gtttatcgag cactagcata gtctacatcc tgattgcagt  10320
gtgtcttgga gggttgatag ggatccccgc tttaatatgt tgctgcaggg gcgttgtaa  10380 caaaaaggga gaacaagttg gtatgtcaag accaggccta aagcctgatc ttacgggaac  10440
atcaaaatcc tatgtaaggt cgctctgatc ctctacaact cttgaaacac aaatgtccca  10500
caagtctcct cttcgtcatc aagcaaccac cgcacccagc atcaagccca cctgaaatta  10560
tctccggctt ccctctggcc gaacaatatc ggtagttaat caaaacttag ggtgcaagat  10620
catccacaat gtcaccacaa cgagaccgga taaatgcctt ctacaaagat aaccccccatc 10680 ccaagggaag taggatagtc attaacagag aacatcttat gattgataga ccttatgttt  10740
tgctggctgt tctgtttgtc atgtttctga gcttgatcgg gttgctagcc attgcaggca  10800
```

```
ttagacttca tcgggcagcc atctacaccg cagagatcca taaaagcctc agcaccaatc    10860
tagatgtaac taactcaatc gagcatcagg tcaaggacgt gctgacacca ctcttcaaaa    10920
tcatcggtga tgaagtgggc ctgaggacac ctcagagatt cactgaccta gtgaaattaa    10980
tctctgacaa gattaaattc cttaatccgg atagggagta cgacttcaga gatctcactt    11040
ggtgtatcaa cccgccagag agaatcaaat tggattatga tcaatactgt gcagatgtgg    11100
ctgctgaaga gctcatgaat gcattggtga actcaactct actggagacc agaacaacca    11160
atcagttcct agctgtctca aagggaaact gctcagggcc cactacaatc agaggtcaat    11220
tctcaaacat gtcgctgtcc ctgttagact tgtatttagg tcgaggttac aatgtgtcat    11280
ctatagtcac tatgacatcc cagggaatgt atgggggaac ttacctagtg aaaagccta    11340 atctgagcag caaaaggtca gagttgtcac aactgagcat gtaccgagtg tttgaagtag    11400
gtgttatcag aaatccgggt ttgggggctc cggtgttcca tatgacaaac tatcttgagc    11460
aaccagtcag taatgatctc agcaactgta tggtggcttt gggggagctc aaactcgcag    11520
ccctttgtca cggggaagat tctatcacaa ttccctatca gggatcaggg aaaggtgtca    11580
gcttccagct cgtcaagcta ggtgtctgga atccccaac cgacatgcaa tcctgggtcc    11640
ccttatcaac ggatgatcca gtgatagaca ggctttacct ctcatctcac agaggtgtta    11700
tcgctgacaa tcaagcaaaa tgggctgtcc cgacaacacg aacagatgac aagttgcgaa    11760
tggagacatg cttccaacag gcgtgtaagg gtaaaatcca agcactctgc gagaatcccg    11820
agtgggcacc attgaaggat aacaggattc cttcatacgg ggtcttgtct gttgatctga    11880
gtctgacagt tgagcttaaa atcaaaattg cttcgggatt cgggccattg atcacacacg    11940
gttcagggat ggacctatac aaatccaacc acaacaatgt gtattggctg actatcccgc    12000
caatgaagaa cctagcctta ggtgtaatca acacattgga gtggatacct agattcaagg    12060
ttagtcccta cctcttcact gtcccaatta aggaagcagg cgaagactgc catgccccaa    12120
catacctacc tgcggaggtg gatggtgatg tcaaactcag ttccaatctg gtgattctac    12180
ctggtcaaga tctccaatat gttttggcaa cctacgatac ttccagggtt gaacatgctg    12240
tggtttatta cgtttacagc ccaagccgct cattttctta ctttatcct tttaggttgc    12300 ctataaaggg ggtccccatc gaattacaag tggaatgctt cacatgggac caaaaactct    12360
ggtgccgtca cttctgtgtg cttgcggact cagaatctgg tggacatatc actcactctg    12420
ggatggtggg catgggagtc agctgcacag tcacccggga agatggaacc aatcgcagat    12480
agggctgcta gtgaaccaat cacatgatgt cacccagaca tcaggcatac ccactagtgt    12540
gaaatagaca tcagaattaa gaaaacgta gggtccaagt ggttccccgt tatggactcg    12600
ctatctgtca accagatctt ataccctgaa gttcacctag atagcccgat agttaccaat    12660
aagatagtag ccatcctgga gtatgctcga gtccctcacg cttacagcct ggaggaccct    12720
acactgtgtc agaacatcaa gcaccgccta aaaacggat tttccaacca atgattata    12780 aacaatgtgg aagttgggaa tgtcatcaag tccaagctta ggagttatcc ggcccactct    12840
catattccat atccaaattg taatcaggat ttatttaaca tagaagacaa agagtcaacg    12900
aggaagatcc gtgaactcct caaaaagggg aattcgctgt actccaaagt cagtgataag    12960
gttttccaat gcttaaggga cactaactca cggcttggcc taggctccga attgagggag    13020
gacatcaagg agaaagttat taacttggga gtttacatgc acagctccca gtggtttgag    13080
ccctttctgt tttggtttac agtcaagact gagatgaggt cagtgattaa atcacaaacc    13140
```

-continued

```
catacttgcc ataggaggag acacacacct gtattcttca ctggtagttc agttgagttg   13200
ctaatctctc gtgaccttgt tgctataatc agtaaagagt ctcaacatgt atattacctg   13260
acatttgaac tggttttgat gtattgtgat gtcatagagg ggaggttaat gacagagacc   13320
gctatgacta ttgatgctag gtatacagag cttctaggaa gagtcagata catgtggaaa   13380
ctgatagatg gtttcttccc tgcactcggg aatccaactt atcaaattgt agccatgctg   13440
gagcctcttt cacttgctta cctgcagctg agggatataa cagtagaact cagaggtgct   13500
ttccttaacc actgctttac tgaaatacat gatgttcttg accaaaacgg gttttctgat   13560
gaaggtactt atcatgagtt aactgaagct ctagattaca ttttcataac tgatgacata   13620
catctgacag gggagatttt ctcattttc agaagtttcg gccaccccag acttgaagca   13680
gtaacggctg ctgaaaatgt taggaaatac atgaatcagc ctaaagtcat tgtgtatgag   13740
actctgatga aaggtcatgc catattttgt ggaatcataa tcaacggcta tcgtgacagg   13800
cacggaggca gttggccacc gctgaccctc cccctgcatg ctgcagacac aatccggaat   13860
gctcaagctt caggtgaagg gttaacacat gagcagtgcg ttgataactg gaaatctttt   13920
gctggagtga aatttggctg ctttatgcct cttagcctgg atagtgatct gacaatgtac   13980
ctaaaggaca aggcacttgc tgctctccaa agggaatggg attcagttta cccgaaagag   14040
ttcctgcgtt acgaccctcc caagggaacc gggtcacgga ggcttgtaga tgttttcctt   14100
aatgattcga gctttgaccc atatgatgtg ataatgtatg ttgtaagtgg agcttacctc   14160
catgaccctg agttcaacct gtcttacagc ctgaaagaaa aggagatcaa ggaaacaggt   14220 agacttttg ctaaaatgac ttacaaaatg agggcatgcc aagtgattgc tgaaaatcta   14280
atctcaaacg ggattggcaa atattttaag gacaatggga tggccaagga tgagcacgat   14340
ttgactaagg cactccacac tctagctgtc tcaggagtcc ccaaagatct caaagaaagt   14400
cacagggggg ggccagtctt aaaaacctac tcccgaagcc cagtccacac aagtaccagg   14460
aacgtgagag cagcaaaagg gtttataggg ttccctcaag taattcggca ggaccaagac   14520
actgatcatc cggagaatat ggaagcttac gagacagtca gtgcatttat cacgactgat   14580
ctcaagaagt actgccttaa ttggagatat gagaccatca gcttgtttgc acagaggcta   14640
aatgagattt acggattgcc ctcatttttc cagtggctgc ataagaggct tgagacctct   14700
gtcctgtatg taagtgaccc tcattgcccc cccgaccttg acgcccatat cccgttatat   14760
aaagtcccca atgatcaaat cttcattaag taccctatgg gaggtataga agggtattgt   14820
cagaagctgt ggaccatcag caccattccc tatctatacc tggctgctta tgagagcgga   14880
gtaaggattg cttcgttagt gcaaggggac aatcagacca tagccgtaac aaaaagggta   14940
cccagcacat ggccctacaa ccttaagaaa cgggaagctg ctagagtaac tagagattac   15000
tttgtaattc ttaggcaaag gctacatgat attggccatc acctcaaggc aaatgagaca   15060
attgtttcat cacatttttt tgtctattca aaaggaatat attatgatgg gctacttgtg   15120
tcccaatcac tcaagagcat cgcaagatgt gtattctggt cagagactat agttgatgaa   15180
acaagggcag catgcagtaa tattgctaca acaatggcta aaagcatcga gagaggttat   15240
gaccgttacc ttgcatattc cctgaacgtc ctaaaagtga tacagcaaat tctgatctct   15300
cttggcttca caatcaattc aaccatgacc cgggatgtag tcatacccct cctcacaaac   15360
aacgacctct taataaggat ggcactgttg cccgctccta ttgggggat gaattatctg   15420 aatatgagca ggctgtttgt cagaaacatc ggtgatccag taacatcatc aattgctgat   15480
ctcaagagaa tgattctcgc ctcactaatg cctgaagaga ccctccatca agtaatgaca   15540
```

```
caacaaccgg gggactcttc attcctagac tgggctagcg acccttactc agcaaatctt   15600
gtatgtgtcc agagcatcac tagactcctc aagaacataa ctgcaaggtt tgtcctgatc   15660
catagtccaa acccaatgtt aaaaggatta ttccatgatg acagtaaaga agaggacgag   15720
ggactggcgg cattcctcat ggacaggcat attatagtac ctagggcagc tcatgaaatc   15780
ctggatcata gtgtcacagg gcaagagag tctattgcag gcatgctgga taccacaaaa    15840
ggcttgattc gagccagcat gaggaagggg gggttaacct ctcgagtgat aaccagattg   15900
tccaattatg actatgaaca attcagagca gggatggtgc tattgacagg aagaaagaga   15960
aatgtcctca ttgacaaaga gtcatgttca gtgcagctgg cgagagctct aagaagccat   16020
atgtgggcga ggctagctcg aggacggcct atttacggcc ttgaggtccc tgatgtacta   16080
gaatctatgc gaggccacct tattcggcgt catgagacat gtgtcatctg cgagtgtgga   16140
tcagtcaact acggatggtt ttttgtcccc tcgggttgcc aactggatga tattgacaag   16200
gaaacatcat ccttgagagt cccatatatt ggttctacca ctgatgagag aacagacatg   16260
aagcttgcct tcgtaagagc cccaagtcga tccttgcgat ctgctgttag aatagcaaca   16320
gtgtactcat gggcttacgg tgatgatgat agctcttgga acgaagcctg gttgttggct   16380
aggcaaaggg ccaatgtgag cctggaggag ctaagggtga tcactcccat ctcaacttcg   16440
actaatttag cgcataggtt gagggatcgt agcactcaag tgaaatactc aggtacatcc   16500
cttgtccgag tggcgaggta taccacaatc tccaacgaca atctctcatt tgtcatatca   16560
gataagaagg ttgatactaa ctttatatac aacaaggaa tgcttctagg gttgggtgtt    16620
ttagaaacat tgtttcgact cgagaaagat accggatcat ctaacacggt attacatctt   16680
cacgtcgaaa cagattgttg cgtgatcccg atgatagatc atcccaggat acccagctcc   16740
cgcaagctag agctgagggc agagctatgt accaacccat tgatatatga taatgcacct   16800
ttaattgaca gagatgcaac aaggctatac acccagagcc ataggaggca ccttgtggaa   16860
tttgttacat ggtccacacc ccaactatat cacattttag ctaagtccac agcactatct   16920
atgattgacc tggtaacaaa atttgagaag gaccatatga atgaaatttc agctctcata   16980
ggggatgacg atatcaatag tttcataact gagtttctgc tcatagagcc aagattattc   17040
actatctact tgggccagtg tgcggccatc aattgggcat tgatgtaca ttatcataga    17100 ccatcaggga aatatcagat gggtgagctg ttgtcatcgt tcctttctag aatgagcaaa   17160
ggagtgttta aggtgcttgt caatgctcta agccacccaa agatctacaa gaaattctgg   17220
cattgtggta ttatagagcc tatccatggt ccttcacttg atgctcaaaa cttgcacaca   17280
actgtgtgca acatggttta cacatgctat atgacctacc tcgacctgtt gttgaatgaa   17340
gagttagaag agttccacat tctcttgtgt gaaagcgacg aggatgtagt accggacaga   17400
ttcgacaaca tccaggcaaa acacttatgt gttctggcag atttgtactg tcaaccaggg   17460
acctgcccac caattcgagg tctaagaccg gtagagaaat gtgcagttct aaccgaccat   17520
atcaaggcag aggctatgtt atctccagca ggatcttcgt ggaacataaa tccaattatt   17580
gtagaccatt actcatgctc tctgacttat ctccggcgag gatcgatcaa acagataaga   17640
ttgagagttg atccaggatt catttttcgac gccctcgctg aggtaaatgt cagtcagcca   17700
aagatcggca gcaacaacat ctcaaatatg agcatcaagg ctttcagacc cccacacgat   17760
gatgttgcaa aattgctcaa agatatcaac acaagcaagc acaatcttcc catttcaggg   17820
ggcaatctcg ccaattatga aatccatgct ttccgcagaa tcgggttgaa ctcatctgct   17880
```

```
tgctacaaag ctgttgagat atcaacatta attaggagat gccttgagcc aggggaggac   17940
ggcttgttct tgggtgaggg atcgggttct atgttgatca cttataaaga gatacttaaa   18000
ctaaacaagt gcttctataa tagtggggtt tccgccaatt ctagatctgg tcaaagggaa   18060
ttagcaccct atccctccga agttggcctt gtcgaacaca gaatgggagt aggtaatatt   18120
gtcaaagtgc tctttaacgg gaggcccgaa gtcacgtggg taggcagtgt agattgcttc   18180
aatttcatag ttagtaatat ccctacctct agtgtggggt ttatccattc agatatagag   18240
accttgcctg acaaagatac tatagagaag ctagaggaat tggcagccat cttatcgatg   18300
gctctgctcc tgggcaaaat aggatcaata ctggtgatta agcttatgcc tttcagcggg   18360
gattttgttc agggatttat aagttatgta gggtctcatt atagagaagt gaaccttgta   18420
taccctagat acagcaactt catctctact gaatcttatt tggttatgac agatctcaag   18480
gctaaccggc taatgaatcc tgaaaagatt aagcagcaga taattgaatc atctgtgagg   18540
acttcacctg gacttatagg tcacatccta tccattaagc aactaagctg catacaagca   18600
attgtgggag acgcagttag tagaggtgat atcaatccta ctctgaaaaa acttacacct   18660
atagagcagg tgctgatcaa ttgcggggttg gcaattaacg gacctaagct gtgcaaagaa   18720
ttgatccacc atgatgttgc ctcagggcaa gatggattgc ttaattctat actcatcctc   18780
tacagggagt tggcaagatt caaagacaac caaagaagtc aacaagggat gttccacgct   18840
taccccgtat tggtaagtag caggcaacga gaacttatat ctaggatcac ccgcaaattc   18900
tgggggcaca ttcttcttta ctccgggaac aaaaagttga taaataagtt tatccagaat   18960
ctcaagtccg gctatctgat actagactta caccagaata tcttcgttaa gaatctatcc   19020
aagtcagaga aacagattat tatgacgggg ggtttgaaac gtgagtgggt ttttaaggta   19080
acagtcaagg agaccaaaga atggtataag ttagtcggat acagtgccct gattaaggac   19140
taattggttg aactccggaa ccctaatcct gccctaggtg gttaggcatt atttgcaata   19200
tattaaagaa aactttgaaa atacgaagtt ctattccca gctttgtctg gtggccggca   19260
tggtcccagc ctcctcgctg gcgccggctg ggcaacattc cgaggggacc gtcccctcgg   19320
taatggcgaa tgggacgcgg ccgatccggc tgctaacaaa gcccgaaagg aagctgagtt   19380
ggctgctgcc accgctgagc aataactagc ataacccctt ggggcctcta acgggtctt   19440
gagggttttt tgctgaaaag gaggaactat atccggatgc ggcgcgcggc cctatggtac   19500
ccagcttttg ttccctttag tgagggttaa ttccgagctt ggcgtaatca tggtcatagc   19560
tgttcctgt gtgaaattgt tatccgctca caattccaca caacatagga gccggaagca   19620
taaagtgtaa agcctggggt gcctaatgag tgaggtaact cacattaatt gcgttgcgct   19680
cactgcccgc tttccagtcg ggaaacctgt cgtgccagct gcattaatga atcggccaac   19740
gcgcggggag aggcggtttg cgtattgggc gctcttccgc ttcctcgctc actgactcgc   19800
tgcgctcggt cgttcggctg cggcgagcgg tatcagctca ctcaaaggcg gtaatacggt   19860
tatccacaga atcaggggat aacgcaggaa agaacatgtg agcaaaaggc cagcaaaagg   19920
ccaggaaccg taaaaaggcc gcgttgctgg cgtttttcca taggctcggc cccctgacg   19980
agcatcacaa aaatcgacgc tcaagtcaga ggtggcgaaa cccgacagga ctataaagat   20040
accaggcgtt ccccctgga agctccctcg tgcgctctcc tgttccgacc ctgccgctta   20100
ccggatacct gtccgccttt ctcccttcgg gaagcgtggc gctttctcaa tgctcacgct   20160
gtaggtatct cagttcggtg taggtcgttc gctccaagct gggctgtgtg cacgaacccc   20220
ccgttcagcc cgaccgctgc gccttatccg gtaactatcg tcttgagtcc aacccggtaa   20280
```

```
gacacgactt atcgccactg gcagcagcca ctggtaacag gattagcaga gcgaggtatg   20340
taggcggtgc tacagagttc ttgaagtggt ggcctaacta cggctacact agaaggacag   20400
tatttggtat ctgcgctctg ctgaagccag ttaccttcgg aaaaagagtt ggtagctctt   20460
gatccggcaa acaaaccacc gctggtagcg gtggttttt tgtttgcaag cagcagatta    20520
cgcgcagaaa aaaaggatct caagaagatc ctttgatctt ttctacgggg tctgacgctc   20580
agtggaacga aaactcacgt taagggattt tggtcatgag attatcaaaa aggatcttca   20640
cctagatcct tttaaattaa aaatgaagtt ttaaatcaat ctaaagtata tatgagtaaa   20700
cttggtctga cagttaccaa tgcttaatca gtgaggcacc tatctcagcg atctgtctat   20760
ttcgttcatc catagttgcc tgactgcccg tcgtgtagat aactacgata cgggagggct   20820
taccatctgg ccccagtgct gcaatgatac cgcgagaccc acgctcaccg gctccagatt   20880
tatcagcaat aaaccagcca gccggaaggg ccgagcgcag aagtggtcct gcaactttat   20940
ccgcctccat ccagtctatt aattgttgcc gggaagctag agtaagtagt tcgccagtta   21000
atagtttgcg caacgttgtt gccattgcta caggcatcgt ggtgtcacgc tcgtcgtttg   21060
gtatggcttc attcagctcc ggttcccaac gatcaaggcg agttacatga tcccccatgt   21120
tgtgaaaaaa agcggttagc tccttcggtc ctccgatcgt tgtcagaagt aagttggccg   21180
cagtgttatc actcatgctt atggcagcac tgcataattc tcttactgtc atgccatccg   21240
taagatgctt ttctgtgact ggtgagtact caaccaagtc attctgagaa tagtgtatgc   21300
ggcgaccgag ttgctcttgc ccggcgtcaa tacgggataa taccgcgcca catagcagaa   21360
ctttaaaagt gctcatcatt ggaaaacgtt cttcggggcg aaaactctca aggatcttac   21420
cgctgttgag atccagttcg atgtaaccca ctcgtgcacc caactgatct tcagcatctt   21480
ttactttcac cagcgtttct gggtgagcaa aaacaggaag gcaaaatgcc gcaaaaaagg   21540
gaataagggc gacacggaaa tgttgaatac tcatactctt cctttttcaa tattattgaa   21600
gcatttatca gggttattgt ctcatgagcg gatacatatt tgaatgtatt tagaaaaata   21660
aacaaatagg ggttccgcgc acatttcccc gaaaagtgcc acctgaaatt gtaaacgtta   21720
atattttgtt aaaattcgcg ttaaattttt gttaaatcag ctcattttt aaccaatagg    21780 ccgaaatcgg caaaatccct tataaatcaa agaatagac cgagataggg ttgagtgttg    21840
ttccagtttg gaacaagagt ccactattaa agaacgtgga ctccaacgtc aaagggcgaa   21900
aaaccgtcta tcagggcgat ggcccactac gtgaaccatc accctaatca agttttttgg   21960
ggtcgaggtg ccgtaaagca ctaaatcgga accctaaagg gagcccccga tttagagctt   22020
gacggggaaa gccggcgaac gtggcgagaa aggaagggaa gaaagcgaaa ggagcgggcg   22080
ctagggcgct ggcaagtgta gcggtcacgc tgcgcgtaac caccacaccc gccgcgctta   22140
atgcgccgct acagggcgcg tcccattcgc cattcaggct gcgcaactgt tgggaagggc   22200
gatcggtgcg ggcctcttcg ctattacgcc agccaccgcg gtg                    22243
```

<210> SEQ ID NO 150
<211> LENGTH: 9
<212> TYPE: PRT
<213> ORGANISM: Artificial Sequence
<220> FEATURE:
<223> OTHER INFORMATION: Synthetic peptide HBSP A2-2

<400> SEQUENCE: 150

Thr Leu Cys Ile Pro His Val Ala Val
1               5

-continued

```
<210> SEQ ID NO 151
<211> LENGTH: 9
<212> TYPE: PRT
<213> ORGANISM: Artificial Sequence
<220> FEATURE:
<223> OTHER INFORMATION: Synthetic peptide Sv B7-3

<400> SEQUENCE: 151

Ser Pro Phe Leu Pro Leu Leu Pro Ile
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic furin sites

<400> SEQUENCE: 152

Arg Arg Asp Lys Arg
1               5
```

DENGUE VIRUS CHIMERIC POLYEPITOPE COMPOSED OF FRAGMENTS OF NON-STRUCTURAL PROTEINS AND ITS USE IN AN IMMUNOGENIC COMPOSITION AGAINST DENGUE VIRUS INFECTION

FIELD OF THE INVENTION

The present invention is directed to a dengue virus chimeric polyepitope composed of fragments of non-structural proteins and its use in an immunogenic composition against dengue virus infection. The present invention provides means, in particular polynucleotides, vectors, cells and methods to produce vectors expressing said chimeric polyepitopes, in particular vectors consisting of recombinant measles virus (also designated MV) particles. The present invention also relates to the use of the recombinant MV particles, in particular under the form of a composition or of a vaccine, for the prevention and/or treatment of a dengue virus infection.

BACKGROUND OF THE INVENTION

Dengue virus (DENV) belongs to the Flaviviridae family of enveloped, positive-strand RNA viruses, and is transmitted by *Aedes* mosquitoes. DENV infection is the most important arthropod-borne viral disease, with about 390 million infections every year, that can result in dengue fever (DF), and in 1-5% of cases in dengue hemorrhagic fever (DHF) and dengue shock syndrome (DSS), characterized by vascular leak leading to hypotensive shock (World Health Organization (WHO) Press 2009, *WHO/HTM/NTD/DEN/ 2009. 1 ed.*; Bhatt S et al., *Nature* 2013, 496(7446):504-507). Over 2 million cases of severe dengue disease and over 20,000 deaths are estimated to occur each year (Gubler D J, The American journal of tropical medicine and hygiene 2012, 86(5):743-744).

There are four main DENV serotypes (designated DENV1-4) that are 67-75% identical at the amino acid level. The viral RNA genome is translated as a single polyprotein that is cleaved by viral and host proteases into three structural proteins (capsid (C), premembrane (prM), and envelope (E)) and seven non-structural (NS) proteins (NS1, NS2A, NS2B, NS3, NS4A, NS4B, NS5). Complete nucleotide sequences of the reference genomes of the 4 dengue virus serotypes can be accessed from the Genbank database under accession numbers NC_001477.1, NC_001474.2, NC_001475.2 and NC_002640.1 respectively. During infection, the E protein interacts with cellular receptors and viral uptake occurs via receptor-mediated endocytosis (Heinz F X et al., *Archives of virology Supplementum* 1994, 9:339-348; Mukhopadhyay S et al., *Nat Rev Microbiol* 2005, 3(1):13-22). The E protein is structurally conserved among flaviviruses and consists of three domains (EDI, EDII, and EDIII) (Rey F A et al., *Nature* 1995, 375(6529):291-298). Notably, the EDIII domain induces the most potent neutralizing and serotype-specific antibodies (Beltramello M et al., *Cell host & microbe* 2010, 8(3):271-283; Shrestha B et al., *PLoS Pathog* 2010, 6(4):e1000823; Sukupolvi-Petty S et al., *J Virol* 2010, 84(18):9227-9239; Wahala W M et al., *PLoS Pathog* 2010, 6(3):e1000821; de Alwis R et al, *PLoS neglected tropical diseases* 2011, 5(6):e1188; Yauch L E et al., *Advances in virus research* 2014, 88:315-372).

A single minimal tetravalent DENV antigen composed of the four envelope domain III (EDIII) from the four DENV serotypes fused to the ectodomain of the membrane protein (ectoM) has been previously described (Brandler et al., *PLoS* 2007, 1(3), e96; Brandler et al., *Vaccine*, 2010, 28, 6730-6739). When expressed by a replicating viral vector derived from live-attenuated MV vaccine, this antigen induced neutralizing antibodies against the four serotypes of dengue virus (Brandler et al., *Vaccine*, 2010, 28, 6730-6739). However, evaluated in a non-human primate model of DENV infection, a recombinant MV vector expressing the tetravalent EDIII-ectoM antigen provided only partial protection. This observation indicated that an additional DENV antigen was missing to provide full protection.

The NS proteins are involved in viral replication and assembly and are usually not incorporated in mature viral particles. Strikingly, while a primary infection by one DENV serotype induces a lasting protective immunity against reinfection by the same serotype, not only it does not protect against infection with other serotypes but it increases also the risk to develop a more severe disease upon secondary infection, a phenomenon attributed to non-neutralizing or sub-neutralizing antibodies and called Antibody-Dependent Enhancement (ADE) (Halstead S B et al. *Nature* 1977, 265(5596):739-741; Dejnirattisai W et al. *Science* 2010, 328(5979):745-748). In support of the ADE hypothesis, it was proposed that the low levels of serotype cross-reactive antibodies produced following a primary infection, can enhance the secondary infections through the formation of DENV-antibody complexes that bind to the Fcγ receptors (FcγR) on myeloid cells. This process leads to higher viral load and higher production of inflammatory mediators responsible of vascular permeability (Halstead S B et al. *Nature* 1977, 265(5596):739-741; Morens D M et al., *Clinical infectious diseases: an official publication of the Infectious Diseases Society of America* 1994, 19(3):500-512; Halstead S B et al., *Advances in virus research* 2003, 60:421-467).

Mechanistically, ADE was shown to be critically dependent on the activation of FcγRIIa receptor expressed by monocytes, macrophages and dendritic cells (DCs) which produce high amounts of cytokines (TNF-α and IL-6) and chemokines (MIP-1a) upon stimulation (Wong K L et al., *PLoS ONE* 2012, 7(5):e36435; Boonnak K et al., *J Immunol* 2013, 190(11):5659-5665; Guilliams M et al., *Nat Rev Immunol* 2014, 14(2):94-108). The increased viral loads in ADE were also shown to result from the binding of immune complexes (between the virus and sub-neutralizing antibodies) to the leukocyte Ig-like receptor B1 (LILR-B1) on human primary monocytes, leading to the inhibition of the early antiviral responses mediated by the activated FcγRIIa (Chan K R et al., *Proc Natl Acad Sci USA* 2014, 111(7):2722-2727).

Thus, depending on the nature of the DENV-specific antibody response, the adaptive immunity can induce either protection against infection or enhancement of infection and disease progression.

Like B cells, a pathogenic role of virus-specific T cells during secondary infection was also suggested. The hypothesis, called "original antigenic sin" postulated that, after a primary infection, cross-reactive memory T cells, with low avidity for the serotype of the secondary infection, dominate and mask the specific T cell response, leading to a less efficient killing of infected target cells (Mongkolsapaya J et al. *Nat Med* 2003, 9(7):921-927). These cross-reactive CD8+ T cells, stimulated upon a secondary infection with a different serotype, displayed also quantitative and qualitative differences in their response to the cross-reactive epitope or the altered peptide ligand (Bashyam H S et al., *J Immunol* 2006, 176(5):2817-2824).

However, in spite of these studies, the direct demonstration of a pathogenic role of DENV-specific T cells is still missing, and recent reports did not support a causative role for cross-reactive CD8+ T cells in the pathogenesis of dengue hemorrhagic fever during secondary infections. Indeed, a study in adults experiencing a secondary infection did not reveal any correlation between the magnitude and specificity of T-cell responses and clinical disease grade (Simmons C P et al., *J Virol* 2005, 79(9):5665-5675), and an important protective role for CD8+ T cells during primary DENV infection was also identified in a mouse model (Yauch L E et al. *J Immunol* 2009, 182(8):4865-4873). More strikingly, a detailed analysis of HLA-restricted T-cell responses in donors from hyperendemic area even reinforces the protective role of CD8+ T cells during DENV infection (Weiskopf D et al., *Proc Natl Acad Sci USA* 2013, 110(22): E2046-2053). It appears that, whereas serotype-specific responses are a hallmark of primary infection, there is a shift towards a response against conserved epitopes following secondary infection, without any difference in the avidity or functionality in CD8+ T cells among serotype-specific or conserved responses. In addition, a significant correlation was established between a weak T-cell response and disease susceptibility (Weiskopf D et al., *Proc Natl Acad Sci USA* 2013, 110(22):E2046-2053). Collectively, these studies highlight the beneficial effect of CD8+ T cells against disease progression in dengue virus infection.

BRIEF DESCRIPTION OF THE FIGURES

FIG. 1. Immunogenicity of non-structural proteins NS3, NS4a, NS4b and NS5 of DENV1 and intra-serotype and inter-serotype amino acid sequence conservation of DENV. A. Weiskopf D et al., *Proc Natl Acad Sci USA* 2013, 110(22):E2046-2053; B. Rivino L et al., *J Virol* 2013, 87(5):2693-2706.

FIG. 3. Amino acid consensus sequences of DENV2-NS, DENV3-NS and DENV4-NS polyepitopes (SEQ ID NOs: 146, 147 and 148 respectively).

FIG. 4. Alignment comparing the amino acid sequences of DENV1-NS, DENV2-NS, DENV3-NS and DENV4-NS consensus polyepitopes (SEQ ID NOs: 3, 146, 147 and 148 respectively).

FIG. 5. Native nucleotide sequence of the polynucleotide encoding DENV1-NS polyepitope (SEQ ID NO: 1).

FIG. 6. Optimised nucleotide sequence of the polynucleotide encoding DENV1-NS polyepitope (human codon optimized, measles optimized) (SEQ ID NO: 2).

FIG. 7. Schematic representation of recombinant MV vectors expressing DENV antigens. The NS polyepitopic synthetic sequence was inserted into the ATU position 2 or 3 of MV vectors in combination or not with DENV EDIII tetrameric antigen. The MV genes are indicated as follows: nucleoprotein (N), phosphoprotein and V/C accessory proteins (PVC), matrix (M), fusion (F), hemagglutinin (H) and polymerase (L). T7 RNA polymerase promoter (T7), T7 RNA polymerase terminator (T7t), hepatitis delta virus ribozyme (a), hammerhead ribozyme (hh). In MVDVax9, the combined antigen inserted into the ATU position 2 is composed of a secreted DENV EDIII tetrameric protein fused to a secreted NS polyepitopic sequence with furin sites (having the amino acid sequence RRDKR as defined in SEQ ID NO: 152) inserted to separate the different components. In MVDVax11, on the contrary, the NS polyepitopic synthetic sequence is not secreted (no peptide leader sequence) and is fused in 3' to the exported DENV EDIII tetrameric protein (starting with peptide leader sequence).

FIG. 9. DENV NS polyepitope peptides used for ELISPOT assays in CD46-IFNAR mice. Sequences 1-36 are 15-mer peptides overlapping of 5 aminoacids covering the entire DENV NS polyepitopic antigen. Peptides 37-41 were identified using prediction algorithms for their ability to bind H2-Db and H2-Kb T cell receptors expressed in CD46-IFNAR mice. These peptides have amino acid sequences as defined in SEQ ID NOs: 98-138.

FIG. 14. Identification and HLA restriction of the immunogenic epitopes of the DENV1-NS polyepitopic construct (SEQ ID NO: 3)

FIG. 18 presents Table 1: DENV CD8 T+ cell epitopes having amino acid sequences as defined in SEQ ID NOs: 16-68. Amino acids differing from the described epitope are underlined; bCD8 T cell epitopes with positive score in the Elispot test are highlighted; cNT: not tested. References for HLA resctriction are as follows: (1) Rivino L et al., *J Virol* 2013, 87(5):2693-2706; (2) Simmons C P et al. *J Virol* 2005, 79(9):5665-5675; (3) Imrie A et al. *J Virol* 2007, 81(18): 10081-10091; (4) Boucherma R et al., *J Immunol* 2013, 191(2):583-593; (5) Weiskopf D et al., *Proc Natl Acad Sci USA* 2013, 110(22):E2046-2053; (6) Lund O et al., *PLoS ONE* 2011, 6(10):e26494; (7) Rivino L et al., *J Immunol* 2013, 191(8):4010-4019; (8) Nascimento E J et al., *PLoS neglected tropical diseases* 2013, 7(10):e2497; (9) Immune Epitope Database (IEDB); (10) Weiskopf D et al., *J Immunol* 2011, 187(8):4268-4279; (11) Yauch L E et al., *J Immunol* 2009, 182(8):4865-4873.

FIGS. 20A to 20D present Tables 3A-3D. Sequence conservation among the 4 DENV serotypes of epitopes of the NS polyepitope sequence identified in mice with 4 different HLA-restrictions. Predicted anchor residues are underlined and highlighted in grey. A) Peptides HLA-A*02:01; B) Peptides HLA-A*24:02; C) Peptides HLA-B*07:02;

DESCRIPTION OF THE INVENTION

The inventors have analyzed transcripts differentially expressed in peripheral blood mononuclear cells (PBMCs) from either asymptomatic or symptomatic infected donors from a cohort in Cambodia and observed a significant number of genes corresponding to CD8+ T cell activation overexpressed in asymptomatic individuals, in comparison with symptomatic donors, with Dengue Fever (DF) or Dengue Hemorrhagic Fever (DHF). A higher number of transcripts associated with TH17 and neutrophil activation were also observed in PBMC from these symptomatic patients with DHF and dengue shock syndrome (DSS), in agreement with the strong inflammatory response observed in severe dengue cases. Taken together, these observations strongly support an HLA-linked protective role for CD8+ T cells in anti-DENV immunity.

Figure 1:
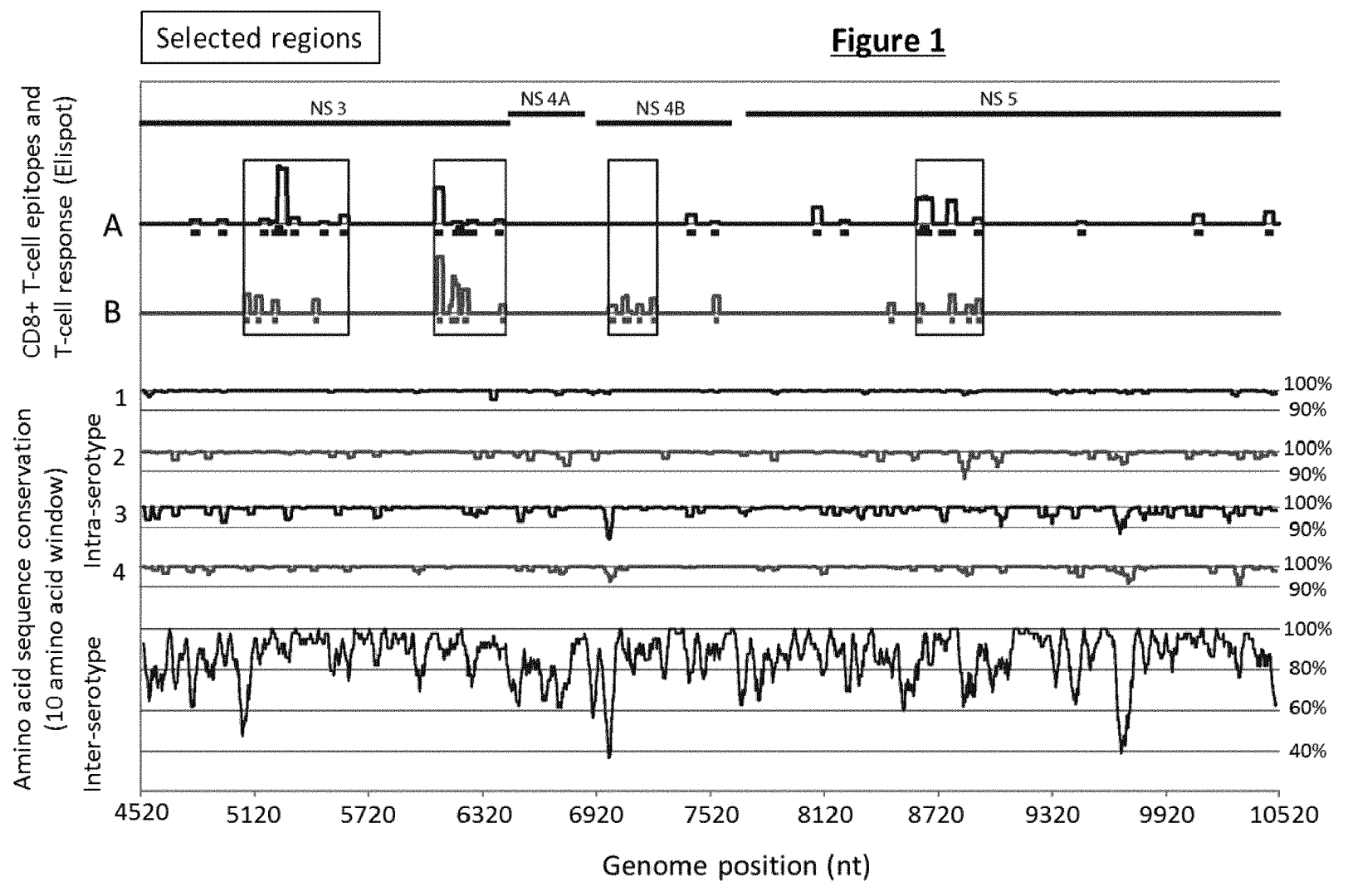
Figure 2:
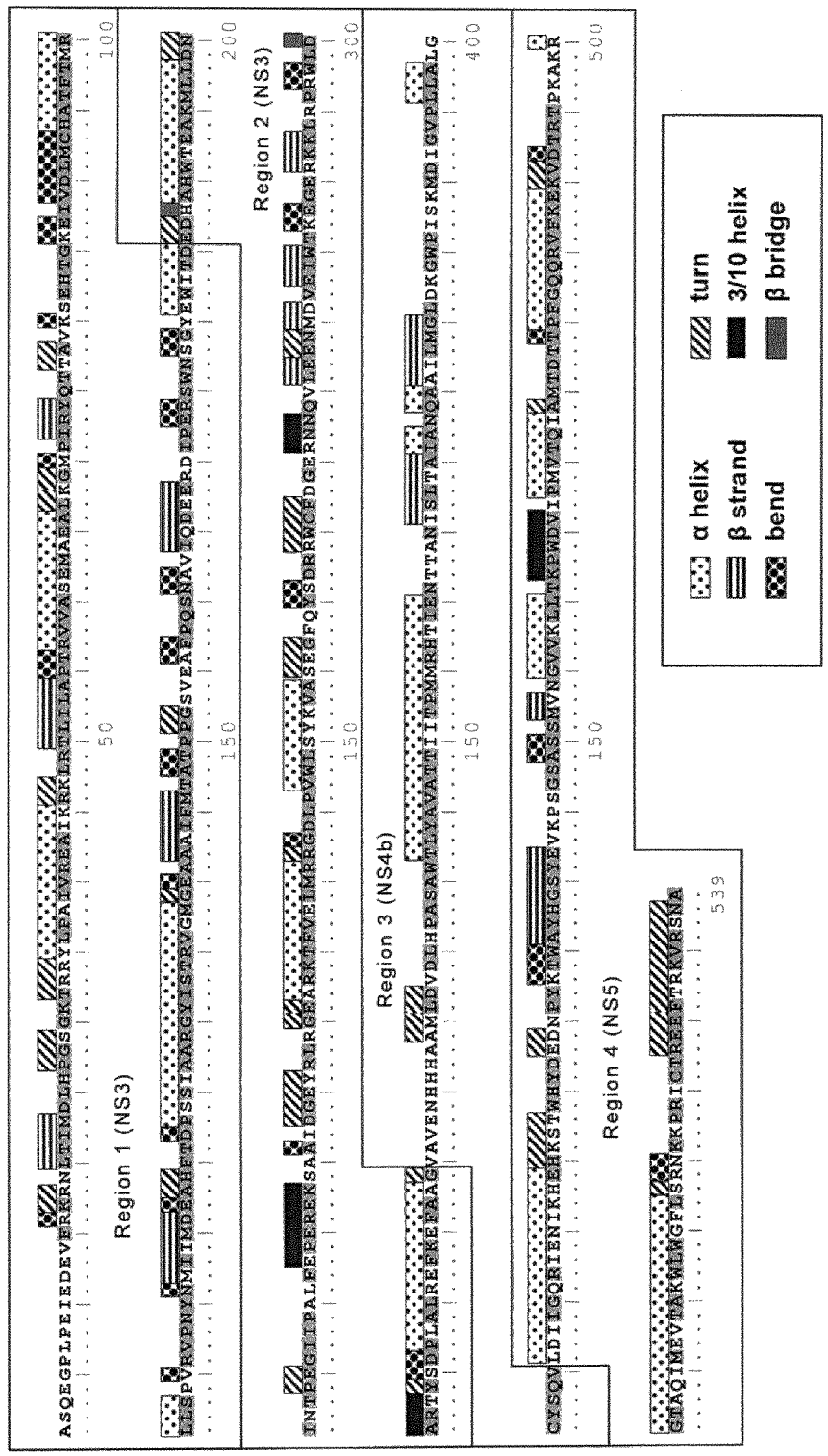
FIG. 2. Amino acid sequence and secondary structure of NS DENV1 polyepitopic combined polyepitopic antigen (SEQ ID NO: 3). The following recitation of positions of amino acids in the sequence indicates the type of secondary structure in which the amino acid(s) is(are) involved in the corresponding full length protein as predicted for NS4B, or described in published crystallography studies for NS3 and NS5 (PDB ID 2VBC, *J Virol.* 2008 January; 82(1):173-183 and 2J7W, *J Virol.* 2007 May; 81(9):4753-65, respectively). In particular, alpha-helices are observed at the following segments of amino acid(s): 35-45; 57-66; 94-103; 123-138; 181-185; 189-198; 232-241; 247-254; 307-318; 342-360; 371-372; 374-375; 396-398; 406-419; 455-460; 468-473; 480-489; 500-517. Beta strands are observed at the following segments of amino acid(s): 20-23; 50-54; 72-74; 112-116; 142-146; 164-168; 276-277; 280-281; 283-285; 291-293; 366-370; 376-380; 436-442; 452-453. Bends are observed at the following segments of amino acid(s): 16; 55-56; 70; 80; 86-87; 89-93; 105; 111; 117; 122; 140; 148-49; 156-157; 161-162; 173-174; 178-179; 221; 243; 260-261; 287-288; 297-298; 305-306; 433-35; 449-450; 479; 492; 519-520. Turns are observed at the following segments of amino acid(s): 17-18; 27-29; 32-34; 46-47; 67-69; 77-78; 118-119; 139; 151-152; 186-187; 199-200; 204-205; 223-226; 230-231; 242; 255-257; 264-267; 278-279; 304; 319; 329-332; 420-423; 428-429; 474; 490-491; 518; 528-538. Moreover, 3/10 helices are observed at the following segments of amino acid(s): 213-218; 271-273; 301-303; 462-466 and 13 bridge is observed at the amino acids 188 and 300. Positions with conserved amino acids (found in more than 99.9% of a representative panel of 2033 sequences that include the 4 serotypes) are highlighted in dark grey.

The inventors designed an antigen capable of inducing CD8+ T cell immunity to DENV. Most importantly, this antigen has a small size compared to the full length of the DENV genome, or to the full length of DENV NS proteins, so that it can be inserted in any vaccine vector, such as for example, a replicating viral vector derived from live-attenuated MV vaccine. Furthermore, this design aims at providing a DENV antigen enriched in highly antigenic epitopes, with the idea of limiting the exposure of the immune system to weakly immunogenic epitopes, and prevent the dispersion or dilution of the immune response. This antigen is composed of polyepitopic regions from NS proteins of DENV. Using compiled anti-DENV T-cell epitope distribution and strength (Simmons C P et al., *J Virol* 2005, 79(9):5665-5675; Yauch L E et al., *J Immunol* 2009, 182(8):4865-4873; Weiskopf D et al., *Proc Natl Acad Sci USA* 2013, 110(22): E2046-2053; Imrie A et al., *J Virol* 2007, 81(18):10081-10091; Lund O et al., *PLoS ONE* 2011, 6(10):e26494; Weiskopf D et al., *J Immunol* 2011, 187(8):4268-4279; Boucherma R et al., *J Immunol* 2013, 191(2):583-593; Nascimento E J et al., *PLoS neglected tropical diseases* 2013, 7(10):e2497; Rivino L et al., *J Virol* 2013, 87(5):2693-2706; Rivino L et al., *J Immunol* 2013, 191(8):4010-4019; Immune Epitope Database (IEDB)), the inventors selected four regions that are enriched in CD8 epitopes, for a total of 539 amino acids: two regions in NS3 (185 and 134 amino acids, respectively), one region in NS4b (86 amino acids) and one in NS5 (135 amino acids) (FIG. 1). Borders of these 4 regions were chosen based on the secondary structure and amino acid sequence properties of the respective polyproteins, using crystallographic data for NS3 and NS5 (PDB ID 2VBC and 2J7W respectively), and using prediction tools such as JPRED (Cole C, Barber J D & Barton G J. *Nucleic Acids Res*. 2008. 35 (suppl. 2) W197-W201) or GOR IV (GOR secondary structure prediction method version IV, Methods in Enzymology 1996 R. F. Doolittle Ed., vol 266, 540-553, Garnier J, Gibrat J-F, Robson B) for NS4B, (FIG. 2). Notably, the design carefully avoided the disruption of secondary structure elements such as α-helices or β-strands (FIG. 2). A total of 2033 full-length dengue genome sequences (865 for serotype 1, 678 for serotype 2, 427 for serotype 3 and 63 for serotype 4) were aligned using MUSCLE 3.7 (Edgar R C, *Nucleic Acids Res* 2004, 32(5): 1792-1797), with manual adjustments according to the amino acid sequence. Sequence similarity was evaluated intra- and inter-serotypes at the nucleic and amino acid levels. Analysis of the concatenated regions of interest revealed strong intra-serotype conservation, and generally a higher degree of sequence identity compared to the genome as a whole, including for inter subtypes comparisons (FIGS. 1 and 2). Based on the genetic diversity of the four serotypes of DENV, and with the idea that T cell epitopes are either conserved among different serotypes, or are serotype-specific with nevertheless the ability to induce cross-reactive CD8+ T-cell responses, a prototype consensus sequence based on epidemic strains of DENV1 was selected, the DENV1 NS T cell polyepitope (FIGS. 1 and 2).

A serotype 1 consensus sequence was selected, as it presented the highest average genetic identity with the 4 serotypes (versus serotype 1: 99.48%; serotype 2: 83.48%; serotype 3: 89.39%; serotype 4: 76.96%).

Average genetic identity was estimated for each serotype as the percent sequence identity (ratio of identical positions over the total of aligned positions constituting the NS polyepitope) pairwise for each sequence of the serotype, and the average was reported. This percentage given corresponds only to the concatenation of the selected fragments of NS3, NS4B and NS5.

The invention thus relates to a chimeric polyepitope having less than 600 amino acid residues comprising or consisting of the following fragments of (a), (b) and (c) assembled in a fusion polypeptide wherein the fragments of (a), (b) and (c) are directly or indirectly fused in this order:

(a) two fragments of the non-structural (NS) NS3 protein of the dengue virus (DENV) serotype 1 (DENV1) comprising or consisting of two regions, wherein the first region has an amino acid sequence as defined in SEQ ID NO: 6, and the second region has an amino acid sequence as defined in SEQ ID NO: 9, (b) a fragment of the NS4b protein of DENV1 having an amino acid sequence as defined in SEQ ID NO: 12, (c) a fragment of the NS5 protein of DENV1 having an amino acid sequence as defined in SEQ ID NO: 15, or a polyepitope variant thereof, which (i) comprises or consists of the assembly in a fusion polypeptide, of DENV NS fragments, the sequences of which are obtained by alignment of the NS3 DENV1, NS4b DENV1, NS5 DENV1 fragments recited in (a), (b) and (c) with the respective NS3, NS4b and NS5 sequences of the NS proteins of a virus of the DENV2, DENV3 or DENV4 serotype or (ii) consists of a chimeric polyepitope having an amino acid sequence which has more than 75% identity, in particular more than 80% or more than 85% or more than 90% identity with the sequence of the fusion polypeptide consisting of fused fragments (a), (b) and (c) (from which it derives by mutation of amino acid residues), over its whole length.

In a particular embodiment, the present invention relates to a chimeric polyepitope having a size of less than 600 amino acid residues, in particular consisting of a strand of 539 amino acid residues and comprising or consisting of the fusion of fragments named (a), (b) and (c) hereafter and obtained from or representative of several non-structural (NS) proteins of any DENV genome, namely fragments consisting of:

(a) the NS3 protein consisting of amino acids 1645 to 1829 and 1959 to 2092 in the polyprotein sequence of DENV1 (Genbank accession number NP_059433.1), or amino acids 1645 to 1828 and 1958 to 2091 in the polyprotein sequence of DENV2 (Genbank accession number NP_056776.2), or amino acids 1643 to 1827 and 1957 to 2090 in the polyprotein sequence of DENV3 (Genbank accession number YP_001621843.1), or amino acids 1644 to 1827 and 1957 to 2090 in the polyprotein sequence of DENV4 (Genbank accession number NP_073286.1), (b) the NS4b protein consisting of amino acids 2262 to 2347 in the polyprotein sequence of DENV1 (Genbank accession number NP_059433.1), or amino acids 2260 to 2345 in the polyprotein sequence of DENV2 (Genbank accession number NP_056776.2), or amino acids 2260 to 2344 in the polyprotein sequence of DENV3 (Genbank accession number YP_001621843.1), or amino acids 2259 to 2341 in the polyprotein sequence of DENV4 (Genbank accession number NP_073286.1), and (c) the NS5 protein consisting of amino acids 2766 to 2899 in the polyprotein sequence of DENV1 (Genbank accession number NP_059433.1), or amino acids 2765 to 2898 in the polyprotein sequence of DENV2 (Genbank accession number NP_056776.2), or amino acids 2763 to 2896 in the polyprotein sequence of DENV3 (Genbank accession number YP_001621843.1), or amino acids 2761 to 2894 in the polyprotein sequence of DENV4 (Genbank accession number NP_073286.1), wherein each fragment (a), (b) and (c) comprises a plurality of epitopes suitable for the elicitation of an immune response, especially an immune T-cell response against all DENV serotypes, said polyepitope resulting from direct or indirect fusion of the plurality of said fragments, in particular said fragments originating from a unique dengue virus serotype.

In a particular embodiment, the present invention relates to a chimeric polyepitope having a size of 539 amino acids, and comprising or consisting of the fusion of fragments named (a), (b) and (c) hereafter and obtained from or representative of several non-structural (NS) proteins of any DENV genome, namely fragments consisting of:

(a) the NS3 protein encoded by nucleotides 5027 to 5581 and 5969 to 6370 in the nucleotide sequence of DENV1 (Genbank accession number NC_001477.1), or nucleotides 5026 to 5580 and 5968 to 6369 in the nucleotide sequence of DENV2 (Genbank accession number NC_001474.2), or nucleotides 5021 to 5575 and 5963 to 6364 in the nucleotide sequence of DENV 3 (Genbank accession number NC_001475.2), or nucleotides 5028 to 5582 and 5970 to 6371 in the nucleotide sequence of DENV 4 (Genbank accession number NC_002640.1), (b) the NS4b protein encoded by nucleotides 6878 to 7135 in the nucleotide sequence of DENV1 (Genbank accession number NC_001477.1), or nucleotides 6874 to 7131 in the nucleotide sequence of DENV2 (Genbank accession number NC_001474.2), or nucleotides 6872 to 7126 in the nucleotide sequence of DENV 3 (Genbank accession number NC_001475.2), or nucleotides 6876 to 7124 in the nucleotide sequence of DENV 4 (Genbank accession number NC_002640.1), and (c) the NS5 protein encoded by nucleotides 8390 to 8791 in the nucleotide sequence of DENV1 (Genbank accession number NC_001477.1), or nucleotides 8389 to 8790 in the nucleotide sequence of DENV2 (Genbank accession number NC_001474.2), or nucleotides 8381 to 8782 in the nucleotide sequence of DENV 3 (Genbank accession number NC_001475.2), or nucleotides 8382 to 8783 in the nucleotide sequence of DENV 4 (Genbank accession number NC_002640.1), wherein each translated fragment (a), (b) and (c) comprises a plurality of epitopes suitable for the elicitation of an immune response, especially an immune T-cell response against all DENV serotypes, said polyepitope resulting from direct or indirect fusion of the plurality of said fragments in particular said fragments originating from a unique dengue virus serotype.

As defined herein, the term "polyepitope" refers to a polypeptide with advantageously at least 3 and in particular at least 5 and preferably more than 10 or more than 13 epitopes identified in DENV1 NS3, NS4b and NS5 proteins, in particular T-cell epitopes of DENV1 NS3, NS4b or NS5 consensus sequence provided in FIG. 1. Epitopes within the present invention are, either linear or conformational, preferably linear, and are any peptide or polypeptide involved in the induction of a cell-mediated immune response, especially a T cell immune response against a DENV and in particular against anyone of DENV1, DENV2, DENV3, DENV4 or against multiple, in particular all DENV serotypes. Accordingly, epitopes described herein include those which are processed by APC (Antigen Presenting Cells) in a host, especially T epitopes recognized in association with class I MHC (Major Histocompatibility Complex) molecules, such as epitopes which target cells are CD8+T lymphocytes or T epitopes recognized in association with class II MHC molecules, such as those which target cells are CD4+T lymphocytes.

The term "chimeric polyepitope" means any polyepitopic polypeptide comprising sub-portions of different DENV NS proteins selected among NS3, NS4b and NS5 proteins, for example a polyepitope deriving from a first DENV NS protein and a polyepitope deriving from a second DENV NS protein as defined herein. A polyepitope is also considered to be a chimeric polyepitope if it includes sub-portions deriving from different polyepitopes from the same DENV NS protein, or even from the same polyepitopes from different DENV NS proteins. The chimeric polyepitope of the invention includes the polyepitope variant. Accordingly each definition or embodiment disclosed herein applies to the variant polyepitope unless it is technically irrelevant.

In a particular embodiment of the invention, the chimeric polyepitope comprises human leukocyte antigen (HLA)-restricted epitopes. The expression "HLA-restricted" refers to the capacity for a particular epitope to have an affinity for this type of HLA molecule. The HLA molecules used in the invention encompass either class I molecules (designated HLA-A, B or C) or class II molecules (designated DP, DQ or DR).

In another particular embodiment of the invention, the chimeric polyepitope elicits a human leukocyte antigen (HLA)-restricted CD8+ and/or CD4+ T cell response against DENV1, DENV2, DENV3 and DENV4. A non-exhaustive list of DENV CD8 T cell epitopes is provided in Table 1.

In another particular embodiment of the invention, the chimeric polyepitope elicits a human leukocyte antigen (HLA)-restricted CD4+ T cell response against DENV1, DENV2, DENV3 and DENV4. A non-exhaustive list of DENV CD4 T cell epitopes is provided in Table 2.

In a particular embodiment, the NS chimeric polyepitope sequence has been shown to elicit antigenic responses in mice with HLA restriction such as HLA-A*02:01, HLA-A*24:02, HLA-B*07:02 or HLA-B*35:01.

In a particular embodiment, the present invention relates to a chimeric polyepitope, whose size is 539 amino acids, comprising or consisting of:

(a) two fragments of the non-structural (NS) NS3 protein of the dengue virus (DENV) serotype 1 (DENV1), having amino acid sequences as defined in SEQ ID NO: 6, SEQ ID NO: 9, respectively, (b) a fragment of the NS4b protein of DENV1 comprising amino acid sequences as defined in SEQ ID NO: 12, (c) a fragment of the NS5 protein of DENV1 comprising amino acid sequences as defined in SEQ ID NO: 15, and wherein each NS fragment (a), (b) and (c) is fused directly or indirectly with another NS fragment (a), (b) and (c) in the polyepitope, preferably in this order.

Nucleotide sequences of the polyprotein of DENV1, DENV2, DENV3 and DENV4 can be accessed from the Genbank accession numbers NP_059433.1, NP_056776.2, YP_001621843.1 and NP_073286.1 respectively.

Amino acid sequences of DENV2-NS, DENV3-NS and DENV4-NS polyepitopes of SEQ ID NO: 146, 147 and 148 respectively which are variant polyepitopes of the invention are disclosed in FIG. 3. The inventors have carried out an alignment showing conserved amino acid residues in sequences of DENV1-NS, DENV2-NS, DENV3-NS and DENV4-NS polyepitopes (FIG. 4).

In a preferred embodiment of the invention, the chimeric polyepitope comprises at least the P30, P451, P36, P453, P49, P50, P32, P17, P21, P51, P33, P56 and P15 epitopes disclosed herein. In particular, the P30, P451 and P56 epitopes are restricted by HLA-A*02:01, the P17, P32 and P33 epitopes are restricted by HLA-A*24:02, the P15, P30 and P36 epitopes are restricted by HLA-B*07:02 and the P21, P49, P50, P51 and P453 epitopes are restricted by HLA-B*35:01. The chimeric polyepitope is expected to contain a number of additional epitopes at least equal to the number of existing HLA, with examples provided in Tables 1 and 2.

The epitopes of the invention can have amino acid sequences that are distinct or that differ by one or more amino acids in the consensus NS determined for DENV1 within the frame of the invention. Alternatively or in addition, two epitopes of the polyepitope of the invention can have overlapping sequences in one NS fragment, and accordingly share some amino acids.

Chimeric polyepitopes of the invention can be synthesized chemically, or produced either in vitro (cell free system) or in vivo after expression of the nucleic acid molecule encoding the polyepitope in a cell system.

As defined herein, the term "fragment" refers to parts or portions of NS proteins (i.e. NS3, NS4b or NS5 protein), in particular portions having from 86 to 185 amino acids. Any sequence or combination of sequences of any dengue virus isolate corresponding to the fragments of the invention (as delimited by the positions in the NS proteins as identified using nucleotide and amino acid numbering on DENV1 reference sequence deposited in Genbank (NP_059433.1) or as disclosed with respect to its SEQ ID NO. is shorter in length than the NS protein from which it originates.

According to a particular embodiment of the invention, one NS fragment is fused "directly" with another NS fragment, i.e. the 3' end of the NS fragment is directly linked to the 5' end of the second fragment (and so on), corresponding to a chimeric polyepitope composed of consecutive NS fragments from the same and/or from different NS proteins chosen among NS3, NS4b and NS5, in particular originating from NS consensus sequence of DENV1. According to an alternative embodiment, the fusion of the fragments is "indirect" and accordingly involves the presence of non-NS amino acid residues segment(s), i.e., amino acid residues segments which do not read on the NS protein providing the sequence of the considered fragment.

As defined herein, the term "region" refers to contiguous amino acid strand of a NS protein as defined herein, having at least 86 amino acids. A fragment of a NS protein may comprise or consist of a plurality of regions as for the NS3 fragment.

The term "percentage identity" between two compared nucleotidic sequences or respectively two amino acid sequences as used in the present invention means a percentage of identical nucleotides or amino acids between the two sequences to be compared, obtained after best alignment, that percentage being purely statistical and the differences between the two sequences being randomly distributed and over their entire length. The term "best alignment" or "optimum alignment" means the alignment at which the percentage of identity is the highest. Sequence comparisons between two nucleic acid or amino acid sequences are traditionally carried out by comparing these sequences after having aligned them in an optimum manner, said comparison being carried out using comparison segments or windows to identify and compare local regions with sequence similarity. The optimum sequence alignment for comparison may be carried out manually or using a Smith and Waterman (1981) local homology algorithm, using the Neddleman and Wunsch (1970) local homology algorithm, using the Pearson and Lipman (1988) sequence similarity search method, or using software employing these algorithms (GAP, BEST-FIT, BLAST P, BLAST N, FASTA and TFASTA in the Wisconsin Genetics Software Package, Genetics Computer Group, 575 Science Dr, Madison, Wis.). To obtain an optimal alignment, the BLAST program may be used, with the BLOSUM 62 matrix. It is also possible to use PAM or PAM250 matrices. A total of 2033 full-length dengue genome sequences (865 for serotype 1, 678 for serotype 2, 427 for serotype 3 and 63 for serotype 4) were aligned using MUSCLE 3.7 (Edgar R C, *Nucleic Acids Res* 2004, 32(5): 1792-1797), with manual adjustments according to the amino acid sequence.

The percentage identity between two nucleic acid or two amino acid sequences is determined by comparing these two sequences aligned in an optimum manner. The percentage identity is calculated by determining the number of identical positions for which the nucleotide or amino acid residue is identical between the two sequences, dividing this number of identical positions by the total number of compared positions and multiplying the result obtained by 100 to obtain the percentage identity between these two sequences.

In a particular embodiment of the invention, the first region of NS3 of DENV1 has an amino acid sequence as defined in SEQ ID NO: 6, the second region of NS3 of DENV1 has an amino acid sequence as defined in SEQ ID NO: 9, the NS4b fragment of DENV1 has an amino acid sequence as defined in SEQ ID NO: 12 and the NS5 fragment of DENV1 has an amino acid sequence as defined in SEQ ID NO: 15.

In another particular embodiment of the invention, the native and optimised sequences of the polynucleotide encoding the first region of NS3 of DENV1 are as defined in SEQ ID NOs: 4 and 5 respectively, the native and optimised sequences of the polynucleotide encoding the second region of NS3 of DENV1 are as defined in SEQ ID NOs: 7 and 8 respectively, the native and optimised sequences of the polynucleotide encoding the NS4b fragment of DENV1 are as defined in SEQ ID NOs: 10 and 11 respectively, and the native and optimised sequences of the polynucleotide encoding the NS5 fragment of DENV1 are as defined in SEQ ID NOs: 13 and 14 respectively.

The term "variants" encompasses the assembly of the other fragments of the NS3, NS4b and NS5 proteins of a virus of the DENV serotype 2, 3 or 4, as disclosed herein.

In a preferred embodiment of the invention, the chimeric polyepitope comprises or consists of a polypeptide having an amino acid sequence selected from the group consisting of SEQ ID NOs: 3, 146, 147 and 148.

The present invention also relates to an association of the chimeric polyepitope of the invention, with a distinct immunogenic polypeptide hereafter designated as tetravalent EDIII/ectoM. In a particular embodiment of the invention, said distinct immunogenic polypeptide (tetravalent EDIII/ectoM) consists of chimeric DENV antigens composed of the fusion of the EOM polypeptides representative of the four DENV serotypes, fused to ectoM of DENV1, and has an amino acid sequence as disclosed in SEQ ID NO: 145, and is encoded by the polynucleotide having SEQ ID NO: 144.

Said association of polypeptides may be achieved as a result of expression of the polynucleotides encoding each of said chimeric polyepitope and distinct immunogenic polypeptide, from a vector as disclosed herein. Alternatively, said association may result from an amino acid construct encompassing said chimeric polyepitope and distinct immunogenic polypeptide.

The present invention also relates to viral particles, in particular recombinant measles virus (MV) particles expressing a chimeric polypeptide of the invention or said chimeric polypeptide in association with the tetravalent EDIII/ectoM polypeptide.

The present invention also relates to a vector comprising or consisting of recombinant measles virus (MV) particles expressing the chimeric polyepitope of the invention and optionally the tetravalent EDIII/ectoM immunogenic polypeptide.

The thus produced recombinant viral particles, in particular measles virus particles have proved to enhance the immune response elicited by the DENV antigens when used alone, in particular by impacting the immunogenic T-cell response elicited following administration of the particles to a host in need thereof.

In order to prepare the viral particles, in particular MV particles expressing the chimeric polyepitope of the invention in association with the so-called tetravalent EDIII/ectoM polypeptide as disclosed herein, the polynucleotide(s) encoding said polyepitope and polypeptide are recombined into a polynucleotide encompassing the genome of the virus, especially the genome of the measles virus.

According to a preferred embodiment of the invention, the recombinant MV genome is provided as a cDNA encoding the full-length RNA genome of a live-attenuated Schwarz or Moraten virus.

A live-attenuated MV strain refers to a strain which has been serially passaged on selected cells and, preferably, adapted to other cells such as primary cells with an IFN a/β response, i.e. CEF cells, to produce seed strains suitable for the preparation of vaccine strains, harboring a stable genome which would not allow reversion to pathogenicity nor integration into host chromosomes, in particular human host chromosomes. In a particular embodiment of the invention, a live-attenuated MV is one which has been selected on primary cells such as CEF cells.

As defined herein, the expression "live-attenuated Schwarz or Moraten virus" designates a Schwarz or Moraten virus originating from a strain that is avirulent or less virulent than a determined parent strain in the same host, especially in human, while maintaining infectious properties and immunogenicity and possibly adjuvancy when administered in a host, especially in human. In particular, the Schwarz strain or the Moraten strain is from the Rouvax® vaccine (Aventis). It has been demonstrated that the Schwarz strain has a perfect identity of sequence with the Moraten strain (Parks, C. L. et al., 2001, *J Virol*, 75(2): 910-920; Schwarz, A. J., 1962, *Am J Dis Child*, 103, 386-389). The Schwarz/Moraten strains are currently widely-used since they induce long-term cell and humoral immune responses and present an important genetic stability since no reversion to a pathogenic form has ever been observed (Hilleman, M., 2002, *Vaccine*, 20:651-665).

The measles virus genome is obtained as a result of preparation of a cDNA molecule encoding the full-length MV genome as disclosed in the art especially in WO 2004/001051 and WO 2004/000876. Said cDNA molecule has been included as an insert in a plasmid designated pTM-MVSchw deposited on Jun. 12, 2002 with the CNCM under No. 1-2889 (Institut Pasteur-Paris-France). The sequence of the MV cDNA encoding the genome is provided in the figures illustrating the constructs prepared with the chimeric polyepitope of the invention and the distinct so-called tetravalent EDIII/ectoM polypeptide. The position of the MV sequences is disclosed in said figures.

In order to express the chimeric polyepitope of the invention and optionally the distinct so-called tetravalent EDIII/ectoM polypeptide, said cDNA molecule encoding the full-length MV genome is recombined with a DNA molecule encoding the chimeric polyepitope of the invention and optionally in a DNA molecule encoding the so-called tetravalent EDIII/ectoM polypeptide as disclosed herein, using methods and protocols well-known from the person skilled in the art. The DNA molecules encoding said polypeptides are prepared according to known techniques, by the skilled person.

In a particular embodiment, a DNA molecule corresponding to the chimeric polyepitope of the invention can be generated by chemical synthesis. Preferably, this sequence is codon-optimized for expression in mammalian cells and preferably its length fulfills the "rule of six" which stipulates that the total number of nucleotides is a multiple of 6, which rules is known to impact the proper expression of the MV proteins from the MV genome (Calain, P. et al. *J Virol.*, 1993, 67:4822-4830).

In a particular embodiment, all nucleic acid constructs inserted in the cDNA encoding the full-length MV genome, in particular coding sequences for the chimeric polyepitope and for the so-called tetravalent EDIII/ectoM polypeptide have a number of nucleotides which is a multiple of six.

The present invention thus relates to an isolated or purified polynucleotide encoding the chimeric polyepitope of the invention, and having preferably a total number of nucleotides which complies with the rule of six. This polynucleotide is in particular a DNA or a cDNA. In a particular embodiment, MV editing- and polyadenylation-like sequences of the sequence encoding the NS fragments of the polynucleotide of the invention are mutated (Lamb, R. A. et al. In Fields Virology, 4th edition, 1305-1340; Schneider, H. et al. *Virology*, 1997, 227: 314-322). In addition, to allow its future cloning into a plasmid such as pUC into a mammalian expression plasmid such as pcDNA3, or into MV vector, the DNA encoding the chimeric polyepitope of the invention was flanked by sequences of restriction sites such as BgIII, ApaI, BsiWI and BssHII.

The invention accordingly concerns in particular the native and codon optimized nucleotide sequences encoding the chimeric polyepitope of DENV1 which are the sequences disclosed as SEQ ID NO: 1 and SEQ ID NO: 2 respectively (FIGS. 5 and 6). Amino acid sequence of the chimeric polyepitope of DENV1 is the sequence disclosed as SEQ ID NO: 3.

The present invention also relates to an isolated or purified polynucleotide encoding the chimeric polyepitope of the invention, in a nucleic acid construct further comprising a polynucleotide encoding tetravalent DENV antigens composed of the fusion of the EDIII polypeptides of the four serotypes, fused to ectoM of DENV1, wherein the polynucleotide obtained has preferably a total number of nucleotides which complies with the rule of six. In a particular embodiment, this polynucleotide has the sequence of SEQ ID NO: 144. Such a construct may in particular comprise the polynucleotide encoding tetravalent DENV antigens composed of the fusion of the EDIII polypeptides of the four serotypes, fused to ectoM of DENV1 upstream from the polynucleotide encoding the chimeric polyepitope of the invention.

The invention also relates to a nucleic acid molecule comprising the herein disclosed polynucleotide encoding the chimeric polyepitope of the invention and optionally comprising the polynucleotide encoding tetravalent DENV antigens composed of the fusion of the EDIII polypeptides of the four serotypes, fused to ectoM of DENV1 recombined with the cDNA molecule encoding the full-length MV genome.

As defined herein, the term "isolated or purified" means molecules which have been altered by man from their native state, i.e. if the molecules exist in nature, they have been changed and/or withdrawn from their initial environment. As an example, a polynucleotide naturally present and found in the biological environment of a living organism which naturally expresses it is not "isolated" in this context. However, the same polynucleotide when separated from its natural environment and/or obtained by cloning, amplification and/or chemical synthesis is considered in the present invention to be "isolated". Further, a polynucleotide which is introduced into an organism by transformation, gene manipulation or any other recombination method is "isolated" even if it is present in said organism.

The term "encoding" used in the present application defines the ability of the nucleic acid molecules to be transcribed and where appropriate translated for product expression into selected cells or cell lines, when said molecule is placed under expression control sequences including promoter for transcription. Accordingly a "polynucleotide encoding" according to the invention is either limited to the nucleic acid having the sequence translated into the amino acid sequence or alternatively when specified comprises also the expression control sequences.

The invention also relates to a vector. As used herein, the term "vector" refers to a polynucleotide construct designed for transduction/transfection of one or more cell types. Vectors may be, for example, "cloning vectors" which are designed for isolation, propagation and replication of inserted polynucleotides (designated as the insert), "expression vectors" which are designed for expression of a polynucleotide molecule especially for expression of the insert in a host cell, or a "viral vector" which is designed to result in the production of recombinant virus particles or virus-like particles, or "shuttle vectors", which comprise the attributes of more than one type of vector.

A number of vectors suitable for transduction or for transfection of cells, in particular for stable transfection of cells and bacteria are available to the public (e.g. plasmids, viruses), as are methods for constructing such cell lines. It will be understood that the present invention encompasses any type of vector comprising any of the polynucleotides of the invention.

The present invention accordingly relates to a vector, in particular an expression vector, which may be a plasmid comprising as polynucleotide insert(s), one or a plurality of the nucleic acid molecules defined herein. In a particular embodiment, the plasmid comprises as an insert a polynucleotide encoding the chimeric polyepitope of the invention as defined herein and optionally comprises the polynucleotide encoding tetravalent DENV antigens composed of the fusion of the EDIII polypeptides of the four serotypes, fused to ectoM of DENV1.

In a particular embodiment, the present invention concerns a plasmid (designated measles genome vector) comprising (i) a cDNA encoding the full-length RNA genome of a measles virus (MV), which cDNA is recombined with (ii) a polynucleotide according to the invention encoding the chimeric polyepitope of the invention as defined herein and optionally (iii) a polynucleotide encoding tetravalent DENV antigens composed of the fusion of the EDIII polypeptides of the four serotypes, fused to ectoM of DENV1 as defined herein. In a particular embodiment when the sequences of (i), (ii) and optionally (iii) are present in the MV genome vector, they comply together with the rule of six.

In a particular embodiment said polynucleotide(s) is(are) located as separate insert(s) between the P and M genes of the MV genome, or between the H and L genes of the MV genome. Optionally said insert(s) is(are) located in an Additional Transcription Unit (ATU) such as the ATU having the sequence of ATU 2 or ATU3 illustrated in the construct MDVVax6. The location of the ATU within the cDNA derived from the antigenomic RNA of MV can vary along said cDNA.

In a particular embodiment, the present invention concerns a recombinant measles virus (MV) genome vector, which is a plasmid comprising (i) a cDNA encoding the full-length RNA genome of a MV virus and (ii) the polynucleotide encoding the chimeric polyepitope according to the invention, said polynucleotide being located as an insert between the P and M genes of the MV genome or between the H and L genes of the MV genome, optionally in an Additional Transcription Unit (ATU), wherein the sequences of (i) and (ii) when recombined in the plasmid together comply with the rule of six.

The present invention also concerns a recombinant MV genome vector, which is a plasmid comprising (a) a cDNA encoding the full-length RNA genome of a MV virus, (b) a polynucleotide encoding tetravalent DENV antigens composed of the fusion of the envelope domain III (EDIII) polypeptides of the four DENV serotypes, fused to the ectodomain of the membrane protein (ectoM) of DENV1, in particular DENV antigens having the sequence of SEQ ID NO: 145 and (c) the polynucleotide according to the invention, wherein:

the polynucleotide (b) is located as an insert between the P and M genes of the MV genome and the polynucleotide (c) is located as an insert between the H and L genes of the MV genome, or the polynucleotide (b) is located as an insert between the P and M genes of the MV genome and the polynucleotide (c) is located as an insert between the P and M genes of the MV genome, or the polynucleotide (b) is located as an insert between the H and L genes of the MV genome and the polynucleotide (c) is located as an insert between the P and M genes of the MV genome and wherein the sequences of (a), (b) and (c) when recombined in the plasmid together comply with the rule of six.

In a particular embodiment, when the sequences of (a), (b) and (c) are recombined in a plasmid they together comply with the rules of six.

The nucleotide sequences of particular vectors of the invention comprising both polynucleotides are the sequences disclosed as SEQ ID NO: 139, SEQ ID NO: 140, SEQ ID NO: 141, SEQ ID NO: 142, SEQ ID NO: 143 and SEQ ID NO: 149.

The present invention also relates to a host cell genetically transformed with the polynucleotide encoding the chimeric polyepitope of the invention and optionally with the polynucleotide encoding the tetravalent EDIII/ectoM according to the invention, in particular a polynucleotide encoding tetravalent DENV antigens composed of the fusion of the envelope domain III (EDIII) polypeptides of the four DENV serotypes, fused to the ectodomain of the membrane protein (ectoM) of DENV1. A particular host cell may thus be genetically transformed with a vector of the invention, in particular with a recombinant MV genome vector of the invention.

The host cell of the invention is transfected with a genome vector of the invention, by methods well known to the man skilled in the art, i.e. by chemical transfection (calcium phospate, lipofectamine), lipid-based techniques (liposome), electroporation, photoporation, use of viral vectors . . . .

In a particular embodiment, a cell is transformed or transduced with a polynucleotide of the invention, in a way enabling integration of the polynucleotide in the cell genome either by a recombination with the homologous cellular sequence or by insertion in the cellular genome. The transfection, infection or transduction can occur ex vivo, i.e. in an artificial environment outside the living organism.

As used herein, the terms "transfected", "transformed" or infected" refer to a cell comprising a vector of the invention (transient expression), whereas the term "genetically transformed" refers to a cell whose genome has been definitively modified by a polynucleotide of the invention (permanent expression).

Said transitory or stably transformed cells can be any prokaryotic (bacteria) or eukaryotic (yeast, insect or animal including mammal especially human) cells. In an embodiment, cells are non-human cells. In a particular embodiment, cells of the invention are isolated human cells, "isolated" meaning outside of their natural environment.

In a particular embodiment of the invention, the cell is HEK-293-T7-MV cell line.

More preferably, an infectious recombinant MV genome vector suitable to carry out the invention is produced using a cDNA of MV Schwarz strain cloned into the plasmid pTM-MVSchw, deposited by Institut Pasteur at the CNCM (Paris, France) under number 1-2889 on Jun. 12, 2002, the sequence of which is described by Combredet (Combredet, C. et al., 2003, *J Virol,* 77(21): 11546-11554), and also disclosed in WO2004/000876. The plasmid pTM-MVSchw has been obtained from a Bluescript plasmid, and comprises the polynucleotide coding for the full-length MV (+) RNA strand of the Schwarz strain placed under the control of the promoter of the T7 RNA polymerase, and has 18967 nucleotides. cDNAs from other MV strains may be similarly obtained starting from the nucleic acid purified from viral particles of live-attenuated MV. Accordingly a recombinant MV genome vector of the invention is pTM-MVDVax6 as illustrated by SEQ ID NO: 139, pTM-MVDVax7 as illustrated by SEQ ID NO: 140, pTM-MVDVax8 as illustrated by SEQ ID NO: 141, pTM-MVDVax9 as illustrated by SEQ ID NO: 142, pTM-MVDVax10 as illustrated by SEQ ID NO: 143 or pTM-MVDVax11 as illustrated by SEQ ID NO: 149.

The plasmid comprising the recombinant MV genome thus defined (genome vectors) are suitable for use in a rescue system for the preparation of recombinant measles virus particles.

Rescue of recombinant MV viruses can be performed as previously described (Combredet et al., *J Virol.*, 2003, 77(21): 11546-11554), in particular using stable HEK293-T7-MV helper cells (WO2004/000876).

In order for the rescue of recombinant MV particles to be achieved and enable the assembly of recombinant MV particles of the invention, helper cells (host cells) are used which express an RNA polymerase such as the T7 RNA polymerase and the N, P and L proteins of MV and which are genetically transformed with a MV genome vector according to the invention. The expression of the MV proteins by the helper cell may be obtained by genetically transforming the helper cell with additional, vectors such as transcomplementation plasmids, expressing an RNA polymerase such as the T7 RNA polymerase and the N, P and L proteins of MV.

In a particular embodiment of the invention, the helper cell line is the 293-T7-NP cell line deposited with the Collection Nationale de Cultures de Micro-organismes (CNCM) on Jun. 14, 2006, under number 1-3618 or the 293-nIsT7-NP MV cell line deposited with the CNCM on Aug. 4, 2006, under number 1-3662.

The present invention also relates to recombinant MV particles, which are rescued from a helper cell line expressing the T7 RNA polymerase and the N, P and L proteins of MV, and which further expresses a nucleic acid encoding a vector of the invention or a nucleic acid encoding a recombinant MV genome vector of the invention.

In a further aspect, the present invention relates to an immunogenic composition comprising (a) DENV antigens composed of the fusion of the EDIII polypeptides of the four DENV serotypes, fused to ectoM of DENV1, in particular DENV antigens having the sequence of SEQ ID NO: 145 and (b) the chimeric polyepitope according to the invention, which optionally does not comprise an accessory adjuvant.

The present invention also relates to an immunogenic composition comprising recombinant MV particles according to the invention, which composition optionally does not comprise an accessory adjuvant. Interestingly, the recombinant MV particles of the invention are capable of eliciting a humoral and/or a cellular immune response(s) against the dengue virus infection or against both MV and the dengue virus infection, in a host upon administration. In a particular embodiment, the immunogenic composition of the invention elicits an immune response, in particular a T-cell immune response against the DENV1, DENV2, DENV3 and DENV4 and accordingly may elicit a protective response against infection by any virus of these DENV 1 to 4 serotypes.

According to a particular embodiment of the invention, the immunogenic composition is formulated for an administration through parenteral route such as subcutaneous (s.c.), intradermal (i.d.), intramuscular (i.m.), intraperitoneal (i.p.) or intravenous (i.v.) injection.

According to another particular embodiment of the invention, the immunogenic composition is administered in one or multiple administration dose(s), in particular in a prime-boost administration regime.

In a particular embodiment, the immunogenic composition does not comprise an accessory adjuvant.

The quantity to be administered (dosage) depends on the subject to be treated, including the condition of the patient, the state of the individual's immune system, the route of administration and the size of the host. Suitable dosages range from $10^3$ TCID50 to $10^7$ TCID50 and can be modified by one skilled in the art, depending on circumstances.

The present invention also relates to a vaccine composition comprising (a) DENV antigens composed of the fusion of the EDIII polypeptides of the four DENV serotypes, fused to ectoM of DENV1, and (b) the chimeric polyepitope according to the invention, which optionally does not comprise an accessory adjuvant.

The present invention also relates to a vaccine composition comprising recombinant MV particles according to the invention, which optionally does not comprise an accessory adjuvant.

The present invention also relates to a method to prevent and/or treat a dengue virus infection in a human subject comprising administering a pharmaceutically effective quantity of recombinant MV particles according to the invention or an immunogenic composition according to the invention, wherein said particles or composition are in admixture with a pharmaceutically acceptable vehicle; and/ or an adjuvant.

As used herein, the term "to prevent" refers to a method by which a dengue virus infection is obstructed or delayed.

As used herein, the term "to treat" refers to a method by which the symptoms of a dengue virus infection are either alleviated, i.e. decrease of the dengue virus infection in the host or improvement of the clinical condition of the patient, or completely eliminated.

As defined herein, a pharmaceutically acceptable vehicle encompasses any substance that enables the formulation of the chimeric polyepitope, the polynucleotide, the vector, in particular the recombinant MV genome vector according to the invention within a composition. A vehicle is any substance or combination of substances physiologically acceptable i.e., appropriate for its use in a composition in contact with a host, especially a human, and thus non-toxic. Examples of such vehicles are phosphate buffered saline solutions, distilled water, emulsions such as oil/water emulsions, various types of wetting agents sterile solutions and the like.

As defined herein, an adjuvant includes, for example, liposomes, oily phases, such as Freund type adjuvants, generally used in the form of an emulsion with an aqueous phase or can comprise water-insoluble inorganic salts, such as aluminium hydroxide, zinc sulphate, colloidal iron hydroxide, calcium phosphate or calcium chloride.

The present invention also relates to a method to produce recombinant MV particles for the preparation of an anti-dengue virus vaccine, comprising or consisting of:

a) transfecting a recombinant MV genome vector according to the invention, in a helper cell line which expresses the T7 RNA polymerase and the N, P and L proteins of MV;

b) transferring said helper cell line onto cells competent to sustain the replication and production of recombinant MV particles expressing a chimeric polyepitope according to the invention and optionally a polypeptide comprising a tetravalent DENV antigen composed of the fusion of the EDIII polypeptides of the four serotypes, fused to ectoM of DENV1, in particular DENV antigens having the sequence of SEQ ID NO: 145; and c) recovering the recombinant MV particles produced in step b).

In a preferred embodiment of the invention, the competent cells in step b) are Vero (African green monkey kidney) cells, CEF (chick embryo fibroblast) cells or MRC5 cells.

EXAMPLES

Cell Culture

Vero cells were maintained in DMEM Glutamax (Gibco-BRL) supplemented with 5% heat-inactivated fetal calf serum (FCS, Invitrogen, Frederick, Md.). Stable HEK293-17-MV helper cells used for viral rescue (WO2004/000876) were grown in DMEM supplemented with 10% FCS.

Construction and Rescue of Recombinant MV Vectors

Figure 7:
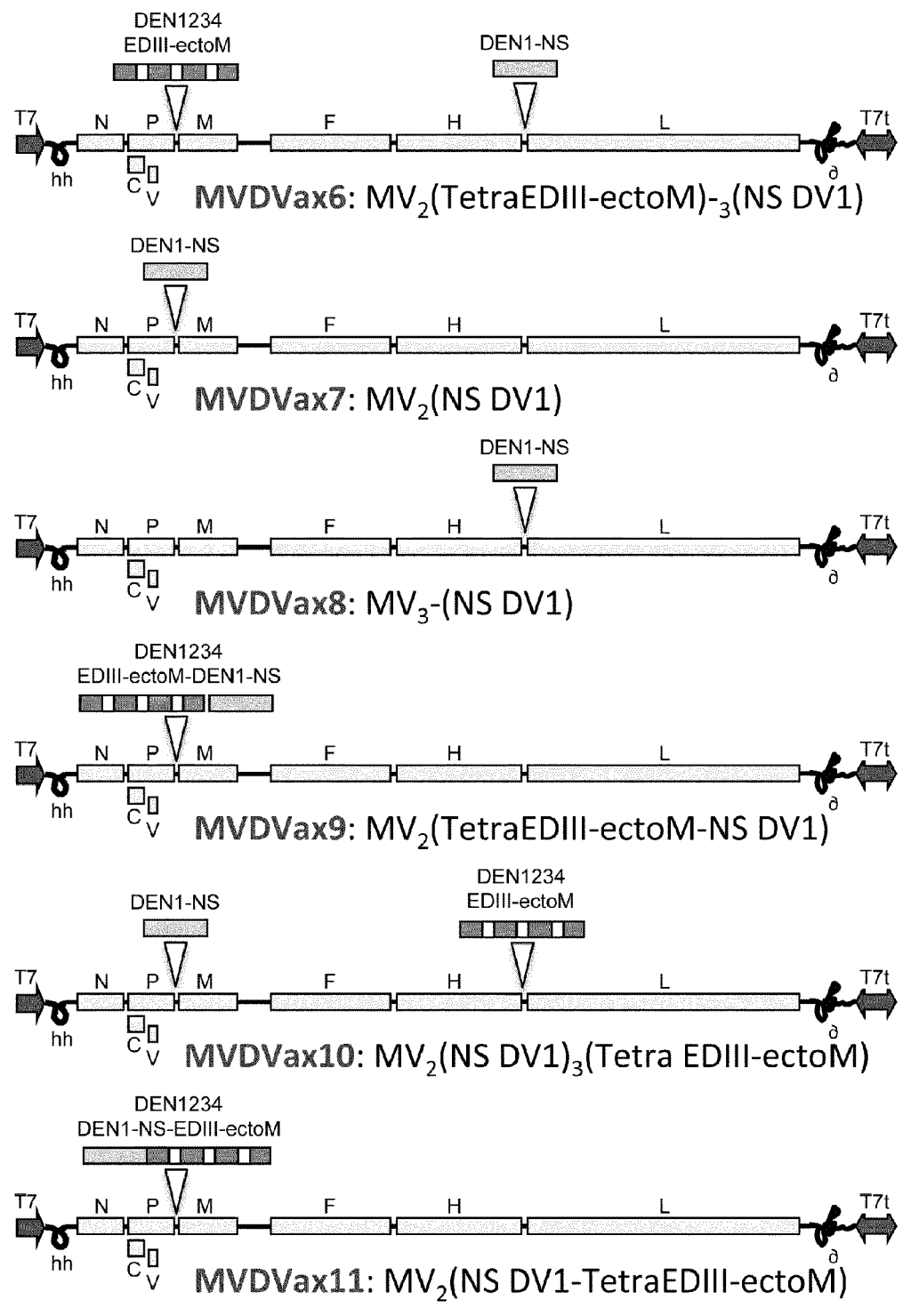

The plasmid pTM-MVSchw, which contains an infectious MV cDNA corresponding to the anti-genome of the Schwarz MV vaccine strain, has been previously described (Combredet et al., *J Virol.*, 2003, 77(21): 11546-11554). The synthetic cDNA encoding for the polyepitopic construct of non-structural proteins from DENV1 was inserted into BsiWI/BssHII-digested pTM-MVSchw vectors in different positions, in combination or not with tetrameric EDIII antigen previously described (Brand/er et al., *PLoS* 2007, 1(3), e96; Brandler et al., *Vaccine*, 2010, 28, 6730-6739) (FIG. 7). Rescue of recombinant viruses was performed as previously described (Combredet et al., *J Virol.*, 2003, 77(21): 11546-11554) using stable HEK293-T7-MV helper cells (WO2004/000876). The recombinant viruses were grown on Vero cells and viral titers were determined by end point dilution assay on Vero cells.

Western Blot

Figure 8:
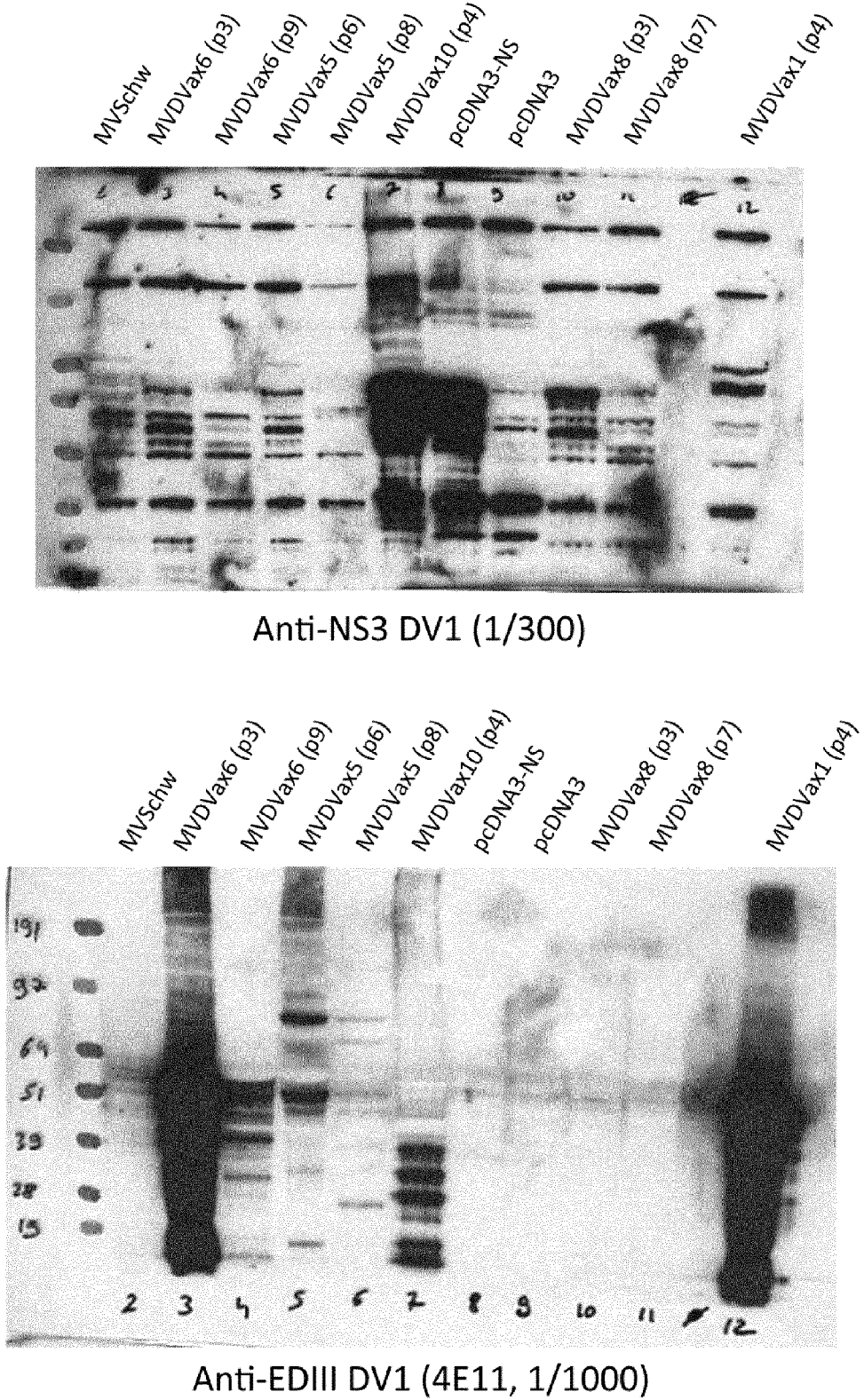
FIG. 8. Detection by western blot of the expression of DENV NS polyepitopic antigen (top) and DENV EDIII tetrameric antigen (bottom) in cell lysates of Vero cells infected by MV-DENV recombinant viruses or HEK293 cells transfected with pcDNA3-NS plasmid. DENV proteins were probed with specific Mabs.

To evidence the expression of DENV antigens by MV vectors or pcDNA3 expression plasmid, lysates from Vero cells infected with MV-DENV or from HEK293 cells transfected with pcDNA3-NS plasmid were fractionated by SDS-PAGE, transferred to cellulose membranes (Amersham Pharmacia Biotech), and probed with anti-EDIII DENV1 mAb 4E11 or anti-NS3 antibody. A goat anti-mouse IgG-horseradish peroxidase (HRP) conjugate (Amersham) was used as secondary antibody. Peroxidase activity was visualized with an enhanced chemiluminescence detection kit (Pierce). This analysis showed that MV vectors expressed both EDIII tetrameric antigen and NS polyepitopic antigen. Similarly, the pcDNA3-NS plasmid expressed a high level of NS polyepitopic antigen (FIG. 8).

Mice Experiments and Cellular Immune Responses

Mice deficient for IFNα/β receptors and expressing human MV receptor (hCD46+/− IFNα/β−/− or CD46-IFNAR) were produced as previously described (Combredet et al., *J Virol.*, 2003, 77(21): 11546-11554) and housed under pathogen-free conditions at the Institut Pasteur animal facility. Experiments were conducted following the guidelines of the Office of Laboratory Animal Care at Institut Pasteur. Group of six 6-week-old CD46-IFNAR mice were inoculated via the intraperitoneal (ip) route with a single administration of $10^5$ TCID50 of MV-DENV vectors or empty MV. Mice were euthanized 7 days post-immunization and spleens were collected. Freshly extracted splenocytes were specifically stimulated for 18 h with DENV peptides (2 µg/ml) or MV (MOI 1). Cells were also stimulated by concanavalin A (5 µg/ml, Sigma) as a positive control and by RPMI-IL-2 (10 U/ml) as a negative control. Their capacity to secrete IFN-γ upon stimulation was tested by ELISPOT assay as previously described (Guerbois et al., *Virology*, 2009, 388(1): 191-203).

Peptides

A series of 36 overlapping peptides (9 to 15 amino acids overlapping of 5 amino acids) covering the entire NS polyepitopic sequence were synthesized (FIG. 9). Five specific peptides were also identified with prediction algorithms able to bind to H2-Db and H2-Kb T cell receptors expressed in CD46-IFNAR mice (FIG. 9). These peptides were used in ELISPOT experiments either in pools or as individual peptides to restimulate T cell responses in splenocytes from immunized CD46-IFNAR mice.

Immunogenicity in CD46-IFNAR Mice

Figure 10:
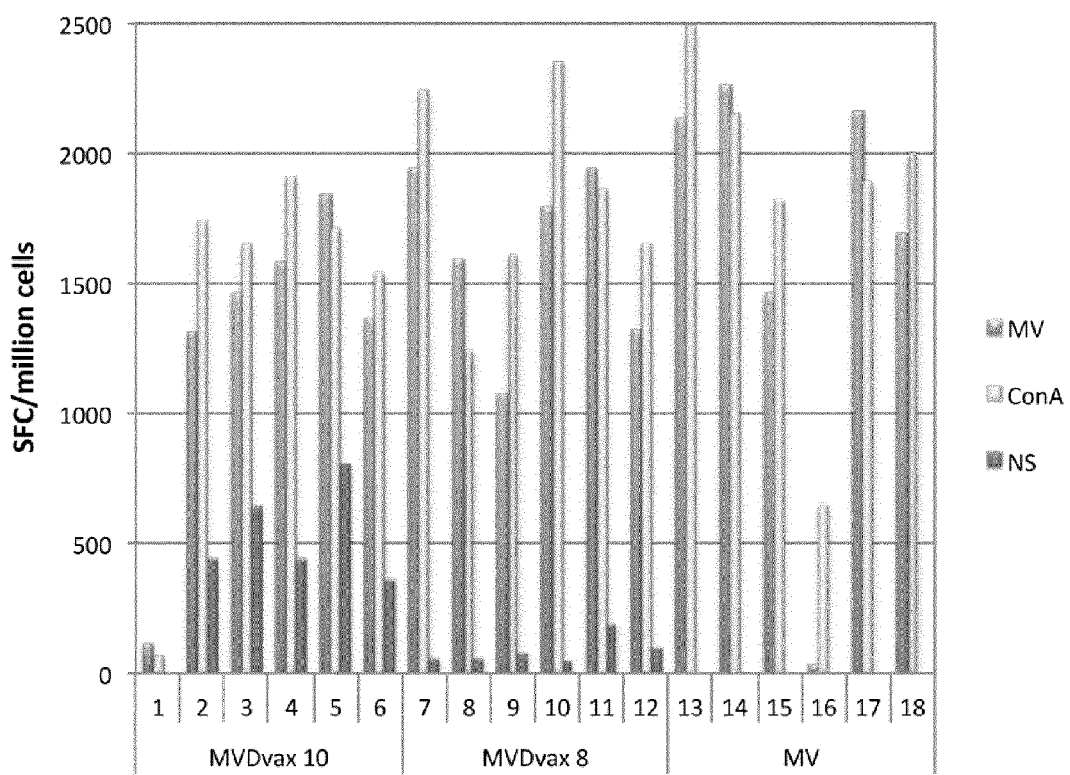
FIG. 10. ELISPOT quantification of T-cell responses in CD46-IFNAR mice immunized by MV-DENV vectors. Groups of six mice were immunized with MVDVax10, MVDVax8 or empty MV. ELISPOTS were quantified in splenocytes collected 7 days after a single immunization. Responses to DENV NS peptides, MV and concavalin A as a positive control are shown.
Figure 11:
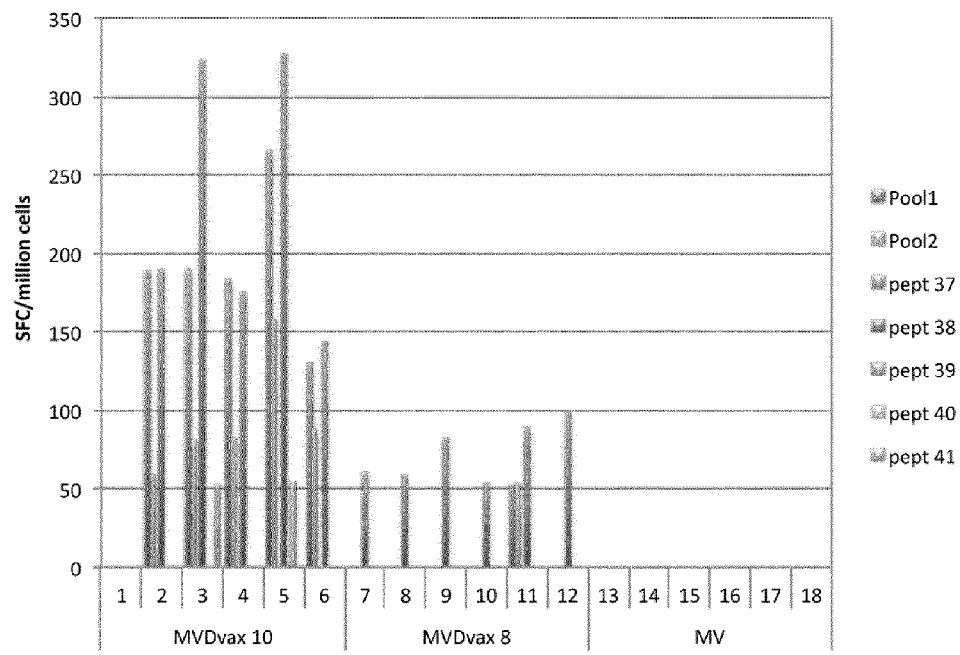
FIG. 11. ELISPOT quantification of T-cell responses in CD46-IFNAR mice immunized by MV-DENV vectors. The responses to different peptide pools or individual peptides covering the NS polyepitopic antigen are shown.
Figure 12:
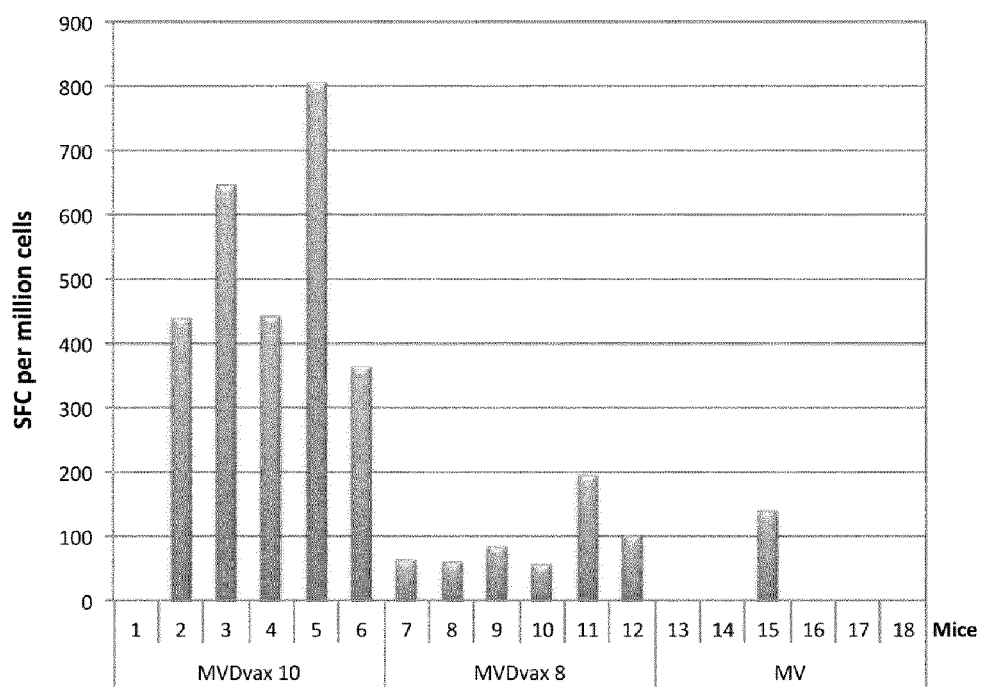
FIG. 12. ELISPOT responses in CD46-IFNAR mice immunized by MV-DEBNV vectors cumulating the responses to individual peptides or pools.

Cell-mediated immune response (CMI) elicited by immunization with MV-DENV was assessed using IFN-γ ELISPOT assay on splenocytes collected 7 days after a single immunization. After ex vivo stimulation by DENV NS peptides or MV, a significant number of DENV-specific IFN-γ secreting cells (400-800 spot forming cells/$10^6$ splenocytes) were detected in MV-DENV immunized mice (FIGS. 10, 11, 12), which represented one third of MV-specific response in similar stimulation condition (1500 spot forming cells/$10^6$ splenocytes). Most mice immunized with MV-DENV (5/6) had a significant CMI response to DENV, demonstrating that a single MV-DENV immunization in this experimental model was able to prime anti-DENV cellular immunity within a week.

Immunogenicity in Humanized Mice.

Figure 13:
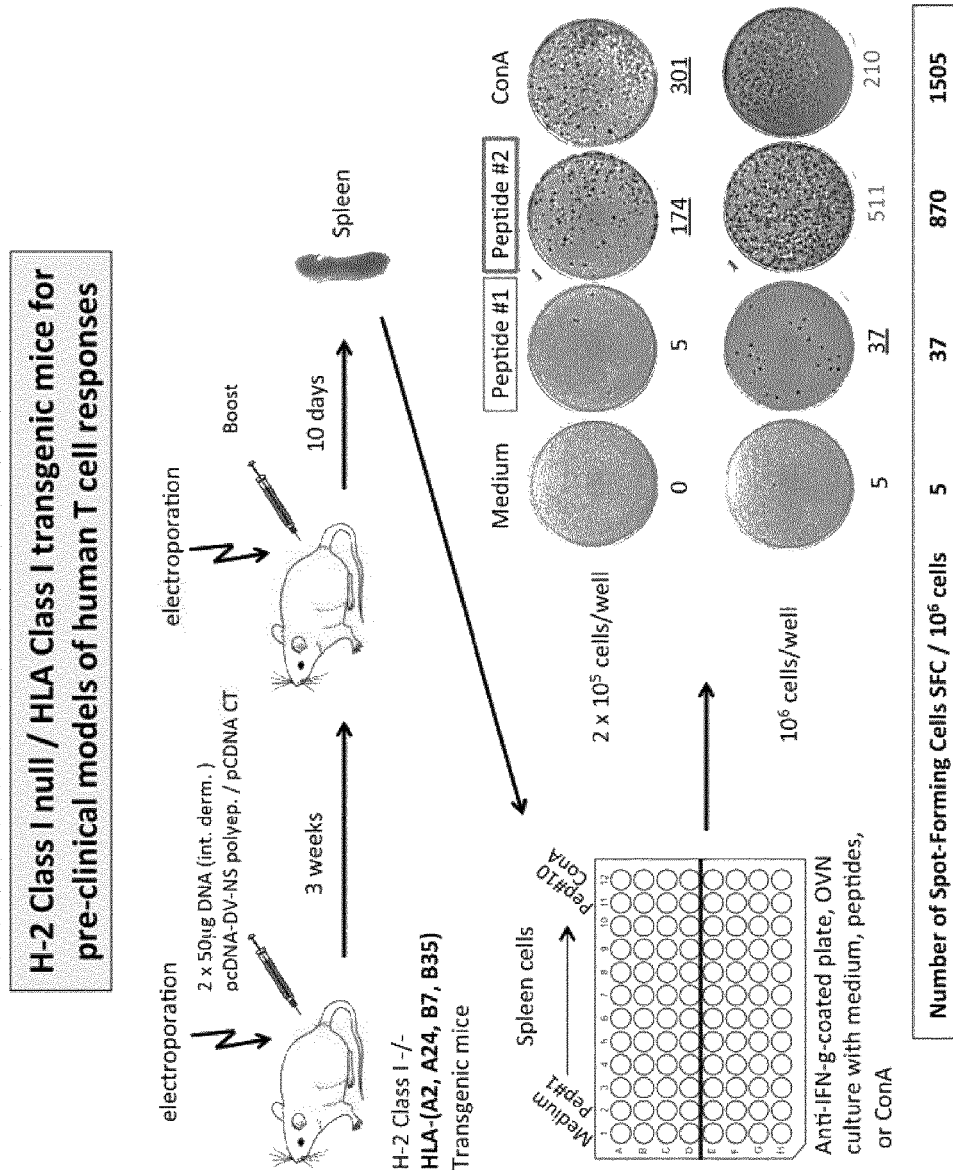
FIG. 13. Procedure for eliciting CD8+ T cell responses in H-2 Class I null/HLA Class I transgenic mice and quantification of IFN-γ response by ELISPOT assay.

The pcDNA3 plasmid expressing the DENV1 NS polyepitope sequence under a CMV promoter was injected by electroporation in HLA-A*02-01, HLA-A*24:02, HLA-B*07:02 and HLA-B*35:01 monochain transgenic/H-2 Class I null mice, and the INF-γ response of spleen cells was quantified by ELISPOT assay against individual peptides (FIG. 13).

Among 47 potential epitopes described to elicit an HLA-restricted T cell response in human donors previously exposed to DENV, 13 epitopes were identified in immunized mice: four in the first domain of NS3, and restricted by HLA-A*02:01, HLA-B*07:02 and HLA-13*35:01, four in the second domain of NS3, restricted by HLA-A*24:02 and HLA-B*35:01, three in NS4b, restricted by HLA-A*24:02 and HLA-B*35:01, and two in NS5 and restricted by HLA-A*02:01 and HLA-B*07:02 (FIG. 14).

Figure 15A:
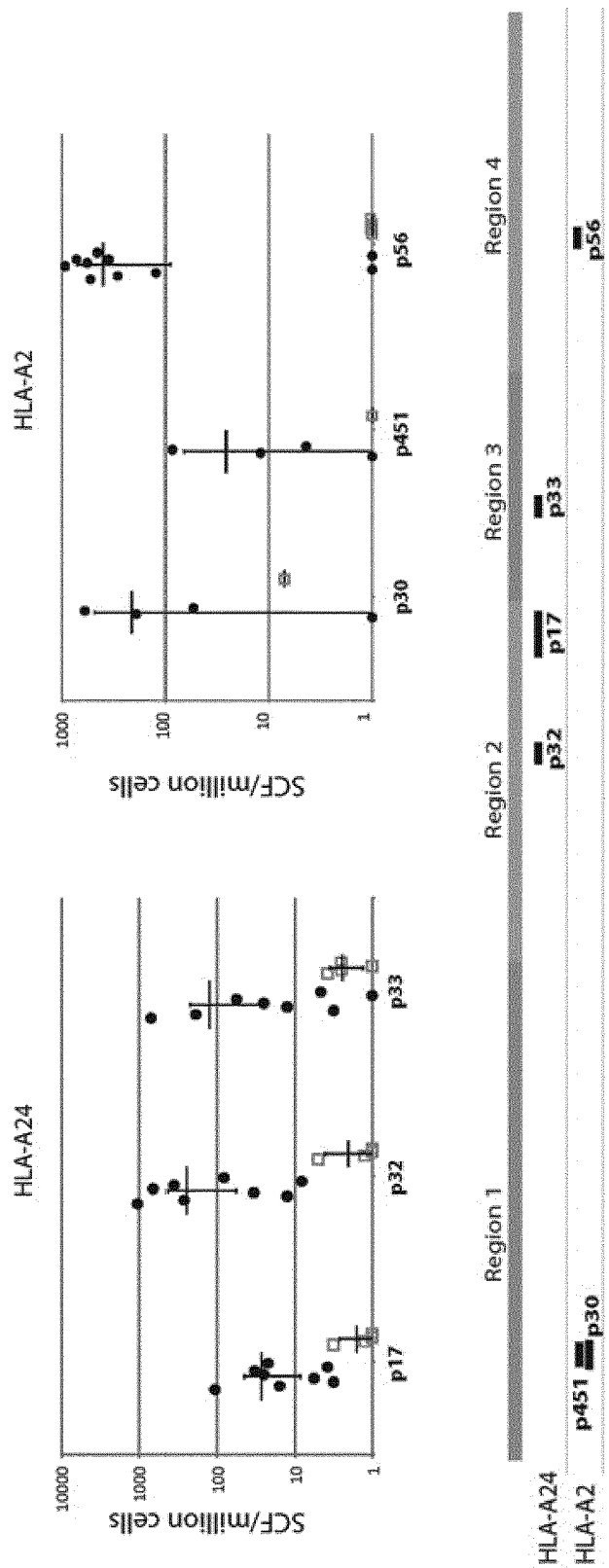
FIG. 15. Quantification of the T-cell responses in HLA-A2, A24, B7 and B35 transgenic mice by ELISPOT assay. Three independent experiments have been performed, in which a total of ten and four HLA-A*02:01 transgenic mice received the DENV1-NS polyepitopic construct (SEQ ID NO: 3) and the control plasmid, respectively, eight and four HLA-A*24:02 transgenic mice received the DENV1-NS polyepitopic construct and the control plasmid, respectively, five and four HLA-B*07:02 received the DENV1-NS polyepitopic construct and the control plasmid, respectively and five and three HLA-B*35:01 transgenic mice received the DENV1-NS polyepitopic construct and the control plasmid, respectively. All the animals were immunized by intradermic injection (100 µg DENV1-NS polyepitopic construct, or 100 µg pcDNA3.1 control plasmid) followed by in vivo electroporation. Two immunizations were performed at 3 week interval, and spleen cells were tested for IFN-γ secretion by ELISPOT 10 days after the second injection. Individual mice were tested in parallel with different peptides at 2 µg/ml and with concanavalin A (ConA) at 5 µg/ml, final concentration.
Figure 15B:
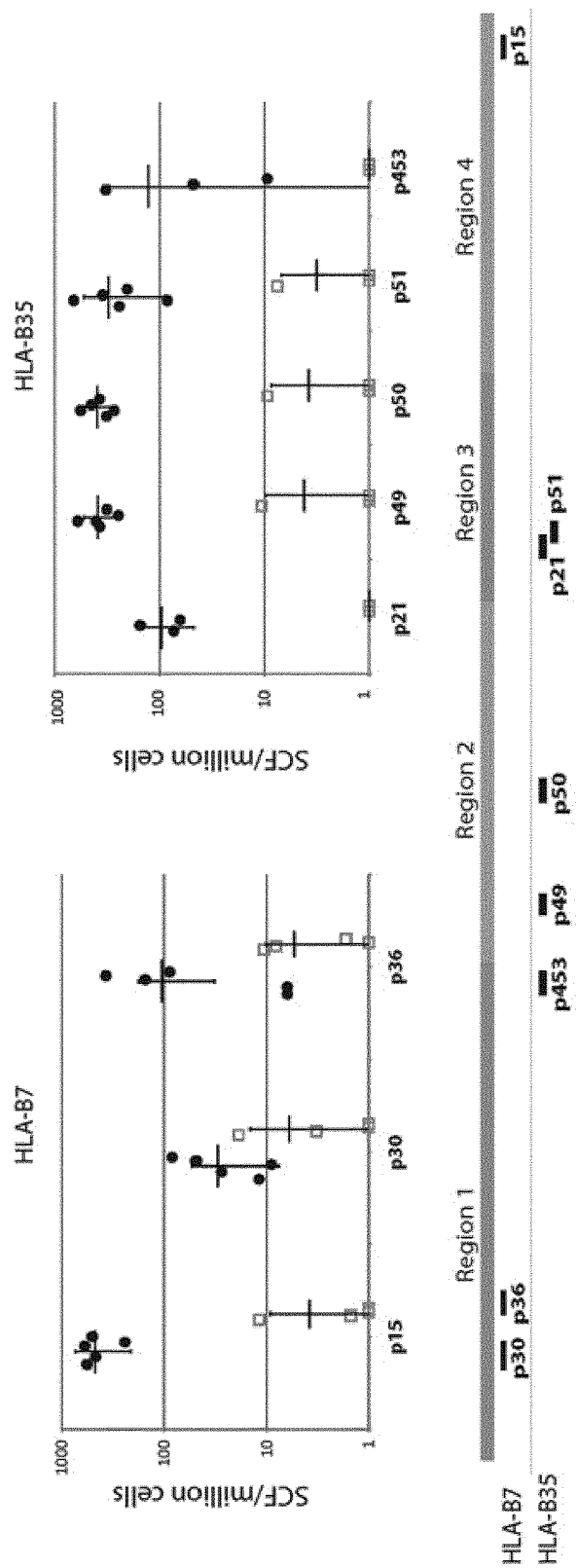

Comparison of the T cell response elicited in the different transgenic mice revealed a higher number of peptides with a higher magnitude in the HLA-B*35:01 mice, in agreement with the high response frequency and magnitude associated with this allele in human donors from hyperendemic area (Weiskopf D et al., *Proc Natl Acad Sci USA* 2013, 110(22): E2046-2053) (FIG. 15).

Interestingly, and in agreement with the conserved antigenic regions selected from the different serotypes (FIGS. 1 and 14), the amino acid sequence of the antigenic epitopes present in the polyepitopic construct was conserved among the other dengue serotypes, in particular for the two anchor residues involved in HLA binding (Table 3). This suggested that the CD8+ T cells induced by the DENV1-based construct could also recognize peptides derived from DENV2, 3 and 4. This T-cell cross reactivity may be verified using human EBV-transformed B cell line C1R (Zemmour J et al., *J Immunol* 1992, 148(6):1941-1948) expressing a single HLA allele, and pulsed with the cognate peptide, or infected with DENV1, 2, 3 and 4.

Evidence of an In Vitro and In Vivo Immune Protection Induced after DNA Immunization with the DENV1-NS Polyepitopic Construct (SEQ ID NO: 3)

A. Induction of DENV-Specific Cytotoxic T Cells in HLA Class I Transgenic Mice.

To investigate a role of CD8 T cells in a protective immune response, four groups of H-2 Class I null/HLA Class I transgenic mice (HLA-A*02:01, HLA-A*24:02, HLA-B*07:02 and HLA-B*35:01) were vaccinated by DNA immunization. In each group made up of seven transgenic animals, five and two mice received the DENV1-NS polyepitopic construct and the control plasmid, respectively. All animals were immunized by intradermic injection (100 µg DENV1-NS polyepitopic or control plasmid) followed by in vivo electroporation. Two immunizations were performed at three weeks interval, and spleen cells were tested for in vitro and in vivo cytotoxic activity as well as IFN-γ secretion by ELISPOT assay ten days after the second injection.

1—Evaluation of DENV-Specific Cytotoxic T Cell Responses In Vitro.

Figure 16A:
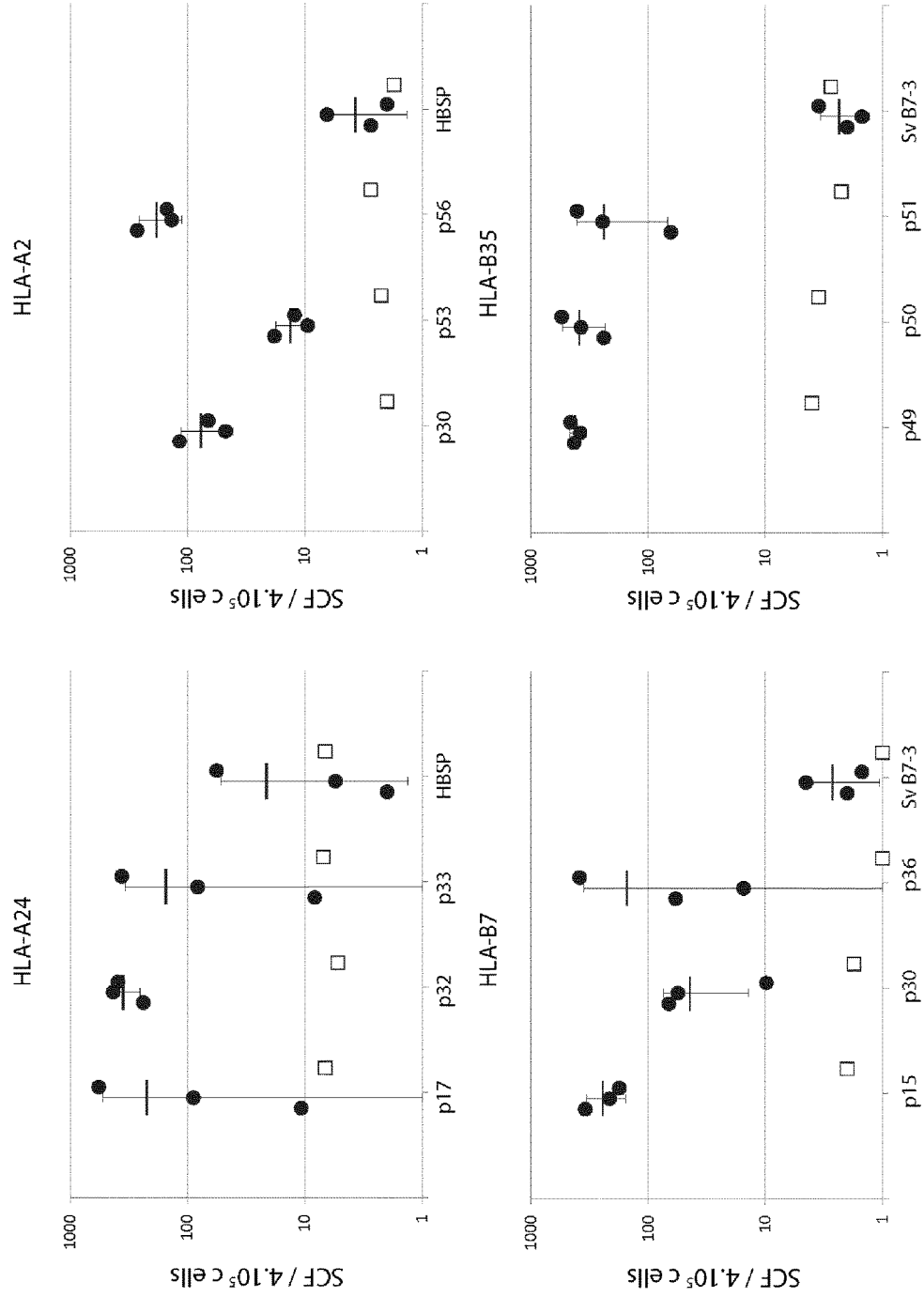
FIG. 16. A) IFN-γ and B) Granzyme B (GrB) ELISPOT responses cumulating the responses to individual peptides. In these assays, the peptides used were: For HLA-A24 transgenic mice, peptides P17, P32 and P33 (having the amino acid sequences as defined in SEQ ID NO: 39, 33 and 47 respectively) were used as cognate, and peptide HBSP A2-2 (having the amino acid sequence TLCIPHVAV as defined in SEQ ID NO: 150) as control. For HLA-A2 transgenic mice, peptides P30, P53 and P56 were used as cognate (having the amino acid sequences as defined in SEQ ID NO: 18, 51 and 55 respectively), and peptide HBSP A2-2 as control. For HLA-B7 transgenic mice, peptides P15, P30 and P36 were used as cognate (having the amino acid sequences as defined in SEQ ID NO: 68, 18 and 21 respectively), and peptide Sv B7-3 (having the amino acid sequence SPFLPLLPI as defined in SEQ ID NO: 151) as control. For HLA-B35 transgenic mice, peptides P49, P50 and P51 were used as cognate (having the amino acid sequences as defined in SEQ ID NO: 28, 32 and 45 respectively), and peptide Sv B7-3 as control.
Figure 16B:
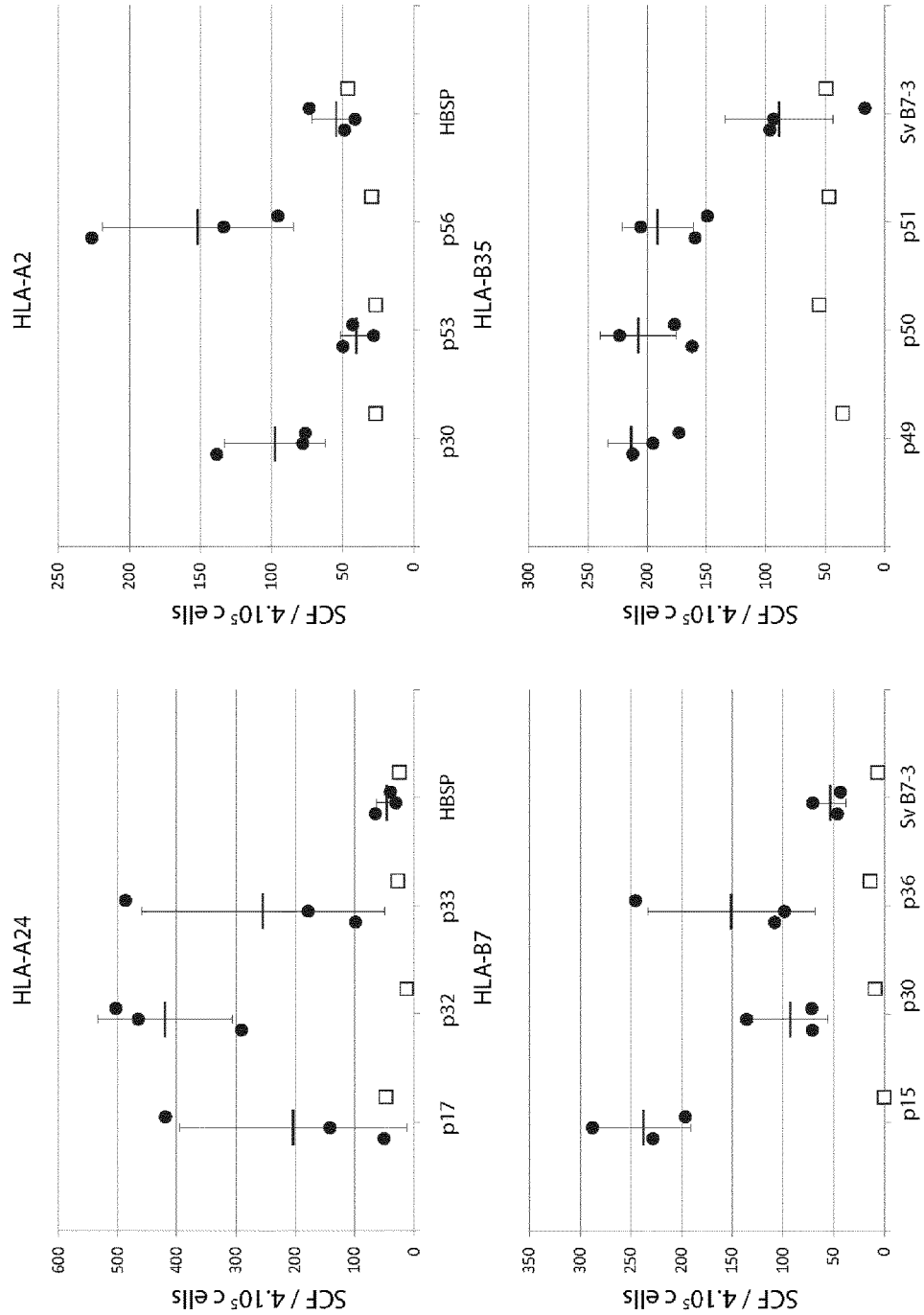

In each group of HLA Class I transgenic animals, three and one mouse that received the DENV1-NS polyepitopic construct and the control plasmid, respectively, were tested for their antigen-specific cytotoxic T cell responses. Quantification of the T cell response was obtained using the Granzyme B (GrB) ELISPOT assay, which measures at a single cell level the release of the cytotoxic mediator Granzyme B, and which was shown to correlate strongly with the ability of T cells to lyse target cells (Ewen C L et al., 2006, J Immunol Methods, 308(1-2): 156-166; Kalia V et al., 2010, Adv Exp Med Biol, 684: 79-95; Zanetti M, et al. 2010, Adv Exp Med Biol, 684:108-125) and to inhibit viral production (Marcet-Palacios M, et al., 2011, PLoS Pathog, 7(12):e1002447). In this assay, the frequency of spleen cells releasing Granzyme B upon in vitro stimulation with cognate or irrelevant peptides was measured in parallel with the frequency of cells secreting IFN-γ. Results showed a significant INF-γ and GrB response in mice immunized with the DENV1-NS polyepitopic construct, in comparison to the animals immunized with the control pcDNA3.1 plasmid (FIGS. 16A and 16B). There was also a correlation between the IFN-γ response and the release of GrB, with the highest response for both IFN-γ and GrB obtained for peptides P32 in HLA-A24 mice, P56 in HLA-A2 mice, P15 in HLA-B7 mice, and P49, P50 and P51 in HLA-B35 mice.

2—Evaluation of DENV-Specific Cytotoxic T Cells In Vivo.

Figure 17:
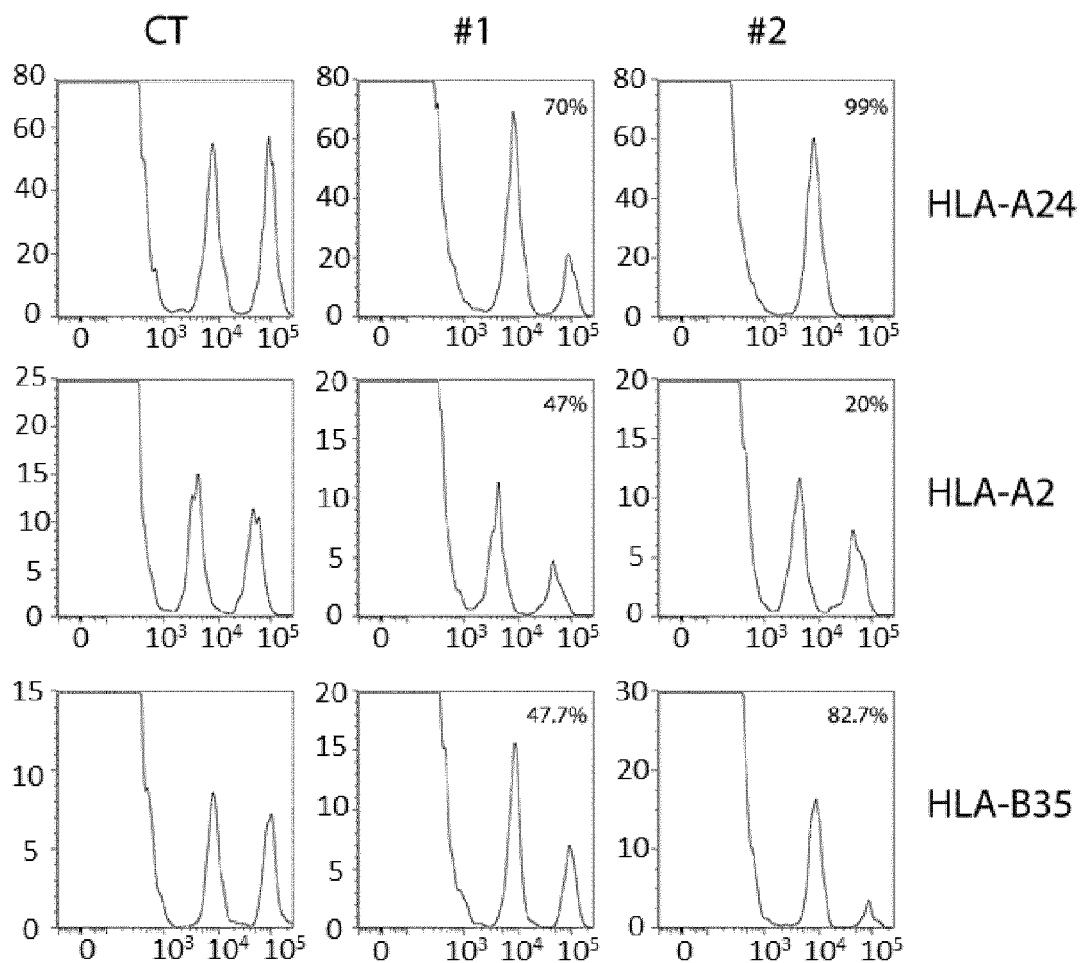
FIG. 17. In vivo cytotoxic activity of T cells from animals immunized with the DENV1-NS polyepitopic construct (SEQ ID NO: 3) or the control plasmid. For HLA-A24 mice, high stained target cells were pulsed with a mix of P17, P32 and P33 cognate peptides (having the amino acid sequences as defined in SEQ ID NO: 39, 33 and 47 respectively), while low stained control cells were not pulsed. For HLA-A2 mice, high stained target cells were pulsed with a mix of P30, P53 and P56 cognate peptides (having the amino acid sequences as defined in SEQ ID NO: 18, 51 and 55 respectively), while low stained control cells were pulsed with the HBSP A2-2 control peptide. For HLA-B35 mice, high stained target cells were pulsed with a mix of P49, P50 and P51 cognate peptides (having the amino acid sequences as defined in SEQ ID NO: 28, 32 and 45 respectively), while low stained control cells were not pulsed.
Figure 19:
FIG. 19 presents Table 2. DENV CD4 T+ cell epitopes having amino acid sequences as defined in SEQ ID NOs: 69-97.

The in vivo cytotoxic assay was performed as previously described (Clemente T. et al., 2013, Methods, 61(2):105-109). Briefly, mice immunized with the DENV1-NS polyepitopic construct or the control plasmid were adoptively transferred with syngeneic cells loaded with peptides and labeled with a fluorescent dye (Cell trace violet). A mix of $10^7$ high- and $10^7$ low-fluorescent stained cells, pulsed with specific and control peptides, respectively, was injected intravenously into recipient animals. Eighteen hours after the injection, spleen cells of recipient mice were analyzed by flow cytometry and the ratio between Cell trace high (cells pulsed with a mix of specific peptides) and Cell trace low donor cells (not pulsed or pulsed with control peptides) was determined. As an equivalent number of high and low stained cells were injected into recipient mice, a specific killing activity in immunized mice resulted in a lower fraction of high stained cells loaded with the mix of specific peptides (FIG. 17). The percentage of specific lysis was determined using the formula:

$$1 - \frac{\% \text{ Cell trace violet high immunized}/ \% \text{ Cell trace violet low immunized}}{\% \text{ Cell trace violet high naive}/ \% \text{ Cell trace violet low naive}} \times 100$$

B. Induction of a Protective Immune Response in Humanized Mice

Because type I IFN-sufficient mice are resistant to DENV infection, a vaccine-induced protective immune response against a challenge with DENV can only be considered in type I-deficient mice, or in alymphoid mice engrafted with human hematopoietic stem cells. In line with the recent development of new generations of humanized mice reconstituted with human myeloid and lymphoid compartments with HLA-restricted responses (Legrand N, et al., 2011, Proc Natl Acad Sci USA, 108(32): 13224-13229; Garcia S, et al., 2012, Immunol Lett, 146(1-2): 1-7; Serra-Hassoun M, et al., 2014, J Immunol, 193(3): 1504-1511), the inventors will use RAG$^{-/-}$ γc$^{-/-}$ mice transgenic for human SIRPalpha, in which mouse MHC class I and class II molecules have been replaced by human HLA-A2 and DR1 molecules, respectively (CH1-2hSa).

In a first setting, HLA-A2 molecules will be in the HHD configuration (with the human α1 and α2 domains of HLA-A2 linked to the murine α3 domain of H-2Db) (Pascolo S, et al., 1997, J Exp Med, 185(12): 2043-2051). The CH1-2hSa HHD mice are currently available. Three months after human hematopoietic cord blood progenitor engraftment, when all the human subsets have been reconstituted in the host, the mice will first be infected with Dengue virus to verify the in vivo viral replication in the human dendritic cell compartment. Briefly, two groups of three mice each will be injected intravenously with $10^5$ or $10^6$ PFU of the DENV1 strain KDH0026A (derived from a human clinical isolate). Virus titers will be monitored by quantitative reverse transcription (qRT)-PCR.

In a second setting, the HLA-A2 molecules will consist of the full human HHH version of the class I molecule. These new CH1-2hSa HHH hosts, which are currently under development, should improve the binding of the human CD8/TCR molecules to the MHC-peptide complexes allowing a more efficient stimulation of DENV-specific CD8 T cells. Two groups of 6 humanized CH1-2hSa HHH mice each will be immunized with the DENV1-NS polyepitopic and the control plasmid constructs, as described in FIG. 13. Within each group of 6 reconstituted mice, protection will be assessed by quantifying viral mRNA by qRT-PCR in the blood of infected animals at day 2, 4 and 7 after intravenous injection of $10^5$ or $10^6$ PFU of DENV1 strain KDH0026A within each group of three mice.

C. MVDVax Protective Efficacy in CD46-IFNAR Mice

The inventors evaluated the protective efficacy in CD46-IFNAR mice of recombinant MVDVax vectors expressing a tetravalent DENV antigen composed of the fusion of the envelope domain III (EDIII) of the four DENV serotypes fused to the ectodomain of the membrane protein (ectoM) of DENV1 and expressing simultaneously the DENV1 NS antigen of the invention (described in FIG. 7). CD46-IFNAR mice were produced as previously described (Combredet, C. et al., 2003, *J Virol,* 77(21): 11546-11554) and housed under pathogen-free conditions at the Institut Pasteur animal facility. Experiments were conducted following the guidelines of the Office of Laboratory Animal Care at Institut Pasteur. Group of six 6-week-old CD46-IFNAR mice were inoculated via the intraperitoneal (ip) route with $10^5$ TCID50 of MV-DENV vectors or empty MV. A second administration of the same dose was performed 1 month after priming. To analyze the presence of anti-MV and anti-DENV antibodies, blood was regularly collected by the periorbital route. Two months after the last immunization, all animals were experimentally challenged by intraperitoneal injection of $10^5$ TCID50 of mouse-neuro adapted DENV1 Hawaï strain grown on Vero cells (Despres et al, *J. Virol.*, 1998, 72(1), 823-829). After challenge, blood was collected by the periorbital route at day 1, 2, 3, 5, 7 and the animals were followed for clinical signs and weight for the 15 following days. DENV1 genomic viral load was determined in mice sera by one-step qRT-PCR as described below. Sera were heat inactivated at 56° C. for 30 min and the presence of anti-MV antibodies was detected using ELISA (Trinity Biotech). HRP-conjugated anti-mouse immunoglobulin (Jackson Immuno Research) was used as secondary antibody. Anti-DENV antibodies were detected as previously described (Brandler et al., Vaccine, 2010, 28, 6730-6739) by ELISA using 96-well plates coated with recombinant EDIII proteins from DENV1, DENV2, DENV3, and DENV4 produced in *E. coli* or synthesized in vitro. HRP-conjugated anti-mouse immunoglobulin was used as secondary antibody. The endpoint titers of pooled sera were calculated as the reciprocal of the last dilution giving twice the absorbance of sera from MV inoculated mice that served as negative controls.

D. MVDVax Protective Efficacy in Non-Human Primates

The inventors will evaluate in non-human primates (NHP) the protective efficacy of recombinant MVDVax vectors.

Experiments will be conducted as follows:

Viruses.

Challenge viruses: DENV1 Jamaica strain CVI 1636 3P, isolated in 1977, passages 2/3 MP/3P C6/36HT 2P Vero cells culture supernatant. DENV1 strain KDH0026A, C6/36 cell culture supernatant. DENV2 DJ.M.O.1.7.12, C6/36 cell culture supernatant. DENV4 Dominica 814669 strain, isolated in 1981, passages 4P C6/36 HT 2P Vero cells culture supernatant. These viruses are used for neutralization tests. The recombinant MVDVax vaccine virus is prepared as previously described (Brandler et al., *Vaccine,* 2010, 28, 6730-6739) and viral titer is determined by endpoint limit-dilution assay on Vero cells.

Animals.

Mauritian-derived cynomolgus macaques (*Macaca fascicularis*) are housed in BSL-3 animal care facility at the CEA. The Ile-de-France region ethics committee will approve experimental methods that are conducted in accordance with the European Directive 2010-63-UE. The animals are juvenile male and female adults (0.8-1 kg). To evaluate the immunogenicity of the vaccine candidate, 12 animals are inoculated subcutaneously with two 200-μL doses containing $10^5$ TCID50 of MVDvax vaccine virus one month apart and are boosted six month later with a third dose of $10^6$ TCID50 of MVDVax. Similarly, eight control animals receive two administrations of empty MVSchw vaccine (200 μL containing $10^5$ TCID50) and a third dose of $10^6$ TCID50 six months later. Five months after the last immunization, the animals are divided in two groups and challenged by intravenous inoculation of $1.0\times10^4$ pfu of wild type DENV1 or DENV4 suspended in 200 μL PBS. Monkeys are monitored for viremia, clinical signs, and cellular and antibody response. Peripheral blood mononuclear cells (PBMC) are isolated by Percoll density gradient centrifugation (Sigma-Aldrich). Serum and plasma are collected and stored at −20° C. for later analysis.

Humoral Responses.

Anti-DENV and anti-MV antibodies are detected in heat-inactivated sera by use of an enzyme-linked immunosorbant assay (ELISA) as previously described (Brand/er et al., *Vaccine,* 2010, 28, 6730-6739). Sera are considered positive when the optical density (OD) is twice the OD of sera from control animals.

DENV Neutralization Test.

Anti-DENV neutralizing antibodies are detected using a focus reduction neutralization test (PRNT) in Vero cells as previously described (Brandler et al., *PLoS* 2007, 1(3), e96). Briefly, anti-DENV neutralizing antibodies are detected on Vero cells using 50 FFU of Vero-adapted DENV1 Hawaï strain (WHO reference strain, Genbank accession no. AF226687), DENV2 Jamaica strain N.1409, DENV3 strain PaH881/88 Thailand, or DENV4 strain 63632/76 Burma. The endpoint titer is calculated as the highest serum dilution that reduces the number of FFU by at least 50%. The neutralizing antibody titer is also tested at the Center for Vaccine Development (CVD, Mahidol University, Thailand). In the tests conducted at the CVD, monkey kidney-derived LLC-MK2 cells and the following DENV are used: DENV1 (16007), DENV2 (16681), DENV3 (16562), and DENV4 (1036), and the PRNT titer is calculated based on a 50% reduction in plaque count (PRNT50) as previously described (Sirivichayakul et al. *Virol. J.* 2014, 11-48).

Cellular Immune Responses.

Cellular responses are detected by Elispot assay and by polyfunctional flow cytometry following stimulation of lymphocytes from peripheral blood with synthetic peptide pools covering the DENV1-NS insert of MVDVax, as previously described (Stebbings et al, *PLoS-One,* 2012, 7(11), e50397). Cells are stimulated in triplicate with synthetic 15-mer (overlapping by 11aa) peptide pools (BEI, http://www.beiresources.org) at 1 μg/ml/peptide or a live-attenuated empty MV at $10^4$ TCID50/$10^6$ cells, in the presence of 1 μg/ml of the co-stimulatory antibodies anti-CD28 and CD49d (Biolegend). Negative controls are incubated with an equal volume of DMSO (0.15% v/v) without peptide and positive controls with 1 μg/ml Staphylococcal Enterotoxin B (Sigma-Aldrich).

Quantification of DENV Viral RNA and DENV Titration.

Sera (25 μL) are diluted in 0.5 mL Dulbecco's modified Eagle's medium (DMEM)/5% fetal calf serum (FCS). Viral RNA is extracted (QIAamp viral RNA extraction kit, Qiagen) and analyzed by one step DENV qRT-PCR, using high fidelity enzymes (Roche, Mannheim, Germany). Real-time qRT-PCR of DENV RNA is performed with RealArt™ WNV LC real-time PCR kit (Qiagen). For virus titration, samples are diluted in 250 μL of medium, and infectivity of serial dilutions is assayed on Vero cells overlaid with DMEM Glutamax/2% FCS containing 0.8% final (weight/volume) carboxy methylcellulose. After 4 days of incubation, cells are fixed and plaques are visualized by an immuno-focus assay as previously described (Brandler et al., *PLoS* 2007, 1(3), e96).

The invention claimed is:

1. A chimeric polyepitope polypeptide having an amino acid sequence of less than 600 amino acid residues comprising polypeptide fragments (a), (b), (c), and (d) directly or indirectly fused in this order:

(a) a first fragment of the non-structural (NS) NS3 protein of dengue virus (DENV) serotype 1 (DENV1) comprising an amino acid sequence as defined in SEQ ID NO: 6, (b) a second fragment of the NS3 protein of DENV1 comprising an amino acid sequence as defined in SEQ ID NO: 9, (c) a fragment of the NS4b protein of DENV1 comprising an amino acid sequence as defined in SEQ ID NO: 12, and (d) a fragment of the NS5 protein of DENV1 comprising an amino acid sequence as defined in SEQ ID NO: 15;

or a variant of the chimeric polyepitope polypeptide having an amino acid sequence more than 80% identical to the amino acid sequence of the chimeric polyepitope polypeptide over its whole length;

wherein the chimeric polyepitope polypeptide elicits a human leukocyte antigen (HLA)-restricted $CD8^+$ and/or $CD4^+$ T cell response against DENV1, DENV2, DENV3 and DENV4.

2. The chimeric polyepitope polypeptide according to claim 1, which comprises an amino acid sequence selected from the group consisting of SEQ ID NO: 3, SEQ ID NOs: 146, SEQ ID NO: 147 and SEQ ID NO: 148.

3. Recombinant measles virus (MV) particles, which are rescued from a helper cell line expressing the T7 RNA polymerase and the N, P and L proteins of MV, and which further expresses a polynucleotide encoding the chimeric polyepitope polypeptide of claim 1.

4. An immunogenic composition comprising (a) DENV antigens composed of the fusion of the EDIII polypeptides of the four DENV serotypes, fused to ectoM of DENV1, wherein the DENV antigens have the sequence of SEQ ID NO: 145; and (b) the chimeric polyepitope polypeptide according to claim 1.

5. An immunogenic composition comprising recombinant MV particles according to claim 3.

6. The immunogenic composition according to claim 4, wherein said composition is formulated for an administration through parenteral route such as subcutaneous (s.c.), intradermal (i.d.), intramuscular (i.m.), intraperitoneal (i.p.) or intravenous (i.v.) injection.

7. The immunogenic composition according to claim 4, wherein said composition is formulated for administration in one or multiple administration dose(s) in a prime-boost administration regime.

8. The chimeric polyepitope polypeptide according to claim 1, wherein the chimeric polyepitope polypeptide consists of polypeptide fragments (a), (b), (c), and (d).

9. A method to immunize a human subject against a dengue virus infection comprising administering a pharmaceutically effective quantity of recombinant MV particles according to claim 3, wherein said particles are in admixture with a pharmaceutically acceptable vehicle and/or an adjuvant.

10. A method to treat a dengue virus infection in a human subject comprising administering a pharmaceutically effective quantity of recombinant MV particles according to claim 3, wherein said particles are in admixture with a pharmaceutically acceptable vehicle and/or an adjuvant.

* * * * *